(12) United States Patent
Neya et al.

(10) Patent No.: US 6,333,324 B1
(45) Date of Patent: *Dec. 25, 2001

(54) PIPERAZINE COMPOUNDS AS INHIBITORS OF MMP OR TNF

(75) Inventors: Masahiro Neya, Tsuchiura; Hitoshi Yamazaki, Tsukuba; Natsuko Kayakiri, Suita; Kentaro Sato, Tsukuba; Teruo Oku, Takatsuki, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,928

(22) PCT Filed: Dec. 15, 1997

(86) PCT No.: PCT/JP97/04613
  § 371 Date: Jul. 26, 1999
  § 102(e) Date: Jul. 26, 1999

(87) PCT Pub. No.: WO98/27069
  PCT Pub. Date: Jun. 25, 1998

(30) Foreign Application Priority Data

Dec. 17, 1996 (AU) .................................................. PO4249
Jun. 3, 1997 (AU) .................................................. PO7156
Aug. 14, 1997 (AU) .................................................. PO8568

(51) Int. Cl.[7] ..................... C07D 241/04; C07D 409/14; C07D 409/12; C07D 405/12; A61K 31/495

(52) U.S. Cl. ..................... 514/235.5; 544/383; 544/375; 544/379; 544/367; 544/121; 544/364; 544/366; 514/252.13; 514/252.12; 514/254.1; 514/253.01; 514/254.06

(58) Field of Search ..................... 544/383, 375, 544/379, 367, 121, 364, 366; 514/252.12, 254.1, 252.13, 235.5, 253.01, 254.06

(56) References Cited

U.S. PATENT DOCUMENTS 5,753,653 * 5/1998 Bender et al. ..................... 514/227.5

FOREIGN PATENT DOCUMENTS

| | | |
|---|---|---|
| 0 606 046 | 7/1994 | (EP) . |
| WO 96/33172 | 10/1996 | (WO) . |
| 96/33172 * | 10/1996 | (WO) . |
| WO 97/20824 | 6/1997 | (WO) . |
| WO 98/08825 | 3/1998 | (WO) . |

* cited by examiner

*Primary Examiner*—Mukund J. Shah
*Assistant Examiner*—Hong Liu
(74) *Attorney, Agent, or Firm*—Oblon, Spivak, McClelland, Maier & Neustadt, P.C.

(57) ABSTRACT

A compound of formula (I) wherein A is a sulfonyl or a carbonyl; $R^1$ is an optionally substituted aryl, an optionally substituted heterocyclic group, an optionally substituted lower alkyl or an optionally substituted lower alkenyl; $R^2$ is a hydrogen, an optionally substituted lower alkyl, an optionally substituted aryl or an optionally substituted heterocyclic group; $R^3$ is an optionally substituted lower alkyl, an optionally substituted lower alkoxy, an optionally substituted aryloxy, an optionally substitued lower alkenyl, an optionally substituted aryl, an optionally substituted heterocyclic group or an optionally substitued amino; $R^4$ is a hydrogen, an optionally substituted lower alkyl, an optionally substituted aryl or an optionally substituted heterocyclic group; $R^5$ is a hydrogen, an optionally substituted lower alkyl, an optionally substituted aryl or an optionally substituted heterocyclic group; and $R^{10}$ is a hydroxy or a protected hydroxy, and a pharmaceutically acceptable salt thereof. The compound of the present invention is useful as a medicament for prophylactic and therapeutic treatment of MMP- or TNFα-mediated diseases.

(I)

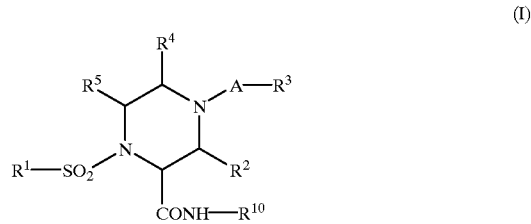

9 Claims, No Drawings

PIPERAZINE COMPOUNDS AS INHIBITORS OF MMP OR TNF

FIELD OF THE INVENTION

The present invention relates to new compounds and pharmaceutically acceptable salts thereof.

More particularly, it relates to new compounds and pharmaceutically acceptable salts thereof which are useful as inhibitors of matrix metalloproteinases (hereinafter to be referred to as MMP) or the production of tumor necrosis factor α (hereinafter to be referred to as TNFα), to pharmaceutical compositions comprising the same, to use of the same as medicaments, and to methods for using the same therapeutically in the treatment and/or the prevention of MMP- or TNFα-mediated diseases.

BACKGROUND ART

Some piperazine compounds to be useful as metalloproteinase inhibitors, or the like are known (WO 97/20824, etc.).

DISCLOSURE OF THE INVENTION

One object of the present invention is to provide new and useful compounds and pharmaceutically acceptable salts thereof, and to provide a process for preparing said new compound and salts thereof, which have pharmacological activities such as MMP- or TNFα-inhibitory activity and the like.

Another object of the present invention is to provide a pharmaceutical composition comprising, as an active ingredient, said compound or a pharmaceutically acceptable salt thereof.

A further object of the present invention is to provide use of said compounds and pharmaceutically acceptable salts thereof as medicaments for prophylactic and therapeutic treatment of MMP- or TNFα-mediated diseases.

A still further object of the present invention is to provide a method for using the same for the treatment and/or the prevention of MMP- or TNFα-mediated diseases in mammals, especially humans.

The compounds of the present invention have inhibitory activity on MMP or the production of TNFα, and are useful for the treatment and/or prevention of diseases such as stroke, arthritis, cancer, tissue ulceration, decubitus ulcer, restenosis, periodontal disease, epidermolysis bullosa, scleritis, psoriasis and other diseases characterized by matrix metalloproteinase activity, as well as AIDS, sepsis, septic shock and other diseases caused by the production of TNFα.

There are a number of structurally related metalloproteases which effect the breakdown of structural proteins. Matrix-degrading metalloproteases, such as gelatinase (MMP-2, MMP-9), stromelysin (MMP-3) and collagenase (MMP-1, MMP-8, MMP-13), are involved in tissue matrix degradation and have been implicated in many pathological conditions involving abnormal connective tissue and basement membrane matrix metabolism, such as arthritis (e.g., osteoarthritis and rheumatoid arthritis), cerebral disease (e.g., stroke, etc.), tissue ulceration (e.g., corneal, epidermal and gastric ulcerations), abnormal wound healing, periodontal disease, bone disease (e.g., Paget's disease and osteoporosis), tumor metastasis or invasion and HIV-infection.

A tumor necrosis factor is recognized to be involved in many infections and autoimmune diseases. Furthermore, it has been shown that TNF is the prime mediator of the inflammatory response seen in sepsis and septic shock.

The object compounds of the present invention are novel and can be represented by the following formula (I):

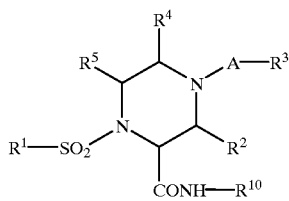

(I)

wherein
A is a sulfonyl or a carbonyl;
$R^1$ is an optionally substituted aryl, an optionally substituted heterocyclic group, an optionally substituted lower alkyl or an optionally substituted lower alkenyl;
$R^2$ is a hydrogen, an optionally substituted lower alkyl, an optionally substituted aryl or an optionally substituted heterocyclic group;
$R^3$ is an optionally substituted lower alkyl, an optionally substituted lower alkoxy, an optionally substituted aryloxy, an optionally substituted lower alkenyl, an optionally substituted aryl, an optionally substituted heterocyclic group or an optionally substituted amino:
$R^4$ is a hydrogen, an optionally substituted lower alkyl, an optionally substituted aryl or an optionally substituted heterocyclic group;
$R^5$ is a hydrogen, an optionally substituted lower alkyl, an optionally substituted aryl or an optionally substituted heterocyclic group; and
$R^{10}$ is a hydroxy or a protected hydroxy, provided that when A—$R^3$ is methylsulfonyl, then $R^1$ is an aryl substituted by a substituent selected from the group consisting of halogen, cyano, nitro, amino, acylamino, lower alkylamino, carbamoyl, hydroxy, lower alkoxy, phenoxy, lower alkyl, aryl and heterocyclic group, an optionally substituted heterocyclic group, an optionally substituted lower alkyl or an optionally substituted lower alkenyl, and the above-mentioned heterocyclic group is each selected from the group consisting of
unsaturated 3- to 8-membered heteromonocyclic group containing 1 to 4 nitrogen atoms,
saturated 3- to 8-membered heteromonocyclic group containing 1 to 4 nitrogen atoms,
unsaturated condensed 7- to 13-membered heterocyclic group containing 1 to 5 nitrogen atoms,
unsaturated 3- to 8-membered heteromonocyclic group containing 1 or 2 oxygen atoms and 1 to 3 nitrogen atoms,
saturated 3- to 8-membered heteromonocyclic group containing 1 or 2 oxygen atoms and 1 to 3 nitrogen atoms,
unsaturated condensed 7- to 13-membered heterocyclic group containing 1 or 2 oxygen atoms and 1 to 3 nitrogen atoms,
unsaturated 3- to 8-membered heteromonocyclic group containing 1 or 2 sulfur atoms and 1 to 3 nitrogen atoms,
saturated 3- to 8-membered heteromonocyclic group containing 1 or 2 sulfur atoms and 1 to 3 nitrogen atoms,
unsaturated 3- to 8-membered heteromonocyclic group containing sulfur atom, unsaturated 3- to 8-membered heteromonocyclic group containing oxygen atom, saturated 3- to 8-membered heteromonocyclic group containing oxygen atom, unsaturated condensed 7- to 13-membered heterocyclic group containing 1 or 2 sulfur atoms and 1 to 3 nitrogen atoms and unsaturated condensed 7- to 13-membered heterocyclic group containing 1 or 2 oxygen atoms, and a pharmaceutically acceptable salt thereof.

The object compounds of the present invention can be prepared by the following processes.

Process 1

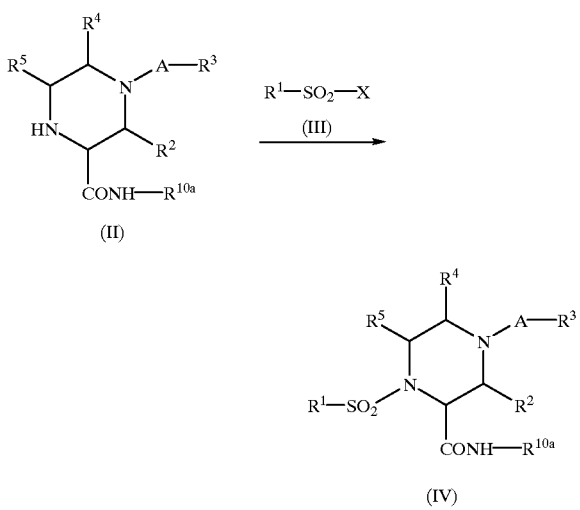

Process 2

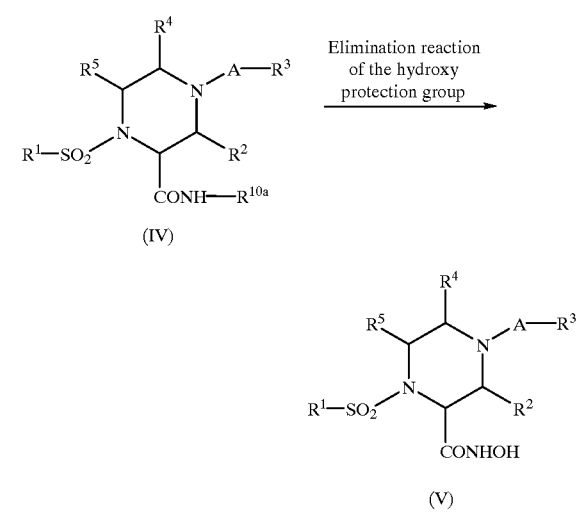

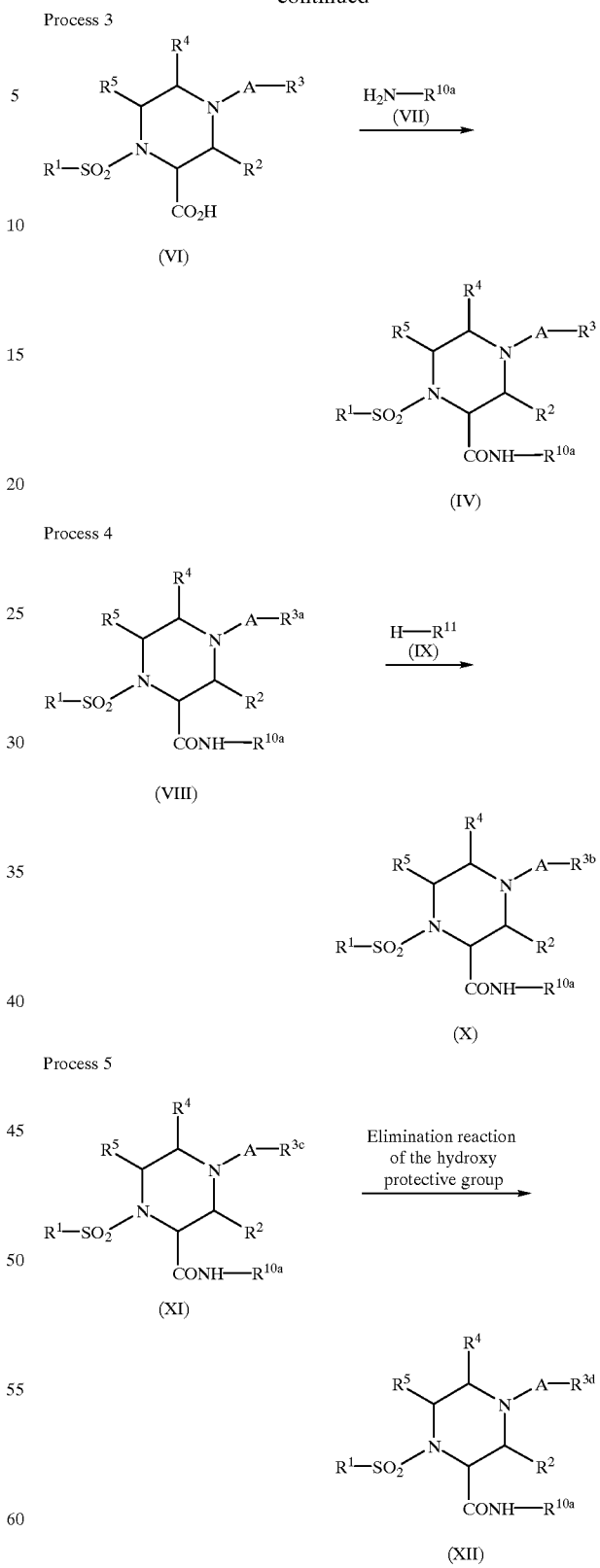

Process 6

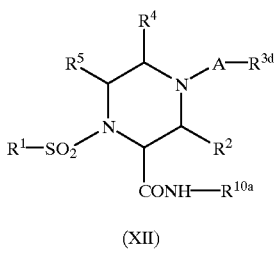

(XII)

amidation reaction →

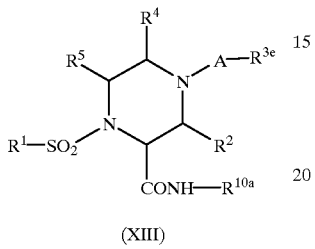

(XIII)

Process 7

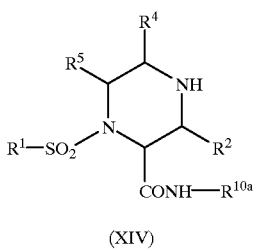

(XIV)

$R^3-A-X$
(XV)
→

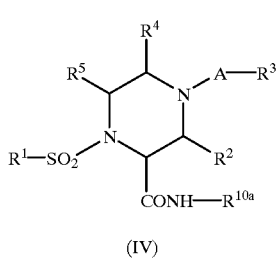

(IV)

Process 8

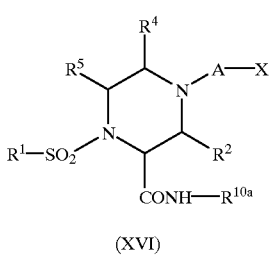

(XVI)

$H_2N-R^{3f}$
(XVII)
→

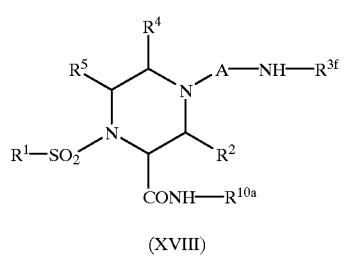

(XVIII)

Process 9

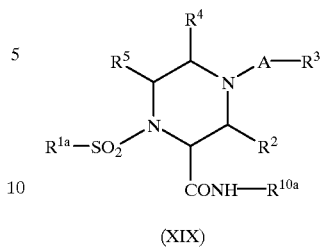

(XIX)

Elimination reaction of the hydroxy protective group →

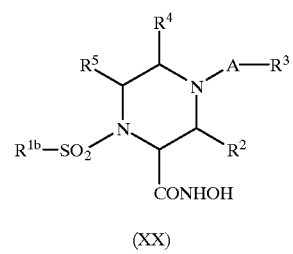

(XX)

Process 10

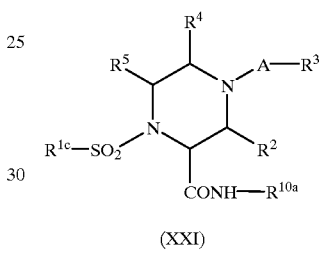

(XXI)

solvolysis →

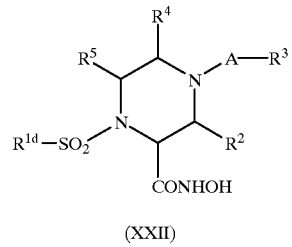

(XXII)

In the above formulas (II), (III), (IV), (V), (VI), (VII), (VIII), (X), (XI), (XII), (XIII), (XIV), (XV), (XVI), (XVIII), (XIX), (XX), (XXI) and (XXII), A, $R^1$, $R^2$, $R^3$, $R^4$ and $R^5$ are as defined above, $R^{10a}$ is a protected hydroxy, X is a leaving group, $R^{1a}$ is a heterocyclic group having a substituent which is aryl substituted by acyloxy, $R^{1b}$ is a heterocyclic group having a substituent which is aryl substituted by hydroxy, $R^{1c}$ is a heterocyclic group having a substituent which is aryl substituted by cyanoalkyloxy, $R^{1d}$ is a heterocyclic group having a substituent which is aryl substituted by alkoxycarbonylalkyloxy, $R^{3a}$ is an alkyl substituted by halogen, $R^{3b}$ is a di(lower)alkylamino(lower)alkyl, an N-containing heterocyclic-(lower)-alkyl or an optionally substituted heterocyclic-thio(lower)alkyl, $R^{3c}$ is a protected carboxy(lower)alkyl or a protected carboxy(lower)alkylamino, $R^{3d}$ is a carboxy(lower)alkyl or a carboxy(lower)alkylamino, $R^{3e}$ is an N-containing heterocyclic-carbonyl(lower)alkyl, an optionally substituted amino-carbonyl(lower)alkyl or an optionally substituted amino-carbonyl(lower)alkylamino, $R^{3f}$ is a hydroxy(lower)alkyl, and $R^{11}$ is a di(lower)alkylamino, an N-containing heterocyclic group or an optionally substituted heterocyclic-thiol. Heterocyclic group, aryl, acyl, alkyl, alkoxy, protected carboxy and halogen in the $R^{1a}$, $R^{1b}$, $R^{1c}$, $R^{1d}$, $R^{3a}$, $R^{3b}$, $R^{3c}$, $R^{3d}$, $R^{3e}$, $R^{3f}$ and $R^{11}$ are as defined below.

The starting compounds (II), (VI), (XIV) and (XVI) can be prepared according to the following Preparations or by a conventional method.

Suitable pharmaceutically acceptable salts of the object compounds may be conventional non-toxic salts and include an acid addition salt such as an organic acid salt (e.g., acetate, trifluoroacetate, maleate, tartrate, fumarate, methanesulfonate, benzenesulfonate, formate, toluenesulfonate, etc.), an inorganic acid salt (e.g., hydrochloride, hydrobromide, hydroiodide, sulfate, nitrate, phosphate, etc.), or a salt with a base such as an amino acid (e.g., arginine, aspartic acid, glutamic acid, etc.), an alkali metal salt (e.g., sodium salt, potassium salt, etc.), an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzyl-ethylenediamine salt, etc.), or the like.

The object compounds and pharmaceutically acceptable salts thereof may include solvates such as enclosure compounds (e.g., hydrate, etc.).

Suitable examples and illustrations of the various definitions, which the present invention includes within its scope and which are shown in the above and subsequent descriptions of the present specification, are as follows.

Suitable "aryl" in the term "optionally substituted aryl" and "optionally substituted aryloxy" includes an aryl having 6 to 10 carbon atoms, such as phenyl, tolyl, xylyl, cumenyl, mesityl, naphthyl and the like, preferably phenyl, and may have one or more substituents. Examples of the substituents for substituted aryl are halogen, cyano, nitro, amino, acylamino, lower alkylamino, carbamoyl, hydroxy, lower alkoxy, aryloxy, lower alkyl, optionally substituted aryl, optionally substituted heterocyclic group and the like, preferably halogen, nitro and lower alkoxy (e.g., methoxy, etc.).

Suitable "heterocyclic group" in the term "optionally substituted heterocyclic group" means saturated or unsaturated, 3- to 8-membered monocyclic or polycyclic heterocyclic group containing at least one hetero atom such as oxygen atom, sulfur atom, nitrogen atom and the like.

More preferable heterocyclic groups are:

unsaturated 3- to 8-membered, preferably 5- or 6-membered, heteromonocyclic group containing 1 to 4 nitrogen atoms, for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), and the like;

saturated 3- to 8-membered, preferably 5- or 6-membered, heteromonocyclic group containing 1 to 4 nitrogen atoms, for example, azetidinyl, pyrrolidinyl, imidazolidinyl, piperidinyl, piperidino, pyrazolidinyl, piperazinyl, and the like;

unsaturated condensed 7- to 13-membered, preferably 9- or 10-membered, heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, and the like;

unsaturated 3- to 8-membered, preferably 5- or 6-membered, heteromonocyclic group containing 1 or 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), and the like;

saturated 3- to 8-membered, preferably 5- or 6-membered, heteromonocyclic group containing 1 or 2 oxygen atoms and 1 to 3 nitrogen atoms, for example, morpholinyl, morpholino, and the like;

unsaturated condensed 7- to 13-membered, preferably 9- or 10-membered, heterocyclic group containing 1 or 2 oxygen atoms and 1 to 3 nitrogen atoms, for example, benzoxazolyl, benzoxadiazolyl, and the like;

unsaturated 3- to 8-membered, preferably 5- or 6-membered, heteromonocyclic group containing 1 or 2 sulfur atoms and 1 to 3 nitrogen atoms, for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), and the like;

saturated 3- to 8-membered, preferably 5- or 6-membered, heteromonocyclic group containing 1 or 2 sulfur atoms and 1 to 3 nitrogen atoms, for example, thiazolidinyl, and the like;

unsaturated 3- to 8-membered, preferably 5- or 6-membered, heteromonocyclic group containing sulfur atom, for example, thienyl, and the like;

unsaturated 3- to 8-membered, preferably 5- or 6-membered, heteromonocyclic group containing oxygen atom, for example, furyl, and the like;

saturated 3- to 8-membered, preferably 5- or 6-membered, heteromonocyclic group containing oxygen atom, for example, oxolanyl, and the like;

unsaturated condensed 7- to 13-membered, preferably 9- or 10-membered, heterocyclic group containing 1 or 2 sulfur atoms and 1 to 3 nitrogen atoms, for example, benzothiazolyl, benzothiadiazolyl, and the like;

unsaturated condensed 7- to 13-membered, preferably 9- or 10-membered, heterocyclic group containing 1 or 2 oxygen atoms, for example, benzodihydrofuranyl, benzodioxolenyl, and the like;

The most preferable heterocyclic groups may be unsaturated 5- or 6-membered heteromonocyclic group containing 1 to 4 nitrogen atoms, saturated 5- or 6-membered, heteromonocyclic group containing 1 to 4 nitrogen atoms, unsaturated 5- or 6-membered heteromonocyclic group containing 1 or 2 oxygen atoms and 1 to 3 nitrogen atoms, saturated 5- or 6-membered heteromonocyclic group containing 1 or 2 oxygen atoms and 1 to 3 nitrogen atoms, unsaturated 5- or 6-membered heteromonocyclic group containing 1 or 2 sulfur atoms and 1 to 3 nitrogen atoms, unsaturated 5- or 6-membered heteromonocyclic group containing a sulfur atom, and unsaturated 9- or 10-membered heterobicyclic group containing 1 or 2 oxygen atoms.

These heterocyclic groups may have one or more substituents. Examples of the substituents for substituted heterocyclic group are halogen, cyano, nitro, amino, acylamino, lower alkylamino, carbamoyl, hydroxy, lower alkoxy, aryloxy, lower alkyl, aryl, optionally substituted heterocyclic group, haloaryl, hydroxyaryl, lower alkoxyary, lower alkylaryl, nitroaryl, biphenylyl, aryloxyaryl, trihaloalkylaryl, cyano(lower)alkoxyaryl, cyanoaryl, cyano(lower)alkylaryl, lower alkanoyloxyaryl, lower alkanoyloxy(lower)alkylaryl, di(lower)-alkylaminosulfonylaryl, hydroxy(lower)alkylaryl, lower alkoxycarbonylaryl, lower alkoxycarbonyl(lower)alkoxyaryl, lower alkoxysulfonyloxyaryl, aryl substituted by halogen and hydroxy, aryl substituted by halogen and alkanoyloxy, aryl substituted by halogen and lower alkoxy, lower alkyl-heterocyclic group and aryl-heterocyclic group and the like, preferably halogen; phenyl; halophenyl; hydroxyphenyl; lower alkoxyphenyl; lower alkylphenyl; nitrophenyl; biphenylyl; phenoxyphenyl; trihalo(lower)alkylphenyl; cyano(lower)alkoxyphenyl; cyanophenyl; cyano(lower)alkylphenyl; lower alkanoyloxyphenyl; lower alkanoyloxy(lower)alkylphenyl; di(lower)alkylaminosulfonylphenyl; hydroxy(lower)alkylphenyl; lower alkoxycarbonylphenyl; lower alkoxycarbonyl(lower)alkoxyphenyl; lower alkoxysulfonyloxyphenyl; phenyl substituted by halogen and hydroxy, phenyl substituted by halogen and lower alkanoyloxy; phenyl substituted by halogen and lower alkoxy; heterocyclic group selected from the group consisting of unsaturated 9- or 10-membered heterobicyclic group containing 1 or 2 oxygen atoms, unsaturated 5- or 6-membered heteromonocyclic group containing 1 to 4 nitrogen atoms, unsaturated 5- or 6-membered heteromonocyclic group containing 1 or 2 oxygen atoms and 1 to 3 nitrogen atoms and unsaturated 5- or 6-membered heteromonocyclic group containing 1 or 2 sulfur atoms and 1 to 3 nitrogen atoms; and a lower alkyl- or (phenyl-)heterocyclic group, said heterocyclic group being unsaturated 5- or 6-membered heteromonocyclic group containing 1 or 2 oxygen atoms and 1 to 3 nitrogen atoms.

Suitable "lower alkyl" in the term "optionally substituted lower alkyl" is a straight or branched alkyl having 1 to 6 carbon atoms, and exemplified by methyl, ethyl, propyl, isopropyl, butyl, isobutyl, tert-butyl, pentyl, hexyl and the like, preferably methyl and propyl, which may have one or more substituents. Examples of the substituents for substituted alkyl are halogen, cyano, nitro, acylamino, carbamoyl, hydroxy, lower alkoxy, optionally substituted aryloxy, optionally substituted aryl, heterocyclic group, heterocyclic-carbonyl, lower alkylcarbamoyl, carboxy, protected carboxy, di(lower)alkylamino, lower alkylamino, protected amino, arylcarbonylamino, heterocyclic-carbonylamino, lower alkanoylamino, lower alkylsulfonylamino, di(lower)alkylaminosulfonylamino, heterocyclic-sulfonylamino, heterocyclic-thio, lower alkylheterocyclic-thio and the like, preferably halogen for $R^1$, and halogen, carbamoyl, heterocyclic group, heterocyclic-carbonyl, lower alkylcarbamoyl, carboxy, protected carboxy, di(lower)alkylamino, lower alkylamino, protected amino, arylcarbonylamino, heterocyclic-carbonylamino, lower alkanoylamino, lower alkylsulfonylamino, di(lower)alkylaminosulfonylamino, heterocyclic-sulfonylamino, heterocyclic-thio and lower alkylheterocyclic-thio for $R^3$.

Suitable "lower alkenyl" in the term "optionally substituted lower alkenyl" is a straight or branched alkenyl having 2 to 6 carbon atoms, and exemplified by ethenyl, 1-propenyl, 2-propenyl, 1-butenyl, 2-butenyl, 1-pentenyl, 2-pentenyl and the like, preferably ethenyl, which may have one or more substituents. Examples of the substituents for substituted alkyl are halogen, cyano, nitro, acylamino, lower alkylamino, carbamoyl, hydroxy, lower alkoxy, optionally substituted aryloxy, optionally substituted aryl, heterocyclic group, heterocyclic-carbonyl and the like, preferably aryl (e.g., phenyl, etc.) for $R^1$, and heterocyclic group (e.g., pyridyl, etc.) for $R^3$.

Suitable "lower alkoxy" in the term "optionally substituted alkoxy" is a straight or branched alkenyl having 1 to 6 carbon atoms, and exemplified by methoxy, ethoxy, propoxy, isopropoxy, butoxy, isobutoxy, tert-butoxy, pentyloxy, tert-pentyloxy, hexyloxy and the like, preferably methoxy, which may have one or more substituents. Examples of the substituents for substituted alkoxy are halogen, cyano, nitro, acylamino, lower alkylamino, carbamoyl, hydroxy, lower alkoxy, optionally substituted aryloxy, optionally substituted aryl, heterocyclic group, heterocyclic-carbonyl and the like, preferably aryl (e.g., fluorenyl, etc.).

Suitable "optionally substituted amino" includes a group of the formula:

wherein $R^8$ and $R^9$ are the same or different and each is hydrogen, lower alkyl, carboxy(lower)alkyl, lower alkoxycarbonyl(lower)alkyl, carbamoyl(lower)alkyl, hydroxy(lower)alkyl, aryl or cyclo(lower)alkyl.

Suitable "protected hydroxy" includes hydroxy protected by a conventional protective group, for example, substituted lower alkoxy such as lower alkoxy(lower)alkoxy (e.g., methoxymethoxy), lower alkoxy(lower)alkoxy(lower)alkoxy (e.g., methoxyethoxymethoxy) and substituted or unsubstituted aryl(lower)alkoxy (e.g., benzyloxy, nitrobenzyloxy); acyloxy such as lower alkanoyloxy (e.g., acetoxy, propionyloxy, pivaloyloxy), aroyloxy (e.g., benzoyloxy, fluorenecarbonyloxy), lower alkoxycarbonyloxy (e.g., methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy), substituted or unsubstituted aryl(lower)alkoxycarbonyloxy (e.g., benzyloxycarbonyloxy, bromobenzyloxycarbonyloxy), arenesulfonyloxy (e.g., benzenesulfonyloxy, tosyloxy) and alkanesulfonyloxy (e.g., methanesulfonyloxy, ethanesulfonyloxy); tri(lower)alkylsilyloxy (e.g., trimethylsilyloxy); tetrahydropyranyloxy; and the like.

The term "lower" is intended to mean 1 to 6 carbon atoms, preferably 1 to 4 carbon atoms, unless otherwise indicated.

Suitable "halogen" includes fluorine, bromine, chlorine and iodine.

Suitable acyl moiety of "acylamino" includes acyl such as aliphatic acyl, aromatic acyl, heterocyclic acyl and aliphatic acyl substituted by aromatic or heterocyclic group(s) derived from carboxylic, carbonic, sulfonic and carbamic acids.

The aliphatic acyl includes saturated or unsaturated, acyclic or cyclic ones, for example, alkanoyl such as lower alkanoyl (e.g., formyl, acetyl, propionyl, butylyl, isobutylyl, valeryl, isovaleryl, pivaloyl, hexanoyl, etc.), alkylsulfonyl such as lower alkylsulfonyl (e.g., mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g., methylcarbamoyl, ethylcarbamoyl, etc.), alkoxycarbonyl such as lower alkoxycarbonyl (e.g., methoxycarbonyl, ethoxycarbonyl, propoxycarbonyl, butoxycarbonyl, tert-butoxycarbonyl, etc.), alkenyloxycarbonyl such as lower alkenyloxycarbonyl (e.g., vinyloxycarbonyl, allyloxycarbonyl, etc.), alkenoyl such as lower alkenoyl (e.g., acryloyl, methacryloyl, crotonoyl, etc.), cycloalkanecarbonyl such as cyclo(lower)-alkanecarbonyl (e.g., cyclopropanecarbonyl, cyclopentanecarbonyl, cyclohexanecarbonyl, etc.), and the like.

The aromatic acyl may include $C_6$–$C_{10}$ aroyl (e.g., benzoyl, toluoyl, xyloyl, etc.), N-($C_6$–$C_{10}$)arylcarbamoyl (e.g., N-phenylcarbamoyl, N-tolylcarbamoyl, N-naphthylcarbamoyl, etc.), $C_6$–$C_{10}$ arenesulfonyl (e.g., benzenesulfonyl, tosyl, etc.), and the like.

The heterocyclic acyl may include heterocyclic-carbonyl (e.g., furoyl, thenoyl, nicotinoyl, isonicotinoyl, thiazolylcarbonyl, thiadiazolylcarbonyl, tetrazolylcarbonyl, etc.), and the like.

The aliphatic acyl substituted by aromatic group(s) may include aralkanoyl such as phenyl(lower)alkanoyl (e.g., phenylacetyl, phenylpropionyl, phenylhexanoyl, etc.), aralkoxycarbonyl such as phenyl(lower)alkoxycarbonyl (e.g., benzyloxycarbonyl, phenethyloxycarbonyl, etc.), aryloxyalkanoyl such as phenoxy(lower)alkanoyl (e.g., phenoxyacetyl, phenoxypropionyl, etc.), and the like.

The aliphatic acyl substituted by heterocyclic group(s) may include heterocyclic-alkanoyl such as heterocyclic-(lower)alkanoyl (e.g., thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted by one or more suitable substituents such as nitro and the like, and preferable acyl having such substituent(s) may be nitroaralkoxycarbonyl (e.g., nitrobenzyloxycarbonyl, etc.) and the like.

Suitable "lower alkyl" and lower alkyl moiety of "lower alkylamino", "lower alkylaryl", "trihaloalkylaryl", "cyano (lower)alkylaryl", "lower alkanoyloxy(lower)alkylaryl", "lower alkylsulfonyloxyaryl", "di(lower) alkylaminosulfonylaryl", "hydroxy(lower)alkylaryl", "lower alkyl-heterocyclic group", "lower alkylcarbamoyl", "di(lower)alkylamino", "lower alkylsulfonylamino", "di (lower)alkylaminosulfonylamino", "lower alkylheterocyclic-thio", "carboxy(lower)alkyl", "lower alkoxycarbonyl(lower)alkyl", "carbamoyl(lower)alkyl" and "hydroxy(lower)-alkyl" are the same as lower alkyl defined above with regard to "optionally substituted lower alkyl".

Suitable "lower alkoxy" and lower alkoxy moiety of "lower alkoxyaryl", "cyano(lower)alkoxyaryl", "lower alkoxycarbonylaryl", "lower alkoxycarbonyl(lower) alkoxyaryl" and "lower alkoxycarbonyl(lower)alkyl" are the same as alkoxy defined above with regard to "optionally substituted alkoxy".

Suitable "aryl" and aryl moiety of "aryloxy", "haloaryl", "hydroxyaryl", "lower alkoxyaryl", "lower alkylaryl", "nitroaryl", "aryloxyaryl", "trihaloalkylaryl", "cyano(lower) alkoxyaryl", "cyanoaryl", "cyano(lower)alkylaryl", "lower alkanoyloxyaryl", "lower alkanoyloxy(lower)alkylaryl", "di (lower)alkylaminosulfonylaryl", "hydroxy(lower) alkylaryl", "lower alkoxycarbonylaryl", "lower alkoxycarbonyl(lower)alkoxyaryl", "lower alkylsulfonyloxyaryl", "aryl substituted by halogen and hydroxy", "aryl substituted by halogen and alkanoyloxy", "aryl substituted by halogen and lower alkoxy", "arylheterocyclic group" and "arylcarbonylamino" are the same as aryl defined above with regard to "optionally substituted aryl".

Suitable "heterocyclic group" of the substituent and heterocyclic group moiety of "heterocyclic-carbonyl", "lower alkyl-heterocyclic group", "aryl-heterocyclic group", "heterocyclic-carbonylamino", "heterocyclic-sulfonylamino", "heterocyclic-thio", "lower alkylheterocyclic-thio", "heterocyclic-(lower)alkyl" and "heterocyclic-thio" are the same as heterocyclic group defined above with regard to "optionally substituted heterocyclic group".

Suitable halo moiety of "haloaryl" and "trihaloalkylaryl" is halogen defined above.

Suitable alkanoyl moiety of "lower alkanoyloxyaryl", "lower alkanoyloxy(lower)alkyl", "alkanoyloxy" and "lower alkanoylamino" is a straight or branched alkanoyl having 1 to 10, preferably 1 to 6, carbon atoms. Such group includes, for example, formyl, acetyl, propionyl, isopropionyl, butyryl, isobutyryl, valeryl, pivaloyl, hexanoyl and the like, preferably acetyl.

Suitable "protected carboxy" includes esterified carboxy wherein "esterified carboxy" is as defined below.

Suitable examples of the ester moiety of the esterified carboxy are lower alkyl ester (e.g., methyl ester, ethyl ester, propyl ester, isopropyl ester, butyl ester, isobutyl ester, tert-butyl ester, pentyl ester, hexyl ester, etc.) and the like, which may have at least one suitable substituent. Examples of the substituted lower alkyl ester are lower alkanoyloxy (lower)alkyl ester [e.g., acetoxymethyl ester, propionyloxymethyl ester, butyryloxymethyl ester, valeryloxymethyl ester, pivaloyloxymethyl ester, hexanoyloxymethyl ester, 1-(or 2-)-acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethylester, 2-ethylbutyryloxymethyl ester, 3,3-dimethylbutyryloxymethylester, 1-(or 2-)pentanoyloxyethyl ester, etc.], lower alkanesulfonyl (lower)-alkyl ester (e.g., 2-mesylethyl ester, etc.), mono(or di or tri)halo(lower)alkyl ester (e.g., 2-iodoethyl ester, 2,2, 2-trichloroethyl ester, etc.); lower alkoxycarbonyloxy (lower)alkyl ester [e.g., methoxycarbonyloxymethyl ester, ethoxycarbonyloxymethyl ester, propoxycarbonyloxymethyl ester, tert-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidylidene (lower)alkyl ester, (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g., vinyl ester, allyl ester, etc.); lower alkynyl ester (e.g., ethynyl ester, propynyl ester, etc.); ar(lower)alkyl ester which may have at least one suitable substituent (e.g., benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-tert-butylbenzyl ester, etc.); aryl ester which may have at least one suitable substituent (e.g., phenyl ester, 4-chlorophenyl ester, tolyl ester, tert-butylphenyl ester, xylyl ester, mesityl ester, cumenyl ester, etc.); phthalidyl ester; and the like.

More preferable examples of the protected carboxy thus defined may be $C_2$–$C_4$ alkenyloxycarbonyl and phenyl(or nitrophenyl)($C_1$–$C_4$)alkoxycarbonyl, and the most preferable one may be ethoxycarbonyl.

Suitable "amino-protective group" includes "acyl" mentioned above.

More preferable examples of "amino-protective group" are $C_2$–$C_4$ alkoxycarbonyl and phenyl(or nitrophenyl) ($C_1$–$C_4$)alkoxycarbonyl, and the most preferable one is tert-butoxycarbonyl.

Suitable "cyclo(lower)alkyl" is, for example, cyclopropyl, cyclobutyl, cyclopentyl, cyclohexyl, and the like.

Suitable "leaving group" includes halogen as mentioned above, acyloxy such as sulfonyloxy (e.g., mesyloxy, tosyloxy, etc.), alkoxy (e.g., tert-butoxy, etc.), aralkoxy (e.g., benzyloxy, etc.), and the like.

Of the object compounds (I),
(1) the preferred one may be the compound of the formula (I) wherein
$R^2$ is a hydrogen or an optionally substituted lower alkyl, and
$R^4$ is a hydrogen or an optionally substituted lower alkyl,
(2) the more preferred one may be the compound of the formula (I) wherein
A is a sulfonyl or a carbonyl;
$R^1$ is an aryl optionally substituted by a substituent selected from the group consisting of halogen, cyano, nitro, amino, acylamino, lower alkylamino, carbamoyl, hydroxy, lower alkoxy, phenoxy, lower alkyl, aryl and heterocyclic group; a heterocyclic group optionally substituted by a substituent selected from the group consisting of halogen, cyano, nitro, amino, acylamino, lower alkylamino, carbamoyl, hydroxy, lower alkoxy, aryloxy, lower alkyl, aryl, heterocyclic group, haloaryl, hydroxyaryl, lower alkoxyaryl, lower alkylaryl, nitroaryl, biphenylyl, aryloxyaryl, trihaloalkylaryl, cyano(lower)alkoxyaryl, cyanoaryl, cyano(lower)alkylaryl, lower alkanoyloxyaryl, lower alkanoyloxy(lower)alkylaryl, di(lower)alkylaminosulfonylaryl, hydroxy(lower)alkylaryl, lower alkoxycarbonylaryl, lower alkoxycarbonyl(lower)alkoxyaryl, lower alkylsulfonyloxyaryl, aryl substituted by halogen and hydroxy, aryl substituted by halogen and alkanoyloxy, aryl substituted by halogen and lower alkoxy, lower alkyl-heteromonocyclic group and aryl-heterocyclic group; a lower alkyl optionally substituted by halogen; or a lower alkenyl optionally substituted by aryl;
$R^2$ is a hydrogen or an optionally substituted lower alkyl;
$R^3$ is a lower alkyl optionally substituted by a substituent selected from the group consisting of halogen, heterocyclic group, carbamoyl, lower alkylcarbamoyl, carboxy, protected carboxy, heterocyclic-carbonyl, di(lower)alkylamino, protected amino, arylcarbonylamino, heterocyclic-carbonylamino, lower alkanoylamino, lower alkylsulfonylamino, di(lower)alkylaminosulfonylamino, heterocyclic-sulfonyl amino, heterocyclic-thio, lower alkylheterocyclic-thio and heterocyclic-thio; a lower alkoxy; an aryloxy; an aryl(lower)alkoxy; an optionally substituted lower alkenyl; an optionally substituted heterocyclic group; or a group of the formula:

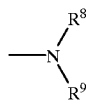

wherein
$R^8$ and $R^9$ are the same or different and each is hydrogen, lower alkyl, carboxy(lower)alkyl, lower alkoxycarbonyl(lower)alkyl, carbamoyl(lower)alkyl, hydroxy(lower)alkyl, aryl, cyclo(lower)alkyl or heterocyclic-(lower)alkyl;
$R^4$ is a hydrogen or an optionally substituted lower alkyl;
$R^5$ is a hydrogen, an optionally substituted lower alkyl, an optionally substituted aryl or an optionally substituted heterocyclic group and
$R^{10}$ is a hydroxy or a protected hydroxy; and
(3) the most preferred one may be the compound of the formula (I)

wherein
A is a sulfonyl or a carbonyl;
$R^1$ is a thienyl substituted by a substituent selected from the group consisting of halogen, phenyl, halophenyl, hydroxyphenyl, lower alkoxyphenyl, lower alkylphenyl, nitrophenyl, biphenylyl, phenoxyphenyl, trihalo(lower)alkylphenyl, cyano(lower)alkoxyphenyl, cyanophenyl, cyano(lower)alkylphenyl, lower alkanoyloxyphenyl, lower alkanoyloxy(lower)alkylphenyl, di(lower)alkylaminosulfonylphenyl, hydroxy(lower)alkylphenyl, lower alkoxycarbonylphenyl, lower alkoxycarbonyl(lower)alkoxyphenyl, lower alkylsulfonyloxyphenyl, phenyl substituted by halogen and hydroxy, phenyl substituted by halogen and lower alkanoyloxy, phenyl substituted by halogen and lower alkoxy, thiazolyl, oxazolyl, pyridyl, benzodihydrofuranyl, benzodioxolenyl, lower alkyloxadiazolyl and phenyloxadiazolyl, a thiazolyl substituted by phenyl or a thiadiazolyl substituted by phenyl;
$R^2$ is a hydrogen;
$R^3$ is a lower alkyl, a halo(lower)alkyl, a morpholinyl (lower)-alkyl, a piperidinyl(lower)alkyl, a pyridyl (lower)alkyl, a carbamoyl(lower)alkyl, a lower alkylcarbamoyl(lower)alkyl, a carboxy(lower)alkyl, a phenyl(lower)alkoxycarbonyl(lower)alkyl, a morpholinylcarbonyl(lower)alkyl, a di(lower)alkylamino(lower)alkyl, a phenyl(lower)alkoxycarbonylamino(lower)alkyl, a lower alkoxycarbonylamino(lower)alkyl, a benzoylamino (lower)alkyl, a pyridyl-carbonylamino(lower)alkyl, a lower alkanoylamino(lower)alkyl, a lower alkylsulfonylamino(lower)alkyl, a di(lower) alkylaminosulfonylamino(lower)alkyl, a pyridyl-sulfonylamino(lower)alkyl, a triazolylthio(lower)alkyl, an imidazolylthio(lower)alkyl, a thiazolylthio(lower) alkyl, a benzimidazolylthio(lower)alkyl, a lower alkyltriazolylthio(lower)alkyl, a lower alkoxy, a fluorenyl(lower)alkoxy, a phenoxy, a pyridyl(lower) alkenyl, a pyridyl, a piperidinyl, a thienyl substituted by oxazolyl, a mono- (or di-)(lower)alkylamino, a carboxy(lower)alkylamino, a lower alkoxycarbonyl (lower)alkylamino, an N-(lower)alkyl-N-(lower) alkoxycarbonyl(lower)alkylamino, a carbamoyl(lower) alkylamino, a hydroxy(lower)alkylamino, a phenylamino or a cyclo(lower)alkylamino;
$R^4$ is a hydrogen;
$R^5$ is a hydrogen and
$R^{10}$ is a hydroxy.

The processes for preparing the object compounds are explained in detail in the following.

Process 1

The compound (IV) or a salt thereof can be prepared by reacting the compound (II) or a salt thereof with the compound (III) or a salt thereof.

Suitable salts of the compounds (II), (III) and (IV) may be the same as those exemplified with respect to the compound (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine and dichloromethane, a mixture thereof, or any other organic solvents which do not adversely affect the reaction.

This reaction can be carried out in the presence of an organic or inorganic base such as alkali metal (e.g., lithium, sodium, potassium, etc.), alkaline earth metal (e.g., calcium, etc.), alkali metal hydride (e.g., sodium hydride, etc.), alkaline earth metal hydride (e.g., calcium hydride, etc.), alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), alkali metal alkoxide (e.g., sodium methoxide, sodium ethoxide, potassium tert-butoxide, etc.), alkali metal alkanoic acid (e.g., sodium acetate, etc.), trialkylamine (e.g., triethylamine, etc.), pyridine compound (e.g., pyridine, lutidine, picoline, 4-dimethylaminopyridine, etc.), quinoline, lithium diisopropylamide, and the like.

The reaction temperature is not critical, and the reaction is usually carried out under cooling to heating.

Process 2

The compound (V) and a salt thereof can be prepared by eliminating the hydroxy protective group of the compound (IV) or a salt thereof.

Suitable salts of the compounds (IV) and (V) may be the same as those exemplified above with regard to the compound (I).

Suitable method of this elimination reaction includes conventional ones such as hydrolysis, reduction and the like.

The hydrolysis is preferably carried out in the presence of a base or an acid including Lewis acid.

Suitable base includes an inorganic base and an organic base such as an alkali metal (e.g., sodium, potassium, etc.), an alkaline earth metal (e.g., magnesium, calcium, etc.), the hydroxide or carbonate or hydrogencarbonate thereof, trialkylamine (e.g., trimethylamine, triethylamine, etc.), picoline, 1,5-diazabicyclo[4.3.0]non-5-one, and the like.

Suitable acid includes an organic acid (e.g., formic acid, acetic acid, propionic acid, trichloroacetic acid, trifluoroacetic acid, etc.), and an inorganic acid (e.g., hydrochloric acid, hydrobromic acid, sulfuric acid, hydrogen chloride, hydrogen bromide, etc.).

The elimination using Lewis acid such as trihaloacetic acid (e.g., trichloroacetic acid, trifluoroacetic acid, etc.) and the like is preferably carried out in the presence of cation trapping agent (e.g., anisole, phenol, etc.). This reaction is usually carried out without solvent.

Alternatively, the reaction may be carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide and N,N-dimethylacetamide, a mixture thereof, or any other organic solvents which do not adversely affect the reaction.

The reaction temperature is not critical and the reaction is usually carried out under cooling to warming.

The reduction is carried out in a conventional manner, including chemical reduction and catalytic reduction.

Suitable reducing reagents to be used in chemical reduction are a hydride (e.g., hydrogen iodide, hydrogen sulfide, lithium aluminum hydride, sodium borohydride, sodium cyanoborohydride, etc.), or a combination of a metal (e.g., tin, zinc, iron, etc.) or a metallic compound (e.g., chromium chloride, chromium acetate, etc.) and an organic acid or an inorganic acid (e.g., formic acid, acetic acid, propionic acid, trifluoroacetic acid, p-toluenesulfonic acid, hydrochloric acid, hydrobromic acid, etc.).

Suitable catalyst to be used in catalytic reduction is conventional one such as platinum catalyst (e.g., platinum plate, spongy platinum, platinum black, colloidal platinum, platinum oxide, platinum wire, etc.), palladium catalyst (e.g., spongy palladium, palladium black, palladium oxide, palladium on carbon, colloidal palladium, palladium on barium sulfate, palladium on barium carbonate, etc.), nickel catalyst (e.g., reduced nickel, nickel oxide, Raney nickel, etc.), cobalt catalyst (e.g., reduced cobalt, Raney cobalt, etc.), iron catalyst (e.g., reduced iron, Raney iron, Ullman iron, etc.), and the like.

The reduction is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide and cyclohexane, a mixture thereof, or any other organic solvents which do not adversely affect the reaction.

When the above-mentioned acids to be used in chemical reduction are liquid, they can also be used as a solvent.

The reaction temperature of this reduction is not critical and the reaction is usually carried out under cooling to warming.

Process 3

The compound (IV) or a salt thereof can be prepared by reacting the compound (VI) or its reactive derivative at the carboxy group, or a salt thereof, with the compound (VII) or its reactive derivative at the amino group, or a salt thereof.

Suitable salts of the compounds (VI) and (VII) may be the same as those exemplified for the compound (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine and dichloromethane, a mixture thereof, or any other organic solvents which do not adversely affect the reaction.

This reaction can be carried out in the presence of an organic or inorganic base such as alkali metal (e.g., lithium, sodium, potassium, etc.), alkaline earth metal (e.g., calcium, etc.), alkali metal hydride (e.g., sodium hydride, etc.), alkaline earth metal hydride (e.g., calcium hydride, etc.), alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), alkali metal alkoxide (e.g., sodium methoxide, sodium ethoxide, potassium tert-butoxide, etc.), alkali metal alkanoic acid (e.g., sodium acetate, etc.), trialkylamine (e.g., triethylamine, etc.), pyridine compound (e.g., pyridine, lutidine, picoline, 4-dimethylaminopyridine, etc.), quinoline, lithium diisopropylamide, and the like.

Suitable reactive derivative at the amino group of the compound (VII) may include Schiff's base type imino or its tautomeric enamine type isomer formed by the reaction of the compound (VII) with a carbonyl compound such as aldehyde, ketone or the like; a silyl derivative formed by the reaction of the compound (VII) with a silyl compound such as bis(trimethylsilyl)acetamide, mono(trimethylsilyl)acetamide, bis(trimethylsilyl)urea or the like; a derivative formed by the reaction of the compound (VII) with phosphorus trichloride or phosgene, and the like.

Suitable reactive derivative at the carboxy group of the compound (VI) may include an acid halide, an acid anhydride, an activated amide, an activated ester, and the like. Suitable examples of the reactive derivative may be an acid chloride; an acid azide; a mixed acid anhydride with acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, sulfonic acid (e.g., methanesulfonic acid, etc.), aliphatic carboxylic acid (e.g., acetic acid, propionic acid, butyric acid, isobutyric acid, pivalic acid, pentanoic acid, isopentanoic acid, 2-ethylbutyric acid, trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenyl azophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-1H-benzotriazole, etc.), and the like. These reactive derivative can be optionally be selected from them according to the kind of the compound (VI) to be used.

The reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclo-hexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate (e.g., ethyl chloroformate, isopropyl chloroformate); triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; 1-hydroxybenzotriazole; or so-called Vilsmeier reagent prepared by the reaction of N,N-dimethylforamide with thionyl chloride, phosgene, trichloromethyl chloroformate, phosphorus oxychloride or oxalyl chloride.

The reaction temperature is not critical, and the reaction is usually carried out under cooling.

Process 4

The compound (X) or a salt thereof can be prepared by reacting the compound (VIII) or a salt thereof with the compound (IX) or a salt thereof.

Suitable salts of the compounds (VIII), (IX) and (X) may be the same as those exemplified for the compound (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine and dichloromethane, a mixture thereof, or any other organic solvents which do not adversely affect the reaction.

This reaction can be carried out in the presence of an organic or inorganic base such as alkali metal (e.g., lithium, sodium, potassium, etc.), alkaline earth metal (e.g., calcium, etc.), alkali metal hydride (e.g., sodium hydride, etc.), alkaline earth metal hydride (e.g., calcium hydride, etc.), alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), alkali metal alkoxide (e.g., sodium methoxide, sodium ethoxide, potassium tert-butoxide, etc.), alkali metal alkanoic acid (e.g., sodium acetate, etc.), trialkylamine (e.g., triethylamine, etc.), pyridine compound (e.g., pyridine, lutidine, picoline, 4-dimethylaminopyridine, etc.), quinoline, lithium diisopropylamide, and the like.

The reaction is carried out in the presence of alkali metal halide (e.g., sodium iodide, potassium iodide, etc.), alkali metal thiocyanate (e.g., sodium thiocyanate, potassium thiocyanate, etc.), di(lower)alkyl azodicarboxylate (e.g., diethyl azodicarboxylate, diisopropyl azodicarboxylate, etc.), and the like.

The reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclo-hexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate (e.g., ethyl chloroformate, isopropyl chloroformate); triphenylphosphine; 2-ethyl-7-hydroxybenz-isoxazolium salt; 2-ethyl-5-(m-sulfophenyl)isoxazolium hydroxide intramolecular salt; 1-(p-chlorobenzenesulfonyloxy)-6-chloro-1H-benzotriazole; 1-hydroxybenzotriazole; or so-called Vilsmeier reagent prepared by the reaction of N,N-dimethylforamide with thionyl chloride, phosgene, trichloromethyl chloroformate, phosphorus oxychloride or oxalyl chloride.

The reaction temperature is not critical, and the reaction is usually carried out under cooling.

Process 5

The compound (XII) or a salt thereof can be prepared by eliminating the hydroxy protective group of the compound (XI) or a salt thereof.

Suitable salts of the compounds (XI) and (XII) may be the same as those exemplified for the compound (I).

The reaction of this process can be carried out in a manner similar to that in Process 2.

Process 6

The compound (XIII) or a salt thereof can be prepared by subjecting the compound (XII) or a salt thereof to amidation reaction.

Suitable salts of the compounds (XII) and (XIII) may be the same as those exemplified for the compound (I).

The reaction of this process can be carried out in a manner similar to that in Process 4.

Process 7

The compound (IV) or a salt thereof can be prepared by reacting the compound (XIV) or a salt thereof with the compound (XV) or a salt thereof.

Suitable salts of the compounds (XIV) and (XV) may be the same as those exemplified for the compound (I).

The reaction of this process can be carried out in a manner similar to that in Process 1.

Process 8

The compound (XVIII) or a salt thereof can be prepared by reacting the compound (XVI) or a salt thereof with the compound (XVII) or its reactive derivative at the carboxy group, or a salt thereof.

Suitable salts of the compounds (XVI), (XVII) and (XVIII) may be the same as those exemplified for the compound (I).

Suitable reactive derivative at the amino group of the compound (XVII) may include Schiff's base type imino or its tautomeric enamine type isomer formed by the reaction of the compound (XVII) with a carbonyl compound such as aldehyde, ketone or the like; a silyl derivative formed by the reaction of the compound (XVII) with a silyl compound such as bis(trimethylsilyl)acetamide, mono(trimethylsilyl) acetamide, bis(trimethylsilyl)urea or the like; a derivative formed by the reaction of the compound (XVII) with phosphorus trichloride or phosgene, and the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine and dichloromethane, a mixture thereof, or any other organic solvents which do not adversely affect the reaction.

This reaction can be carried out in the presence of an organic or inorganic base such as alkali metal (e.g., lithium, sodium, potassium, etc.), alkaline earth metal (e.g., calcium, etc.), alkali metal hydride (e.g., sodium hydride, etc.), alkaline earth metal hydride (e.g., calcium hydride, etc.), alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), alkali metal alkoxide (e.g., sodium methoxide, sodium ethoxide, potassium tert-butoxide, etc.), alkali metal alkanoic acid (e.g., sodium acetate, etc.), trialkylamine (e.g., triethylamine, etc.), pyridine compound (e.g., pyridine, lutidine, picoline, 4-dimethylaminopyridine, etc.), quinoline, lithium diisopropylamide, and the like.

The reaction is carried out in the presence of alkali metal halide (e.g., sodium iodide, potassium iodide, etc.), alkali metal thiocyanate (e.g., sodium thiocyanate, potassium thiocyanate, etc.), di(lower)alkyl azodicarboxylate (e.g., diethyl azodicarboxylate, diisopropyl azodicarboxylate, etc.), and the like.

The reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate (e.g., ethyl chloroformate, isopropyl chloroformate); triphenylphosphine; 2-ethyl-7-hydroxybenz-isoxazolium salt; 2-ethyl-5-(m-sulfophenyl)isoxazolium hydroxide intramolecular salt; 1-(p-chlorobenzenesulfonyloxy)-6-chloro-1H-benzotriazole; 1-hydroxybenzotriazole; or so-called Vilsmeier reagent prepared by the reaction of N,N-dimethylformamide with thionyl chloride, phosgene, trichloromethyl chloroformate, phosphorus oxychloride or oxalyl chloride.

The reaction temperature is not critical, and the reaction is usually carried out under cooling.

Process 9

The compound (XX) or a salt thereof can be prepared by eliminating the hydroxy protective group of the compound (XIX) or a salt thereof.

Suitable salts of the compounds (XIX) and (XX) may be the same as those exemplified for the compound (I).

The reaction of this process can be carried out in a manner similar to that in Process 2.

Process 10

The compound (XXII) or a salt thereof can be prepared by subjecting the compound (XXI) or a salt thereof to solvolysis.

Suitable salts of the compounds (XXII) and (XXI) may be the same as those exemplified for the compound (I).

The solvolysis is carried out in a conventional solvent such as water, alcohol (e.g., methanol, ethanol, etc.), a mixture thereof, or any other organic solvents which do not adversely affect the reaction.

The reaction temperature is not critical, and the reaction is usually carried out under cooling to heating.

The compounds obtained can be isolated and purified by a conventional method such as pulverization, recrystallization, column chromatography, reprecipitation and the like.

The object compounds can be transformed into their salts in a conventional manner.

It is to be noted that the object compounds may include one or more stereoisomers due to asymmetric carbon atoms, and all of such isomers and mixtures thereof are included within the scope of this invention.

Collagenases initiate the degradation of collagen in vertebrates and, in addition to their normal function in the metabolism of connective tissue and wound healing, they have been implicated to be involved in a number of pathological conditions such as joint destruction in rheumatoid arthritis, periodontal disease, corneal ulceration, tumor metastasis, osteoarthritis, decubitus restenosis after percutaneous transluminal coronary angiopsty, osteoporosis, proriasis, chronic active heatitis, autoimmune keratitis, and the like, and therefore the compounds of the present invention are useful for treating and/or preventing such pathological conditions.

For therapeutic purposes, the compounds and pharmaceutically acceptable salts thereof of the present invention can be used in the form of a pharmaceutical preparation containing, as an active ingredient, one of said compounds in admixture with a pharmaceutically acceptable carrier such as an organic or inorganic solid or liquid excipient suitable for oral, parenteral or external administration. The pharmaceutical preparations may be capsules, tablets, dragees, granules, solutions, suspensions, emulsions, sublingual tablets, suppositories, ointments, and the like. If desired, there may be included, in these preparations, auxiliary substances, stabilizing agents, wetting agents, emulsifying agents, buffers and other commonly used additives.

While the dose of the compound will vary depending upon the age and condition of patient and the like, in the case of intravenous administration, a daily dose of 0.01–100 mg of the active ingredient per kg weight of a human being, and in the case of intramuscular administration, a daily dose of 0.05–100 mg of the same per kg weight of a human being, or in the case of oral administration, a daily dose of 0.1–100 mg of the same per kg weight of a human being, is generally given for the treatment of MMP or TNFα mediated diseases.

In order to illustrate the usefulness of the object compound, the pharmacological test data of a representative compound of the compound are shown in the following.

Inhibitory Activity of Collagenase

1. Test Method

Human collagenase was prepared from the culture medium of human skin fibroblast stimulated with interleukin-1β (1 ng/ml). Latent collagenase was activated by incubation with trypsin (200 μg/ml) at 37° C. for 60 minutes and the reaction was stopped by adding soybean trypsin inhibitor (800 μg/ml). Collagenase activity was determined using FTTC-labeled calf skin type I collagen. FITC-collagen (2.5 mg/ml) was incubated at 37° C. for 120 minutes with the activated collagenase and test compound in 50 mM Tris buffer (containing 5 mm $CaCl_2$, 200 mM NaCl and 0.02% $NaN_3$, pH 7.5). After stopping the enzyme reaction by adding the equal volume of 70% ethanol-200 /mM Tris buffer (pH 9.5), the reaction mixture was centrifuged, and collagenase activity was estimated by measuring the fluorescence intensity of supernatant at 495 nm (excitation) and 520 nm (emission).

2. Test Compound

Compound of Example 5

3. Test Result

| Test Compound | Inhibitory activity |
| --- | --- |
| Example 5 | 95.3% at $1 \times 10^{-6}$M |

The following examples are given for the purpose of illustrating the present invention in detail.

Preparation 1

To a solution of pyrazine-2-carboxylic acid (100 g) in ethanol (EtOH, 1000 ml) was added conc. sulfuric acid (45 ml) at room temperature. After refluxing for 8 hours, the reaction mixture was concentrated in vacuo. The residue was dissolved in ethyl acetate (AcOEt, 1500 ml) and water ($H_2O$, 1000 ml), and sodium hydrogencarbonate ($NaHCO_3$) was added to adjust the pH of the mixture to 8. The aqueous layer was extracted with AcOEt (1000 ml), and the combined organic layer was washed with brine and dried over magnesium sulfate ($MgSO_4$). The solution was concentrated in vacuo, and the residue was crystallized from hexane (1000 ml) to give 111.2 g of ethyl pyrazine-2-carboxylate, m.p.: 48–49° C.

Preparation 2

A solution of ethyl pyrazine-2-carboxylate (60 g) in EtOH (500 ml) was subjected to catalytic reduction using palladium hydroxide on carbon (5.0 g), in hydrogen at 3 atm for 4 hours. The catalyst was removed by filtration and the filtrate was concentrated in vacuo to give 62.8 g of ethyl 1,4,5,6-tetrahydropyrazine-2-carboxylate as an oil.

Preparation 3

To a solution of ethyl 1,4,5,6-tetrahydropyrazine-2-carboxylate (61.5 g) in acetonitrile (MeCN, 500 ml) was added a solution of ditert-butyl dicarbonate (85.9 g) in MeCN (100 ml) under cooling on an ice bath. After stirring for 5 hours at room temperature, the solution was concentrated in vacuo. The residue was dissolved in AcOEt (1500 ml). The solution was washed with 5% hydrogen chloride (HCl) solution, 1M $NaHCO_3$ solution and brine, dried over $MgSO_4$ and concentrated in vacuo. The residue was crystallized from AcOEt (100 ml) and diethyl ether ($Et_2O$, 600 ml) to give 77.7 g of ethyl 1-tert-butoxycarbonyl-1,4,5,6-tetrahydropyrazine-2-carboxylate.

m.p.: 127–129° C.

Mass (ESI+): 257 (M+H)

$^1$H-NMR (300 MHz, $CDCl_3$, δ): 1.28(3H, t, J=7.5 Hz), 1.49(9H, s), 3.28–3.34(2H, m), 3.46–3.58(2H, m), 4.19(2H, q, J=7.5 Hz), 4.40–4.52(1H, m), 7.06(1H, d, J=7.0 Hz)

Preparation 4

A solution of ethyl 1-tert-butoxycarbonyl-1,4,5,6-tetrahydropyrazine-2-carboxylate (69.0 g) in acetic acid (AcOH, 500 ml) was subjected to catalytic reduction using platinum dioxide (4.0 g) at 40° C. in hydrogen at 3 atm for 4 hours. The catalyst was removed by filtration, and the filtrate was concentrated in vacuo. The residue was dissolved in $H_2O$ (800 ml) and the solution was washed with $Et_2O$ (500 ml×2). To the aqueous layer was added $NaHCO_3$ to adjust the pH of the solution to 8 and the solution was extracted with AcOEt (800 ml×2). The combined organic layer was washed with saturated aqueous $NaHCO_3$ solution and brine, dried over $MgSO_4$ and concentrated in vacuo to give 62.8 g of ethyl 1-tert-butoxycarbonyl- piperazine-2-carboxylate as an oil.

Mass (ESI+): 259 (M+H)

$^1$H-NMR (300 MHz, $CDCl_3$, δ): 1.30(3H, t, J=7.5 Hz), 1.45(4.5H, s), 1.48(4.5H, s), 2.63–2.68(1H, m), 2.83–3.22 (3H, m), 3.43–3.59(1H, m), 3.70–3.91(1H, m), 4.14–4.30 (2H, m), 4.42–4.70(1H,m)

Preparation 5

To a solution of ethyl 1-tert-butoxycarbonylpiperazine-2-carboxylate (117.5 g, 455 mmol) in EtOH (1.53 l) was added powdered (L)-tartaric acid (37.5 g, 250 mmol, 0.55 eq) at 65° C. After complete dissolution (15 minutes), seed crystals were added. The mixture was stirred at 70–75° C. for 30 minutes to allow precipitation of crystals. After cooling to ambient temperature over 2 hours, the mixture was further stirred for 3 hours. The resulting solid was recovered, washed with EtOH (100 ml, 50 ml×2) and dried for one day to give 71.1 g (174 mmol) of (2R)-1-tert-butoxycarbonyl-2-ethoxycarbonylpiperazine (2R,3R)-(+)-tartrate.

$[α]_D^{20}$=+62.1° (c=1.17, $H_2O$)

$^1$H-NMR (300 MHz, DMSO-$d_6$, δ): 1.20(3H, t, J=7.5 Hz), 1.35(5H, s), 1.40(4H, s), 2.48–2.62(1H, m), 2.78–3.09(3H, m), 3.30–3.40(1H, m), 3.61–3.71(1H, m), 4.05–4.20(2H, m), 4.19(2H, s), 4.44–2.57(1H, m)

Preparation 6

A suspension of (2R)-1-tert-butoxycarbonyl-2-ethoxycarbonyl-piperazine (2R,3R)-(+)-tartrate (18 g) in AcOEt (400 ml) was washed with 1M aqueous $NaHCO_3$ solution (500 ml) and brine. The organic layer was dried over $MgSO_4$ and concentrated in vacuo to give (2R)-1-tert-butoxycarbonyl-2-ethoxycarbonylpiperazine as crystals.

m.p.: 47–48° C.

$[a]_D^{20}$=+66.3° [c=1.0, methanol(MeOH)]

Mass (ESI+): 259.2 (M+H)

$^1$H-NMR (300 MHz, $CDCl_3$, δ): 1.29(3H, t, J=7.5 Hz), 1.45(4.5H, s), 1.48(4.5H, s), 2.63–2.68(1H, m), 2.83–3.22 (3H, m), 3.43–3.59(1H, m), 3.70–3.91(1H, m), 4.14–4.30 (2H, m), 4.42–4.70(1H, m)

Preparation 7

A mixture of (2R)-1-tert-butoxycarbonyl-2-ethoxycarbonylpiperazine (1.67 g) and 1N aqueous sodium hydroxide (9.53 ml) in dioxane (16 ml) was stirred for 2 hours at ambient temperature. The mixture was adjusted to pH 5 with 1N HCl on an ice bath. To the mixture was added sodium carbonate (1.35 g), and then methanesulfonyl chloride (873 mg) dropwise on an ice bath. After stirring at the same temperature for 2 hours, the resulting mixture was acidified with 4N HCl, and extracted with AcOEt. The extract was dried over sodium sulfate and concentrated in vacuo to give 1.95 g of (2R)-1-tert-butoxycarbonyl-4-methanesulfonylpiperazine-2-carboxylic acid as an amorphous powder.

Mass (ESI): 307 (M−1)

$^1$H-NMR (300 MHz, DMSO-$d_6$, δ): 1.39(5H, s), 1.42(4H, s), 2.67–2.78(1H, m), 2.78–2.90(4H, m), 2.90–3.20(2H, m), 3.34–3.57(1H, m), 3.79–4.00(1H, m), 4.60–4.72(1H, m)

Preparation 8

To a mixture of (2R)-1-tert-butoxycarbonyl-4-methanesulfonylpiperazine-2-carboxylic acid (1.95 g), O-benzylhydroxylamine hydrochloride (1.51 g) and 1-hydroxybenzotriazole (HOBT, 1.03 g) in N,N-dimethylformamide (DMF, 20 ml) was added triethylamine (191 mg) on an ice bath. To the mixture was added dropwise 1-(3-dimethylaminopropyl)-3-ethylcarbodiimide (WSCD, 1.18 g) at a temperature below 6° C. After stirring at the same temperature for 4 hours, the mixture was concentrated in vacuo. The residue was partitioned by dissolving same in AcOEt and $H_2O$. The organic layer was washed with 2.5% aqueous citric acid, saturated aqueous $NaHCO_3$ solution and brine, dried over sodium sulfate and concentrated in vacuo. The obtained oil was purified by chromatography on silica gel ($SiO_2$) [eluent: from 0.5 to 1.5% MeOH-chloroform ($CHCl_3$)] to give 1.35 g of (2R)-1-tert-butoxycarbonyl-4-methanesulfonylpiperazine-2-(N-benzyloxy)carboxamide as an amorphous powder.

Mass (ESI): 412 (M−1)
$^1$H-NMR (300 MHz, $CDCl_3$, δ): 1.43(9H, s), 2.78–3.02 (7H, m), 3.60–3.70(1H, m), 4.16–4.23(1H, m), 4.62–4.70 (1H, m), 4.89(1H, d, J=10.5 Hz), 4.98(1H, d, J=10.5 Hz), 7.35–7.41(5H, m)

Preparation 9

To a solution of (2R)-1-tert-butoxycarbonyl-4-methanesulfonylpiperazine-2-(N-benzyloxy)carboxamide (1.34 g) in AcOEt (6.5 ml) was added 4N HCl-AcOEt (6.5 ml) at ambient temperature. The suspension was stirred at the same temperature for 2 hours and concentrated in vacuo to give 1.20 g of (2R)-4-methanesulfonylpiperazine-2-(N-benzyloxy)carboxamide hydrochloride as a solid.

Mass (ESI): 248 (M−1)
$^1$H-NMR (300 MHz, DMSO-$d_6$, δ): 3.00–3.07(4H, m), 3.07–3.16(2H, m), 3.27–3.40(1H, m), 3.58–3.67(1H, m), 3.74–3.83(1H, m), 3.93(1H, dd, J=4, 9 Hz), 4.85(2H, s), 7.38–7.45(5H, m)

EXAMPLE 1

To a mixture of (2R)-4-methanesulfonylpiperazine-2-(N-benzyloxy)carboxamide hydrochloride (1.34 g) and pyridine (13.5 ml) was added 4-methoxybenzenesulfonyl chloride (910 mg) at ambient temperature. After stirring for 2 hours, the mixture was concentrated. The residue was partitioned by dissolving same in AcOEt and $H_2O$. The organic layer was washed with 5% aqueous citric acid, saturated aqueous $NaHCO_3$ solution and brine, dried over sodium sulfate and concentrated in vacuo. The residue was purified by chromatography on $SiO_2$ (eluent: from 0.5 to 1% MeOH-$CHCl_3$) to give 1.46 g of (2R)-4-methanesulfonyl-1-(4-methoxybenzenesulfonyl)piperazine-2-(N-benzyloxy)carboxamide as an amorphous powder.

Mass (ESI): 482 (M−1)
$^1$H-NMR (300 MHz, $CDCl_3$, δ): 2.48–2.61(2H, m), 2.88 (3H, s), 2.95–3.09(1H, m), 3.45–3.55(1H, m), 3.73–3.82 (1H, m), 3.90(3H, s), 4.12–4.20(1H, m), 4.44–4.51(1H, m), 4.89(1H, d, J=10 Hz), 4.99(1H, d, J=10 Hz), 7.00(2H, d, J=8 Hz), 7.36–7.44(5H, m), 7.71(2H, d, J=8 Hz), 9.00(1H, brs)

EXAMPLE 2

A mixture of (2R)-4-methanesulfonyl-1-(4-methoxybenzenesulfonyl)piperazine-2-(N-benzyloxy)carboxamide (1.00 g), 10% palladium on barium sulfate (200 mg) and cyclohexene (3 ml) in EtOH (9 ml) was refluxed for 8 hours. The mixture was filtered and the obtained filtrate was concentrated in vacuo. The residue was purified by chromatography on $SiO_2$ (eluent: from 1 to 6% MeOH-$CHCl_3$) to give 735 mg of (2R)-4-methanesulfonyl-1-(4-methoxybenzenesulfonyl)piperazine-2-(N-hydroxy) carboxamide as an amorphous powder.

Mass (ESI): 392 (M−1)
$^1$H-NMR (300 MHz, DMSO-$d_6$, δ): 2.54–2.67(1H, m), 2.80–2.89(4H, m), 3.40–3.49(1H, m), 3.52–3.71(2H, m), 3.72–3.81(1H, m), 3.85(3H, s), 4.38–4.42(1H, m), 7.10(2H, d, J=8 Hz), 7.74(2H, d, J=8 Hz), 8.91(1H, brs)

EXAMPLE 3

To a solution of (2R)-4-methanesulfonyl-1-(4-methoxybenzenesulfonyl)piperazine-2-(N-hydroxy) carboxamide (1.00 g) in a mixture of EtOH (3 ml) and $H_2O$ (3 ml) was added 1N aqueous sodium hydroxide solution (2.18 ml) at ambient temperature. After the mixture was freeze-dried, the resulting powder was collected with AcOEt to give 825 mg of (2R)-4-methanesulfonyl-1-(4-methoxybenzenesulfonyl)piperazine-2-(N-hydroxy) carboxamide sodium salt as a powder.

Mass (ESI): 392 (M−1)
$^1$H-NMR (300 MHz, DMSO-$d_6$, δ): 2.60(1H, dt, J=4, 10 Hz), 2.74(1H, dd, J=4, 10 Hz), 2.80(3H, s), 3.38–3.48(2H, m), 3.69(1H, dt, J=4, 10 Hz), 3.99(1H, d, J=10 Hz), 4.22(1H, d, J=2 Hz), 7.05(2H, d, J=8 Hz), 7.83(2H, d, J=8 Hz)

Preparation 10

A solution of (2R)-1-tert-butoxycarbonyl-4-methanesulfonylpiperazine-2-carboxylic acid (2.90 g) in 4N HCl-AcOEt solution (40 ml) was stirred at room temperature for 30 minutes. The solution was concentrated in vacuo and the residue was solidified with $Et_2O$ to give 2.15 g of (2R)-4-methanesulfonylpiperazine-2-carboxylic acid hydrochloride as a powder.

Mass (ESI): 207.1 (M−1)
$^1$H-NMR (300 MHz, $D_2O$, δ): 3.02–3.14(2H, m), 3.08 (3H, s), 3.42–3.51(1H, m), 3.52–3.78(3H, m), 3.95–4.05 (1H, m), 4.09–4.18(1H, m)

Preparation 11

To a solution of (2R)-4-methanesulfonylpiperazine-2-carboxylic acid hydrochloride (2.10 g) in $H_2O$ (20 ml) and dioxane (20 ml) were added $NaHCO_3$ (2.38 g) and a solution of benzyloxycarbonyl chloride (1.76 g) in $Et_2O$ (10 ml) at room temperature. After stirring for 2 hours, $Et_2O$ and dioxane were evaporated in vacuo. The solution was acidified with 1N HCl and extracted with AcOEt (80 ml). The organic layer was washed with brine, dried over $MgSO_4$ and concentrated in vacuo to give 3.0 g of (2R)-1-benzyloxycarbonyl-4-methanesulfonylpiperazine-2-carboxylic acid as an amorphous powder.

Mass (ESI−): 341.3 (M−H)
$^1$H-NMR (300 MHz, $CDCl_3$, δ): 2.70–2.85(2H, m), 2.81 (3H, s), 2.90–3.01(1H, m), 3.20–3.42(1H, m), 3.62–3.80 (1H, m), 4.00–4.19(1H, m), 4.20–4.34(1H, m), 4.56–4.78 (2H, m), 5.03(1H, bs), 7.38(5H, bs)

Preparation 12

To a solution of (2R)-1-benzyloxycarbonyl-4-methanesulfonylpiperazine-2-carboxylic acid (3.00 g), O-(2-tetrahydropyranyl)hydroxylamine (1.23 g) and HOBT (1.42 g) in DMF (50 ml) was added WSCD.HCl (2.02 g) under cooling on an ice bath. After stirring for 30 minutes, the solution was concentrated in vacuo. The residue was dissolved in AcOEt (100 ml). The solution was washed with 5% aqueous citric acid solution, 1M $NaHCO_3$ solution and brine, dried over $MgSO_4$, and concentrated in vacuo to give 3.58 g of (2R)-1-benzyloxycarbonyl-4-methanesulfonylpiperazine-2-[N-(2-tetrahydropyranyloxy)] carboxamide as an amorphous powder.

Mass (ESI−): 440.3 (M−H)

¹H-NMR (300 MHz, CDCl₃, δ): 1.49–1.91(6H, m), 2.80–3.32(2H, m), 2.92(3H, bs), 3.52–3.64(1H, m), 3.68–3.78(1H, m), 3.83–3.95(1H, m), 4.00–4.15(1H, m), 4.20(1H, d, J=12 Hz), 4.76–4.86(1H, m), 4.90–4.98(1H, bs), 5.20(2H, s), 7.36(5H, bs)

Preparation 13

A solution of (2R)-1-benzyloxycarbonyl-4-methanesulfonylpiperazine-2-[N-(2-tetrahydropyranyloxy)]carboxamide (3.5 g) in EtOH (50 ml) was subjected to catalytic reduction using palladium hydroxide on carbon (700 mg), in hydrogen at 3 atm for 8 hours. The catalyst was removed by filtration and the filtrate was concentrated in vacuo to give 1.87 g of (2R)-4-methanesulfonylpiperazine-2-[N-(2-tetrahydropyranyloxy)]carboxamide.

Mass (ESI+): 308.2 (M+H)

¹H-NMR (300 MHz, DMSO-d₆, δ): 1.45–1.78(6H, m), 2.88–3.09(2H, m), 2.99(3H, s) 3.15–3.32(2H, m), 3.46–3.60 (2H, m), 3.68–3.82(2H, m), 3.86–4.00(1H, m), 4.88(1H, d, J=12 Hz)

EXAMPLE 4

To a solution of (2R)-4-methanesulfonylpiperazine-2-[N-(2-tetrahydropyranyloxy)]carboxamide (1.80 g) in pyridine (30 ml) was added 4-nitrobenzenesulfonyl chloride (1.56 g) in dichloromethane (CH₂Cl₂, 10 ml) under cooling on an ice bath. After stirring for 2 hours, the solution was concentrated in vacuo. The residue was dissolved in AcOEt (50 ml). The solution was washed with 5% aqueous citric acid solution, 1M NaHCO₃ solution and brine, dried over MgSO₄ and concentrated in vacuo. The residue was purified by SiO₂ column chromatography (eluent: CHCl₃) to give 2.15 g of (2R)-1-(4-nitrobenzenesulfonyl)-4-methanesulfonylpiperazine-2-[N-(2-tetrahydropyranyloxy)]carboxamide as an amorphous powder.

Mass (ESI−): 491.3 (M−H)

¹H-NMR (300 MHz, CDCl₃, δ): 1.50–1.90(6H, m), 2.84–3.09(2H, m), 2.86(3H, s), 3.23–3.47(1H, m), 3.58–3.69(1H, m), 3.72–3.82(1H, m), 3.84–3.95(1H, m), 4.09–4.22(1H, m), 4.62–4.78(1H, br), 4.90(1H, bs), 7.95–8.13(2H, m), 8.32–8.42(2H, m), 9.11(1H, bs)

EXAMPLE 5

To a solution of (2R)-1-(4-nitrobenzenesulfonyl)-4-methanesulfonylpiperazine-2-[N-(2-tetrahydropyranyloxy)]carboxamide (2.0 g) in MeOH (10 ml) was added 10% HCl-MeOH (30 ml) at room temperature. After stirring for 30 minutes, the solution was concentrated in vacuo. The residue was purified by SiO₂ column chromatography (eluent: CHCl₃) to give 1.33 g of (2R)-1-(4-nitrobenzenesulfonyl)-4-methanesulfonylpiperazine-2-(N-hydroxy)carboxamide as an amorphous powder.

Mass (ESI−): 407.2 (M−H)

¹H-NMR (300 MHz, DMSO-d₆, δ): 2.63–2.78(1H, m), 2.86(3H, s), 2.98(1H, dd, J=4.5, 12 Hz), 3.80(2H, d, J=12 Hz), 3.45–3.69(2H, m), 4.49(1H, bs), 8.05(2H, d, J=7.5 Hz), 8.40(2H, d, J=7.5 Hz), 8.94(1H, s)

EXAMPLE 6

(2R)-1-(4-Nitrobenzenesulfonyl)-4-methanesulfonylpiperazine-2-(N-hydroxy)carboxamide sodium salt (310 mg) was obtained in substantially the same manner as in Example 3.

Mass (ESI−): 407.2 (M−H)

¹H-NMR (300 MHz, CD₃OD, δ): 2.62(3H, s), 2.64–2.73 (1H, m), 2.80(1H, dd, J=3.5, 12 Hz), 3.44(1H, d, J=12 Hz), 3.50–3.59(2H, m), 3.83(1H, d, J=12 Hz), 4.22(1H, bs), 7.88(2H, d, J=7.5 Hz), 8.17(2H, d, J=7.5 Hz)

EXAMPLE 7

(2R)-1-(4-Bromobenzenesulfonyl)-4-methanesulfonylpiperazine-2-[N-(2-tetrahydropyranyloxy)]carboxamide (300 mg) was obtained in substantially the same manner as in Example 4.

Mass (ESI−): 524.3 (M−H)

¹H-NMR (300 MHz, CDCl₃, δ): 1.53–1.92(6H, m), 2.69–2.87(2H, m), 2.89(1.5H, s), 2.91(1.5H, s), 3.27–3.44 (1H, m), 3.58–3.74(2H, m), 3.82–3.99(2H, m), 4.20(1H, d, J=13 Hz), 4.55–4.66(1H, br), 4.93(1H, bs), 7.70(4H, s), 9.12(1H, bs)

EXAMPLE 8

(2R)-1-(5-Chloro-2-thienylsulfonyl)-4-methanesulfonylpiperazine-2-[N-(2-tetrahydropyranyloxy)]carboxamide was obtained in substantially the same manner as in Example 4.

Mass (ESI): 486 (M−1)

¹H-NMR (300 MHz, CDCl₃, δ): 1.56–1.70(2H, m), 1.70–1.89(4H, m), 2.76–2.95(6H, m), 3.60–3.74(2H, m), 3.87–4.00(2H, m), 4.19–4.28(1H, m), 4.55–4.64(1H, m), 4.93–5.00(1H, m), 6.99(1H, d, J=4 Hz), 7.43–7.51(1H, m), 9.09(1H, brs)

EXAMPLE 9

To a solution of (2R)-4-methanesulfonylpiperazine-2-[N-(2-tetrahydropyranyloxy)]carboxamide (300 mg) in pyridine-CH₂Cl₂ (1:1, 10 ml) was added 5-bromo-2-thienylsulfonyl chloride at 0° C., and the mixture was stirred at room temperature. After 3.5 hours, N,N-dimethyl-1,3-propanediamine was added and the mixture was stirred for 10 minutes. This mixture was diluted with CHCl₃ (20 ml), washed with 5% aqueous citric acid solution, saturated aqueous NaHCO₃ solution and brine, and dried over MgSO₄. The solvent was evaporated to give 478 mg of (2R)-1-(5-bromo-2-thienylsulfonyl)-4-methanesulfonylpiperazine-2-[N-(2-tetrahydropyranyloxy)]carboxamide (containing two diastereoisomers) as a colorless oil.

Mass (ESI): 530, 532

¹H-NMR (300 MHz, CDCl₃, δ): 1.56–1.91(6H, m), 2.74–2.95(2H, m), 2.90(1.5H, s), 2.92(1.5H, s), 3.36–3.51 (1H, m), 3.59–3.71(2H, m), 3.85–4.01(2H, m), 4.21(1H, d, J=13 Hz), 4.62(1H, br), 4.96(1H, br), 7.12(1H, d, J=4 Hz), 7.39–7.48(1H, m)

EXAMPLE 10

(2R)-1-(4-Bromobenzenesulfonyl)-4-methanesulfonylpiperazine-2-(N-hydroxy)carboxamide (155 mg) was obtained in substantially the same manner as in Example 5.

Mass (ESI−): 440.2 (M−H)

¹H-NMR (300 MHz, DMSO-d₆, δ): 2.62–2.67(1H, m), 2.85(1.5H, s), 2.94(1H, dd, J=4.5, 12 Hz), 3.44–3.66(2H, m), 3.69–3.85(2H, m), 4.43(1H, bs), 7.71(2H, d, J=8.5 Hz), 7.81(2H, d, J=8.5 Hz), 8.95(1H, s)

EXAMPLE 11

(2R)-1-(5-Chloro-2-thienylsulfonyl)-4-methanesulfonylpiperazine-2-(N-hydroxy)carboxamide was obtained in substantially the same manner as in Example 5.

Mass (ESI): 402 (M−1)

¹H-NMR (300 MHz, DMSO-$d_6$, δ): 2.68–2.82(1H, m), 2.98(3H, s), 3.01(1H, dd, J=4, 10 Hz), 3.49–3.59(1H, m), 3.59–3.75(2H, m), 3.80(1H, d, J=10 Hz), 4.40–4.47(1H, m), 7.30(1H, d, J=4 Hz), 7.59(1H, d, J=4 Hz), 9.00(1H, brs)

EXAMPLE 12

(2R)-1-(5-Bromo-2-thienylsulfonyl)-4-methanesulfonylpiperazine-2-(N-hydroxy)carboxamide was obtained in substantially the same manner as in Example 5.

Mass (ESI): 446, 448

¹H-NMR (300 MHz, DMSO-$d_6$, δ): 2.70–2.82(1H, m), 2.88(3H, s), 3.02(2H, dd, J=4, 13 Hz), 3.54(1H, d, J=15 Hz), 3.68–3.78(2H, m), 3.80(1H, d, J=14 Hz), 4.35(1H, t, J=6 Hz), 4.44(1H, bs), 7.38(1H, d, J=4 Hz), 7.51(1H, d, J=4 Hz), 9.00(1H, s)

Preparation 14

N-[N-(tert-Butoxycarbonyl)-O-benzyl-L-seryl]-D-leucine methyl ester (545 mg) was dissolved in 4N HCl-AcOEt (5 ml), and the solution was stirred at ambient temperature for 1.5 hours. The solvent was evaporated in vacuo. The resulting oil was dissolved in dry MeOH (5 ml). Benzaldehyde (205 mg) and sodium cyanoborohydride (NaBH₃CN, 97 mg) were added to this solution, and the reaction mixture was stirred at ambient temperature for 3 hours. Benzaldehyde (60 mg) and NaBH₃CN (30 mg) were added to the reaction mixture and the mixture was stirred at ambient temperature for 1.5 hours. After evaporation of the solvent in vacuo, the residue was partitioned by dissolving same in AcOEt and saturated aqueous NaHCO₃ solution. The organic layer was washed with saturated sodium chloride (NaCl) solution, dried over MgSO4, and concentrated in vacuo. The residue was purified by SiO₂ column chromatography (eluent: CHCl₃) to give 376 mg of N-(N,O-dibenzyl-L-seryl)-D-leucine methyl ester as an oil.

Mass (ESI+): 413 (M+H)

¹H-NMR (300 MHz, CDCl₃, δ): 1.43(6H, d, J=6 Hz), 1.50–1.70(3H, m), 3.43(1H, m), 3.60–3.80(4H, m), 3.72(3H, s), 4.45(1H, d, J=12 Hz), 4.51(1H, d, J=12 Hz), 4.58(1H, m), 7.20–7.40(10H, m), 7.79(1H, d, J=10 Hz)

Preparation 15

N-(N,O-Dibenzyl-L-seryl)-D-leucine methyl ester (376 mg) was dissolved in toluene. AcOH (0.06 ml) was added and the mixture was stirred at 100° C. for one hour and at 110° C. for 5 hours. The reaction mixture was partitioned by dissolving same in AcOEt and saturated aqueous NaHCO₃ solution. The organic layer was washed with saturated NaCl solution, dried over MgSO₄, and concentrated in vacuo. The residue was purified by SiO₂ column chromatography (eluent: n-hexane/AcOEt=3/2, then 1/1). After evaporation of the solvent, the crystals were collected using isopropyl ether to give 312 mg of (2S,5R)-1-benzyl-2-benzyloxymethyl-5-(2-methylpropyl)-3,5-dioxopiperazine as a slightly yellowish powder.

m.p.: 95–97° C.

Mass (ESI−): 379 (M−H)

¹H-NMR (300 MHz, CDCl₃, δ): 0.86(3H, d, J=7 Hz), 0.95(3H, d, J=7 Hz), 1.50–1.75(2H, m), 2.02(1H, m), 3.66 (1H, d, J=10 Hz), 3.86(1H, d, J=10 Hz), 3.89(1H, s), 4.10(1H, d, J=15 Hz), 4.23(1H, dd, J=5, 10 Hz), 4.35(1H, d, J=12 Hz), 4.47(1H, d, J=12 Hz), 5.13(1H, d, J=15 Hz), 5.84(1H, s), 7.15–7.40(10H, m)

Preparation 16

A solution of (2S,5R)-1-benzyl-2-benzyloxymethyl-5-(2-methylpropyl)-3,5-dioxopiperazine (12.5 g) in dry tetrahydrofuran (THF, 100 ml) was dropwise added to a suspension of lithium aluminum hydride (4.99 g) in dry THF (90 ml) at 55° C. over 1 hour. The reaction mixture was further stirred at 55° C. for 2 hours, and then cooled on an ice bath. The reaction was quenched by careful dropwise addition of 10% H₂O-THF (100 ml). AcOEt (700 ml) and MgSO₄ (20 g) were added, and the mixture was stirred at ambient temperature for one hour and at 55° C. for 30 minutes. Insoluble matter was filtered off through a celite pad and the cake was washed several times with AcOEt. The filtrate and combined washings were concentrated in vacuo to give 11.0 g of (2R,5R)-1-benzyl-2-benzyloxymethyl-5-(2-methylpropyl)piperazine as an oil.

Mass (ESI+): 353 (M+H)

¹H-NMR (300 MHz, CDCl₃, δ): 1.30(3H, d, J=7 Hz), 1.33(3H, d, J=7 Hz), 1.00–1.65(3H, m), 1.37(1H, t, J=12 Hz), 2.45(1H, m), 2.65–2.85(2H, m), 3.10(1H, dd, J=4, 12 Hz), 3.18(1H, d, J=15 Hz), 3.49(1H, dd, J=5, 10 Hz), 3.63(1H, dd, J=2, 10 Hz), 4.15(1H, d, J=15 Hz), 4.51(2H, s), 7.20–7.40(10H, m)

Preparation 17

A solution of (2R,5R)-1-benzyl-2-benzyloxymethyl-5-(2-methylpropyl)piperazine (7.0 g) and di-tert-butyl dicarbonate (5.2 g) in CH₂Cl₂ (50 ml) was stirred at ambient temperature for 3 hours. The solvent was evaporated in vacuo and the residue was purified by SiO₂ column chromatography (eluent: CHCl₃/n-hexane=1/1, then CHCl₃) to give 8.1 g of (2R,5R)-1-benzyl-2-benzyloxymethyl-4-(tert-butoxycarbonyl)-5-(2-methylpropyl)piperazine as an oil.

Mass (ESI+): 453 (M+H)

¹H-NMR (300 MHz, CDCl₃, δ): 0.85(3H, d, J=7 Hz), 0.86(3H, d, J=7 Hz), 1.28(1H, m), 1.40–1.70(2H, m), 1.47 (9H, s), 2.28(1H, d, J=12 Hz), 2.62(1H, dd, J=5, 12 Hz), 3.00(1H, br), 3.20(1H, brd, J=13 Hz), 3.55(1H, t, J=10 Hz), 3.60(1H, d, J=13 Hz), 3.77(1H, dd, J=5, 10 Hz), 3.85(1H, d, J=13 Hz), 4.00–4.15(1H, br), 4.10(1H, d, J=13 Hz), 4.49 (1H, d, J=12 Hz), 4.57(1H, d, J=12 Hz), 7.20–7.40(10H, m)

Preparation 18

10% Palladium on carbon (0.8 g) was added to a solution of (2R,5R)-1-benzyl-2-benzyloxymethyl-4-(tert-butoxycarbonyl)-5-(2-methylpropyl)piperazine (8.1 g) in AcOH (80 ml), and the mixture was hydrogenated in hydrogen at 3 atm for 4 hours at ambient temperature. The catalyst was removed by filtration through a celite pad and the filtrate was washed with AcOH. The filtrate and combined washings were concentrated in vacuo, and the residue was partitioned by dissolving same in saturated aqueous NaHCO₃ solution and AcOEt. The organic layer was washed with NaCl solution, dried over MgSO₄, and concentrated in vacuo to give 5.8 g of (2R,5R)-2-benzyloxymethyl-4-(tert-butoxycarbonyl)-5-(2-methylpropyl)piperazine as an oil.

Mass (ESI+): 363 (M+H)

¹H-NMR (300 MHz, CDCl₃, δ): 0.82(3H, d, J=7 Hz), 0.85(3H, d, J=7 Hz), 1.44(9H, s), 1.40–1.80(3H, m), 2.50 (1H, d, J=12 Hz), 3.03(1H, dd, J=5, 12 Hz), 3.10(1H, m), 3.20(1H, dd, J=5, 13 Hz), 3.39(1H, dd, J=5, 10 Hz), 3.68 (1H, t, J=10 Hz), 3.79(1H, d, J=13 Hz), 4.10(1H, m), 4.51(1H, d, J=12 Hz), 4.58(1H, d, J=12 Hz), 7.25–7.40(5H, m)

Preparation 19

(2R,5R)-2-Benzyloxymethyl-4-(tert-butoxycarbonyl)-1-(4-methoxybenzenesulfonyl)-5-(2-methylpropyl)piperazine (6.4 g) was obtained in substantially the same manner as in Example 1.

m.p.: 119–120° C.

Mass (ESI+): 555 (M+Na), 578 (M+2Na)

¹H-NMR (300 MHz, CDCl₃, δ): 0.83–0.90(6H, br), 1.20–1.50(3H, m), 1.41, 1.43(9H, s), 2.97–3.14(2H, m), 3.20–3.50(3H, m), 3.83(3H, s), 4.00–4.50(5H, m), 6.86(2H, d, J=8 Hz), 7.20–7.40(5H, m), 7.18, 7.22(2H, d, J=8 Hz)

Preparation 20

Palladium hydroxide on carbon (700 mg) was added to a solution of (2R,5R)-2-benzyloxymethyl-4-(tert-butoxycarbonyl)-1-(4-methoxybenzenesulfonyl)-5-(2-methylpropyl)piperazine (6.4 g) in MeOH (60 ml), and the mixture was hydrogenated in hydrogen at 3.5 atm for 4 hours at ambient temperature. The catalyst was removed by filtration through a celite pad and the filtrate was washed with MeOH. The filtrate and combined washings were concentrated in vacuo to give 5.3 g of (2R,5R)-4-(tert-butoxycarbonyl)-2-hydroxymethyl-1-(4-methoxybenzenesulfonyl)-5-(2-methylpropyl)piperazine as white crystals.

m.p.: 90–93° C.

Mass (ESI–): 441 (M–H), (ESI+): 465 (M+Na)

$^1$H-NMR (300 MHz, CDCl$_3$, δ): 0.80–0.90(6H, br), 1.44 (9H, s), 1.10–1.70(3H, m), 2.73–3.11(2H, m), 3.20(1H, dd, J=5, 13 Hz), 3.36–3.65(3H, m), 3.88(3H, s), 3.94(1H, m), 4.05–4.36(3H, m), 6.97(2H, d, J=8 Hz), 7.75(2H, d, J=8 Hz)

Preparation 21

Ruthenium (IV) oxide hydrate (238 mg) was added to a solution of (2R,5R)-4-(tert-butoxycarbonyl)-2-hydroxymethyl-1-(4-methoxybenzenesulfonyl)-5-(2-methylpropyl)piperazine (5.3 g) in acetone (50 ml) and H$_2$O (20 ml), followed by addition of sodium periodate (5.1 g) with cooling on an ice bath. After stirring at the same temperature for 40 minutes, the reaction was quenched with 2-propanol (50 ml). Insoluble matter was removed by filtration through a celite pad, and the filtrate was washed with acetone and AcOEt. The filtrate and combined washings were concentrated in vacuo, and the residue was partitioned by dissolving same in 5% aqueous sodium bisulfite and AcOEt. The organic layer was washed with saturated NaCl solution, dried over MgS04, and concentrated in vacuo to give 5.6 g of (2R,5R)-4-(tert-butoxycarbonyl)-1-(4-methoxybenzenesulfonyl)-5-(2-methylpropyl)piperazine-2-carboxylic acid as an amorphous powder.

Mass (ESI–): 455 (M–H), (ESI+): 479 (M+Na)

$^1$H-NMR (300 MHz, CDCl$_3$, δ): 0.89(6H, d, J=7 Hz), 1.30–1.65(3H, m), 1.38(9H, s), 2.90–3.60(3H, m), 3.86(3H, s), 4.10–4.62(3H, m), 6.93(2H, d, J=8 Hz), 7.70(2H, d, J=8 Hz)

Preparation 22

(2R,5R)-4-(tert-Butoxycarbonyl)-1-(4-methoxybenzenesulfonyl)-5-(2-methylpropyl)piperazine-2-(N-benzyloxy)carboxamide (5.3 g) was obtained in substantially the same manner as in Preparation 8.

m.p.: 178–179° C.

Mass (ESI+): 584 (M+Na)

$^1$H-NMR (300 MHz, CDCl$_3$, δ): 0.75–0.96(6H, br), 0.90–1.70(3H, m), 1.44(9H, s), 2.80–3.70(ca. 3H, br), 3.87 (3H, s), 4.00–4.70(ca. 3H, br), 4.88(2H, s), 6.97(2H, d, J=8 Hz), 7.39(5H, m), 7.63–7.83(2H, br), 8.77, 9.18(1H, br)

Preparation 23

(2R,5R)-1-(4-Methoxybenzenesulfonyl)-5-(2-methylpropyl)piperazine-2-(N-benzyloxy)carboxamide hydrochloride (5.2 g) was obtained in substantially the same manner as in Preparation 10.

m.p.: 168–173° C.

Mass (ESI+): 462 (M+H)

$^1$H-NMR (300 MHz, DMSO-d$_6$, δ): 0.83(3H, d, J=7 Hz), 0.84(3H, d, J=7 Hz), 1.36(1H, m), 1.90–2.15(2H, m), 3.15 (1H, dd, J=4, 12 Hz), 3.25(1H, dd, J=4, 12 Hz), 3.30–3.50 (2H, m), 3.75(1H, d, J=12 Hz), 3.83(3H, s), 4.18(1H, t, J=4 Hz), 4.77(2H, s), 7.13(2H, d, J=8 Hz), 7.79(2H, d, J=8 Hz)

EXAMPLE 13

(2R,5R)-4-Methanesulfonyl-1-(4-methoxybenzenesulfonyl)-5-(2-methylpropyl)piperazine-2-(N-benzyloxy)carboxamide (0.37 g) was obtained in substantially the same manner as in Example 1.

m.p.: 165–166° C.

Mass (ESI–): 538 (M–H)

$^1$H-NMR (300 MHz, CDCl$_3$, δ): 0.77(3H, d, J=5 Hz), 0.83(3H, d, J=5 Hz), 1.11(1H, m), 1.18–1.40(2H, m), 2.91 (3H, s), 2.85–3.20(2H, m), 3.56(1H, d, J=13 Hz), 3.77(1H, m), 3.88(3H, s), 4.12(1H, d, J=13 Hz), 4.36(1H, m), 4.86 (1H, d, J=10 Hz), 4.95(1H, d, J=10 Hz), 6.98(2H, d, J=8 Hz), 7.40(5H, m), 7.71(2H, d, J=8 Hz), 9.20(1H, brs)

EXAMPLE 14

(2R,5R)-4-Methanesulfonyl-1-(4-methoxybenzenesulfonyl)-5-(2-methylpropyl)piperazine-2-(N-hydroxy)carboxamide (188 mg) was obtained in substantially the same manner as in Example 2.

m.p.: 68–93° C.

Mass (ESI–): 448 (M–H)

$^1$H-NMR (300 MHz, DMSO-d$_6$, δ): 0.76(3H, d, J=5 Hz), 0.80(3H, d, J=5 Hz), 1.17(1H, m), 1.20–1.44(2H, m), 2.87 (3H, s), 3.20–3.44(2H, m), 3.71–3.89(3H, m), 3.83(3H, s), 4.31(1H, d, J=4 Hz), 7.08(2H, d, J=8 Hz), 7.72(2H, d, J=8 Hz), 8.92(1H, brs)

Preparation 24

Ethyl 1-(tert-butoxycarbonyl)-4-methanesulfonylpiperazine-2-carboxylate was obtained in substantially the same manner as in Example 4.

$^1$H-NMR (300 MHz, CDCl$_3$, δ): 1.28(3H, t, J=8 Hz), 1.43(4H, s), 1.47(5H, s), 2.73(1H, t, J=14 Hz), 2.89(1H, d, J=14 Hz), 3.08–3.34(1H, m), 3.61–3.78(1H, m), 3.86–4.09 (1H, m), 4.12–4.29(2H, m), 4.22(2H, q, J=8 Hz), 4.67(0.5H, bs), 4.86(0.5H, bs)

Preparation 25

Ethyl 4-methanesulfonylpiperazine-2-carboxylate hydrochloride was obtained in substantially the same manner as in Preparation 9.

$^1$H-NMR (300 MHz, DMSO-d$_6$, δ): 1.26(3H, t, J=8 Hz), 3.02(3H, s), 3.09–3.30(2H,m), 3.33–3.59(3H, m), 3.76(1H, dd, J=4, 16 Hz), 4.26(2H, q, J=8 Hz), 4.50(1H, dd, J=4, 11 Hz)

Preparation 26

Ethyl (2RS)-1-(3-chloropropylsulfonyl)-4-methanesulfonylpiperazine-2-carboxylate (224 mg) was obtained in substantially the same manner as in Example 4.

m.p.: 144–145° C.

$^1$H-NMR (300 MHz, CDCl$_3$, δ): 1.33(3H, t, J=7 Hz), 2.25–2.40(2H, m), 2.75–2.90(1H, overlapping), 2.80(3H, s), 3.00(1H, dd, J=4, 12 Hz), 3.20–3.40(2H, m), 3.48(1H, dt, J=4, 12 Hz), 3.68(2H, t, J=7 Hz), 3.76(1H, d, J=12 Hz), 3.83(1H, d, J=12 Hz), 4.15–4.40(3H, m), 4.75(1H, brs)

Preparation 27

A mixture of ethyl (2RS)-1-(3-chloropropylsulfonyl)-4-methanesulfonylpiperazine-2-carboxylate (203 mg) and 1N aqueous sodium hydroxide (0.9 ml) in dioxane (2 ml) and EtOH (1 ml) was stirred for 2 hours at ambient temperature. The mixture was acidified with 1N HCl (0.9 ml) and concentrated in vacuo. The resulting crystals were collected with H$_2$O, and washed with H$_2$O and Et$_2$O to give 165 mg of (2RS)-1-(3-chloropropylsulfonyl)-4-methanesulfonylpiperazine-2-carboxylic acid.

m.p.: 188–189° C.

Mass (ESI–): 347 (M–H)

¹H-NMR (300 MHz, DMSO-d$_6$, δ): 2.14(2H, m), 2.78 (1H, dt, J=4, 12 Hz), 2.91(3H, s), 2.99(1H, dd, J=4, 12 Hz), 3.20–3.45(3H, overlapping with H$_2$O), 3.53(1H, d, J=12 Hz), 3.68(1H, d, J=12 Hz), 3.76(2H, t, J=6 Hz), 4.00(1H, d, J=12 Hz), 4.62(1H, brs)

EXAMPLE 15

(2RS)-1-(3-Chloropropylsulfonyl)-4-methanesulfonylpiperazine-2-[N-(2-tetrahydropyranyloxy)]carboxamide (172 mg) was obtained in substantially the same manner as in Preparation 12.

Mass (ESI-): 446, 448 (M-H)

¹H-NMR (300 MHz, CDCl$_3$, δ): 1.50–2.00(6H, m), 2.33 (2H, m), 2.90(3H, s), 2.83–3.00(1H, overlapping), 3.13(1H, brd, J=12 Hz), 3.20–4.00(7H, br), 3.68(2H, t, J=5 Hz), 4.14(1H, br), 4.65(1H, br), 5.01(1H, br), 9.26(1H, br)

EXAMPLE 16

(2RS)-1-(3-Chloropropylsulfonyl)-4-methanesulfonylpiperazine-2-(N-hydroxy)carboxamide (95 mg) was obtained in substantially the same manner as in Example 5.

Mass (ESI-): 362 (M-H)

¹H-NMR (300 MHz, DMSO-d$_6$, δ): 2.15(2H, m), 2.78 (1H, dt, J=4, 10 Hz), 2.90(3H, s), 3.06(1H, d, J=4, 10 Hz), 3.15–3.45(2H, overlapping with H$_2$O), 3.53(1H, d, J=12 Hz), 3.73(2H, t, J=6 Hz), 3.57–3.80(2H, m), 3.88(1H, d, J=12 Hz), 4.39(1H, s), 9.06(1H, s)

Preparation 28

Ethyl 1-tert-butoxycarbonyl-1,4,5,6-tetrahydropyrazinecarboxylate (60 g) was dissolved in AcOH (400 ml), and the solution was subjected to catalytic reduction using 10% palladium on carbon (12 g)-H$_2$O (30 ml), in hydrogen at 3 atm for 4 hours. The catalyst was removed by filtration and the filtrate was concentrated under reduced pressure. The residue was dissolved in AcOEt (1000 ml), and the organic layer was washed with saturated aqueous NaHCO$_3$ solution by stirring carefully to avoid foaming. The organic layer was further washed with saturated brine, and dried over anhydrous MgSO$_4$. The solvent was evaporated under reduced pressure to give 59.2 g of ethyl 1-tert-butoxycarbonyl-2-piperazinecarboxylate as an oil (yield 97.9%).

TLC Rf 0.44 (CHCl$_3$:MeOH, 9:1)

Mass (ESI+): 259 (M+H)

¹H-NMR (300 MHz, CDCl$_3$, δ): 1.30(3H, t, J=7.5 Hz), 1.45(4.5H, s), 1.48(4.5H, s), 2.63–2.68(1H, m), 2.83–3.22 (3H, m), 3.43–3.59(1H, m), 3.70–3.91(1H, m), 4.14–4.30 (2H, m), 4.42–4.70(1H, m)

EXAMPLE 17

(2R)-4-Methanesulfonyl-1-(4-phenoxybenzenesulfonyl)piperazine-2-(N-benzyloxy)carboxamide (39.5 g) was obtained in substantially the same manner as in Example 1.

Mass (ESI+): 546 (M+H)

¹H-NMR (300 MHz, CDCl$_3$, δ): 2.52–2.70(2H, m), 2.98–3.15(1H, m), 2.89(3H, s), 3.52(1H, d, J=12 Hz), 3.78 (1H, d, J=13 Hz), 4.26(1H, d, J=13 Hz), 4.50(1H, br), 4.92(2H, dd, J=11 and 14 Hz), 7.01(2H, d, J=8 Hz), 7.10(2H, d, J=8 Hz), 7.26(1H, dd, J=8, 8 Hz), 7.35–7.49(7H, m), 7.70(2H, d, J=8 Hz)

EXAMPLE 18

A solution of (2R)-4-methanesulfonyl-1-(4-phenoxybenzenesulfonyl)-piperazine-2-(N-benzyloxy) carboxamide (39.0 g) in dioxane (156 ml) and EtOH (156 ml) was subjected to catalytic reduction using 10% palladium on barium sulfate (3.9 g) in hydrogen at 3 atm for 4 hours. The catalyst was removed by filtration and the filtrate was concentrated in vacuo. The residue was purified by chromatography on SiO$_2$ (eluent: from 0.5 to 2% MeOH-CHCl$_3$) to give 31.5 g of (2R)-4-methanesulfonyl-1-(4-phenoxybenzenesulfonyl)piperazine-2-(N-hydroxy)-carboxamide as an amorphous powder.

Mass (ESI-): 454 (M-H)

m.p. 112–114° C.

¹H-NMR (300 MHz, DMSO-d$_6$, δ): 2.63(1H, td, J=5, 13 Hz), 2.84(3H, s), 2.90(1H, dd, J=5, 14 Hz), 3.46(1H, d, J=12 Hz), 3.53–3.72(3H, m), 4.40(1H, bs), 7.07–7.19(4H, m), 7.25(1H, dd, J=7, 7 Hz), 7.42–7.51(2H, m), 7.78(2H, d, J=8 Hz), 8.90(1H, s)

EXAMPLE 19

(2R)-4-Methanesulfonyl-1-(4-phenoxybenzenesulfonyl)piperazine-2-(N-hydroxy)carboxamide sodium salt (25.9 g) was obtained in substantially the same manner as in Example 3.

Mass (ESI-): 454 (M-H)

¹H-NMR (300 MHz, DMSO-d$_6$, δ): 2.65(1H, td, J=4, 13 Hz), 2.78(1H, dd, J=5, 14 Hz), 2.80(3H, s), 3.45(2H, d, J=11 Hz), 3.72(1H, td, J=4, 11 Hz), 3.99(1H, d, J=14 Hz), 4.21(1H, s), 7.03(2H, d, J=8 Hz), 7.14(2H, d, J=8 Hz), 7.24(1H, dd, J=8, 8 Hz), 7.45(2H, dd, J=8, 8 Hz), 7.90(2H, d, J=8 Hz)

Preparation 29

N-(tert-Butoxycarbonyl)-O-benzyl-L-serine N,O-dimethylhydroxyl-amine amide (2.5 g) was obtained in substantially the same manner as in Preparation 8.

¹H-NMR (300MHz, CDCl$_3$, δ): 1.43(9H, s), 3.20(3H, s), 3.60–3.72(2H, m), 3.70(3H, s), 4.49(1H, d, J=10 Hz), 4.57 (1H, d, J=10 Hz), 4.88(1H, m), 5.43(1H, d, J=7 Hz), 7.22–7.37(5H, m)

Preparation 30

0.9M Methylmagnesium bromide (MeMgBr) in THF (100 ml) was added dropwise to a solution of N-(tert-butoxycarbonyl)-O-benzyl-L-serine N,O-dimethylhydroxylamine amide (5.0 g) in dry THF (25 ml) with cooling on an ice bath. The reaction mixture was stirred at the same temperature for 2 hours. The reaction was quenched by adding saturated aqueous ammonium chloride (NH$_4$Cl) solution and the resulting mixture was extracted with AcOEt. The organic layer was washed with saturated aqueous NaHCO$_3$ solution and saturated aqueous NaCl solution, dried over MgSO$_4$ and concentrated in vacuo to give 4.3 g of (3S)-4-benzyloxy-3-tert-butoxycarbonylamino-2-butanone as an oil.

¹H-NMR (300 MHz, CDCl$_3$, δ): 1.43(9H, s), 2.20(3H, s), 3.68(1H, dd, J=3.8 Hz), 3.91(1H, dd, J=3.8 Hz), 4.34(1H, m), 4.47(1H, d, J=10 Hz), 4.57(1H, d, J=10 Hz), 7.20–7.40 (5H, m)

Preparation 31

A solution of (3S)-4-benzyloxy-3-tert-butoxycarbonylamino-2-butanone (4.3 g) in dry MeOH (20 ml) was added to a solution of 2-aminoethanol (2.0 g) in AcOH (1.8 g) in dry MeOH (20 ml). NaBH$_3$CN (1.4 g) was added and the mixture was stirred at ambient temperature overnight. The mixture was concentrated in vacuo and the residue was partitioned between AcOEt and aqueous NaHCO$_3$ solution. The organic layer was washed with saturated aqueous NaHCO$_3$ solution and saturated aqueous NaCl solution. The organic layer was mixed with 1N HCl (50 ml) and the mixture was stirred vigorously for 1 hour. The organic layer was separated, washed with saturated aqueous NaHCO$_3$ solution and saturated aqueous NaCl solution, dried over MgSO$_4$ and concentrated in vacuo to give 4.1 g of (2R, 3RS)-O-benzyl-2-tert-butoxycarbonylamino-3-(2-hydroxyethylamino)butanol as an oil.

Mass (ESI+): 339 (M+H)

$^1$H-NMR (300 MHz, CDCl$_3$, δ): 1.11, 1.18, 1.23(3H, d, J=5 Hz), 1.45(9H, s), 2.60–3.00(3H, m), 3.45–3.95(5H, m), 4.48(1H, d, J=10 Hz), 4.54(1H, d, J=10 Hz), 5.00–5.35(1H, m), 7.20–7.40(5H, m)

Preparation 32

A solution of triethylamine (7.6 g) in dioxane (20 ml) was added to dropwise a solution of (2R,3RS)-O-benzyl-2-tert-butoxycarbonyl-amino-3-(2-hydroxyethylamino)butanol (8.4 g) and methanesulfonyl chloride (8.6 g) in dioxane (40 ml) with cooling on an ice bath. The reaction mixture was stirred at ambient temperature for 2 hours and the reaction was quenched by adding 3-(N,N-dimethylamino) propylamine (5 ml). The mixture was concentrated in vacuo and the residue was partitioned between 0.6N HCl and AcOEt. The organic layer was washed with saturated aqueous NaHCO$_3$ solution and saturated aqueous NaCl solution, dried over MgSO$_4$ and concentrated in vacuo. The residue was purified by SiO$_2$ column chromatography (eluent: AcOEt in n-hexane 40%, 50% and then 60%). The fraction containing the desired product was concentrated in vacuo and was further purified by SiO$_2$ column chromatography (eluent: acetone in toluene 16%) to give 2.7 g of (2R, 3R)-O-benzyl-2-tert-butoxycarbonylamino-3-[N-(2-methanesulfonyloxy-ethyl)-N-methanesulfonylamino] butanol as an oil.

$^1$H-NMR (300 MHz, CDCl$_3$, δ): 1.28(3H, d, J=5 Hz), 1.43(9H, s), 2.88(3H, s), 3.02(3H, s), 3.40–3.65(3H, m), 3.75–3.94(2H, m), 3.99(1H, m), 4.28–4.50(2H, m), 4.49(1H, d, J=10 Hz), 4.54(1H, d, J=10 Hz), 4.98(1H, d, J=8 Hz), 7.27–7.40(5H, m)

Preparation 33

(2R,3S)-O-Benzyl-2-tert-butoxycarbonylamino-3-[N-(2-methane-sulfonyloxyethyl)-N-methanesulfonylamino] butanol (5.7 g) was obtained in substantially the same manner as in Preparation 32.

$^1$H-NMR (300 MHz, CDCl$_3$, δ): 1.23(3H, d, J=5 Hz), 1.43(9H, s), 2.92(3H, s), 3.05(3H, s), 3.37–3.60(4H, m), 3.69(1H, m), 4.05(1H, m), 4.25–4.50(2H, m), 4.45(1H, d, J=10 Hz), 4.56(1H, d, J=10 Hz), 5.24(1H, d, J=7 Hz), 7.25–7.40(5H, m)

Preparation 34

A solution of (2R,3R)-O-benzyl-2-tert-butoxycarbonylamino-3-[N-(2-methanesulfonyloxyethyl)-N-methanesulfonylamino]butanol (2.6 g) in dry DMF (15 ml) was added dropwise to a suspension of sodium hydride (60% dispersion in mineral oil, 189 mg) in dry DMF (10 ml) at 4° C. over 20 minutes. The mixture was stirred at same temperature for 45 minutes and then poured into a mixture of ice and 1N HCl (8 ml). The mixture was extracted with AcOEt. The organic layer was washed with saturated aqueous NaCl solution, dried over MgSO$_4$ and concentrated in vacuo. The residue was purified by SiO$_2$ column chromatography (eluent: AcOEt in n-hexane 40% and 50%) to give 2.1 g of (2R,3R)-2-benzyloxymethyl-1-tert-butoxycarbonyl-4-methanesulfonyl-3-methylpiperazine as an oil.

m.p.: 62–68° C.

Mass (ESI+): 399 (M+H), 421 (M+Na)

$^1$H-NMR (300 MHz, CDCl$_3$, δ): 1.36(3H, d, J=6 Hz), 1.43(9H, s), 2.84(3H, s), 3.11(1H, m), 3.43(1H, m), 3.52–3.68(2H, m), 3.70–3.85(3H, m), 4.09(1H, m), 4.50(1H, d, J=10 Hz), 4.57(1H, d, J=10 Hz), 7.27–7.38(5H, m)

Preparation 35

10% Palladium on activated carbon (1.5 g) was suspended in H$_2$O (10 ml) and the suspension was added to a solution of (2R,3R)-2-benzyloxymethyl-1-tert-butoxycarbonyl-4-methanesulfonyl-3-methyl-piperazine (2.1 g) and ammonium formate (3.3 g) in MeOH (25 ml). The mixture was refluxed for 1.5 hours. Ammonium formate (3.4 g) in H$_2$O (10 ml) and MeOH (10 ml) were added to the reaction mixture, and the mixture was refluxed for 1.5 hours. 10% Palladium on activated carbon (1.5 g) in H$_2$O (10 ml) and ammonium formate (3.4 g) were added to the reaction mixture and the mixture was refluxed for 2.5 hours. The catalyst was removed by filtration through a celite pad and the pad was washed with MeOH. The combined filtrate and washings were concentrated in vacuo. The residue was partitioned between AcOEt and brine. The organic layer was dried over MgSO$_4$ and concentrated in vacuo to give 1.5 g of (2R,3R)-1-tert-butoxycarbonyl-2-hydroxymethyl-4-methane-sulfonyl-3-methylpiperazine as a solid.

m.p.: 84–90° C.

Mass (ESI+): 309 (M+H), 331 (M+Na)

$^1$H-NMR (300 MHz, CDCl$_3$, δ): 1.32(3H, d, J=5 Hz), 1.47(9H, s), 2.87(3H, s), 3.25–3.48(3H, m), 3.70–3.90(4H, m), 4.07(1H, m)

Preparation 36

(2R,3R)-1-tert-Butoxycarbonyl-4-methanesulfonyl-3-methyl-2-piperazinecarboxylic acid (1.0 g) was obtained in substantially the same manner as in Preparation 21.

m.p.: 158° C.

$^1$H-NMR (300 MHz, CDCl$_3$, δ): 1.47(9H, s), 1.49(3H, d, J=6 Hz), 2.90(3H, s), 3.43(1H, m), 3.54(1H, m), 3.60–3.80 (2H, m), 4.20(1H, m), 4.48(1H, d, J=3 Hz)

Preparation 37

(2R,3R)-N-Benzyloxy-1-tert-butoxycarbonyl-4-methanesulfonyl-3-methyl-2-piperazinecarboxamide (690 mg) was obtained in substantially the same manner as in Preparation 8.

m.p.: 156–159° C.

Mass (ESI+): 428 (M+H), 450 (M+Na)

$^1$H-NMR (300 MHz, CDCl$_3$, δ): 1.21(3H, d, J=6 Hz), 1.37(9H, s), 2.94(3H, s), 3.25–3.55(3H, m), 3.84(1H, m), 3.98(1H, m), 4.25(1H, d, J=6 Hz), 4.81(2H, s), 7.30–7.50 (5H, m)

Preparation 38

(2R,3R)-N-Benzyloxy-4-methanesulfonyl-3-methyl-2-piperazine-carboxamide hydrochloride (559 mg) was obtained in substantially the same manner as in Preparation 10.

Mass (ESI+): 328 (M+H)

$^1$H-NMR (300 MHz, DMSO-d$_6$, δ): 1.10(3H, d, J=6 Hz), 3.00–3.30(3H, m), 3.13(3H, s), 3.69(3H, d, J=11 Hz), 4.00 (1H, d, J=5 Hz), 4.32(1H, m), 4.86(2H, s), 7.35–7.50(5H, m)

EXAMPLE 20

A solution of 4-methoxybenzenesulfonyl chloride (284 mg) in dioxane (2 ml) was added to a solution of (2R,3R)-N-benzyloxy-4-methanesulfonyl-3-methyl-2-piperazinecarboxamide hydrochloride (200 mg) in pyridine (2 ml) with cooling on an ice bath. The mixture was stirred at ambient temperature for 3.5 hours. 4-Methoxybenzenesulfonyl chloride (60 mg) in dioxane (1 ml) was added thereto, and the mixture was stirred at ambient temperature for 2 hours. 4-Methoxybenzenesulfonyl chloride (60 mg) in dioxane (1 ml) was added to the mixture. The reaction mixture was stirred at ambient temperature for 2 hours, and the reaction was quenched by adding 3-(N,N-dimethyl-amino)propylamine (0.1 ml). The mixture was partitioned between 0.6N HCl and AcOEt. The organic layer was washed with 0.6N HCl, saturated aqueous NaHCO$_3$ solution and saturated aqueous NaCl solution, dried over MgSO$_4$ and concentrated in vacuo. The residue was purified by SiO$_2$ column chromatography (eluent: AcOEt in n-hexane 60% to 80%) to give 273 mg of (2R,3R)-N-benzyloxy-4-methanesulfonyl-1-(4-methoxy-benzenesulfonyl)-3-methyl-2-piperazinecarboxamide as an amorphous powder.

Mass (ESI−): 496 (M−H)

$^1$H-NMR (300 MHz, CDCl$_3$, δ): 1.38(3H, d, J=5 Hz), 2.77(3H, s), 3.17(1H, m), 3.40(1H, m), 3.55–3.75(2H, m), 3.86(3H, s), 3.93(1H, m), 4.26(1H, m), 4.85(1H, d, J=10 Hz), 4.92(1H, d, J=10 Hz), 6.99(2H, d, J=8 Hz), 7.40(5H, s), 7.76(2H, d, J=8 Hz), 8.86(1H, brs)

EXAMPLE 21

(2R,3R)-N-Hydroxy-4-methanesulfonyl-1-(4-methoxybenzenesulfonyl)-3-methyl-2-piperazinecarboxamide (106 mg) was obtained in substantially the same manner as in Example 18.

Mass (ESI−): 406 (M−H)

$^1$H-NMR (300 MHz, DMSO-d$_6$, δ): 1.74(3H, d, J=5 Hz), 2.78(3H, s), 3.07(1H, m), 3.55–3.75(4H, m), 3.84(3H, s), 4.19(1H, d, J=4 Hz), 7.09(2H, d, J=8 Hz), 7.72(2H, d, J=8 Hz), 8.97(1H, br)

Preparation 39

A solution of (2R,3S)-O-benzyl-2-tert-butoxycarbonylamino-3-[N-(2-methanesulfonyloxyethyl)-N-methanesulfonylamino]butanol (1.1 g) in dry THF (15 ml) was added dropwise to a suspension of sodium hydride (60% dispersion in mineral oil, 80.1 mg) in dry THF (8 ml) at 4° C. over 15 minutes. The mixture was stirred at the same temperature for 3.5 hours and then poured into saturated aqueous NH$_4$Cl solution. The mixture was extracted with AcOEt. The organic layer was washed with saturated aqueous NaCl solution, dried over MgSO$_4$ and concentrated in vacuo. The residue was purified by SiO$_2$ column chromatography (eluent: AcOEt in n-hexane 40% and 50%) to give 0.80 g of (2R,3S)-2-benzyloxy-methyl-1-tert-butoxycarbonyl-4-methanesulfonyl-3-methylpiperazine as an oil.

Mass (ESI+): 399 (M+H), 421 (M+Na)

$^1$H-NMR (300 MHz, CDCl$_3$, δ): 1.30(3H, d, J=5 Hz), 1.43(9H, s), 2.81(3H, s), 2.85–3.30(2H, m), 3.35–3.93(4H, m), 4.08(1H, m), 4.27(1H, m), 4.50(1H, d, J=10 Hz), 4.59 (1H, d, J=10 Hz), 7.25–7.40(5H, m)

Preparation 40

(2R,3S)-2-Benzyloxymethyl-4-methanesulfonyl-1-(4-methoxybenzene-sulfonyl)-3-methylpiperazine (320 mg) was obtained in substantially the same manner as in Preparation 10.

Mass (ESI+): 469 (M+H), 491 (M+Na)

$^1$H-NMR (300 MHz, CDCl$_3$, δ): 1.31(3H, d, J=7 Hz), 2.81(3H, s), 2.97(1H, dt, J=2, 12 Hz), 3.19(1H, dt, J=2, 12 Hz), 3.38(1H, dd, J=5, 8 Hz), 3.50–3.70(3H, m), 3.83(3H, s), 4.01(1H, m), 4.26(1H, q, J=7 Hz), 4.37(1H, d, J=11 Hz), 4.49(1H, d, J=11 Hz), 6.85(2H, d, J=8 Hz), 7.25–7.40(5H, m), 7.71 (2H, d, J=8 Hz)

Preparation 41

A mixture of (2R,3S)-2-benzyloxymethyl-4-methanesulfonyl-1-(4-methoxybenzenesulfonyl)-3-methylpiperazine (330 mg) and palladium hydroxide (40 mg) in dioxane (5 ml) and MeOH (5 ml) was hydrogenated in hydrogen at 3.5 atm and ambient temperature for 1 day. The catalyst was removed by filtration through a celite pad and the pad was washed with MeOH. The filtrate and combined washings were concentrated in vacuo. The residue was purified by SiO$_2$ column chromatography (eluent: AcOEt/n-hexane 60%, then MeOH/AcOEt 1%) to give 253 mg of (2R,3S)-2-hydroxymethyl-4-methanesulfonyl-1-(4-methoxybenzene-sulfonyl)-3-methylpiperazine.

Mass (ESI−): 377 (M−H)

$^1$H-NMR (300 MHz, CDCl$_3$, δ): 1.30(3H, d, J=5 Hz), 2.08(1H, t, J=4 Hz), 2.88(3H, s), 3.08(1H, dt, J=2, 10 Hz), 3.20(1H, dt, J=2, 10 Hz), 3.48(1H, m), 3.62(1H, dd, J=2, 10 Hz), 3.69(1H, dd, J=2, 10 Hz), 3.70–3.90(2H, m), 3.87(3H, s), 4.26(1H, q, J=5 Hz), 6.98(2H, d, J=8 Hz), 7.76(2H, d, J=8 Hz)

Preparation 42

(2R,3S)-4-Methanesulfonyl-1-(4-methoxybenzenesulfonyl)-3-methyl-2-piperazinecarboxylic acid (231 mg) was obtained in substantially the same manner as in Preparation 21.

m.p.: 150–152° C.

Mass (ESI−): 391 (M−H)

$^1$H-NMR (300 MHz, CDCl$_3$, δ): 1.42(3H, d, J=5 Hz), 2.83(3H, s), 3.24(1H, dt, J=2, 11 Hz), 3.36(1H, dt, J=2, 11 Hz), 3.56(1H, dd, J=2, 11 Hz), 3.70(1H, dd, J=2, 11 Hz), 3.88(3H, s), 4.55(1H, brs), 4.66(1H, q, J=5 Hz), 6.97(2H, d, J=8 Hz), 7.73(2H, d, J=8 Hz)

EXAMPLE 22

(2R,3S)-4-Methanesulfonyl-1-(4-methoxybenzenesulfonyl)-3-methyl-N-(2-tetrahydropyranyloxy)-2-piperazinecarboxamide (235 mg) was obtained in substantially the same manner as in Preparation 12.

Mass (ESI−): 490 (M−H)

$^1$H-NMR (300 MHz, DMSO-d$_6$, δ): 1.17, 1.20(3H, d, J=5 Hz), 1.45–1.70(6H, m), 2.86(3H, s), 3.10, 3.15(1H, m), 3.45–3.65(3H, m), 3.68, 3.73(1H, m), 3.83(3H, s), 3.86(1H, m), 4.09, 4.15(1H, s), 4.05–4.25(1H, m), 4.63, 4.71(1H, s), 7.07, 7.09(2H, d, J=8 Hz), 7.64, 7.67(2H, d, J=8 Hz)

EXAMPLE 23

(2R,3S)-N-Hydroxy-4-methanesulfonyl-1-(4-methoxybenzenesulfonyl)-3-methyl-2-piperazinecarboxamide (164 mg) was obtained in substantially the same manner as in Example 5.

Mass (ESI−): 406 (M−H)

$^1$H-NMR (300 MHz, CDCl$_3$, δ): 1.08(3H, d, J=5 Hz), 2.90(3H, s), 3.16(1H, dt, J=2, 10 Hz), 3.28(1H, dt, J=2, 10 Hz), 3.52 (1H, d, J=10 Hz), 3.67(1H, d, J=10 Hz), 3.89(3H, s), 4.32(1H, s), 4.68(1H, q, J=5 Hz), 7.03(2H, d, J=8 Hz), 7.80(2H, d, J=8 Hz)

Preparation 43

A solution of sodium carbonate (1.63 g) in H$_2$O (7.65 ml), 4-fluorobenzeneboronic acid (1.03 g) and tetrakis (triphenylphosphine) palladium(0) (70.9 mg) were added successively to a solution of 2-bromothiophene (1.00 g) in dimethoxyethane (12.3 ml). The mixture was refluxed for 4 hours. The mixture was cooled to ambient temperature and partitioned between AcOEt and H$_2$O. The organic layer was washed with 0.5N aqueous NaOH solution and saturated aqueous NaCl solution, dried over MgSO$_4$ and concentrated in vacuo. The residue was purified by SiO$_2$ column chromatography (eluent: n-hexane and then AcOEt in n-hexane 10%). The solvent was evaporated in vacuo to give 1.05 g of 2-(4-fluorophenyl)thiophene as a white solid.

m.p.: 51–52° C.

¹H-NMR (300 MHz, CDCl₃, δ): 7.01–7.14(3H, m), 7.21–7.29(2H, m), 7.52–7.62(2H, m)

Preparation 44

2-(4-Fluorophenyl)thiophene (538 mg) was added to a solution of sulfur trioxide N,N-dimethylformamide complex in dichloroethane (5 ml). The reaction mixture was stirred at 50° C. for 3 hours and at 70° C. for 2 hours. Sulfur trioxide N,N-dimethylformamide complex (231 mg) was added to the reaction mixture and the mixture was stirred at 80° C. overnight. The reaction mixture was cooled to ambient temperature. Thionyl chloride (0.27 ml) was added to the reaction mixture and the mixture was stirred at 70° C. for 3 hours. The mixture was concentrated in vacuo and the residue was partitioned between AcOEt and ice water. The organic layer was washed with H₂O, saturated aqueous NaHCO₃ solution and saturated aqueous NaCl solution, dried over MgSO₄ and concentrated in vacuo to give 694 mg of 5-(4-fluoro-phenyl)-2-thiophenesulfonyl chloride as a blue-gray solid.

m.p.: 82–85° C.

¹H-NMR (300 MHz, CDCl₃, δ): 7.17(2H, t, J=8 Hz), 7.25(1H, d, J=1 Hz), 7.61(2H, d, J=3.8 Hz), 7.83(1H, d, J=1 Hz)

Preparation 45

2-(3-Fluorophenyl)thiophene (1.12 g) was obtained in substantially the same manner as in Preparation 43.

¹H-NMR (300 MHz, CDCl₃, δ): 6.96(1H, t, J=8 Hz), 7.09(1H, t, J=4 Hz), 7.22–7.40(5H, m)

Preparation 46

2-(3-Fluorophenyl)thiophene-5-sulfonylchloride (1.54 g) was obtained in substantially the same manner as in Preparation 44.

m.p.: 75–84° C.

¹H-NMR (300 MHz, CDCl₃, δ): 7.20–7.30(1H, m), 7.40–7.47(1H, m), 7.50(1H, d, J=4 Hz), 7.68(1H, t, J=8 Hz), 7.88(1H, d, J=4 Hz)

EXAMPLE 24

(2R)-4-Methanesulfonyl-1-(5-phenylthiophene-2-sulfonyl)-N-(2-tetrahydropyranyloxy)-2-piperazinecarboxamide (273 mg) was obtained in substantially the same manner as in Example 4.

Mass (ESI): 528 (M–1)

¹H-NMR (300 MHz, CDCl₃, δ): 1.51–1.67(4H, m), 1.70–1.90(2H, m), 2.78–2.95(5H, m), 3.32–3.49(1H, m), 3.55–3.72(2H, m), 3.86–4.03(2H, m), 4.20–4.30(1H, m), 4.60–4.69(1H, m), 4.94–5.01(1H, m), 7.30(1H, d, J=3 Hz), 7.40–7.49(3H, m), 7.58–7.65(3H, m), 9.11–9.21 (1H, m)

EXAMPLE 25

(2R)-N-Hydroxy-4-methanesulfonyl-1-(5-phenylthiophene-2-sulfonyl)-2-piperazinecarboxamide (153 mg) was obtained in substantially the same manner as in Example 5.

Mass (ESI): 444 (H–1)

¹H-NMR (300 MHz, DMSO-d₆, δ): 2.69–2.80(1H, m), 2.86(3H, s), 3.00(1H, dd, J=6, 14 Hz), 3.54(1H, d, J=14 Hz), 3.69–3.88(3H, m), 4.49(1H, d, J=2 Hz), 7.40–7.52(3H, m), 7.62(1H, d, J=3 Hz), 7.70(1H, d, J=3 Hz), 7.76(2H, d, J=8 Hz), 9.00 (1H, brs)

EXAMPLE 26

(2R)-1-{5-(3-Fluorophenyl)thiophene-2-sulfonyl}-4-methanesulfonyl-N-(2-tetrahydropyranyloxy)-2-piperazinecarboxamide (370 mg) was obtained in substantially the same manner as in Example 4.

Mass (ESI): 546 (M–1)

¹H-NMR (300 MHz, CDCl₃, δ): 1.51–1.67(4H, m), 1.71–1.90(2H, m), 2.78–2.95(5H, m), 3.30–3.50(1H, m), 3.57–3.73(2H, m), 3.87–4.03(2H, m), 4.20–4.29(1H, m), 4.59–4.69(1H, m), 4.94–5.00(1H, m), 7.08–7.16(1H, m), 7.28–7.33(2H, m), 7.36–7.47(2H, m), 7.60–7.68(1H, m), 9.10–9.20(1H, m)

EXAMPLE 27

(2R)-1-{5-(3-Fluorophenyl)thiophene-2-sulfonyl}-N-hydroxy-4-methanesulfonyl-2-piperazinecarboxamide (282 mg) was obtained in substantially the same manner as in Example 5.

Mass (ESI): 462 (M–1)

¹H-NMR (300 MHz, DMSO-d₆, δ): 2.69–2.80(1H, m), 2.86(3H, s), 3.00(1H, dd, J=6, 14 Hz), 3.53(1H, d, J=14 Hz), 3.67–3.86(3H, m), 4.48(1H, d, J=2 Hz), 7.28(1H, t, J=8 Hz), 7.49–7.61(2H, m), 7.61–7.72(3H, m), 9.00 (1H, brs)

EXAMPLE 28

(2R)-1-[5-(4-Fluorophenyl)thiophene-2-sulfonyl]-4-methanesulfonyl-N-(2-tetrahydropyranyloxy)-2-piperazinecarboxamide (224 mg) was obtained in substantially the same manner as in Example 4.

Mass (ESI–): 546 (M–H)

¹H-NMR (300 MHz, CDCl₃, δ): 1.53–1.90(6H, m), 2.75–2.95(2H, m), 2.91, 2.94(3H, s), 3.32–3.50(1H, m), 3.55–3.75(2H, m), 3.85–4.05(2H, m), 4.23(1H, d, J=10 Hz), 4.55–4.68(1H, br), 4.97(1H, m), 7.15(2H, t, J=8 Hz), 7.23 (1H, d, J=1 Hz), 7.58(2H, d, J=3.8 Hz), 7.55–7.65(1H, m), 9.13, 9.16(1H, brs)

EXAMPLE 29

(2R)-1-[5-(4-Fluorophenyl)thiophene-2-sulfonyl]-N-hydroxy-4-methanesulfonyl-2-piperazinecarboxamide (103 mg) was obtained in substantially the same manner as in Example 5.

Mass (ESI–): 462 (M–H)

¹H-NMR (300 MHz, CDCl₃, δ): 2.65–2.90(2H, m), 2.85 (3H, s), 3.35–3.53(1H, m), 3.66(1H, d, J=12 Hz), 3.95(1H, d, J=12 Hz), 4.25(1H, d, J=12 Hz), 4.73(1H, s), 7.13(2H, t, J=8 Hz), 7.22(1H, d, J=1 Hz), 7.52–7.65(3H, m)

EXAMPLE 30

(2R)-1-[5-(4-Fluorophenyl)thiophene-2-sulfonyl]-N-hydroxy-4-methanesulfonyl-2-piperazinecarboxamide (0.90 g) and 1N NaOH (1.95 ml) were used to give 0.94 g of (2R)-1-[5-(4-fluorophenyl)thiophene-2-sulfonyl]-N-hydroxy-4-methanesulfonyl-2-piperazinecarboxamide sodium salt.

¹H-NMR (300 MHz, DMSO-d₆, δ): 2.71(1H, t, J=10 Hz), 2.83(3H, s), 2.76–2.88(1H, m), 3.52(2H, d, J=10 Hz), 3.81 (1H, t, J=10 Hz), 4.04(1H, d, J=10 Hz), 4.24(1H, s), 7.32 (2H, t, J=8 Hz), 7.52(1H, d, J=3 Hz), 7.73–7.87 (4H, m)

Preparation 47

2-(4-Chlorophenyl)thiophene (1.52 g) was obtained in substantially the same manner as in Preparation 43.

¹H-NMR (300 MHz, CDCl₃, δ): 7.07(1H, dd, J=4, 4 Hz), 7.25–7.37(4H, m), 7.53(2H, d, J=8 Hz)

Preparation 48

5-(4-Chlorophenyl)-2-thiophenesulfonyl chloride (1.55 g) was obtained in substantially the same manner as in Preparation 44.

¹H-NMR (300 MHz, CDCl₃, δ): 7.30(1H, d, J=4 Hz), 7.45(2H, d, J=9 Hz), 7.57(2H, d, J=9 Hz), 7.86(1H, d, J=4 Hz)

EXAMPLE 31

(2R)-1-[5-(4-Chlorophenyl)thiophene-2-sulfonyl]-4-methanesulfonyl-N-(2-tetrahydropyranyloxy)-2-piperazinecarboxamide (424 mg) was obtained in substantially the same manner as in Example 4.

Mass (ESI-): 562, 564 (M-H)

¹H-NMR (300 MHz, CDCl₃, δ): 1.52–1.90(6H, m), 2.77–2.95(5H, m), 3.38–3.49(1H, m), 3.57–3.75(2H, m), 3.86–4.00(2H, m), 4.24(1H, d, J=13 Hz), 4.58–4.65(1H, br), 4.92–4.98(1H, m), 7.07(1H, d, J=8 Hz), 7.41(2H, d, J=8 Hz), 7.52(2H, d, J=8 Hz), 7.60(1H, d, J=8 Hz), 9.17–9.27(1H, m)

Preparation 49

5-(4-Methoxyphenyl)-2-thiophenesulfonyl chloride (1.64 g) was obtained in substantially the same manner as in Preparation 44.

¹H-NMR (300 MHz, CDCl₃, δ): 3.85(3H, s), 6.98(2H, d, J=8 Hz), 7.20(1H, d, J=4 Hz), 7.57(1H, d, J=8 Hz), 7.81(1H, d, J=4 Hz)

EXAMPLE 32

(2R)-1-[5-(4-Methoxyphenyl)thiophene-2-sulfonyl]-4-methanesulfonyl-N-(2-tetrahydropyranyloxy)-2-piperazinecarboxamide (454 mg) was obtained in substantially the same manner as in Example 4.

Mass (ESI-): 558 (M-H)

¹H NMR (300 MHz, CDCl₃, δ): 1.55–1.91(6H, m), 2.76–2.95(5H, m), 3.38–3.49(1H, m), 3.55–3.72(2H, m), 3.85(3H, s), 3.90–4.05(2H, m), 4.23(1H, d, J=13 Hz), 4.60–4.67(1H, br), 4.96–5.01(1H, m), 6.93(2H, d, J=8 Hz), 7.19(1H, d, J=4 Hz), 7.52(2H, d, J=8 Hz), 7.60(1H, d, J=4 Hz), 9.25–9.39(1H, m)

Preparation 50

5-(4-Tolyl)-2-thiophenesulfonyl chloride (782 mg) was obtained in substantially the same manner as in Preparation 44.

¹H-NMR (300 MHz, CDCl₃, δ): 2.44(3H, s), 7.26(2H, d, J=13 Hz), 7.27(1H, d, J=6 Hz), 7.50(2H, d, J=13 Hz), 7.81(1H, d, J=6 Hz)

EXAMPLE 33

(2R)-1-[5-(4-Methylphenyl)thiophene-2-sulfonyl]-4-methanesulfonyl-N-(2-tetrahydropyranyloxy)-2-piperazinecarboxamide (372 mg) was obtained in substantially the same manner as in Example 4.

Mass (ESI-): 542 (M-H)

¹H-NMR (300 MHz, CDCl₃, δ): 1.50–1.90(6H, m), 2.75–3.00(5H, m), 3.35–3.51(1H, m), 3.56–3.75(2H, m), 3.85(3H, s), 3.87–4.04(2H, m), 4.23(1H, d, J=13 Hz), 4.60–4.69(1H, br), 4.95–5.02(1H, m), 7.20–7.28(4H, m), 7.49(1H, d, J=11 Hz), 9.15–9.28(1H, m)

Preparation 51

5-(4-Nitrophenyl)-2-thiophenesulfonyl chloride (915 mg) was obtained in substantially the same manner as in Preparation 44.

¹H-NMR (300 MHz, CDCl₃, δ): 7.48(2H, d, J=4 Hz), 7.84(1H, d, J=9 Hz), 7.91(1H, d, J=4 Hz), 8.47(1H, d, J=9 Hz)

EXAMPLE 34

(2R)-1-[5-(4-Nitrophenyl)thiophene-2-sulfonyl]-4-methanesulfonyl-N-(2-tetrahydropyranyloxy)-2-piperazinecarboxamide (242 mg) was obtained in substantially the same manner as in Example 4.

Mass (ESI-): 573 (M-H)

¹H-NMR (300 MHz, CDCl₃, δ): 1.54–1.84(6H, m), 2.79–2.95(5H, m), 3.34–3.49(1H, m), 3.56–3.75(2H, m), 3.89–4.00(2H, m), 4.22(1H, d, J=13 Hz), 4.62–4.71(1H, br), 4.94–5.00(1H, m), 7.43(1H, d, J=4 Hz), 7.62–7.69(1H, br), 7.77(1H, d, J=11 Hz), 8.29(1H, d, J=11 Hz), 9.17–9.30(1H, br)

Preparation 52

2-(2-Fluorophenyl)thiophene (1.56 g) was obtained in substantially the same manner as in Preparation 43.

¹H-NMR (300 MHz, CDCl₃, δ): 6.96(1H, t, J=8 Hz), 7.09(1H, t, J=4 Hz), 7.22–7.40(5H, m)

Preparation 53

2-(2-Fluorophenyl)thiophene-5-sulfonylchloride (1.10 g) was obtained in substantially the same manner as in Preparation 44.

¹H-NMR (300 MHz, CDCl₃, δ): 7.20–7.30(1H, m), 7.40–7.47(1H, m), 7.50(1H, d, J=4 Hz), 7.68(1H, t, J=8 Hz) 7.88(1H, d, J=4 Hz)

EXAMPLE 35

(2R)-1-[5-(3-Fluorophenyl)thiophene-2-sulfonyl]-4-methanesulfonyl-N-(2-tetrahydropyranyloxy)-2-piperazinecarboxamide (384 mg) was obtained in substantially the same manner as in Example 4.

Mass (ESI): 546 (M-1)

¹H-NMR (300 MHz, CDCl₃, δ): 1.50–1.68(4H, m), 1.70–1.90(2H, m), 2.72–2.95(5H, m), 3.32–3.49(1H, m), 3.54–3.72(2H, m), 3.88–4.05(2H, m), 4.20–4.30(1H, m), 4.59–4.70(1H, m), 4.95–5.00(1H, m), 7.15–7.28(2H, m), 7.33–7.41(1H, m), 7.46(1H, d, J=4 Hz), 7.60–7.69(2H,m), 9.10–9.21(1H, m)

Preparation 54

Into a mixture of 2-mercapto-4-phenylthiazole (2.00 g) and 4N hydrochloric acid (20 ml) in 1,2-dichloroethane (10 ml) was introduced Cl₂ gas over 1 hour at below 15° C. The organic layer was separated, washed with H₂O and brine and dried over sodium sulfate. After concentration, the obtained residue was crystallized from hexane to give 1.21 g of 4-phenylthiazole-2-sulfonylchloride.

¹H-NMR (300 MHz, CDCl₃, δ): 7.41–7.53(3H, m), 7.92 (1H, s), 7.96(2H, d, J=8 Hz)

EXAMPLE 36

(2R)-4-Methanesulfonyl-1-(4-phenylthiazole-2-sulfonyl)-N-(2-tetrahydropyranyloxy)-2-piperazinecarboxamide (177 mg) was obtained in substantially the same manner as in Example 4.

Mass (ESI): 529 (M-1)

¹H-NMR (300 MHz, CDCl₃, δ): 1.40–1.80(6H, m), 2.90–2.97(3H, m), 3.32–3.49(1H, m), 3.54–3.72(2H, m), 3.88–4.05(2H, m), 4.20–4.30(1H, m), 4.59–4.70(1H, m), 4.95–5.00(1H, m), 7.15–7.28(2H, m), 7.33–7.41(1H, m), 7.46(1H, d, J=4 Hz), 7.60–7.69(2H,m), 9.10–9.21(1H, m)

EXAMPLE 37

(2R)-1-[5-(3-Isoxazolyl)thiophene-2-sulfonyl]-4-methanesulfonyl-N-(2-tetrahydropyranyloxy)-2-piperazinecarboxamide (348 mg) was obtained in substantially the same manner as in Example 4.

Mass (ESI): 519 (M-1)

¹H-NMR (300 MHz, CDCl₃, δ): 1.51–1.69(4H, m), 1.70–1.90(2H, m), 2.78–2.95(5H, m) 3.35–3.52(1H, m), 3.58–3.79(2H, m), 3.86–4.01(2H, m), 4.19–4.29(1H, m), 4.58–4.72(1H, m), 4.93–5.00(1H, m) 6.57(1H, s), 7.50(1H, d, J=3 Hz), 7.60–7.70(1H, m), 8.33(1H, s), 9.05–9.18(1H,m)

Preparation 55

2-(4-Trifluoromethylphenyl)thiophene (1.57 g) was obtained in substantially the same manner as in Preparation 43.

$^1$H-NMR (300 MHz, CDCl$_3$, δ): 7.10–7.14(1H, m), 7.34 (1H, d, J=4 Hz), 7.40(1H, d, J=4 Hz), 7.62(2H, d, J=8 Hz), 7.71(2H, d, J=8 Hz)

Preparation 56

To a mixture of 2-(4-trifluoromethylphenyl)thiophene (1.56 g) and acetic anhydride (1.05 g) in AcOEt (7.8 ml) was added a solution of sulfonic acid (637 mg) in AcOEt (1.5 ml) with ice-cooling. After being allowed to ambient temperature, the mixture was stirred for 2 hours and poured into cold water. The resulting mixture was adjusted to have a pH of 7 with 3N aqueous sodium hydroxide, then a pH of 2 with concentrated hydrochloric acid. The separated solid was recoverd and washed with 4N aqueous hydrochloric acid. The obtained solid was dried in vacuo to give 1.55 g of sodium 5-(4-trifluoromethylphenyl)-thiophene sulfonate.

$^1$H-NMR (300 MHz, D$_2$O, δ): 7.40(1H, d, J=4 Hz), 7.47(1H, d, J=4 Hz), 7.72(2H, d, J=8 Hz), 7.78(2H, d, J=8 Hz)

Preparation 57

A mixture of sodium 5-(4-trifluoromethylphenyl) thiophene sulfonate (1.50 g) and DMF (498 mg) in thionyl chloride (7.5 ml) was stirred for 2 hours at 50° C. The mixture was concentrated and partitioned between AcOEt and 3% aqueous sodium bicarbonate. The organic layer was separated, washed with 3% aqueous NaHCO$_3$ solution and brine, dried over sodium sulfate and evaporated in vacuo after filtration to give 1.39 g of 5-(4-trifluoromethylphenyl) thiophene-2-sulfonylchloride as a solid.

m.p.: 73–75° C.

$^1$H-NMR (300 MHz, CDCl$_3$, δ): 7.39(1H, d, J=3 Hz), 7.74(4H, s), 7.89(1H, d, J=3 Hz)

EXAMPLE 38

(2R)-4-Methanesulfonyl-N-(2-tetrahydropyranyloxy)-1-[5-(4-trifluoromethylphenyl)thiophene-2-sulfonyl]-2-piperazinecarboxamide was obtained in substantially the same manner as in Example 4.

Mass (ESI): 596 (M–1)

$^1$H-NMR (300 MHz, CDCl$_3$, δ): 1.51–1.67(4H, m), 1.70–1.90(2H, m), 2.77–2.95(5H, m), 3.33–3.50(1H, m), 3.56–3.73(2H, m), 3.86–4.03(2H, m), 4.20–4.28(1H, m), 4.60–4.70(1H, m), 4.94–5.00(1H, m), 7.38(1H, d, J=3 Hz), 7.61–7.70(1H, m), 7.51(4H, s), 9.08–9.17(1H,m)

Preparation 58

2-[3,4-(Methylenedioxy)phenyl]thiophene (1.53 g) was obtained in substantially the same manner as in Preparation 43.

$^1$H-NMR (300 MHz, CDCl$_3$, δ): 5.98(2H, s), 6.81(1H, d, J=8 Hz), 7.03(1H, t, J=4 Hz), 7.07–7.12(2H, m), 7.18(1H, d, J=4 Hz), 7.21(1H, d, J=4 Hz)

Preparation 59

Sodium 2-[3,4-(methylenedioxy)phenyl]thiophene sulfonate (1.89 g) was obtained in substantially the same manner as in Preparation 56.

$^1$H-NMR (300 MHz, D$_2$O, δ): 5.99(2H, s), 6.88(1H, d, J=8 Hz), 7.11–7.19(3H, m), 7.40(1H, d, J=4 Hz)

Preparation 60

2-[3,4-(Methylenedioxy)phenyl]thiophene-5-sulfonylchloride (1.58 g) was obtained in substantially the same manner as in Preparation 57.

m.p.: 117–119° C.

$^1$H-NMR (300 MHz, CDCl$_3$, δ): 6.05(2H,s), 6.89(1H, d, J=8 Hz), 7.08(1H, s) 7.14(1H, d, J=8 Hz), 7.17(1H, d, J=4 Hz), 7.80(1H, d, J=4 Hz)

EXAMPLE 39

(2R)-4-Methanesulfonyl-N-(2-tetrahydropyranyloxy)-1-{5-[3,4-(methylenedioxy)phenyl]thiophene-2-sulfonyl}-2-piperazinecarboxamide (307 mg) was obtained in substantially the same manner as in Example 4.

Mass (ESI): 572 (M–1)

$^1$H-NMR (300 MHz, CDCl$_3$, δ): 1.50–1.68(4H, m), 1.71–1.90(2H, m), 2.75–2.95(5H, m), 3.31–3.49(1H, m), 3.56–3.71(2H, m), 3.85–4.03(2H, m), 4.20–4.30(1H, m), 4.56–4.67(1H, m), 4.94–5.01(1H, m), 6.03(2H, s), 6.85(1H, d, J=8 Hz), 7.05(1H,s) 7.10(1H, d, J=8 Hz), 7.15(1H, d, J=3 Hz), 7.53–7.62(1H,m), 9.11–9.27(1H, m)

Preparation 61

To a mixture of 4-iodophenol (2 g) and potassium carbonate (1.88 g) in DMF (20 ml) was added dropwise ethyl iodide (1.83 ml) at room temperature, and the mixture was stirred at 50° C. overnight. The resulting mixture was poured into water (50 ml), and extracted with diethyl ether (25 ml×3). The combined organic layer was washed with 0.5N hydrochloric acid, saturated aqueous NaHCO$_3$ solution and brine, and dried over MgSO$_4$. The solvent was evaporated to give 2.06 g of 1-ethoxy-4-iodobenzene as a slightly brown solid. The product was used for the next reaction without further purification.

$^1$H-NMR (300 MHz, CDCl$_3$, δ): 1.40(3H, t, J=7 Hz), 3.97(2H, q, J=7 Hz), 6.66(2H, d, J=8 Hz), 7.54(2H, d, J=8 Hz)

Preparation 62

2-(4-Ethoxyphenyl)thiophene (1.33 g) was obtained in substantially the same manner as in Preparation 43.

$^1$H-NMR (300 MHz, CDCl$_3$, δ): 1.40(3H, t, J=7 Hz), 4.05(2H, q, J=7 Hz), 6.90(2H, d, J=8 Hz), 7.02–7.04 (1H, m), 7.16–7.21 (2H, m), 7.51(2H, d, J=8 Hz)

Preparation 63

5-(4-Ethoxyphenyl)-2-thiophenesulfonyl chloride (766 mg) was obtained in substantially the same manner as in Preparation 44.

$^1$H-NMR (300 MHz, CDCl$_3$, δ): 1.42(3H, t, J=7 Hz), 4.09(2H, q, J=7 Hz), 6.94(2H, d, J=8 Hz), 7.19(1H, d, J=4 Hz), 7.55(2H, d, J=8 Hz), 7.80(1H, d, J=4 Hz)

EXAMPLE 40

(2R)-1-[5-(4-Ethoxyphenyl)thiophene-2-sulfonyl]-4-methanesulfonyl-N-(2-tetrahydropyranyloxy)-2-piperazinecarboxamide (273 mg) was obtained in substantially the same manner as in Example 4.

$^1$H-NMR (300 MHz, CDCl$_3$, δ): 1.45(3H, t, J=7 Hz), 1.52–1.89(6H, m), 2.73–2.96(2H, m), 2.88(1.5H, s), 2.94 (1.5H, s), 3.35–3.49(1H, m), 3.59–3.72(2H, m), 3.87–4.05 (2H, m), 4.09(2H, q, J=7 Hz), 4.27(1H, d, J=13 Hz), 4.59–4.68(1H, br), 5.02(1H, bs), 6.95(2H, d, J=8 Hz), 7.16 (1H, d, J=4 Hz), 7.51(2H, d, J=8 Hz), 7.60(1H, d, J=4 Hz), 9.15–9.26(1H, m)

Preparation 64

4-(2-Thienyl)benzonitrile (1.58 g) was obtained in substantially the same manner as in Preparation 43.

$^1$H-NMR (300 MHz, CDCl$_3$, δ): 7.13(1H, t, J=3 Hz), 7.40–7.48(2H, m), 7.51–7.82(4H, m)

Preparation 65

2-(4-Cyanophenyl)thiophene-5-sulfonylchloride (2.01 g) was obtained in substantially the same manner as in Preparation 44.

¹H-NMR (300 MHz, CDCl₃, δ): 7.42(1H, d, J=3 Hz), 7.74(2H, d, J=8 Hz), 7.79(2H, d, J=8 Hz) 7.90(1H, d, J=3 Hz)

EXAMPLE 41

(2R)-1-[5-(4-Cyanophenyl)thiophene-2-sulfonyl]-4-methanesulfonyl-N-(2-tetrahydropyranyloxy)-2-piperazinecarboxamide (296 mg) was obtained in substantially the same manner as in Example 4.

Mass (ESI): 553 (M−1)

¹H-NMR (300 MHz, CDCl₃, δ): 1.53–1.66(4H, m), 1.72–1.87(2H, m), 2.78–2.95(5H, m), 3.34–3.50(1H, m), 3.58–3.75(2H, m), 3.88–4.02(2H, m), 4.18–4.25(1H, m), 4.60–4.70(1H, m), 4.93–5.00(1H, m), 7.40(1H, d, J=3 Hz), 7.62–7.78(5H, m), 9.08–9.19(1H, m)

Preparation 66

2-(4-Cyanomethylphenyl)thiophene (1.32 g) was obtained in substantially the same manner as in Preparation 43.

¹H-NMR (300 MHz, CDCl₃, δ): 3.78(2H, s), 7.10(1H, t, J=3 Hz), 7.30–7.38(4H, m), 7.52(2H, d, J=8 Hz)

Preparation 67

2-(4-Cyanomethylphenyl)thiophene-5-sulfonylchloride (2.21 g) was obtained in substantially the same manner as in Preparation 44.

¹H-NMR (300 MHz, CDCl₃, δ): 3.82(2H, s), 7.32(1H, d, J=3 Hz), 7.46(2H, d, J=8 Hz), 7.68(2H, d, J=8 Hz), 7.86(1H, d, J=3 Hz)

EXAMPLE 42

(2R)-1-[5-(4-Cyanomethylphenyl)thiophene-2-sulfonyl]-4-methanesulfonyl-N-(2-tetrahydropyranyloxy)-2-piperazinecarboxamide (293 mg) was obtained in substantially the same manner as in Example 4.

Mass (ESI): 567 (M−1)

¹H-NMR (300 MHz, CDCl₃, δ): 1.52–1.69(4H, m), 1.71–1.90(2H, m), 2.77–2.98(5H, m), 3.33–3.50(1H, m), 3.58–3.73(2H, m), 3.82(2H, s), 3.88–4.06(2H, m), 4.20–4.29(1H, m), 4.60–4.70(1H, m) 4.94–5.01(1H, m), 7.31(1H, d, J=3 Hz), 7.42(2H, d, J=8 Hz), 7.60–7.69(3H, m), 9.08–9.19(1H, m)

Preparation 68

4-(2-Thienyl)phenol (10.2 g) was obtained in substantially the same manner as in Preparation 43.

Mass (ESI): 175 (M−1)

¹H-NMR (300 MHz, DMSO-d₆, δ): 6.80(2H, d, J=8 Hz), 7.07(1H, t, J=3 Hz), 7.30(1H, d, J=3 Hz) 7.40(1H, d, J=3 Hz), 7.46(2H, d, J=8 Hz), 9.63(1H, brs)

Preparation 69

To a mixture of 4-(2-thienyl)phenol (1.00 g) and acetic anhydride (869 mg) in tetrahydrofuran (10 ml) was added pyridine (494 mg) with ice-cooling. The mixture was stirred for 1 hour at said temperature and 1 hour at ambient temperature. After concentration, the mixture was partitioned between AcOEt and H₂O. The separated organic layer was washed with 1% aqueous citric acid, 3% aqueous NaHCO₃ solution and brine, dried over sodium sulfate and concentrated. The residue was triturated with hexane to give 985 mg of 2-(4-acetoxyphenyl)thiophene as a powder.

¹H-NMR (300 MHz, CDCl₃, δ): 2.32(3H, s), 7.05–7.16 (3H, m), 7.24–7.30(2H, m), 7.61(2H, d, J=8 Hz)

Preparation 70

2-(4-Acetoxyphenyl)thiophene-5-sulfonylchloride (1.14 g) was obtained in substantially the same manner as in Preparation 44.

¹H-NMR (300 MHz, CDCl₃, δ): 2.33(3H, s), 7.21(2H, d, J=8 Hz), 7.29(1H, d, J=3 Hz), 7.63(2H, d, J=8 Hz), 7.84(1H, d, J=3 Hz)

EXAMPLE 43

(2R)-1-[5-(4-Acetoxyphenyl)thiophene-2-sulfonyl]-4-methanesulfonyl-N-(2-tetrahydropyranyloxy)-2-piperazinecarboxamide (262 mg) was obtained in substantially the same manner as in Example 4.

Mass (ESI): 586 (M−1)

¹H-NMR (300 MHz, CDCl₃, δ): 1.53–1.69(4H, m), 1.72–1.90(2H, m), 2.35(3H, s), 2.77–2.97(5H, m), 3.36–3.50(1H, m), 3.58–3.72(2H, m), 3.87–4.04(2H, m), 4.20–4.29(1H, m), 4.59–4.69(1H, m), 4.94–5.01(1H, m), 7.20(2H, d, J=8 Hz), 7.24–7.30(1H, m), 7.59–7.67(3H, m), 9.08–9.19(1H, m)

Preparation 71

2-(4-Hydroxymethylphenyl)thiophene (2.23 g) was obtained in substantially the same manner as in Preparation 43.

¹H-NMR (300 MHz, CDCl₃, δ): 1.70(1H, t, J=8 Hz), 4.71(2H, s), 7.06–7.10(1H, m), 7.18(1H, d, J=3 Hz), 7.31 (1H, d, J=3 Hz), 7.38(2H, d, J=8 Hz), 7.61(2H, d, J=8 Hz)

Preparation 72

2-(4-Acetoxymethylphenyl)thiophene (2.55 g) was obtained in substantially the same manner as in Preparation 69.

¹H-NMR (300 MHz, CDCl₃, δ): 2.12(3H, s), 5.12(2H, s), 7.09(1H, t, J=3 Hz), 7.30(1H, d, J=3 Hz), 7.33(1H, d, J=3 Hz), 7.48(2H, d, J=8 Hz), 7.61(2H, d, J=8 Hz)

Preparation 73

2-(4-Acetoxymethylphenyl)thiophene-5-sulfonylchloride (3.00 g) was obtained in substantially the same manner as in Preparation 44.

¹H-NMR (300 MHz, CDCl₃, δ): 2.14(3H, s), 5.16(2H, s), 7.32(1H, d, J=3 Hz), 7.47(2H, d, J=8 Hz), 7.63(2H, d, J=8 Hz), 7.87(1H, d, J=3 Hz)

EXAMPLE 44

(2R)-1-[5-(4-Acetoxymethylphenyl)thiophene-2-sulfonyl]-4-methanesulfonyl-N-(2-tetrahydropyranyloxy)-2-piperazinecarboxamide was obtained in substantially the same manner as in Example 4.

Mass (ESI): 600 (M−1)

¹H-NMR (300 MHz, CDCl₃, δ): 1.52–1.89(6H, m), 2.13 (3H, s), 2.76–2.96(5H, m), 3.34–3.50(1H, m), 3.57–3.72 (2H, m), 3.87–4.04(2H, m), 4.20–4.28(1H, m), 4.59–4.68 (1H, m), 4.94–5.00(1H, m), 5.13(2H, s), 7.30(1H, d, J=3 Hz), 7.42(2H, d, J=8 Hz), 7.58–7.65(3H, m), 9.08–9.19(1H, m)

Preparation 74

2-(3-Fluoro-4-methoxyphenyl)thiophene (435 mg) was obtained in substantially the same manner as in Preparation 43.

¹H-NMR (300 MHz, CDCl₃, δ): 3.94(3H, s), 6.93–7.07 (2H, m), 7.17–7.36(4H, m)

Preparation 75

5-(3-Fluoro-4-methoxyphenyl)-2-thiophenesulfonyl chloride (318 mg) was obtained in substantially the same manner as in Preparation 44.

¹H-NMR (300 MHz, CDCl₃, δ): 3.97(3H, s), 7.05(2H, t, J=7 Hz), 7.21(1H, d, J=4 Hz), 7.36(1H, d, J=4 Hz), 7.39(1H, s), 7.83(2H, d, J=7 Hz)

EXAMPLE 45

(2R)-1-[5-(3-Fluoro-4-methoxyphenyl)thiophene-2-sulfonyl]-4-methanesulfonyl-N-(2-tetrahydropyranyloxy)-2-piperazinecarboxamide (396 mg) was obtained in substantially the same manner as in Example 4.

Mass (ESI−): 576 (M−H)

¹H-NMR (300 MHz, CDCl₃, δ): 1.57–1.93(6H, m), 2.79–2.91(2H, m), 2.88(1.5H, s), 2.94(1.5H, s), 3,34–3.48 (1H, m), 3.57–3.69(2H, m), 3.84–4.03(2H, m), 3.93(3H, s), 4.22(1H, d, J=13 Hz), 4.55–4.63(1H, br), 4.94–5.00(1H, m), 6.99(1H, dd, J=9, 9 Hz), 7.18(1H, d, J=4 Hz), 7.30(1H, s), 7.33(1H, d, J=4 Hz), 7.55–7.61(1H, m), 9.12–9.20(1H, br)

Preparation 76

2-(3-Methoxyphenyl)thiophene (1.60 g) was obtained in substantially the same manner as in Preparation 43.

$^1$H-NMR (300 MHz, CDCl$_3$, δ): 3.85(3H, s), 6.83(1H, dd, J=3, 8 Hz), 7.08(1H, t, J=3 Hz), 7.15(1H, d, J=3 Hz), 7.21(1H, d, J=8 Hz), 7.23–7.32(3H, m)

Preparation 77

Sodium 5-(3-methoxyphenyl)thiophene-2-sulfate (1.85 g) was obtained in substantially the same manner as in Preparation 56.

Mass (ESI): 269 (M−1)

$^1$H-NMR (300 MHz, D$_2$O, δ): 3.87(3H, s), 6.99(1H, s), 7.20(1H, s), 7.29(1H, d, J=8 Hz), 7.33(1H, t, J=3 Hz), 7.39(1H, t, J=8 Hz), 7.46(1H, d, J=3 Hz)

Preparation 78

2-(3-Methoxyphenyl)thiophene-5-sulfonylchloride (1.75 g) was obtained in substantially the same manner as in Preparation 57.

$^1$H-NMR (300 MHz, CDCl$_3$, δ): 3.88(3H, s), 6.99(1H, dd, J=3, 8 Hz), 7.13(1H, d, J=3 Hz), 7.21(1H, d, J=8 Hz), 7.30(1H, d, J=3 Hz), 7.39(1H, t, J=8 Hz), 7.83(1H, d, J=3 Hz)

EXAMPLE 46

(2R)-4-Methanesulfonyl-1-[5-(3-methoxyphenyl)thiophene-2-sulfonyl]-N-(2-tetrahydropyranyloxy)-2-piperazinecarboxamide (349 mg) was obtained in substantially the same manner as in Example 4.

Mass (ESI): 558 (M−1)

$^1$H-NMR (300 MHz, CDCl$_3$, δ): 1.51–1.65(4H, m), 1.71–1.87(2H, m), 2.75–2.95(5H, m), 3.33–3.48(1H, m), 3.56–3.71(2H, m), 3.87(3H, s), 3.89–4.02(2H, m), 4.20–4.28(1H, m), 4.59–4.67(1H, m), 4.93–5.00(1H, m), 6.96(1H, d, J=8 Hz), 7.11(1H, d, J=3 Hz), 7.19(1H, d, J=8 Hz), 7.29(1H, d, J=3 Hz), 7.35(1H, t, J=8 Hz), 7.59–7.65(1H, m), 9.08–9.19(1H, m)

Preparation 79

N,N-Dimethyl-4-(2-thienyl)benzenesulfonamide (1.26 g) was obtained in substantially the same manner as in Preparation 43.

$^1$H-NMR (300 MHz, CDCl$_3$, δ): 2.73(6H, s), 7.14(1H, t, J=3 Hz), 7.40(1H, d, J=3 Hz), 7.43(1H, d, J=3 Hz), 7.78(4H, s)

Preparation 80

2-(4-Dimethylaminosulfonylphenyl)thiophene-5-sulfonylchloride (1.47 g) was obtained in substantially the same manner as in Preparation 44.

$^1$H-NMR (300 MHz, CDCl$_3$, δ): 2.78(6H, s), 7.42(1H, d, J=3 Hz), 7.79(2H, d, J=8 Hz), 7.86–7.91(2H, m)

EXAMPLE 47

(2R)-1-[5-(4-Dimethylaminosulfonylphenyl)thiophene-2-sulfonyl]-4-methanesulfonyl-N-(2-tetrahydropyranyloxy)-2-piperazinecarboxamide (426 mg) was obtained in substantially the same manner as in Example 4.

Mass (ESI): 635 (M−1)

$^1$H-NMR (300 MHz, DMSO-d$_6$, δ): 1.31–1.67(6H, m), 2.64(6H, s), 2.77–2.91(4H, m), 3.02–3.17(1H, m), 3.23–3.37(1H, m), 3.50–3.64(2H, m), 3.72–3.90(3H, m), 4.45–4.55(1H, m), 4.63–4.72(1H, m), 7.68(1H, d, J=3 Hz), 7.70(1H, d, J=3 Hz), 7.83(2H, d, J=8 Hz), 8.03(2H, d, J=8 Hz)

Preparation 81

To a mixture of 4-(2-thienyl)phenol (1.76 g) and triethylamine (1.50 g) in MeCN (10 ml) was added dropwise methanesulfonylchloride (1.26 g) with ice-cooling. The mixture was stirred for 1 hour, then for 1 hour at ambient temperature. The resulting mixture was concentrated and diluted with a mixture of AcOEt and H$_2$O to separate solid. The separated solid was recovered and washed with H$_2$O and AcOEt to give 1.62 g of 2-(4-methanesulfonyloxyphenyl)thiophene.

$^1$H-NMR (300 MHz, CDCl$_3$, δ): 3.17(3H, s), 7.08–7.14 (1H, m), 7.28–7.38(4H, m), 7.65(2H, d, J=8 Hz)

Preparation 82

2-(4-Methanesulfonyloxyphenyl)thiophene-5-sulfonylchloride (2.02 g) was obtained in substantially the same manner as in Preparation 44.

$^1$H-NMR (300 MHz, CDCl$_3$, δ): 3.22(3H, s), 7.31(1H, t, J=3 Hz), 7.40(2H, d, J=8 Hz), 7.70(2H, d, J=8 Hz), 7.87(1H, d, J=8 Hz)

EXAMPLE 48

(2R)-1-[5-(4-Methanesulfonyloxyphenyl)thiophene-2-sulfonyl]-4-methanesulfonyl-N-(2-tetrahydropyranyloxy)-2-piperazinecarboxamide (392 mg) was obtained in substantially the same manner as in Example 4.

Mass (ESI): 622 (M−1)

$^1$H-NMR (300 MHz, CDCl$_3$, δ): 1.53–1.70(4H, m), 1.72–1.91(2H, m), 2.76–2.98(5H, m), 3.20(3H, s), 3.33–3.50(1H, m), 3.58–3.74(2H, m), 3.85–4.05(2H, m), 4.19–4.29(1H, m), 4.58–4.70(1H, m), 4.94–5.02(1H, m), 7.26–7.34(1H, m), 7.40(2H, d, J=8 Hz), 7.61–7.72(3H, m), 9.08–9.21(1H, m)

Preparation 83

2-(2,4-Difluorophenyl)thiophene (863 mg) was obtained in substantially the same manner as in Preparation 43.

$^1$H-NMR (300 MHz, CDCl$_3$, δ): 6.85–6.96(2H, m), 7.11 (1H, t, J=3 Hz), 7.35(1H, d, J=3 Hz) 7.41(1H, d, J=3 Hz), 7.54–7.64(1H, m)

Preparation 84

2-(2,4-Difluorophenyl)thiophene-5-sulfonylchloride (819 mg) was obtained in substantially the same manner as in Preparation 44.

$^1$H-NMR (300 MHz, CDCl$_3$, δ): 6.97–7.06(2H, m), 7.42 (1H, d, J=3 Hz), 7.60–7.70(2H, m), 7.88(1H, d, J=3 Hz)

EXAMPLE 49

(2R)-1-[5-(2,4-Difluorophenyl)thiophene-2-sulfonyl]-4-methanesulfonyl-N-(2-tetrahydropyranyloxy)-2-piperazinecarboxamide (309 mg) was obtained in substantially the same manner as in Example 4.

Mass (ESI): 564 (M−1)

$^1$H-NMR (300 MHz, CDCl$_3$, δ): 1.51–1.90(6H, m), 2.74–2.95(5H, m), 3.34–3.51(1H, m), 3.54–3.71(2H, m), 3.87–4.03(2H, m), 4.19–4.29(1H, m), 4.58–4.69(1H, m), 4.94–5.01(1H, m), 6.93–7.04(2H, m) 7.40(1H, d, J=3 Hz), 7.56–7.67(2H, m), 9.08–9.19(1H, m)

Preparation 85

A mixture of 4-(2-thienyl)phenol (1.30 g), chloroacetonitrile (668 mg) and potassium carbonate (1.53 g) in DMF (7 ml) was stirred for 5 hours at ambient temperature. The mixture was diluted with H$_2$O and the separated solid was recovered to give 1.45 g of 2-(4-cyanomethoxyphenyl)thiophene.

$^1$H-NMR (300 MHz, CDCl$_3$, δ): 4.80(2H, s), 7.00(2H, d, J=8 Hz), 7.08(1H, t, J=3 Hz), 7.22–7.30(2H, m), 7.60(2H, d, J=8 Hz)

Preparation 86

2-(4-Cyanomethoxyphenyl)thiophene-5-sulfonylchloride (1.92 g) was obtained in substantially the same manner as in Preparation 44.

$^1$H-NMR (300 MHz, CDCl$_3$, δ): 4.84(2H, s), 7.08(2H, d, J=8 Hz), 7.24(1H, d, J=3 Hz), 7.62(2H, d, J=8 Hz), 7.84(1H, d, J=3 Hz)

EXAMPLE 50

(2R)-1-[5-(4-Cyanomethoxyphenyl)thiophene-2-sulfonyl]-4-methanesulfonyl-N-(2-tetrahydropyranyloxy)-2-piperazinecarboxamide (266 mg) was obtained in substantially the same manner as in Example 4.

Mass (ESI): 583 (M–1)

$^1$H-NMR (300 MHz, CDCl$_3$, δ): 1.51–1.70(4H, m), 1.72–1.90(2H, m), 2.77–3.00(5H, m), 3.32–3.50(1H, m), 3.58–3.73(2H, m), 3.86–4.05(2H, m), 4.20–4.30(1H, m), 4.58–4.69(1H, m), 4.83(2H, s), 4.94–5.03(1H, m), 7.06(2H, d, J=8 Hz), 7.21(1H, d, J=3 Hz), 7.54–7.64(3H, m), 9.08–9.19(1H, m)

Preparation 87

Methyl 4-(2-thienyl)benzoate (2.07 g) was obtained in substantially the same manner as in Preparation 43.

$^1$H-NMR (300 MHz, CDCl$_3$, δ): 3.93(3H, s), 7.11(1H, t, J=3 Hz), 7.37(1H, d, J=3 Hz), 7.42(1H, d, J=3 Hz), 7.68(2H, d, J=8 Hz), 8.04(2H, d, J=8 Hz)

Preparation 88

2-(4-Methoxycarbonylphenyl)thiophene-5-sulfonylchloride (1.40 g) was obtained in substantially the same manner as in Preparation 44.

$^1$H-NMR (300 MHz, CDCl$_3$, δ): 3.96(3H, s), 7.41(1H, d, J=3 Hz), 7.71(2H, d, J=8 Hz), 7.89(1H, d, J=3 Hz), 8.14(2H, d, J=8 Hz)

EXAMPLE 51

(2R)-4-Methanesulfonyl-1-[5-(4-methoxycarbonylphenyl)thiophene-2-sulfonyl]-N-(2-tetrahydropyranyloxy)-2-piperazinecarboxamide (292 mg) was obtained in substantially the same manner as in Example 4.

Mass (ESI): 586 (M–1)

$^1$H-NMR (300 MHz, CDCl$_3$, δ): 1.52–1.69(4H, m), 1.70–1.90(2H, m), 2.78–2.96(5H, m), 3.33–3.50(1H, m), 3.58–3.75(2H, m), 3.84–4.02(5H, m), 4.19–4.29(1H, m), 4.60–4.70(1H, m), 4.94–5.01(1H, m), 7.41(1H, d, J=3 Hz), 7.40(1H, d, J=3 Hz), 7.61–7.70(3H, m), 8.11(2H, d, J=8 Hz), 9.08–9.19(1H, m)

Preparation 89

4-Biphenylylthiophene (1.27 g) was obtained in substantially the same manner as in Preparation 43.

$^1$H-NMR (300 MHz, CDCl$_3$, δ): 7.10(2H, d, J=8 Hz), 7.28–7.50(5H, m), 7.59–7.70(5H, m)

Preparation 90

Sodium 5-(4-biphenylyl)-2-thiophenesulfonate (922 mg) was obtained in substantially the same manner as in Preparation 56.

$^1$H-NMR (300 MHz, DMSO-d$_6$, δ): 7.11(1H, d, J=4 Hz), 7.37(1H, d, J=4 Hz), 7.39(1H, d, J=8 Hz), 7.42–7.50(2H, m), 7.67–7.74(6H, m)

Preparation 91

5-(4-Biphenylyl)-2-thiophenesulfonyl chloride (824 mg) was obtained in substantially the same manner as in Preparation 57.

$^1$H-NMR (300 MHz, DMSO-d$_6$, δ): 7.34(1H, d, J=7 Hz), 7.39–7.51(3H, m), 7.56–7.65(2H, m) 7.69(4H, s), 7.83(1H, d, J=7 Hz)

EXAMPLE 52

(2R)-1-[5-(4-Biphenylyl)thiophene-2-sulfonyl]-4-methanesulfonyl-N-(2-tetrahydropyranyloxy)-2-piperazinecarboxamide (339 mg) was obtained in substantially the same manner as in Example 4.

Mass (ESI–): 604 (M–H)

$^1$H-NMR (300 MHz, DMSO-d$_6$, δ): 1.38–1.70(6H, m), 2.77–2.91(1H, m), 2.88(3H, s), 3.02–3.19(1H, m), 3.45–3.64(2H, m), 3.72–3.95(2H, m), 4.43–4.53(1H, m), 4.72(1H, bs), 7.40(1H, d, J=8 Hz) 7.45–7.52(2H, m), 7.61–7.86(8H, m)

Preparation 92

2-(4-Pyridyl)thiophene (2.53 g) was obtained in substantially the same manner as in Preparation 43.

$^1$H-NMR (300 MHz, CDCl$_3$, δ): 7.13(1H, d, J=5 Hz), 7.42(1H, d, J=4 Hz), 7.45–7.53(3H, m), 8.59(2H, d, J=5 Hz)

Preparation 93

Chlorosulfonic acid (1.4 ml) was added to 2-(4-pyridyl)thiophene (500 mg) at 0° C. and the mixture was stirred for 5 days at room temperature. Ice-water was carefully added to this mixture at 0° C. to decompose excess reagent. This solution was poured into saturated aqueous NaHCO$_3$ solution (ca. pH 7) and extracted with AcOEt (20 ml×3). The combined organic layer was washed with brine, and dried over MgSO$_4$. After 4N HCl-AcOEt (10 ml) was added to the solution, the solvent was removed in vacuo to give 300 mg of 5-(4-pyridyl)-thiophenesulfonyl chloride as a white solid (yield 32.7%).

$^1$H-NMR (300 MHz, DMSO-d$_6$, δ): 7.30(1H, d, J=4 Hz), 8.05(1H, d, J=4 Hz), 8.27(2H, d, J=8 Hz), 8.81(2H, d, J=8 Hz)

EXAMPLE 53

(2R)-1-[5-(4-Pyridyl)thiophene-2-sulfonyl]-4-methanesulfonyl-N-(2-tetrahydropyranyloxy)-2-piperazinecarboxamide (335 mg) was obtained in substantially the same manner as in Example 4.

Mass (ESI–): 529 (M–H)

$^1$H-NMR (300 MHz, CDCl$_3$, δ): 1.55–1.91(6H, m), 2.79–2.92(2H, m), 2.91(1.5H, s), 2.94(1.5H, s), 3.40–3.56 (1H, m), 3.58–3.77(2H, m), 3.86–4.03(2H, m), 4.21(1H, d, J=13 Hz), 4.53–4.59(1H, br), 4.92–5.00(1H, m), 7.49(2H, d, J=8 Hz), 7.49(1H, d, J=4 Hz), 7.62–7.70(1H, br), 7.69(2H, d, J=8 Hz), 9.18–9.28(1H, br)

Preparation 94

To an ice-cooled dioxane (30 ml) was slowly added liquid bromine (2.66 g) and this mixture was stirred for 30 minutes at said temperature. To the mixture was added dropwise 2,3-dihydrobenzofuran (2 g), and the resulting mixture was stirred for 3 hours at room temperature. The solvent was removed under reduced pressure. The residue was dissolved in AcOEt (50 ml) and the solution was washed with saturated aqueous NaHCO$_3$ solution and brine, and dried over MgSO$_4$. The solvent was evaporated to give an orange oil as a crude product. The crude product was purified on an SiO$_2$ column (hexane-AcOEt 20:1) to give 2.33 g of 5-bromo-2,3 dihydrobenzofuran as white crystals (yield 70.3%).

$^1$H-NMR (300 MHz, CDCl$_3$, δ): 3.11(2H, t, J=11 Hz), 4.57(2H, t, J=11 Hz), 6.66(1H, d, J=8 Hz), 7.20(1H, d, J=8 Hz), 7.30(1H, s)

Preparation 95

2-(2,3-Dihydrobenzofuran-5-yl)thiophene (916 mg) was obtained in substantially the same manner as in Preparation 43.

$^1$H-NMR (300 MHz, CDCl$_3$, δ): 3.22(2H, t, J=11 Hz), 4.60(2H, t, J=11 Hz), 6.78(1H, d, J=8 Hz), 7.03(1H, dd, J=6,

12 Hz), 7.15(1H, d, J=4 Hz), 7.18(1H, d, J=6 Hz), 7.37(1H, d, J=8 Hz), 7.43(1H, s)

Preparation 96

Sodium 5-(2,3-dihydrobenzofuran-5-yl)-2-thiophenesulfonate (1.14 g) was obtained in substantially the same manner as in Preparation 56.

$^1$H-NMR (300 MHz, CDCl$_3$, δ): 3.20(2H, t, J=9 Hz), 4.57(2H, t, J=9 Hz), 6.77(1H, d, J=8 Hz), 7.02(1H, d, J=4 Hz), 7.09(1H, d, J=4 Hz), 7.31(1H, d, J=8 Hz), 7.48(1H, s)

Preparation 97

5-(2,3-Dihydrobenzofuran-5-yl)-2-thiophenesulfonyl chloride (770 mg) was obtained in substantially the same manner as in Preparation 57.

$^1$H-NMR (300 MHz, CDCl$_3$, δ): 3.30(2H, t, J=7 Hz), 4.66(2H, t, J=7 Hz), 6.83(1H, d, J=8 Hz), 7.17(1H, d, J=4 Hz), 7.41(1H, d, J=8 Hz), 7.45(1H, s), 7.79(1H, d, J=4 Hz)

EXAMPLE 54

(2R)-1-[5-(2,3-Dihydrobenzofuran-5-yl)thiophene-2-sulfonyl]-4-methanesulfonyl-N-(2-tetrahydropyranyloxy)-2-piperazinecarboxamide (321 mg) was obtained in substantially the same manner as in Example 4.

Mass (ESI-): 570 (M-H)

$^1$H-NMR (300 MHz, CDCl$_3$, δ): 1.54–1.92(6H, m), 2.76–2.87(2H, m), 2.91(1.5H, s), 2.95(1.5H, s), 3.27(2H, t, J=10 Hz), 3.31–3.47(1H, m), 3.58–3.71(2H, m), 3.86–4.04 (1H, m), 4.20–4.30(1H, m), 4.65(2H, t, J=10 Hz), 4.91–5.00 (1H, m), 6.82(1H, d, J=8 Hz), 7.15(1H, d, J=4 Hz), 7.25(1H, d, J=4 Hz), 7.38(1H, d, J=8 Hz), 7.42(1H, s), 7.52–7.59(1H, m), 9.10–9.25(1H, m)

Preparation 98

2-(4-Phenoxyphenyl)thiophene (2.14 g) was obtained in substantially the same manner as in Preparation 43.

$^1$H-NMR (300 MHz, CDCl$_3$, δ): 6.99–7.09(5H, m), 7.12 (1H, dd, J=8, 8 Hz), 7.25(2H, d, J=5 Hz), 7.37(2H, dd, J=8 Hz), 7.58(2H, d, J=8 Hz)

Preparation 99

Sodium 5-(4-phenoxyphenyl)-2-thiophenesulfonate (717 mg) was obtained in substantially the same manner as in Preparation 56.

$^1$H-NMR (300 MHz, DMSO-d$_6$, δ): 7.01–7.10(4H, m), 7.18(1H, dd, J=8, 8 Hz), 7.22(2H, d, J=4 Hz), 7.42(2H, dd, J=8 Hz), 7.65(2H, d, J=8 Hz)

Preparation 100

5-(4-Phenoxyphenyl)-2-thiophenesulfonyl chloride (677 mg) was obtained in substantially the same manner as in Preparation 57.

$^1$H-NMR (300 MHz, CDCl$_3$, δ):
7.07(2H, d, J=8 Hz), 7.10(1H, d, J=8 Hz), 7.22(1H, dd, J=8, 8 Hz), 7.24(2H, d, J=4 Hz), 7.39(2H, dd, J=8 Hz), 7.60(2H, d, J=8 Hz), 7.85(1H, d, J=4 Hz)

EXAMPLE 55

(2R)-1-[5-(4-Phenoxyphenyl)thiophene-2-sulfonyl)-4-methanesulfonyl-N-(2-tetrahydropyranyloxy)-2-piperazinecarboxamide (311 mg) was obtained in substantially the same manner as in Example 4.

Mass (ESI-): 620 (M-H)

$^1$H-NMR (300 MHz, CDCl$_3$, δ): 1.53–1.91(6H, m), 2.75–2.89(2H, m), 2.90(1.5H, s), 2.94(1.5H, s), 3.35–3.48 (1H, m), 3.57–3.70(2H, m), 3.87–4.04(2H, m), 4.24(1H, d, J=13 Hz), 4.62(1H, bs), 4.98(1H, bs), 7.01–7.08(4H, m), 7.14–7.23(2H, m), 7.39(2H, dd, J=8, 8 Hz), 7.54(1H, d, J=8 Hz), 7.55–7.61(1H, m), 9.07(1H, bs)

Preparation 101

2-(3-Fluoro-4-hydroxyphenyl)thiophene (3.80 g) was obtained in substantially the same manner as in Preparation 43.

$^1$H-NMR (300 MHz, CDCl$_3$, δ): 2.37(3H, s), 7.05–7.17 (2H, m), 7.26–7.42(4H, m)

Preparation 102

2-(3-Fluoro-4-acetoxyphenyl)thiophene (2.39 g) was obtained in substantially the same manner as in Preparation 69.

$^1$H-NMR (300 MHz, CDCl$_3$, δ): 5.18(1H, d, J=3 Hz), 6.96–7.07(2H, m), 7.18(1H, d, J=4 Hz), 7.22–7.35(3H, m)

Preparation 103

2-(3-Fluoro-4-acetoxyphenyl)thiophene-5-sulfonyl chloride (2.91 g) was obtained in substantially the same manner as in Preparation 44.

$^1$H-NMR (300 MHz, CDCl$_3$, δ): 2.47(3H, s), 7.25–7.29 (2H, m), 7.39–7.45(2H, m), 7.85(1H, d, J=4 Hz)

EXAMPLE 56

(2R)-1-[5-(4-Acetoxy-3-fluorophenyl)thiophene-2-sulfonyl]-4-methanesulfonyl-N-(2-tetrahydropyranyloxy)-2-piperazinecarboxamide (314 mg) was obtained in substantially the same manner as in Example 4.

Mass (ESI): 604 (M-1)

$^1$H-NMR (300 MHz, CDCl$_3$, δ): 1.51–1.90(6H, m), 2.36 (3H, s), 2.76–2.96(5H, m), 3.32–3.49(1H, m), 3.57–3.73 (2H, m), 3.84–4.01(2H, m), 4.18–4.28(1H, m), 4.58–4.68 (1H, m), 4.92–5.00(1H, m), 7.19–7.28(2H, m), 7.35–7.44 (2H, m), 7.58–7.67(1H, m), 9.05–9.15(1H, m)

Preparation 104

A mixture of N-(2-thienylcarbonylamino)ethanamide (5.37 g) and phosphorus oxychloride (15 ml) was stirred for 8 hours at 90° C. After cooling to ambient temperature, the mixture was concentrated. The residue was partitioned between AcOEt and saturated aqueous NaHCO$_3$ solution. The organic layer was separated and washed with saturated aqueous NaHCO$_3$ solution and brine. The resulting solution was dried over sodium sulfate and concentrated to give 3.65 g of 2-methyl-5-(2-thienyl)-1,3,4-oxadiazole as a solid.

$^1$H-NMR (300 MHz, CDCl$_3$, δ): 2.61(3H, s), 7.17(1H, t, J=3 Hz), 7.54(1H, d, J=3 Hz), 7.74(1H, d, J=3 Hz)

Preparation 105

2-(5-Methyl-1,3,4-oxadiazol-2-yl)thiophene-5-sulfonylchloride (1.06 g) was obtained in substantially the same manner as in Preparation 44.

$^1$H-NMR (300 MHz, CDCl$_3$, δ): 2.67(3H, s), 7.73(1H, d, J=3 Hz), 7.90(1H, d, J=3 Hz)

EXAMPLE 57

(2R)-4-Methanesulfonyl-1-[5-(5-methyl-1,3,4-oxadiazol-2-yl)-thiophene-2-sulfonyl]-N-(2-tetrahydropyranyloxy)-2-piperazinecarboxamide (327 mg) was obtained in substantially the same manner as in Example 4.

Mass (ESI): 534 (M-1)

$^1$H-NMR (300MHz, CDCl$_3$, δ): 1.53–1.88(6H, m), 2.63 (3H, s), 2.79–2.98(5H, m), 3.38–3.53(1H, m), 3.60–3.80 (2H, m), 3.88–4.01(2H, m), 4.18–4.26(1H, m), 4.62–4.72 (1H, m), 4.92–4.99(1H, m), 7.62–7.71(2H, m), 9.08–9.19 (1H, m)

Preparation 106

To a mixture of acetic hydrazide (2.63 g) and NaHCO$_3$ (3.44 g) in a solution of dioxane (40 ml) and H$_2$O (4 ml) was added dropwise 2-thiophenecarbonyl chloride (4.00 g) with ice-cooling. After stirring for 2 hours at ambient temperature, the mixture was diluted with AcOEt and filtered. After concentration of the filtrate, the obtained residue was crystallized from a mixture of AcOEt and hexane to give 5.38 g of N-(2-thienylcarbonylamino)ethanamide.

Mass (ESI): 183 (M-1)

¹H-NMR (300 MHz, DMSO-d₆, δ): 1.91(3H, s), 7.18(1H, t, J=3 Hz), 7.82(2H, d, J=3 Hz), 9.88(1H, brs), 10.33(1H, brs)

Preparation 107

N-(2-Thienylcarbonylamino)benzamide (5.72 g) was obtained in substantially the same manner as in Preparation 106.

¹H-NMR (300 MHz, DMSO-d₆, δ): 3.57(2H, s), 7.22(1H, t, J=3 Hz), 7.49–7.64(3H, m), 7.86–7.95(4H, m)

Preparation 108

2-Phenyl-5-(2-thienyl)-1,3,4-oxadiazole (4.08 g) was obtained in substantially the same manner as in Preparation 104.

¹H-NMR (300 MHz, CDCl₃, δ): 7.21(1H, t, J=3 Hz), 7.50–7.60(4H, m), 7.85(1H, d, J=3 Hz), 8.12(2H, d, J=8 Hz)

Preparation 109

2-(5-Phenyl-1,3,4-oxadiazol-2-yl)thiophene-5-sulfonylchloride (3.21 g) was obtained in substantially the same manner as in Preparation 44.

¹H-NMR (300 MHz, CDCl₃, δ): 7.49–7.65(4H, m), 7.94 (2H, d, J=3 Hz), 8.10–8.20(2H, m)

EXAMPLE 58

(2R)-4-Methanesulfonyl-1-[5-(5-phenyl-1,3,4-oxadiazol-2-yl)-thiophene-2-sulfonyl]-N-(2-tetrahydropyranyloxy)-2-piperazinecarboxamide (198 mg) was obtained in substantially the same manner as in Example 4.

Mass (ESI): 596 (M−1)

¹H-NMR (300 MHz, CDCl₃, δ): 1.48–1.89(6H, m), 2.80–3.03(5H, m), 3.38–3.54(1H, m), 3.60–3.81(2H, m), 3.87–4.03(2H, m), 4.19–4.29(1H, m), 4.62–4.77(1H, m), 4.91–5.01(1H, m), 7.50–7.76(4H, m), 7.72(1H, d, J=3 Hz), 8.13(2H, d, J=8 Hz), 9.08–9.19(1H, m)

Preparation 110

A mixture of phenyl 2-bromothiophene-5-sulfate (4.06 g), hexamethylditin (5.00 g) and tetrakis(triphenylphosphine) palladium (0) (735 mg) in toluene (245 ml) was stirred for 15 minutes at ambient temperature and refluxed for 1 hour under nitrogen atmosphere. The mixture was concentrated and purified by chromatography on SiO₂ (AcOEt/hexane 1:20, then 1:10) to give 2.34 g of phenyl 5-trimethylstannylthiophene-2-sulfate as an oil.

¹H-NMR (300 MHz, CDCl₃, δ): 0.48(9H, s), 7.02(2H, d, J=8 Hz), 7.13(1H, d, J=3 Hz), 7.20–7.41(3H, m), 7.63(1H, d, J=3 Hz)

Preparation 111

A mixture of 2-bromothiazole (200 mg), phenyl 5-trimethylstannylthiophene-2-sulfate (491 mg) and tetrakis (triphenylphosphine)palladium (0) (42.3 mg) in dioxane (4 ml) was stirred for 24 hours at 90° C. The mixture was concentrated and purified by chromatography on SiO₂ (AcOEt/hexane 1:10, then 1:4). The obtained oil was crystallized from hexane to give 231 mg of phenyl 5-(2-thiazolyl)thiophene-2-sulfate.

Mass (ESI): 324 (M+1):

¹H-NMR (300 MHz, CDCl₃, δ): 7.12(2H, d, J=8 Hz), 7.27–7.38(3H, m), 7.40–7.44(2H, m), 7.51(1H, d, J=3 Hz), 7.87(1H, d, J=2 Hz)

Preparation 112

A mixture of phenyl 5-(2-thiazolyl)thiophene-2-sulfate (210 mg) and 1N aqueous sodium hydroxide (4 ml) in EtOH (6 ml) was stirred for 4 hours at 80° C. The mixture was adjusted to pH 3 with 4N aqueous hydrochloric acid and concentrated. The residue was partitioned between AcOEt and H₂O. The aqueous layer was separated and washed with AcOEt. The obtained aqueous layer was concentrated to give 290 mg of sodium 5-(2-thiazolyl)thiophene-2-sulfate as a solid.

Mass (ESI): 246 (M−1)

¹H-NMR (300 MHz, D₂O, δ): 7.48(1H, d, J=3 Hz), 7.58(1H, d, J=3 Hz), 7.69(1H, d, J=3 Hz) 7.84(1H, d, J=3 Hz)

Preparation 113

2-(2-Thiazolyl)thiophene-5-sulfonylchloride (128 mg) was obtained in substantially the same manner as in Preparation 44.

¹H-NMR (300 MHz, CDCl₃, δ): 7.49(2H, d, J=3 Hz), 7.84(1H, d, J=3 Hz), 7.92(1H, d, J=3 Hz)

EXAMPLE 59

(2R)-4-Methanesulfonyl-N-(2-tetrahydropyranyloxy)-1-[5-(2-thiazolyl)thiophene-2-sulfonyl]-2-piperazinecarboxamide (153 mg) was obtained in substantially the same manner as in Example 4.

Mass (ESI): 535 (M−1)

¹H-NMR (300 MHz, CDCl₃, δ): 1.50–1.90(6H, m), 2.74–3.00(5H, m), 3.32–3.51(1H, m), 3.58–3.76(2H, m), 3.86–4.05(2H, m), 4.19–4.30(1H, m), 4.58–4.70(1H, m), 4.93–5.01(1H, m), 7.41(1H, d, J=3 Hz), 7.57(1H, d, J=3 Hz), 7.57–7.68(1H, m), 7.85(1H, d, J=3 Hz), 9.08–9.19(1H, m)

EXAMPLE 60

(2R)-4-Methanesulfonyl-1-[5-phenyl-1,3,4-thiadiazol-2-sulfonyl]-N-(2-tetrahydropyranyloxy)-2-piperazinecarboxamide (117 mg) was obtained in substantially the same manner as in Example 4.

Mass (ESI): 530 (M−1)

¹H-NMR (300 MHz, CDCl₃, δ): 1.60–2.00(6H, m), 2.96–3.02(3H, m), 3.05–3.17(2H, m), 3.44–3.58(1H, m), 3.66–3.81(1H, m), 3.81–3.90(1H, m), 3.92–4.02(1H, m), 4.11–4.27(1H, m), 4.50–4.60(1H, m), 4.90–4.99(1H, m), 5.06–5.12(1H, m), 7.51–7.65(3H, m), 7.97(2H, d, J=8 Hz)

Preparation 114

To a mixture of 2-bromothiophene-5-sulfonylchloride (5.00 g) and phenol (1.89 g) in MeCN (30 ml) was added dropwise triethylamine (2.51 g) with ice-cooling. The mixture was stirred for 1 hour at said temperature and 1 hour at ambient temperature. The resulting mixture was concentrated and partitioned between AcOEt and H₂O. The organic layer was separated and washed with 1% aqueous citric acid and brine. The resulting solution was dried over sodium sulfate and concentrated to give 6.34 g of phenyl 2-bromothiophene-5-sulfate (6.34 g) as a solid.

¹H-NMR (300 MHz, CDCl₃, δ): 7.05–7.10(3H, m), 7.28–7.40(4H, m)

Preparation 115

Phenyl 4-iodebenzenesulfate (1.6 g) was obtained as crystals in substantially the same manner as in Preparation 114.

m.p.: 124–127° C.

¹H-NMR (300 MHz, CDCl₃, δ): 7.03(2H, d, J=6 Hz), 7.30–7.45(3H, m), 7.59(1H, d, J=8 Hz), 8.05(2H, d, J=8 Hz)

Preparation 116

Phenyl 4-(thiophene-2-yl)benzenesulfate (1.30 g) was obtained as yellow crystals in substantially the same manner as in Preparation 43.

m.p.: 122–124° C.

¹H-NMR (300 MHz, CDCl₃, δ): 7.01(2H, d, J=6 Hz), 7.15(1H, t, J=2 Hz), 7.20–7.35(3H, m), 7.43(1H, d, J=2 Hz), 7.46(1H, d, J=2 Hz), 7.73(2H, d, J=8 Hz), 7.81(2H, d, J=8 Hz)

Preparation 117

4-(Thiophene-2-yl)benzenesulfonic acid sodium salt (0.33 g) was obtained in substantially the same manner as in Preparation 112.

Mass (ESI−): 239(M−Na)
¹H-NMR (300 MHz, D₂O, δ): 7.18(1H, dd, J=1, 2 Hz), 7.51(1H, d, J=2 Hz), 7.55(1H, d, J=1 Hz), 7.82(4H, s)
Preparation 118
4-(Thiophene-2-yl)benzenesulfonyl chloride (320 mg) was obtained as crystals in substantially the same manner as in Preparation 56.
m.p.: 103–104° C.
¹H-NMR (300 MHz, CDCl₃, δ): 7.17(1H, t, J=2 Hz), 7.46(1H, d, J=2 Hz), 7.50(1H, d, J=2 Hz), 7.81(1H, d, J=8 Hz), 8.03(1H, d, J=8 Hz)

EXAMPLE 61

(2R)-4-Methanesulfonyl-1-[4-(thiophen-2-yl)benzenesulfonyl]-N-(2-tetrahydropyranyloxy)-2-piperazinecarboxamide (169 mg) was obtained as crystals in substantially the same manner as in Example 4.
m.p.: 194–195° C.
Mass (ESI−): 528 (M−H)
¹H-NMR (300 MHz, CDCl₃, δ): 1.50–1.93(6H, m), 2.62–2.79(2H, m), 2.88, 2.91(3H, s), 3.35(1H, dt, J=2, 11 Hz), 3.57–3.72(2H, m), 3.84–4.04(2H, m), 4.21(1H, d, J=11 Hz), 4.60(1H, m), 4.96(1H, m), 7.15(1H, t, J=2 Hz), 7.40 (1H, d, J=2 Hz), 7.46(1H, d, J=2 Hz), 7.73–7.89(4H, m), 9.13–9.28(1H, br)
Preparation 119
(2R)-1-Benzyloxycarbonyl-4-(9-fluorenylmethyloxycarbonyl)-2-piperazinecarboxylic acid (7.5 g) was obtained as an amorphous powder in substantially the same manner as in Preparation 11.
Mass (ESI−): 485 (M−H)
¹H-NMR (300 MHz, CDCl₃, δ): 2.79–2.98(1H, m), 3.06–3.34(2H, m), 3.82–4.08(2H, m), 4.30–4.92(5H, m), 5.08–5.24(2H, m), 7.23–7.40(9H, m), 7.47–7.62(2H, m), 7.75(2H, d, J=8 Hz)
Preparation 120
(2R)-1-Benzyloxycarbonyl-4-(9-fluorenylmethyloxycarbonyl)-N-(2-tetrahydropyranyloxy)-2-piperazinecarboxamide (8.5 g) was obtained as an amorphous powder in substantially the same manner as in Preparation 12.
Mass (ESI−): 584 (M−H)
¹H-NMR (300 MHz, CDCl₃, δ): 1.47–1.89(6H, m), 2.97–3.15(1H, m), 3.17–3.40(1H, m), 3.48–3.67(1H, m), 3.74–4.06(4H, m), 4.18–4.75(5H, m), 4.83–5.02(1H, m), 5.19(2H, m), 7.27–7.45(9H, m), 7.49–7.69(2H, m), 7.78(2H, d, J=8 Hz)
Preparation 121
(2R)-1-Benzyloxycarbonyl-N-(2-tetrahydropyranyloxy)-2-piperazinecarboxamide (3.4 g) was obtained as an amorphous powder in substantially the same manner as in Preparation 157 to be mentioned later.
Mass (ESI+): 364 (M+H)
¹H-NMR (300 MHz, CDCl₃, δ): 1.48–1.93(6H, m), 2.16–2.29(1H, m), 2.81–2.92(1H, m), 2.94–3.18(2H, m), 3.32–3.67(2H, m), 3.80–4.08(2H, m), 4.31–4.62(1H, m), 4.95(1H, brs), 5.09–5.23(2H, m), 7.36(5H, s)
Preparation 122
(2R)-1-Benzyloxycarbonyl-4-(N,N-dimethylaminosulfonyl)-N-(2-tetrahydropyranyloxy)-2-piperazinecarboxamide (1.5 g) was obtained as an amorphous powder in substantially the same manner as in Example 220 to be mentioned later.
Mass (ESI−): 469 (M−H)
¹H-NMR (300 MHz, CDCl₃, δ): 1.50–1.88(6H, m), 2.78–2.99(2H, m), 2.87, 2.88(6H, s), 3.09–3.30(1H, m), 3.48–3.64(2H, m), 3.80–4.25(3H, m), 4.75–4.86(1H, m), 4.92(1H, brs), 5.18(2H, s), 7.38(5H, s)
Preparation 123
(2R)-4-(N,N-Dimethylaminosulfonyl)-N-(2-tetrahydropyranyloxy)-2-piperazinecarboxamide (920 mg) was obtained as an amorphous powder in substantially the same manner as in Preparation 13.
Mass (ESI+): 337 (M+H)
¹H-NMR (300 MHz, CDCl₃, δ): 1.52–1.92(6H, m), 2.83 (3H, s), 2.85(3H, s), 2.86–2.95(1H, m), 2.97–3.14(2H, m), 3.19–3.32(2H, m), 3.40–3.58(2H, m), 3.60–3.70(1H, m), 3.92–4.02(1H, m), 4.93–4.98(1H, m)

EXAMPLE 62

(2R)-1-[5-(4-Acetoxyphenyl)thiophene-2-sulfonyl]-4-(N,N-dimethylaminosulfonyl)-N-(2-tetrahydropyranyloxy)-2-piperazinecarboxamide (140 mg) was obtained as an amorphous powder in substantially the same manner as in Example 4.
Mass (ESI−): 615 (M−H)
¹H-NMR (300 MHz, CDCl₃, δ): 1.52–1.92(6H, m), 2.32 (3H, s), 2.62–2.78(2H, m), 2.84(3H, s), 2.86(3H, s), 3.38–3.70(3H, m), 3.84–4.08(3H, m), 4.55–4.66(1H, m), 4.93–5.00(1H, m), 7.09(2H, d, J=8 Hz), 7.23–7.28(2H, m), 7.58–7.65(2H, m), 9.17(1H, brs)

EXAMPLE 63

(2R)-1-[5-(4-Cyanophenyl)thiophene-2-sulfonyl]-4-(N,N-dimethylaminosulfonyl)-N-(2-tetrahydropyranyloxy)-2-piperazinecarboxamide (110 mg) was obtained as an amorphous powder in substantially the same manner as in Example 4.
Mass (ESI−): 582 (M−H)
¹H-NMR (300 MHz, CDCl₃, δ): 1.51–1.92(6H, m), 2.61–2.78(2H, m), 2.82(3H, s), 2.84(3H, s), 3.38–3.70(3H, m), 3.85–4.09(3H, m), 4.55–4.68(1H, m), 4.92–5.01(1H, m), 7.38(1H, d, J=3 Hz), 7.59–7.78(5H, m), 9.18(1H, brs)

EXAMPLE 64

(2R)-1-[5-(4-Cyanomethylphenyl)thiophene-2-sulfonyl]-4-(N,N-dimethylaminosulfonyl)-N-(2-tetrahydropyranyloxy)-2-piperazinecarboxamide (115 mg) was obtained as an amorphous powder in substantially the same manner as in Example 4.
Mass (ESI−): 596 (M−H)
¹H-NMR (300 MHz, CDCl₃, δ): 1.52–1.93(6H, m), 2.62–2.77(2H, m), 2.82(3H, s), 2.85(3H, s), 3.38–3.70(3H, m), 3.81(2H, s), 3.86–4.09(3H, m), 4.55–4.68(1H, m), 4.92–5.02(1H, m), 7.31(1H, d, J=3 Hz), 7.42(2H, d, J=8 Hz), 7.58–7.66(3H, m), 9.17(1H, brs)

EXAMPLE 65

(2R)-1-[5-(4-Acetoxymethylphenyl)thiophene-2-sulfonyl]-4-(N,N-dimethylaminosulfonyl)-N-(2-tetrahydropyranyloxy)-2-piperazinecarboxamide (107 mg) was obtained as an amorphous powder in substantially the same manner as in Example 4.
Mass (ESI−): 629 (M−H)
¹H-NMR (300 MHz, CDCl₃, δ): 1.52–1.93(6H, m), 2.12 (3H, s), 2.62–2.77(2H, m), 2.85(3H, s), 2.87(3H, s), 3.36–3.70(3H, m), 3.84–4.10(3H, m), 4.58–4.67(1H, m), 4.92–5.01(1H, m), 5.13(2H, s), 7.29(1H, d, J=3 Hz), 7.43 (2H, d, J=8 Hz), 7.57–7.65(3H, m), 9.17(1H, brs)

EXAMPLE 66

(2R)-4-(N,N-Dimethylaminosulfonyl)-1-[5-(3-fluoro-4-methoxyphenyl)thiophene-2-sulfonyl]-N-(2- tetrahydropyranyloxy)-2-piperazinecarboxamide (424 mg) was obtained in substantially the same manner as in Example 4.

Mass (ESI): 605 (M−1)

$^1$H-NMR (300 MHz, CDCl$_3$, δ): 1.51–1.94(6H, m), 2.60–2.77(2H, m), 2.80–2.92(6H, m), 3.37–3.71(3H, m), 3.86–4.10(6H, m), 4.56–4.68(1H, m), 4.94–5.02(1H, m), 7.01(1H, t, J=8 Hz), 7.29(1H, d, J=3 Hz), 7.30–7.40(2H, m), 7.60(2H, d, J=3 Hz), 9.10–9.20(1H, m)

EXAMPLE 67

(2R)-4-(N,N-Dimethylaminosulfonyl)-1-(4-methoxybenzenesulfonyl)-N-(2-tetrahydropyranyloxy)-2-piperazinecarboxamide (142 mg) was obtained as an amorphous powder in substantially the same manner as in Example 4.

Mass (ESI−): 505 (M−H)

$^1$H-NMR (300 MHz, CDCl$_3$, δ): 1.54–1.94(6H, m), 2.40–2.58(2H, m), 2.82(3H, s), 2.84(3H, s), 3.28–3.45(2H, m), 3.57–3.72(1H, m), 3.89(3H, s), 3.87–4.05(3H, m), 4.45–4.57(1H, m), 4.92–5.01(1H, m), 7.02(2H, d, J=8 Hz), 7.78(2H, d, J=8 Hz), 9.25(1H, brs)

EXAMPLE 68

(2R)-4-(N,N-Dimethylaminosulfonyl)-1-(4-phenoxybenzenesulfonyl)-N-(2-tetrahydropyranyloxy)-2-piperazinecarboxamide (164 mg) was obtained as an amorphous powder in substantially the same manner as in Example 4.

Mass (ESI−): 567 (M−H)

$^1$H-NMR (300 MHz, CDCl$_3$, δ): 1.52–1.95(6H, m), 2.45–2.64(2H, m), 2.83(3H, s), 2.85(3H, s), 3.29–3.59(2H, m), 3.56–3.71(1H, m), 3.82–4.08(3H, m), 4.47–4.58(1H, m), 4.92–4.99(1H, m), 7.06(2H, d, J=8 Hz), 7.10(2H, d, J=8 Hz), 7.26(1H, dd, J=8, 8 Hz), 7.38–7.49(2H, m), 7.78(2H, d, J=8 Hz), 9.22(1H, brs)

Preparation 124

(2R)-1-Benzyloxycarbonyl-4-ethylaminocarbonyl-N-(2-tetrahydropyranyloxy)-2-piperazinecarboxamide (855 mg) was obtained in substantially the same manner as in Example 225 to be mentioned later.

Mass (ESI−): 433 (M−H)

$^1$H-NMR (300 MHz, CDCl$_3$, δ): 1.14(3H, t, J=5 Hz), 1.50–1.90(6H, m), 2.75–3.17(3H, m), 3.23(2H, m), 3.59(1H, m), 3.84–4.15(2H, m), 4.25–4.40(1H, m), 4.70–5.00(3H, m), 5.20(2H, s), 5.20–5.40(1H, br), 7.37(5H, s)

Preparation 125

(2R)-4-Ethylaminocarbonyl-N-(2-tetrahydropyranyloxy)-2-piperazinecarboxamide (287 mg) was obtained in substantially the same manner as in Preparation 13.

Mass (ESI+): 301 (M+H), 323 (M+Na)

$^1$H-NMR (300 MHz, CDCl$_3$, δ): 1.14(3H, t, J=5 Hz), 1.50–1.94(6H, m), 2.73–2.90(2H, m), 3.15–3.30(3H, m), 3.35(1H, dd, J=2, 12 Hz), 3.45–3.55(2H, m), 3.64(1H, m), 3.84(1H, m), 3.98(1H, m), 4.87(1H, brs), 4.94, 4.99(1H, brs)

EXAMPLE 69

(2R)-1-[5-(4-Acetoxyphenyl)thiophene-2-sulfonyl]-4-ethylaminocarbonyl-N-(2-tetrahydropyranyloxy)-2-piperazinecarboxamide (106 mg) was obtained in substantially the same manner as in Example 4.

Mass (ESI−): 579 (M−H)

$^1$H-NMR (300 MHz, CDCl$_3$, δ): 1.10(3H, t, J=4 Hz), 1.50–1.90(6H, m), 2.35(3H, s), 2.65(1H, dt, J=2, 12 Hz), 2.85(1H, dd, J=2, 12 Hz), 3.10–3.30(1H, m), 3.18(2H, m), 3.63(1H, m), 3.85–4.10(3H, m), 4.28(1H, m), 4.59(1H, m), 4.92, 5.00(1H, brs), 5.23(1H, m), 7.19(2H, d, J=8 Hz), 7.25(1H, m), 7.60(2H, d, J=8 Hz), 7.62(1H, m), 9.32, 9.40(1H, s)

EXAMPLE 70

(2R)-1-[5-(4-Cyanophenyl)thiophene-2-sulfonyl]-4-ethylaminocarbonyl-N-(2-tetrahydropyranyloxy)-2-piperazinecarboxamide (95 mg) was obtained in substantially the same manner as in Example 4.

Mass (ESI−): 546 (M−H)

$^1$H-NMR (300 MHz, CDCl$_3$, δ): 1.10(3H, t, J=4 Hz), 1.50–1.90(6H, m), 2.60–2.75(1H, m), 2.86(1H, dd, J=2, 12 Hz), 3.10–3.32(3H, m), 3.63(1H, m), 3.85–4.07(3H, m), 4.31(1H, m), 4.60(1H, m), 4.93, 5.00(1H, brs), 5.16(1H, m), 7.40(1H, m), 7.67(1H, m), 7.69(2H, d, J=8 Hz), 7.74(2H, d, J=8 Hz), 9.36, 9.50(1H, s)

Preparation 126

Ethyl (2R)-4-benzyloxycarbonyl-1-tert-butoxycarbonyl-2-piperazinecarboxylate (15.0 g) was obtained as an oil in substantially the same manner as in Preparation 24.

Mass (ESI−): 391 (M−H)

$^1$H-NMR (300 MHz, CDCl$_3$, δ): 1.08–1.30(3H, m), 1.45, 1.48(9H, s), 2.80–3.31(3H, m), 3.74–4.22(4H, m), 4.50–4.78(2H, m), 5.09(1H, d, J=9 Hz), 5.16(1H, d, J=9 Hz), 7.28–7.42(5H, m)

Preparation 127

To a solution of ethyl (2R)-4-benzyloxycarbonyl-1-tert-butoxycarbonyl-2-piperazinecarboxylate (15.0 g) in dioxane (100 ml) was added 1N NaOH (76.4 ml) at ambient temperature for 4 hours, the reaction mixture was concentrated in vacuo to remove dioxane. The resulting solution was acidified with 3N HCl to be pH2 and extracted with AcOEt (300 ml). The organic layer was washed with saturated NaCl solution, dried over MgSO$_4$ and evaporated in vacuo to give 12.8 g of (2R)-4-benzyloxycarbonyl-1-tert-butoxycarbonyl-2-piperazinecarboxylic acid as an amorphous powder.

Mass (ESI−): 363 (M−H)

$^1$H-NMR (300 MHz, CDCl$_3$, δ): 1.45, 1.48(9H, s), 2.82–3.02(1H, m), 3.09–3.30(2H, m), 3.76–4.18(2H, m), 4.59–4.85(2H, m), 5.04–5.24(2H, m), 7.34(5H, s)

Preparation 128

(2R)-4-Benzyloxycarbonyl-N-tert-butoxy-1-tert-butoxycarbonyl-2-piperazinecarboxamide (554 mg) was obtained as an amorphous powder in substantially the same manner as in Preparation 8.

Mass (ESI−): 434 (M−H)

$^1$H-NMR (300 MHz, CDCl$_3$, δ): 1.23(9H, s), 1.48(9H, s), 2.90–3.40(4H, m), 3.80–4.15(1H, br), 4.40–4.65 (2H, m), 5.05–5.25 (2H, m), 7.27–7.45(5H, m)

Preparation 129

(2R)-N-tert-Butoxy-1-tert-butoxycarbonyl-2-piperazinecarboxamide (249 mg) was obtained as crystals in substantially the same manner as in Preparation 13.

m.p.: 113–114° C.

Mass (ESI+): 302 (M+H)

$^1$H-NMR (300 MHz, CDCl$_3$, δ): 1.27(9H, s), 1.48(9H, s), 2.65–3.04(4H, m), 3.43(1H, d, J=12 Hz), 3.72–3.90(1H, br), 4.22–4.40(1H, br), 8.67(1H, brs)

Preparation 130

(2R)-4-[2-(Benzyloxycarbonylamino)ethanesulfonyl]-N-tert-butoxy-1-tert-butoxycarbonyl-2-piperazinecarboxamide (213 mg) was obtained as amorphous powder in substantially the same manner as in Example 4.

Mass (ESI−): 541 (M−H)

¹H-NMR (300 MHz, CDCl₃, δ): 1.23(9H, s), 1.49(9H, s), 2.84–3.10(3H, m), 3.25–3.75(5H, m), 3.75–4.20(2H, m), 4.64(1H, brs), 5.04(1H, d, J=10 Hz), 5.13(1H, d, J=10 Hz), 5.70–5.95(1H, br), 7.26–7.38(5H, m), 8.50–8.70(1H, br)

Preparation 131

(2R)-4-(2-Aminoethanesulfonyl)-N-tert-butoxy-1-tert-butoxycarbonyl-2-piperazinecarboxamide (150 mg) was obtained as crystals in substantially the same manner as in Preparation 13.

m.p.: 171–172° C.
Mass (ESI+): 409 (M+H)
¹H-NMR (300 MHz, DMSO-d₆, δ): 1.15(9H, s), 1.37(9H, s), 2.79(1H, dt, J=1, 11 Hz), 2.88(2H, t, J=4 Hz), 3.07(2H, t, J=4 Hz), 3.15–3.55(2H, m), 2.72–3.93(2H, m), 4.38–4.55 (1H, m)

Preparation 132

Acetic anhydride (36 mg) was added to a solution of (2R)-4-(2-aminoethanesulfonyl)-N-tert-butoxy-1-tert-butoxycarbonyl-2-piperazinecarboxamide (130 mg) in AcOH (2 ml). The reaction mixture was stirred at ambient temperature for 3 hours. The mixture was concentrated in vacuo, and the residue was partitioned between AcOEt and saturated aqueous NaHCO₃ solution. The organic layer was washed with saturated aqueous NaCl solution, dried over MgSO₄, and concentrated in vacuo to give 142 mg of (2R)-4-[2-(acetylamino)ethanesulfonyl]-N-tert-butoxy-1-tert-butoxycarbonyl-2-piperazinecarboxamide.

Mass (ESI–): 449 (M–H)
¹H-NMR (300 MHz, CDCl₃, δ): 1.26(9H, s), 1.50(9H, s), 1.98(3H, s), 2.75–3.17(3H, m), 3.17–3.45(2H, m), 3.54–3.75(3H, m), 3.93–4.24(2H, m), 4.68(1H, brs), 6.65–6.85(1H, broad), 8.55–8.75(1H, broad)

Preparation 133

(2R)-4-[2-(Acetylamino)ethanesulfonyl]-N-tert-butoxy-2-piperazinecarboxamide hydrochloride (112 mg) was obtained in substantially the same manner as in Preparation 10.

Mass (ESI–): 349 (M–H)
¹H-NMR (300 MHz, DMSO-d₆, δ): 1.20(9H, s), 1.82(3H, s), 3.00–4.10(11H, m), 8.18(1H, t, J=2 Hz)

EXAMPLE 71

(2R)-4-[2-(Acetylamino)ethanesulfonyl]-N-tert-butoxy-1-[5-(4-fluorophenyl)thiophene-2-sulfonyl]-2-piperazinecarboxamide (134 mg) was obtained as amorphous powder in substantially the same manner as in Example 4.

Mass (ESI–): 589 (M–H)
¹H-NMR (300 MHz, CDCl₃, δ): 1.29(9H, s), 1.97(3H, s), 2.82(1H, dt, J=2, 12 Hz), 3.21–3.44(3H, m), 3.52–3.67(3H, m), 4.05(1H, d, J=13 Hz), 4.21(1H, d, J=12 Hz), 4.62(1H, brs), 6.37(1H, br), 7.15(2H, t, J=8 Hz), 7.23(1H, d, J=2 Hz), 7.54–7.65(3H, m), 8.80(1H, s)

Preparation 134

(2R)-N-tert-Butoxy-1-tert-butoxycarbonyl-4-[2-(methanesulfonylamino)ethanesulfonyl]-2-piperazinecarboxamide (1.55 g) was obtained as amorphous powder in substantially the same manner as in Example 4.

Mass (ESI–): 485 (M–H)
¹H-NMR (300 MHz, CDCl₃, δ): 1.25(9H, s), 1.52(9H, s), 2.90–3.10(2H, m), 2.99(3H, s), 3.13–3.68(5H, m), 3.95–4.17(2H, m), 4.66(1H, brs), 6.09(1H, br), 8.76(1H, brs)

Preparation 135

(2R)-N-tert-Butoxy-4-[2-(methanesulfonylamino)ethanesulfonyl]-2-piperazinecarboxamide hydrochloride (1.22 g) was obtained as crystals in substantially the same manner as in Preparation 10.

m.p.: 146–158° C.
Mass (ESI–): 385 (M–H)
¹H-NMR (300 MHz, DMSO-d₆, δ): 1.20(9H, s), 2.97(3H, s), 3.03–3.52(8H, m), 3.68(1H, d, J=11 Hz), 3.90–4.05(2H, m), 7.34(1H, t, J=4 Hz)

EXAMPLE 72

(2R)-N-tert-Butoxy-1-[5-(4-fluorophenyl)thiophene-2-sulfonyl]-4-[2-(methanesulfonylamino)ethanesulfonyl]-2-piperazinecarboxamide (248 mg) was obtained in substantially the same manner as in Example 4.

Mass (ESI–): 625 (M–H)
¹H-NMR (300 MHz, CDCl₃, δ): 1.30(9H, s), 1.59(9H, s), 2.75–2.90(2H, m), 2.98(3H, s), 3.25–3.65(6H, m), 4.03(1H, d, J=12 Hz), 4.19(1H, d, J=12 Hz), 4.62(1H, brs), 5.41(1H, t, J=4 Hz), 7.15(2H, t, J=8 Hz), 7.24(1H, d, J=2 Hz), 7.54–7.63(3H, m), 8.81(1H, s)

EXAMPLE 73

(2R)-N-tert-Butoxy-4-[2-(methanesulfonylamino)ethanesulfonyl]-1-(5-phenylthiophene-2-sulfonyl)-2-piperazinecarboxamide (249 mg) was obtained in substantially the same manner as in Example 4.

Mass (ESI–): 607 (M–H)
¹H-NMR (300 MHz, CDCl₃, δ): 1.30(9H, s), 1.59(9H, s), 2.75–2.90(2H, m), 2.98(3H, s), 3.25–3.65(6H, m), 4.04(1H, d, J=12 Hz), 4.20(1H, d, J=12 Hz), 4.63(1H, brs), 5.40(1H, t, J=4 Hz), 7.31(1H, d, J=2 Hz), 7.37–7.52(3H, m), 7.57–7.65(3H, m), 8.83(1H, s)

EXAMPLE 74

(2R)-N-tert-Butoxy-4-[2-(methanesulfonylamino)ethanesulfonyl]-1-[5-(4-trifluoromethylphenyl)thiophene-2-sulfonyl]-2-piperazinecarboxamide (269 mg) was obtained in substantially the same manner as in Example 4.

Mass (ESI–): 675 (M–H)
¹H-NMR (300 MHz, CDCl₃, δ): 1.30(9H, s), 1.60(9H, s), 2.77–2.90(2H, m), 2.98(3H, s), 3.20–3.65(6H, m), 4.03(1H, d, J=12 Hz), 4.20(1H, d, J=12 Hz), 4.63(1H, brs), 5.42(1H, t, J=4 Hz), 7.38(1H, d, J=2 Hz), 7.65(1H, d, J=2 Hz), 7.72(4H, s), 8.80(1H, s)

EXAMPLE 75

(2R)-N-tert-Butoxy-1-[5-(4-chlorophenyl)thiophene-2-sulfonyl]-4-[2-(methanesulfonylamino)ethanesulfonyl]-2-piperazinecarboxamide (256 mg) was obtained in substantially the same manner as in Example 4.

Mass (ESI–): 641, 643 (M–H)
¹H-NMR (300 MHz, CDCl₃, δ): 1.30(9H, s), 1.60(9H, s), 2.75–2.90(2H, m), 2.98(3H, s), 3.20–3.65(6H, m), 4.03(1H, d, J=12 Hz), 4.20(1H, d, J=12 Hz), 4.62(1H, brs), 5.42(1H, t, J=4 Hz), 7.28(1H, d, J=2 Hz), 7.43(2H, d, J=8 Hz), 7.54(2H, d, J=8 Hz), 7.62(1H, d, J=2 Hz), 8.82(1H, s)

EXAMPLE 76

(2R)-N-tert-Butoxy-1-[5-(4-ethoxyphenyl)thiophene-2-sulfonyl]-4-[2-(methanesulfonylamino)ethanesulfonyl]-2-piperazinecarboxamide (245 mg) was obtained in substantially the same manner as in Example 4.

Mass (ESI–): 651 (M–H)
¹H-NMR (300 MHz, CDCl₃, δ): 1.30(9H, s), 1.45(3H, t, J=5 Hz), 2.75–2.90(2H, m), 2.98(3H, s), 3.25–3.63(6H, m), 4.03(1H, d, J=12 Hz), 4.09(2H, q, J=5 Hz), 4.19(1H, d, J=12

Hz), 4.61(1H, br), 5.37(1H, t, J=4 Hz), 6.94(2H, d, J=8 Hz), 7.18(1H, d, J=2 Hz), 7.51(1H, d, J=8 Hz), 7.59(1H, d, J=2 Hz), 8.81(1H, s)

Preparation 136

(2R)-N-tert-Butoxy-1-tert-butoxycarbonyl-4-{2-[(pyridine-3-sulfonyl)amino]ethanesulfonyl}-2-piperazinecarboxamide (544 mg) was obtained in substantially the same manner as in Example 4.

Mass (ESI-): 548 (M-H)

$^1$H-NMR (300 MHz, CDCl$_3$, δ): 1.28(9H, s), 1.51(9H, s), 2.88–3.11(2H, m), 3.15–3.60(5H, m), 3.61(1H, d, J=11 Hz), 3.95–4.10(2H, m), 4.65(1H, brs), 6.90(1H, br), 7.47(1H, dd, J=4, 8 Hz), 8.24(1H, d, J=8 Hz), 8.81(1H, d, J=4 Hz), 8.84(1H, brs), 9.13(1H, s)

Preparation 137

(2R)-N-tert-Butoxy-4-{2-[(pyridine-3-sulfonyl)amino]ethanesulfonyl}-2-piperazinecarboxamide dihydrochloride (613 mg) was obtained in substantially the same manner as in Preparation 10.

Mass (ESI-): 448 (M-H)

$^1$H-NMR (300 MHz, DMSO-d$_6$, δ): 1.20(9H, s), 3.00–3.27(5H, m), 3.28–3.53(4H, m), 3.66(1H, d, J=11 Hz), 3.93(1H, d, J=11 Hz), 7.68(1H, dd, J=4, 8 Hz), 8.24(1H, dd, J=2, 8 Hz), 8.39(1H, t, J=4 Hz), 8.85(1H, d, J=4 Hz), 8.99(1H, d, J=2 Hz)

EXAMPLE 77

(2R)-N-tert-Butoxy-1-{5-(4-chlorophenyl)thiophene-2-sulfonyl}-4-{2-[(pyridine-3-sulfonyl)amino]ethanesulfonyl}-2-piperazinecarboxamide (140 mg) was obtained in substantially the same manner as in Example 4.

Mass (ESI-): 704, 706 (M-H)

$^1$H-NMR (300 MHz, CDCl$_3$, δ): 1.31(9H, s), 2.75–2.90 (2H, m), 3.25–3.53(5H, m), 3.57(1H, d, J=12 Hz), 4.04(1H, d, J=12 Hz), 4.10(1H, d, J=12 Hz) 4.60(1H, brs), 5.42(1H, br), 7.28(1H, d, J=2 Hz), 7.43(2H, d, J=8 Hz), 7.40–7.50(1H, m), 7.54(1H, d, J=8 Hz), 7.62(1H, d, J=2 Hz), 8.18(1H, d, J=6 Hz), 8.81(1H, d, J=4 Hz), 8.83(1H, s), 9.10(1H, s)

Preparation 138

(2R)-N-tert-Butoxy-1-tert-butoxycarbonyl-4-{2-[(N,N-dimethylaminosulfonyl)amino]ethanesulfonyl}-2-piperazinecarboxamide (523 mg) was obtained in substantially the same manner as in Example 220 to be mentioned later.

Mass (ESI-): 514 (M-H)

$^1$H-NMR (300 MHz, CDCl$_3$, δ): 1.25(9H, s), 1.51(9H, s), 2.81(6H, s), 2.89–3.57(7H, m), 3.67(1H, d, J=11 Hz), 3.95–4.15(2H, m), 4.65(1H, brs), 5.81(1H, br), 8.72(1H, br)

Preparation 139

(2R)-N-tert-Butoxy-4-{2-[(N,N-dimethylaminosulfonyl)amino]ethanesulfonyl}-2-piperazinecarboxamide hydrochloride (395 mg) was obtained in substantially the same manner as Preparation 10.

Mass (ESI-): 414 (M-H)

$^1$H-NMR (300 MHz, DMSO-d$_6$, δ): 1.20(9H, s), 2.69(6H, s), 3.03–3.48(8H, m), 3.67(1H, d, J=11 Hz), 3.88–4.05(2H, m), 7.49(1H, t, J=4 Hz)

EXAMPLE 78

(2R)-N-tert-Butoxy-1-[5-(4-chlorophenyl)thiophene-2-sulfonyl]-4-{2-[(N,N-dimethylaminosulfonyl)amino]ethanesulfonyl}-2-piperazinecarboxamide (168 mg) was obtained in substantially the same manner as in Example 4.

Mass (ESI-): 670, 672 (M-H)

$^1$H-NMR (300 MHz, CDCl$_3$, δ): 1.28(9H, s), 2.75–2.90 (2H, m), 2.78(6H, s), 3.28–3.50(5H, m), 3.62(1H, d, J=12 Hz), 4.04(1H, d, J=12 Hz), 4.18(1H, d, J=12 Hz), 4.61(1H, br), 5.19(1H, t, J=4 Hz), 7.28(1H, d, J=2 Hz), 7.44(2H, d, J=8 Hz), 7.54(1H, d, J=8 Hz), 7.62(1H, d, J=2 Hz), 8.74(1H, s)

Preparation 140

Methyl chloroformate (132 mg) in CHCl$_3$ (3 ml) was added dropwise to (2R)-4-(2-aminoethanesulfonyl)-N-tert-butoxy-1-tert-butoxycarbonyl-2-piperazinecarboxamide (400 mg) in pyridine (2.5 ml) with cooling on an ice bath. After stirring on the ice bath for 3 hours, the reaction mixture was concentrated in vacuo. The residue was partitioned between AcOEt and 3.6% HCl. The organic layer was washed with saturated aqueous NaHCO$_3$ solution and saturated aqueous NaCl solution, dried over MgSO$_4$, and concentrated in vacuo to give 470 mg of (2R)-N-tert-butoxy-1-tert-butoxycarbonyl-4-[2-(methoxycarbonylamino)ethanesulfonyl]-2-piperazinecarboxamide.

Mass (ESI-): 465 (M-H)

$^1$H-NMR (300 MHz, CDCl$_3$, δ): 1.27(9H, s), 1.51(9H, s), 2.81(6H, s), 2.87–3.17(3H, m), 3.25–3.46(2H, m), 3.50–3.78(3H, m), 3.67(3H, s), 3.93–4.20(2H, m), 4.67(1H, brs), 5.72(1H, br), 8.63(1H, br)

Preparation 141

(2R)-N-tert-Butoxy-4-[2-(methoxycarbonylamino)ethanesulfonyl]-2-piperazinecarboxamide hydrochloride (414 mg) was obtaiend in substantially the same manner as in Preparation 10.

Mass (ESI-): 401 (M-H)

$^1$H-NMR (300 MHz, DMSO-d$_6$, δ): 1.20(9H, s), 3.00–3.25(3H, m), 3.25–3.40(5H, m), 3.55(3H, s), 3.67(1H, d, J=11 Hz), 3.88–4.05(2H, m), 7.37(1H, m)

EXAMPLE 79

(2R)-N-tert-Butoxy-1-[5-(4-chlorophenyl)thiophene-2-sulfonyl]-4-[2-(methoxycarbonylamino)ethanesulfonyl]-2-piperazinecarboxamide (253 mg) was obtained in substantially the same manner as in Example 4.

Mass (ESI-): 621, 623 (M-H)

$^1$H-NMR (300 MHz, CDCl$_3$, δ): 1.28(9H, s), 2.75–2.90 (2H, m), 3.24–3.44(3H, m), 3.50–3.65(3H, m), 3.65(3H, s), 4.04(1H, d, J=12 Hz), 4.18(1H, d, J=12 Hz), 4.59(1H, brs), 5.42(1H, br), 7.28(1H, d, J=2 Hz), 7.43(2H, d, J=8 Hz), 7.54(1H, d, J=8 Hz), 7.62(1H, d, J=2 Hz), 8.72(1H, s)

Preparation 142

(2R)-N-tert-Butoxy-1-tert-butoxycarbonyl-4-{2-[(pyridine-3-carbonyl)amino]ethanesulfonyl}-2-piperazinecarboxamide (896 mg) was obtained in substantially the same manner as in Example 4.

Mass (ESI-): 512 (M-H)

$^1$H-NMR (300 MHz, CDCl$_3$, δ): 1.25(9H, s), 1.50(9H, s), 2.88–3.12(3H, m), 3.39–3.70(3H, m), 3.76–4.05(3H, m), 4.17(1H, d, J=11 Hz), 4.70(1H, brs), 7.37(1H, dd, J=2, 6 Hz), 8.66(1H, d, J=6 Hz), 8.73(1H, d, J=2 Hz), 9.08(1H, s)

Preparation 143

(2R)-N-tert-Butoxy-4-{2-[(pyridine-3-carbonyl)amino]ethanesulfonyl}-2-piperazinecarboxamide dihydrochloride (869 mg) was obtained in substantially the same manner as in Preparation 10.

Mass (ESI-): 412 (M-H)

$^1$H-NMR (300 MHz, DMSO-d$_6$, δ): 1.20(9H, s), 1.82(3H, s), 3.00–4.10(11H, m), 7.75(1H, dd, J=2, 6 Hz), 8.47(1H, d, J=6 Hz), 8.84(1H, d, J=2 Hz), 9.14(1H, s), 9.20–9.35(1H, br), 9.30(1H, t, J=4 Hz)

EXAMPLE 80

(2R)-N-tert-Butoxy-1-{5-(4-fluorophenyl)thiophene-2-sulfonyl}-4-{2-[(pyridine-3-carbonyl)amino]

ethanesulfonyl}-2-piperazinecarboxamide (99 mg) was obtained in substantially the same manner as in Example 220 to be mentioned later.

Mass (ESI-): 652 (M-H)

$^1$H-NMR (300 MHz, CDCl$_3$, δ): 1.30(9H, s), 2.76–2.92 (2H, m), 3.33(1H, d, J=12 Hz), 3.42(2H, t, J=4 Hz), 3.62(1H, d, J=12 Hz), 3.65–3.80(1H, m), 3.85–4.00(1H, m), 4.05(1H, d, J=12 Hz), 4.23(1H, d, J=12 Hz), 4.63(1H, brs), 7.15(2H, t, J=8 Hz), 7.24(1H, d, J=2 Hz), 7.36(1H, dd, J=2, 6 Hz), 7.55–7.65(3H, m), 8.13(1H, d, J=6 Hz), 8.73(1H, d, J=2 Hz), 8.84(1H, s), 9.05(1H, s)

EXAMPLE 81

(2R)-1-[5-(4-Acetoxyphenyl)thiophene-2-sulfonyl]-N-tert-butoxy-4-{2-[(pyridine-3-carbonyl)amino]ethanesulfonyl}-2-piperazinecarboxamide (78 mg) was obtained in substantially the same manner as in Example 220 to be mentioned later.

Mass (ESI-): 692 (M-H)

$^1$H-NMR (300 MHz, CDCl$_3$, δ): 1.28(9H, s), 2.34(3H, s), 2.77–2.92(2H, m), 3.33(1H, d, J=12 Hz), 3.42(2H, t, J=4 Hz), 3.62(1H, d, J=12 Hz), 3.67–3.82(1H, m), 3.84–4.00 (1H, m), 4.05(1H, d, J=12 Hz), 4.24(1H, d, J=12 Hz), 4.63(1H, brs), 7.19(2H, d, J=8 Hz), 7.27(1H, d, J=2 Hz), 7.37(1H, dd, J=2, 6 Hz), 7.61(2H, d, J=8 Hz), 8.13(1H, d, J=6 Hz), 8.73(1H, d, J=2 Hz), 8.82(1H, s), 9.05(1H, s)

Preparation 144

(2R)-4-[2-(Benzoylamino)ethanesulfonyl]-N-tert-1-tert-butoxycarbonyl-2-piperazinecarboxamide (867 mg) was obtained in substantially the same manner as in Example 4.

Mass (ESI-): 511 (M-H)

$^1$H-NMR (300 MHz, CDCl$_3$, δ): 1.25(9H, s), 1.50(9H, s), 2.88–3.10(3H, m), 3.37–3.72(3H, m), 3.82–4.05(3H, m), 4.18(1H, d, J=11 Hz), 4.68(1H, brs), 7.43(2H, t, J=7 Hz), 7.50(1H, t, J=7 Hz), 7.84(2H, d, J=7 Hz)

Preparation 145

(2R)-4-[2-(Benzoylamino)ethanesulfonyl]-N-tert-butoxy-2-piperazinecarboxamide hydrochloride (619 mg) was obtained in substantially the same manner as in Preparation 10.

Mass (ESI-): 411 (M-H)

$^1$H-NMR (300 MHz, DMSO-d$_6$, δ): 1.19(9H, s), 3.00–4.10(11H, m), 7.46(2H, t, J=7 Hz), 7.55(1H, t, J=7 Hz), 7.86(2H, d, J=7 Hz), 8.80(1H, t, J=4 Hz), 9.10–9.45(1H, br)

EXAMPLE 82

(2R)-4-[2-(Benzoylamino)ethanesulfonyl]-N-tert-butoxy-1-[5-(4-fluorophenyl)thiophene-2-sulfonyl]-2-piperazinecarboxamide (187 mg) was obtained in substantially the same manner as in Example 4.

Mass (ESI-): 651 (M-H)

$^1$H-NMR (300 MHz, CDCl$_3$, δ): 1.30(9H, s), 2.77–2.90 (2H, m), 3.31(1H, d, J=12 Hz), 3.40(2H, t, J=4 Hz), 3.61(1H, d, J=12 Hz), 3.70–4.00(2H, m), 4.03(1H, d, J=12 Hz), 4.24(1H, d, J=12 Hz), 4.62(1H, brs), 7.09(1H, m), 7.15(2H, t, J=8 Hz), 7.24(1H, d, J=2 Hz), 7.42(2H, d, J=7 Hz), 7.50(1H, t, J=7 Hz), 7.55–7.65(3H, m), 7.81(2H, d, J=7 Hz), 8.78(1H, s)

EXAMPLE 83

(2R)-1-[5-(4-Acetoxyphenyl)thiophene-2-sulfonyl]-4-[2-(benzoylamino)ethanesulfonyl]-N-tert-butoxy-2-piperazinecarboxamide (114 mg) was obtained in substantially the same manner as in Example 4.

Mass (ESI-): 691 (M-H)

$^1$H-NMR (300 MHz, CDCl$_3$, δ): 1.29(9H, s), 2.33(3H, s), 2.77–2.92(2H, m), 3.31(1H, d, J=12 Hz), 3.39(2H, m), 3.61(1H, d, J=12 Hz), 3.67–3.95(2H, m), 4.03(1H, d, J=12 Hz), 4.24(1H, d, J=12 Hz), 4.63(1H, brs), 7.11(1H, t, J=4 Hz), 7.19(2H, d, J=8 Hz), 7.25(1H, d, J=2 Hz), 7.42(2H, t, J=7 Hz), 7.49(1H, t, J=7 Hz), 7.61(2H, d, J=8 Hz), 7.81(2H, d, J=7 Hz), 8.78(1H, s)

EXAMPLE 84

(2R)-4-Methanesulfonyl-N-(2-tetrahydropyranyloxy)-2-piperazinecarboxamide (266 mg) and trans-β-styrenesulfonyl chloride (210 mg) were used to give 271 mg of (2R)-4-methanesulfonyl-1-(2-phenyl-2-trans-ethenylsulfonyl)-N-(2-tetrahydropyranyloxy)-2-piperazinecarboxamide as amorphous powder in substantially the same manner as in Example 4.

Mass (ESI-): 472 (M-H)

$^1$H-NMR (300 MHz, CDCl$_3$, δ): 1.50–1.95(6H, m), 2.92 (3H, s), 2.95(1H, dt, J=2, 12 Hz), 3.11(1H, m), 3.62(1H, m), 3.71–3.85(3H, m), 3.93(1H, m), 4.22(1H, m), 4.62(1H, m), 4.98(1H, m), 6.87(1H, d, J=14 Hz), 6.98(1H, d, J=14 Hz), 7.37–7.57(5H, m), 9.23(1H, brs)

EXAMPLE 85

(2R)-N-Hydroxy-4-[3-(4-morpholino)propanesulfonyl]-1-(5-phenylthiophene-2-sulfonyl)-2-piperazinecarboxamide hydrochloride (280 mg) was obtained as an amorphous powder in substantially the same manner as in Example 5.

Mass (ESI-): 557 (M-H)

$^1$H-NMR (300 MHz, DMSO-d$_6$, δ): 1.95–2.13(3H, m), 2.73–2.90(1H, m), 2.93–3.30(8H, m), 3.55–3.65(1H, m), 3.70–4.00(7H, m), 4.50(1H, brs), 7.38–7.52(3H, m), 7.62 (1H, d, J=3 Hz), 7.68(1H, d, J=3 Hz), 7.76(2H, d, J=8 Hz)

EXAMPLE 86

(2R)-N-Hydroxy-1-(5-phenylthiophene-2-sulfonyl)-4-[2-(4-pyridyl)ethansulfonyl]-2-piperazinecarboxamide hydrochloride (78 mg) was obtained as an amorphous powder in substantially the same manner as in Example 5.

Mass (ESI-): 535 (M-H)

$^1$H-NMR (300 MHz, DMSO-d$_6$, δ): 2.78–2.94(2H, m), 3.01–3.10(2H, m), 3.12–3.37(3H, m), 3.70–4.11(3H, m), 4.52(1H, brs), 7.38–7.52(3H, m), 7.60(1H, d, J=3 Hz), 7.68(1H, d, J=3 Hz), 7.72(2H, d, J=6 Hz), 8.00(2H, d, J=6 Hz), 8.82(2H, d, J=6 Hz)

EXAMPLE 87

(2R)-1-[5-(4-Fluorophenyl)thiophene-2-sulfonyl)-N-hydroxy-4-[2-(4-pyridyl)ethansulfonyl]-2-piperazinecarboxamide hydrochloride (78 mg) was obtained as an amorphous powder in substantially the same manner as in Example 5.

Mass (ESI-): 553 (M-H)

$^1$H-NMR (300 MHz, DMSO-d$_6$, δ): 2.78–2.96(1H, m), 3.03–3.12(1H, m), 3.15–3.29(2H, m), 3.31–3.98(6H, m), 4.51(1H, brs), 7.33(2H, t, J=8 Hz), 7.60(1H, d, J=3 Hz), 7.68(1H, d, J=3 Hz), 7.72–7.85(2H, m), 7.95–8.05(2H, m), 8.83(2H, d, J=6 Hz)

EXAMPLE 88

(2R)-N-Hydroxy-1-(5-phenylthiophene-2-sulfonyl)-4-[3-(1-piperidino)propanesulfonyl]-2-piperazinecarboxamide hydrochloride (115 mg) was obtained as an amorphous powder in substantially the same manner as in Example 5.

Mass (ESI–): 555 (M–H)

¹H-NMR (300 MHz, DMSO-d₆, δ): 1.26–1.42(2H, m), 1.60–1.82(5H, m), 1.98–2.12(3H, m), 2.72–2.91(3H, m), 2.98–3.10(3H, m), 3.12–3.26(3H, m), 3.53–3.64(3H, m), 3.78–3.80(2H, m), 3.87(1H, d, J=12 Hz), 4.50(1H, brs), 7.38–7.52(3H, m), 7.58–7.64(1H, m), 7.67–7.72(1H, m), 7.72–7.79(2H, m), 9.03(1H, brs)

EXAMPLE 89

(2R)-4-(N-Ethylaminocarbonyl)-1-[5-(4-fluorophenyl)thiophene-2-sulfonyl]-N-hydroxy-2-piperazinecarboxamide (98 mg) was obtained as an amorphous powder in substantially the same manner as in Example 5.

Mass (ESI): 455 (M–H)

¹H-NMR (300 MHz, DMSO-d₆, δ): 0.92(3H, t, J=7 Hz), 2.78–3.06(4H, m), 3.50–3.75(3H, m), 3.97–4.08(1H, m), 4.26(1H, brs), 6.35–6.42(1H, m), 7.32(2H, t, J=8 Hz), 7.59 (1H, d, J=3 Hz), 7.67(1H, d, J=3 Hz), 7.78(1H, d, J=3 Hz), 7.82(1H, d, J=3 Hz), 8.93(1H, s)

EXAMPLE 90

(2R)-1-[5-(4-Fluorophenyl)thiophene-2-sulfonyl]-N-hydroxy-4-[3-(3-pyridyl)propionyl]-2-piperazinecarboxamide hydrochloride (136 mg) was obtained as an amorphous powder in substantially the same manner as in Example 5.

Mass (ESI): 517 (M–H)

¹H-NMR (300 MHz, DMSO-d₆, δ): 2.58–3.08(4H, m), 3.22–3.95(3H, m), 4.02–4.23(2H, m), 4.28–4.38(1H, m), 4.43(1H, brs), 7.33(2H, t, J=8 Hz), 7.55–7.72(2H, m), 7.76–7.86(2H, m), 7.90–8.00(1H, m), 8.38–8.50(1H, m), 8.70(1H, d, J=7 Hz), 8.80(1H, s)

EXAMPLE 91

(2R)-4-[3-(N,N-Diethylamino)propanesulfonyl]-1-[5-(4-fluorophenyl)thiophene-2-sulfonyl]-N-hydroxy-2-piperazinecarboxamide hydrochloride (40 mg) was obtained in substantially the same manner as in Example 5.

Mass (ESI): 561 (M–H)

¹H-NMR (300 MHz, DMSO-d₆, δ): 2.19(6H, t, J=7 Hz), 1.89–2.06(2H, m), 2.76–2.88(1H, m), 2.95–3.28(1H, m), 3.49–3.80(3H, m), 3.88(1H, d, J=12 Hz), 4.49(1H, brs), 7.33(2H, t, J=8 Hz), 7.55–7.63(1H, m), 7.69(1H, d, J=3 Hz), 7.78–7.86(2H, m), 9.01(1H, s)

EXAMPLE 92

(2R)-1-[5-(4-Fluorophenyl)thiophene-2-sulfonyl]-N-hydroxy-4-[3-(3-pyridyl)acrylyl]-2-piperazinecarboxamide hydrochloride (120 mg) was obtaiend as an amorphous powder in substantially the same manner as in Example 5.

Mass (ESI): 515 (M–H)

¹H-NMR (300 MHz, DMSO-d₆, δ): 2.92–3.08(1H, m), 3.22–3.90(4H, m), 4.08–4.20(1H, m), 4.33–4.52(2H, m), 7.19–7.36(2H, m), 7.44–7.85(6H, m), 8.18–8.30(2H, m), 8.88(2H, s)

EXAMPLE 93

(2R)-1-[5-(4-Fluorophenyl)thiophene-2-sulfonyl]-N-hydroxy-4-(N-methylaminocarbonyl)-2-piperazinecarboxamide (88 mg) was obtained as an amorphous powder in substantially the same manner as in Example 5.

Mass (ESI): 441 (M–H)

¹H-NMR (300 MHz, DMSO-d₆, δ): 2.44(3H, d, J=3 Hz), 2.77–2.90(1H, m), 2.94–3.07(1H, m), 3.50–3.75(3H, m), 4.02(1H, d, J=12 Hz), 4.25(1H, brs), 6.38(1H, d, J=3 Hz), 7.30(2H, t, J=8 Hz), 7.57(1H, d, J=3 Hz), 7.65(1H, d, J=3 Hz), 7.72–7.85(1H, m), 8.92(1H, s)

EXAMPLE 94

(2R)-1-[5-(4-Fluorophenyl)thiophene-2-sulfonyl]-N-hydroxy-4-methoxycarbonyl-2-piperazinecarboxamide (85 mg) was obtained as an amorphous powder in substantially the same manner as in Example 5.

Mass (ESI): 442 (M–H)

¹H-NMR (300 MHz, DMSO-d₆, δ): 2.80–3.06(1H, m), 3.11–3.23(1H, m), 3.51(3H, m), 3.55–3.74(2H, m), 3.78–3.92(1H, m), 4.05(1H, d, J=12 Hz), 4.28(1H, brs), 7.32(2H, t, J=8 Hz), 7.58(1H, d, J=3 Hz), 7.64(1H, d, J=3 Hz), 7.73–7.87(2H, m), 8.94(1H, s)

EXAMPLE 95

(2R)-1-[5-(4-Fluorophenyl)thiophene-2-sulfonyl]-N-hydroxy-4-(N-propylaminocarbonyl)-2-piperazinecarboxamide (100 mg) was obtained as an amorphous powder in substantially the same manner as in Example 5.

Mass (ESI) : 469 (M–H)

¹H-NMR (300 MHz, DMSO-d₆, δ): 0.77(3H, t, J=8 Hz), 1.23–1.40(2H, m), 2.78–2.96(3H, m), 3.05(1H, dd, J=3, 8 Hz), 3.52–3.76(3H, m), 3.97–4.09(1H, m), 4.27(1H, brs), 6.35–6.46(1H, m), 7.34(2H, t, J=8 Hz), 7.60(1H, d, J=3 Hz), 7.69(1H, d, J=3 Hz), 7.75–7.88(2H, m), 8.94(1H, s)

EXAMPLE 96

(2R)-4-Butyryl-1-[5-(4-fluorophenyl)thiophene-2-sulfonyl]-N-hydroxy-2-piperazinecarboxamide (102 mg) was obtained as an amorphous powder in substantially the same manner as in Example 5.

Mass (ESI) : 454 (M–H)

¹H-NMR (300 MHz, DMSO-d₆, δ): 0.80, 0.84(3H, t, J=8 Hz), 1.32–1.50(2H, m), 2.03–2.28(2H, m), 2.62–2.76(1H, m), 3.02–3.22(1H, m), 3.42–3.87(2H, m), 4.04(1H, d, J=12 Hz), 4.10–4.39(2H, m), 7.32(2H, t, J=8 Hz), 7.51–7.84(4H, m), 8.92, 8.99(1H, s)

EXAMPLE 97

(2R)-4-(N,N-Dimethylaminosulfonyl)-1-[5-(4-fluorophenyl)thiophene-2-sulfonyl]-N-hydroxy-2-piperazinecarboxamide (155 mg) was obtained as an amorphous powder in substantially the same manner as in Example 5.

Mass (ESI): 491 (M–H)

¹H-NMR (300 MHz, CDCl₃, δ): 2.60–2.78(2H, m), 2.72 (6H, m), 3.35–3.52(2H, m), 3.92–4.12(2H, m), 4.59(1H, brs), 7.14(2H, t J=8 Hz), 7.23(1H, d, J=3 Hz), 7.52–7.61(3H, m)

EXAMPLE 98

(2R)-1-[5-(4-Chlorophenyl)thiophene-2-sulfonyl]-4-methanesulfonyl-N-hydroxy-2-piperazinecarboxamide (296 mg) was obtained in substantially the same manner as in Example 5.

Mass (ESI–): 478, 480 (M–H)

¹H-NMR (300 Mz, DMS0-d₆, δ): 2.74–2.85(1H, m), 2.87(3H, s), 3.00(1H, dd, J=4, 10 Hz), 3.52(1H, d, J=8 Hz), 3.70–3.86(3H, m), 4.49(1H, s), 7.54(2H, d, J=8 Hz), 7.60–7.71(4H, m), 7.77(2H, d, J=8 Hz), 9.00(1H, s)

EXAMPLE 99

(2R)-1-[5-(4-Methoxyphenyl)thiophene-2-sulfonyl]-4-methanesulfonyl-N-hydroxy-2-piperazinecarboxamide (252 mg) was obtained in substantially the same manner as in Example 5.

Mass (ESI-): 474 (M–H)

$^1$H-NMR (300 MHz, DMSO-d$_6$, δ): 2.70–2.81(1H, m), 2.85(3H, s), 2.99(1H, dd, J=4, 13 Hz), 3.50–3.60(1H, m), 3.70–3.82(3H, m), 3.82(3H, s), 4.46(1H, s), 7.03(1H, d, J=9 Hz), 7.49(1H, d, J=4Hz), 7.55(1H, d, J=4 Hz), 7.70(1H, d, J=9 Hz), 9.00(1H, s)

EXAMPLE 100

(2R)-1-(5-Phenylthiophene-2-sulfonyl)-4-[3-(4-morpholinocarbonyl)propane]sulfonyl-N-hydroxy-2-piperazinecarboxamide (110 mg) was obtained in substantially the same manner as in Example 5.

Mass (ESI-): 585 (M–H)

$^1$H-NMR (300 MHz, DMSO-d$_6$, δ): 1.75–1.88(2H, m), 2.38(2H, t, J=10 Hz), 2.73–2.87(1H, m), 2.99–3.19(2H, m), 3.35–3.45(4H, m), 3.48–3.60(6H, m), 3.62–3.90(3H, m), 4.46–4.51(1H, m), 7.39–7.52(3H, m), 7.60–7.80(5H, m), 8.99(1H, s)

EXAMPLE 101

(2R)-1-(5-Phenylthiophene-2-sulfonyl)-4-(3-carbamoylpropane)sulfonyl-N-hydroxy-2-piperazinecarboxamide (25 mg) was obtained in substantially the same manner as in Example 5.

Mass (ESI-): 530 (M–H)

$^1$H-NMR (300 MHZ, CDCl$_3$, δ): 1.72–1.86(2H, m), 2.15 (2H, t, J=9 Hz), 2.55(2H, d, J=7 Hz), 2.72–2.85(2H, m), 2.99–3.08(2H, m), 3.52–3.60(1H, m), 3.69–3.90(2H, m), 4.45–4.49(1H, m), 7.39–7.49(3H, m), 7.60(1H, d, J=4 Hz), 7.59(1H, d, J=4 Hz), 7.71–7.80(2H, m), 8.96(1H, br)

EXAMPLE 102

(2R)-1-(5-Phenylthiophene-2-sulfonyl)-4-[3-(N-methylcarbamoyl)propane]sulfonyl-N-hydroxy-2-piperazinecarboxamide (105 mg) was obtained in substantially the same manner as in Example 5.

Mass (ESI-): 529 (M–H)

$^1$H-NMR (300 MHz, CDCl$_3$, δ): 1.72–1.84(2H, m), 2.14 (2H, t, J=9 Hz), 2.52(3H, d, J=6 Hz), 2.73–2.85(2H, m), 2.97–3.05(2H, m), 3.57(1H, d, J=13 Hz), 3.65–3.88(3H, m), 4.46(1H, bs), 7.38–7.49(3H, m), 7.59(1H, d, J=4 Hz), 7.67 (1H, d, J=4 Hz), 7.71–7.76(2H, m), 8.95(1H, bs)

EXAMPLE 103

(2R)-1-[5-(4-Methylphenyl)thiophene-2-sulfonyl]-4-methanesulfonyl-N-hydroxy-2-piperazinecarboxamide (166 mg) was obtained in substantially the same manner as in Example 5.

Mass (ESI-): 458 (M–H)

$^1$H-NMR (300 MHz, DMSO-d$_6$, δ): 2.34(3H, s), 2.69–2.81(1H, m), 2.86(3H, s), 2.98(1H, dd, J=4, 13 Hz), 3.50–3.60(1H, m), 3.71–3.85(3H, m), 4.46(1H, s), 7.28(1H, d, J=11 Hz), 7.53(1H, d, J=4 Hz), 7.54(1H, d, J=4 Hz), 7.57(1H, d, J=9 Hz), 8.97(1H, s)

EXAMPLE 104

(2R)-1-[5-(4-Fluorophenyl)thiophene-2-sulfonyl]-4-(1-propanesulfonyl)-N-hydroxy-2-piperazinecarboxamide (72 mg) was obtained in substantially the same manner as in Example 5.

Mass (ESI-): 490 (M–H)

$^1$H-NMR (300 MHz, DMSO-d$_6$, δ): 0.91(3H, t, J=7 Hz), 1.53–1.69(2H, m), 2.72–2.85(1H, m), 2.91–3.02(3H, m), 3.25–3.40(1H, m), 3.49–3.85(3H, m), 4.44(1H, s), 4.85–4.90(1H, m), 7.30(2H, dd, J=11, 11 Hz), 7.57(1H, d, J=4 Hz), 7.53–7.66(2H, m), 7.73–7.82(2H, m), 8.91–8.99 (1H, m)

EXAMPLE 105

(2R)-1-[5-(4-Nitrophenyl)thiophene-2-sulfonyl]-4-(1-propanesulfonyl)-N-hydroxy-2-piperazinecarboxamide (125 mg) was obtained in substantially the same manner as in Example 5.

Mass (ESI-): 489 (M–H)

$^1$H-NMR (300 MHz, DMSO-d$_6$, δ): 1.53–1.69(2H, m), 2.72–2.85(1H, m), 2.91–3.02(3H, m), 3.25–3.40(1H, m), 3.49–3.85(3H, m), 4.44(1H, s), 4.85–4.90(1H, m), 7.30(2H, dd, J=11, 11 Hz), 7.57(1H, d, J=4 Hz), 7.53–7.66(2H, m), 7.73–7.82(2H, m), 8.91–8.99(1H, m)

EXAMPLE 106

(2R)-N-Hydroxy-1-(5-phenylthiophene-2-sulfonyl)-4-[2-(2-pyridyl)ethanesulfonyl]-2-piperazinecarboxamide (89 mg) was obtained as crystals in substantially the same manner as in Example 5.

Mass (ESI-): 535 (M–H)

m.p. : 170–174° C.

$^1$H-NMR (300 MHz, DMSO-d$_6$, δ): 2.70–2.95(1H, m), 2.97–3.13(3H, m), 3.25–3.53(2H, m), 3.54–3.80(3H, m), 3.87(1H, d, J=12 Hz), 4.47(1H, brs), 7.24(1H, dd, J=4, 6 Hz), 7.34(1H, d, J=6 Hz), 7.37–7.52(3H,m), 7.61(1H, d, J=2 Hz), 7.68(1H, d, J=2 Hz), 7.71–7.78(3H, m), 8.46(1H, d, J=4 Hz)

EXAMPLE 107

(2R)-1-[5-(4-Fluorophenyl)thiophene-2-sulfonyl]-N-hydroxy-4-[3-(1-piperidino)propanesulfonyl]-2-piperazinecarboxamide hydrochloride (135 mg) was obtained as amorphous powder in substantially the same manner as in Example 5.

Mass (ESI-): 573 (M–H)

$^1$H-NMR (300 MHz, DMSO-d$_6$, δ): 1.25–1.45(2H, m), 1.60–1.85(4H, m), 1.95–2.10(2H, m), 2.73–2.93(3H, m), 2.97–3.10(3H, m), 3.10–3.30(3H, m), 3.59(1H, d, J=12 Hz), 3.65–3.80(2H, m), 3.86(1H, d, J=12 Hz), 4.49(1H, s), 7.33 (2H, t, J=8 Hz), 7.59(1H, d, J=2 Hz), 7.68(1H, d, J=2 Hz), 7.82(2H, dd, J=4, 8 Hz)

EXAMPLE 108

(2R)-1-[5-(4-Fluorophenyl)thiophene-2-sulfonyl]-N-hydroxy-4-[(N-phenyl)aminocarbonyl]-2-piperazinecarboxamide (118 mg) was obtained as crystals in substantially the same manner as in Example 5.

Mass (ESI-): 503 (M–H)

m.p.: 187–188° C.

$^1$H-NMR (300 MHz, DMSO-d$_6$, δ): 3.05(1H, m), 3.17 (1H, dd, J=3, 12 Hz), 3.60–3.80(2H, m), 3.94(1H, d, J=12 Hz), 4.69(1H, d, J=12 Hz), 4.33(1H, m), 6.91(1H, t, J=6 Hz), 7.18(2H, t, J=8 Hz), 7.30(2H, t, J=6 Hz), 7.36(2H, d, J=6 Hz), 7.58(1H, d, J=2 Hz), 7.69(1H, d, J=2 Hz), 7.78(2H, dd, J=4, 8 Hz), 8.47(1H, s), 8.95(1H, s)

EXAMPLE 109

(2R)-4-[(N-Cyclohexyl)aminocarbonyl]-1-[5-(4-fluorophenyl)thiophene-2-sulfonyl]-N-hydroxy-2- piperazinecarboxamide (117 mg) was obtained as crystals in substantially the same manner as in Example 5.

m.p.: 111–123° C.

Mass (ESI-): 509 (M–H)

$^1$H-NMR (300 MHz, DMSO-d$_6$, δ): 0.90–1.25(5H, m), 1.43–1.74(5H, m), 2.84(1H, m), 3.04(1H, dd, J=2, 12 Hz), 3.17–3.35(1H, m), 3.50–3.74(3H, m), 3.98(1H, d, J=12 Hz), 4.24(1H, s), 6.07(1H, d, J=6 Hz), 7.32(2H, t, J=8 Hz), 7.58(1H, d, J=2 Hz), 7.67(1H, d, J=2 Hz), 7.80(2H, dd, J=4, 8 Hz), 8.93(1H, s)

EXAMPLE 110

(2R)-4-Ethoxycarbonyl-1-[5-(4-fluorophenyl)thiophene-2-sulfonyl]-N-hydroxy-2-piperazinecarboxamide (85 mg) was obtained in substantially the same manner as in Example 5.

Mass (ESI-): 456 (M–H)

$^1$H-NMR (300 MHz, DMSO-d$_6$, δ): 1.13(3H, t, J=6 Hz), 2.94(1H, m), 3.18(1H, dd, J=2, 12 Hz), 3.75(2H, m), 3.75–3.95(1H, m), 3.94(2H, q, J=6 Hz), 4.07(1H, d, J=12 Hz), 4.26(1H, s), 7.33(2H, t, J=8 Hz), 7.58(1H, d, J=2 Hz), 7.61(1H, d, J=2 Hz), 7.81(2H, dd, J=4, 8 Hz), 8.93(1H, s)

EXAMPLE 111

(2R)-4-Dimethylcarbamoyl-1-[5-(4-fluorophenyl)thiophene-2-sulfonyl]-N-hydroxy-2-piperazinecarboxamide (85 mg) was obtained in substantially the same manner as in Example 5.

Mass (ESI-): 455 (M–H)

$^1$H-NMR (300 MHz, DMSO-d$_6$, δ): 2.65(6H, s), 2.60–2.75(1H, m), 2.89(1H, dd, J=2, 12 Hz), 3.30–3.50(1H, m), 3.57–3.95(3H, m), 4.34(1H, brs), 7.33(2H, t, J=8 Hz), 7.58(1H, d, J=2 Hz), 7.65(1H, d, J=2 Hz), 7.81(2H, dd, J=4, 8 Hz), 8.91(1H, brs)

EXAMPLE 112

(2R)-1-[5-(2-2luorophenyl)thiophene-2-sulfonyl]-4-methanesulfonyl-N-hydroxy-2-piperazinecarboxamide (291 mg) was obtained in substantially the same manner as in Example 5.

$^1$H-NMR (300 MHz, DMSO-d$_6$, δ): 2.73(1H, dt, J=6, 14 Hz), 2.85(3H, s), 3.00(1H, dd, J=6, 14 Hz), 3.53(1H, d, J=14 Hz), 3.67–3.86(3H, m), 4.46–4.51(1H, m), 7.34(1H, t, J=8 Hz), 7.43(1H, d, J=8 Hz), 7.49(1H, t, J=8 Hz), 7.65–7.74 (2H, m), 7.92(1H, t, J=8 Hz), 9.00(1H, brs)

Mass (ESI): 462 (M–1):

EXAMPLE 113

(2R)-N-Hydroxy-4-methanesulfonyl-1-(4-phenylthiazole-2-sulfonyl)-2-piperazinecarboxamide (88 mg) was obtained in substantially the same manner as in Example 5.

Mass (ESI): 445 (M–1)

$^1$H-NMR (300 MHz, DMSO-d$_6$, δ): 2.72–2.88(4H, m), 2.85(3H, s), 3.05(1H, dd, J=6, 14 Hz), 3.58(1H, d, J=14 Hz), 3.71–3.40(3H, m), 4.55–4.61(1H, m), 7.39–7.53(3H, m), 8.00(1H, d, J=8 Hz), 8.54(1H, s), 9.00(11, brs)

EXAMPLE 114

(2R)-4-(2-Benzyloxycarbonylaminoethanesulfonyl)-N-hydroxy-(5-phenylthiophene-2-sulfonyl)-2-piperazinecarboxamide (38 mg) was obtained in substantially the same manner as in Example 5.

Mass (ESI): 607 (M–1)

$^1$H-NMR (300 MHz, DMSO-d$_6$, δ): 2.70–2.90(3H, m), 3.05(1H, dd, J=6, 14 Hz), 3.12–3.20(2H, m), 3.57(1H, d, J=14 Hz), 3.64–3.78(2H, m), 3.83(1H, d, J=14 Hz), 4.42–4.50(1H, m), 4.90–4.98(1H, m), 5.02(2H, s), 7.28–7.51(8H, m), 7.60(1H, d, J=3 Hz), 7.68(1H, d, J=3 Hz), 7.74(2H, d, J=8 Hz), 8.98(1H, brs)

EXAMPLE 115

(2R)-N-Hydroxy-1-(5-phenylthiophene-2-sulfonyl)-4-[3-(1,2,4-triazolyl-3-thio)propanesulfonyl]-2-piperazinecarboxamide hydrochloride (78 mg) was obtained in substantially the same manner as in Example 5.

Mass (ESI): 571 (M–1)

$^1$H-NMR (300 MHz, DMSO-d$_6$, δ): 1.92–2.05(2H, m), 2.71–2.87(1H, m), 3.02(1H, dd, J=6, 14 Hz), 3.08–3.17(4H, m), 3.50–3.60(1H, m), 3.60–3.90(3H, m), 4.43–4.50(1H, m), 7.39–7.51(3H, m), 7.61(1H, d, J=3 Hz), 7.70(1H, d, J=3 Hz), 7.76(2H, d, J=8 Hz), 8.43(1H, brs)

EXAMPLE 116

(2R)-N-Hydroxy-1-[5-(3-isoxazolyl)thiophene-2-sulfonyl]-4-methanesulfonyl-2-piperazinecarboxamide (259 mg) was obtained in substantially the same manner as in Example 5.

Mass (ESI): 435 (M–1)

$^1$H-NMR (300 MHz, DMSO-d$_6$, δ): 2.76(1H, dt, J=6, 14 Hz), 2.87(3H, s), 3.01(1H, dd, J=6, 14 Hz), 3.54(1H, d, J=14 Hz), 3.65–3.85(3H, m), 4.46–4.51(1H, m), 7.12(1H, s), 7,75(1H, d, J=3 Hz), 7.79(1H, d, J=3 Hz), 8.76(1H, s), 9.00(1H, brs)

EXAMPLE 117

(2R)-N-Hydroxy-4-methanesulfonyl-1-[5-(4-trifluoromethylphenyl)thiophene-2-sulfonyl]-2-piperazinecarboxamide (164 mg) was obtained in substantially the same manner as in Example 5.

Mass (ESI): 512 (M–1)

$^1$H-NMR (300 MHz, DMSO-d$_6$, δ): 2.69–2.82(1H, m), 2.86(3H, s), 3.00(1H, dd, J=6, 14 Hz), 3.53(1H, d, J=14 Hz), 3.66–3.85(3H, m), 4.45–4.51(1H, m), 7.73(1H, d, J=3 Hz), 7.78(1H, d, J=3 Hz), 7.84(2H, d, J=8 Hz), 7.99(2H, d, J=8 Hz), 9.00(1H, brs)

EXAMPLE 118

(2R)-N-Hydroxy-4-methanesulfonyl-1-{5-[3,4-(methylenedioxy)phenyl]thiophene-2-sulfonyl}-2-piperazinecarboxamide (215 mg) was obtained in substantially the same manner as in Example 5.

Mass (ESI): 488 (M–1)

$^1$H-NMR (300 MHz, DMSO-d$_6$, δ): 2.67–2.79(1H, m), 2.86(3H, s), 2.98(1H, dd, J=6, 14 Hz), 3.52(1H, d, J=14 Hz), 3.68–3.76(2H, m), 3.81(1H, d, J=14 Hz), 4.42–4.48(1H, m), 6.10(2H, s), 7.00(1H, d, J=8 Hz), 7.23(1H, d, J=8 Hz), 7.48(1H, s), 7,50(1H, d, J=3 Hz), 7.63(1H, d, J=3 Hz), 9.00(1H, brs)

EXAMPLE 119

(2R)-1-[5-(4-Ethoxyphenyl)thiophene-2-sulfonyl]-4-methanesulfonyl-N-hydroxy-2-piperazinecarboxamide (128 mg) was obtained in substantially the same manner as in Example 5.

$^1$H-NMR (300 MHz, DMSO-d$_6$, δ): 1.32(3H, t, J=7 Hz), 2.68–2.80(1H, m), 2.86(3H, s), 2.96(1H, dd, J=4, 13 Hz), 3.51(1H, d, J=12 Hz), 3.69–3.76(2H, m), 3.80(1H, d, J=12 Hz), 4.07(2H, q, J=7 Hz), 4.43(1H, s), 7.00(2H, d, J=8 Hz), 7.44(1H, d, J=4 Hz), 7.63(1H, d, J=4 Hz), 7.68(1H, d, J=8 Hz), 8.99(1H, bs)

EXAMPLE 120

(2R)-1-[5-(4-Cyanophenyl)thiophene-2-sulfonyl]-N-hydroxy-4-methanesulfonyl-2-piperazinecarboxamide (203 mg) was obtained in substantially the same manner as in Example 5.

Mass (ESI): 469 (M−1)

$^1$H-NMR (300 MHz, DMSO-d$_6$, δ): 2.70–2.81(1H, m), 2.87(3H, s), 3.00(1H, dd, J=6, 14 Hz), 3.55(1H, d, J=14 Hz), 3.70–3.86(3H, m), 4.45–4.51(1H, m), 7.72(1H, d, J=3 Hz), 7.81(1H, d, J=3 Hz), 7.97(4H, s), 9.00(1H, brs)

EXAMPLE 121

(2R)-1-[5-(4-Cyanomethylphenyl)thiophene-2-sulfonyl]-N-hydroxy-4-methanesulfonyl-2-piperazinecarboxamide (146 mg) was obtained in substantially the same manner as in Example 5.

Mass (ESI): 483 (M−1)

$^1$H-NMR (300 MHz, DMSO-d$_6$, δ): 2.68–2.80(1H, m), 2.86(3H, s), 3.00(1H, dd, J=6, 14 Hz), 3.53(1H, d, J=14 Hz), 3.70–3.77(2H, m), 3.81(1H, d, J=14 Hz), 4.12(2H, s), 4.44–4.50(1H, m), 7,46(2H, d, J=8 Hz), 7.63(1H, d, J=3 Hz), 7.68(1H, d, J=3 Hz), 7.79(2H, d, J=8 Hz), 9.00(1H, brs)

EXAMPLE 122

(2R)-1-[5-(4-Acetoxymethylphenyl)thiophene-2-sulfonyl]-N-hydroxy-4-methanesulfonyl-2-piperazinecarboxamide (36 mg) was obtained in substantially the same manner as in Example 5.

Mass (ESI): 516 (M−1)

$^1$H-NMR (300 MHz, DMSO-d$_6$, δ): 2.10(3H, s), 2.68–2.80(1H, m), 2.87(3H, s), 3.00(1H, dd, J=6, 14 Hz), 3.49–3.59(1H, m), 3.70–3.85(3H, m), 4.43–4.50(1H, m), 5.11(2H, s), 7.46(2H, d, J=8 Hz), 7.62(1H, d, J=3 Hz), 7.67(1H, d, J=3 Hz), 7.76(2H, d, J=8 Hz), 9.00(1H, brs)

EXAMPLE 123

(2R)-1-[5-(3-Fluoro-4-methoxyphenyl)thiophene-2-sulfonyl]-4-methanesulfonyl-N-hydroxy-2-piperazinecarboxamide (315 mg) was obtained in substantially the same manner as in Example 5.

Mass (ESI−): 492 (M−H)

$^1$H-NMR (300 MHz, DMSO-d$_6$, δ): 2.68–2.80(1H, m), 2.85(3H, s), 2.92–3.02(1H, m), 3.53(1H, d, J=12 Hz), 3.70–3.78(2H, m), 3.81(1H, d, J=12 Hz), 3.89(3H, s), 4.44(1H, s), 7.25(1H, dd, J=11, 11 Hz), 7.48–7.59(2H, m), 7.65(1H, d, J=4 Hz), 7.70(1H, d, J=11 Hz), 9.01(1H, s)

EXAMPLE 124

(2R)-N-Hydroxy-4-methanesulfonyl-1-[5-(3-methoxyphenyl)thiophene-2-sulfonyl]-2-piperazinecarboxamide (239 mg) was obtained in substantially the same manner as in Example 5.

Mass (ESI): 474 (M−1)

$^1$H-NMR (300 MHz, DMSO-d$_6$, δ): 2.69–2.80(1H, m), 2.87(3H, s), 3.00(1H, dd, J=6, 14 Hz), 3.53(1H, d, J=14 Hz), 3.70–3.81(3H, m), 3.85(3H, s), 4.45–4.50(1H, m), 7.00(1H, d, J=8 Hz), 7.30(1H, d, J=8 Hz), 7.40(1H, t, J=8 Hz), 7.73(1H, d, J=3 Hz), 7.78(1H, d, J=3 Hz), 9.00(1H, brs)

EXAMPLE 125

(2R)-1-[5-(4-Dimethylaminosulfonylphenyl)thiophene-2-sulfonyl]-N-hydroxy-4-methanesulfonyl-2-piperazinecarboxamide (264 mg) was obtained in substantially the same manner as in Example 5.

Mass (ESI): 551 (M−1)

$^1$H-NMR (300 MHz, DMSO-d$_6$, δ): 2.64(6H, s), 2.71–2.82(1H, m), 2.88(3H, s), 3.00(1H, dd, J=6, 14 Hz), 3.56(1H, d, J=14 Hz), 3.71–3.87(3H, m), 4.47–4.51(1H, m), 7.72(1H, d, J=3 Hz), 7.79–7.86(3H, m), 8.03(2H, d, J=8 Hz), 9.00(1H, brs)

EXAMPLE 126

(2R)-N-Hydroxy-1-[5-(4-methanesulfonyloxyphenyl)thiophene-2-sulfonyl]-4-methanesulfonyl-2-piperazinecarboxamide (241 mg) was obtained in substantially the same manner as in Example 5.

Mass (ESI): 538 (M−1)

$^1$H-NMR (300 MHz, DMSO-d$_6$, δ): 2.68–2.80(1H, m), 2.86(3H, s), 2.99(1H, dd, J=6, 14 Hz), 3.43(3H, s), 3.53(1H, d, J=14 Hz), 3.68–3.84(3H, m), 4.45–4.50(1H, m), 7.46(2H, d, J=8 Hz), 7.63(1H, d, J=3 Hz), 7.70(1H, d, J=3 Hz), 7.88(2H, d, J=8 Hz), 9.00(1H, s)

EXAMPLE 127

(2R)-1-[5-(2,4-Difluorophenyl)thiophene-2-sulfonyl]-N-hydroxy-4-methanesulfonyl-2-piperazinecarboxamide (251 mg) was obtained in substantially the same manner as in Example 5.

Mass (ESI): 480 (M−1)

$^1$H-NMR (300 MHz, DMSO-d$_6$, δ): 2.68–2.80(1H, m), 2.88(3H, s), 3.00(1H, dd, J=6, 14 Hz), 3.53(1H, d, J=14 Hz), 3.67–3.90(3H, m), 4.47–4.51(1H, m), 7.22–7.30(1H, m), 7.45–7.50(1H, m), 7.67(1H, d, J=3 Hz), 7.72(1H, d, J=3 Hz), 7.94–8.04(1H, m), 9.00(1H, brs)

EXAMPLE 128

(2R)-1-[5-(4-Cyanomethoxyphenyl)thiophene-2-sulfonyl]-N-hydroxy-4-methanesulfonyl-2-piperazinecarboxamide (69 mg) was obtained in substantially the same manner as in Example 5.

Mass (ESI): 499 (M−1)

$^1$H-NMR (300 MHz, DMSO-d$_6$, δ): 2.67–2.80(1H, m), 2.86(3H, s), 3.98(1H, dd, J=6, 14 Hz), 3.52(1H, d, J=14 Hz), 3.69–3.88(3H, m), 4.43–4.50(1H, m), 5.26(2H, s), 7.12(2H, d, J=8 Hz), 7.54(1H, d, J=3 Hz), 7.67(1H, d, J=3 Hz), 7.77(2H, d, J=8 Hz), 9.00(1H, brs)

EXAMPLE 129

(2R)-N-Hydroxy-4-methanesulfonyl-1-[5-(4-methoxycarbonylphenyl)thiophene-2-sulfonyl]-2-piperazinecarboxamide (175 mg) was obtained in substantially the same manner as in Example 5.

Mass (ESI): 502 (M−1)

$^1$H-NMR (300 MHz, DMSO-d$_6$, δ): 2.69–2.83(1H, m), 2.88(3H, s), 3.00(1H, dd, J=6, 14 Hz), 3.54(1H, d, J=14 Hz), 3.70–3.86(3H, m), 3.90(3H, s), 4.45–4.52(1H, m), 7.71(1H, d, J=3 Hz), 7.78(1H, d, J=3 Hz), 7.92(2H, d, J=8 Hz), 8.05(2H, d, J=8 Hz), 9.00(1H, brs)

EXAMPLE 130

(2R)-1-[5-(4-Biphenylyl)thiophene-2-sulfonyl]-4-methanesulfonyl-N-hydroxy-2-piperazinecarboxamide (233 mg) was obtained in substantially the same manner as in Example 5.

Mass (ESI−): 520 (M−H)

¹H-NMR (300 MHz, DMSO-$d_6$, δ): 2.71–2.82(1H, m), 2.87(3H, s), 2.99(1H, dd, J=4, 8 Hz), 3.52(1H, d, J=12 Hz), 3.70–3.77(2H, m), 3.80(1H, d, J=12 Hz), 4.48(1H, s), 7.41 (1H, d, J=8 Hz), 7.48(1H, dd, J=8, 8 Hz), 7.62–7.85(6H, m)

EXAMPLE 131

(2R)-1-[5-(4-Pyridyl)thiophene-2-sulfonyl]-4-methanesulfonyl-N-hydroxy-2-piperazinecarboxamide (225 mg) was obtained in substantially the same manner as in Example 5.

Mass (ESI−): 486 (M−H)

¹H-NMR (300 MHz, DMSO-$d_6$, δ): 2.74–2.86(1H, m), 2.85(3H, s), 3.03–3.09(1H, m), 3.58(1H, d, J=12 Hz), 3.69–3.90(2H, m), 4.56(1H, s), 7 84(1H, d, J=4 Hz), 8.25 (1H, d, J=4 Hz), 8.36(2H, d, J=8 Hz), 8.94(11H, d, J=8 Hz)

EXAMPLE 132

(2R)-1-[5-(2,3-Dihydrobenzofuran-5-yl)thiophene-2-sulfonyl]-4-methanesulfonyl-N-hydroxy-2-piperazinecarboxamide (191 mg) was obtained in substantially the same manner as in Example 5.

Mass (ESI−): 486 (M−H)

¹H-NMR (300 MHz, DMSO-$d_6$, δ): 2.70–2.83(2H, m), 2.87(3H, s), 2.96(1H, dd, J=4, 8 Hz), 3.23(2H, t, J=10 Hz), 3.53(1H, d, J=12 Hz), 3.70–3.77(2H, m), 3 81(1H, d, J=12 Hz), 4.43(1H, s), 4.59(2H, t, J=10 Hz), 6.82(1H, d, J=8 Hz), 7.40(1H, d, J=4 Hz), 7.47(1H, d, J=8 Hz), 7.62(1H, d, J=8 Hz), 7.63(1H, s), 8.97(1H, bs)

EXAMPLE 133

(2R)-1-[5-(4-Phenoxyphenyl)thiophene-2-sulfonyl]-4-methanesulfonyl-N-hydroxy-2-piperazinecarboxamide (250 mg) was obtained in substantially the same manner as in Example 5.

Mass (ESI−): 536 (M−H)

¹H-NMR (300 MHz, DMSO-$d_6$, δ): 2.68–2.80(2H, m), 2.86(3H, s), 2.98(1H, dd, J=5, 13 Hz), 3.53(1H, d, J=13 Hz), 3.70–3.77(2H, m), 3.81(2H, d, J=12 Hz), 4 22(1H, d, J=13 Hz), 4.47(1H, bs), 7.03–7.09(4H, m), 7.20(1H, dd, J=8, 8 Hz), 7.42(2H, dd, J=8, 8 Hz), 7.52(1H, d, J=4 Hz), 7.67(1H, d, J=4 Hz), 7.77(2H, d, J=8 Hz), 8.99(1H, s)

EXAMPLE 134

(2R)-1-[5-(5-Methyl-1,3,4-oxadiazol-2-yl)thiophene-2-sulfonyl]-N-hydroxy-4-methanesulfonyl-2-piperazinecarboxamide (84 mg) was obtained in substantially the same manner as in Example 5.

Mass (ESI): 450 (M−1)

¹H-NMR (300 MHz, DMSO-$d_6$, δ): 2.59(3H, s), 2.68–2.80(1H, m), 2.88(3H, s), 2.98–3.06(1H, m), 3.50–3.59(1H, m), 3.68–3.85(3H, m), 4.48–4.52(1H, m), 7.72–7.75(1H, m), 7.78–7.82(1H, m), 8.97(1H, brs)

EXAMPLE 135

(2R)-1-[5-(5-Phenyl-1,3,4-oxadiazol-2-yl)thiophene-2-sulfonyl]-N-hydroxy-4-methanesulfonyl-2-piperazinecarboxamide (137 mg) was obtained in substantially the same manner as in Example 5.

Mass (ESI): 512 (M−1)

¹H-NMR (300 MHz, DMSO-$d_6$, δ): 2.70–2.83(1H, m), 2.88(3H, s), 3.04(1H, dd, J=6, 14 Hz), 3.57(1H, d, J=14 Hz), 3.68–3.90(3H, m), 4.51–4.56(1H, m), 7.60–7.72(3H, m), 7.84(1H, d, J→3 Hz), 8.01(1H, d, J=3 Hz), 8.13(H, d, J=8 Hz), 9.00(1H, brs)

EXAMPLE 136

(2R)-N-Hydroxy-4-methanesulfonyl-1-[5-(2-thiazolyl)thiophene-2-sulfonyl]-2-piperazinecarboxamide (93 mg) was obtained in substantially the same manner as in Example 5.

Mass (ESI): 451 (M−1)

¹H-NMR (300 MHz, DMSO-$d_6$, δ): 2.68–2.82(1H, m), 2.88(3H, s), 3.02(1H, dd, J=6, 14 Hz), 3.64(1H, d, J=14 Hz), 3.70–3.87(3H, m), 4.47–4.51(1H, m), 7.67(1H, d, J=3 Hz), 7.74(1H, d, J=3 Hz), 7.90(1H, d, J=2 Hz), 7.93(1H, d, J=2 Hz), 9.00(1H, brs)

EXAMPLE 137

(2R)-N-Hydroxy-4-methanesulfonyl-1-[5-phenyl-1,3,4-thiadiazol-2-sulfonyl]-2-piperazinecarboxamide (71 mg) was obtained in substantially the same manner as in Example 5.

Mass (ESI): 446 (M−1)

¹H-NMR (300 MHz, DMSO-$d_6$, δ): 2.82–2.95(4H, m), 3.17(1H, dd, J=6, 14 Hz), 3.61(1X, d, J=14 Hz), 3.73(1H, dt, J=6, 14 Hz), 3.88–4.01(2H, m), 4.58–4.63(1H, m), 7.69–7.70(3H, m), 8.10(2H, d, J=8 Hz), 9.05(1H, brs)

EXAMPLE 138

(2R)-N-Hydroxy-4-methanesulfonyl-1-[4-(thiophene-2-yl)benzenesulfonyl]-2-piperazinecarboxamide (166 mg) was obtained as crystals in substantially the same manner as in Example 5.

m.p.: 201–202° C.

Mass (ESI−): 444 (M−H)

¹H-NMR (300MHz, DMSO-$d_6$, δ): 2.66(1H, dt, J=2, 11 Hz), 2.83(3H, s), 2.93(1H, dd, J=2, 11 Hz), 3.49(1H, d, J=11Hz), 3.63(1H, dt, J=2, 11Hz), 3.70–3.85(2H, m), 4.46 (1H, brs), 7.21(1H, t, J=2 Hz), 7.67–7.77(2H, m), 7.81(2H, d, J=8 Hz), 7.88(2H, d, J=8 Hz), 8.97(1H, s)

EXAMPLE 139

(2R)-N-Hydroxy-4-[5-(isoxazol-3-yl)thiophene-2-sulfonyl]1-1(5-phenylthiophene-2-sulfonyl)-2-piperazinecarboxamide (153 mg) was obtained in substantially the same manner as in Example 5.

m.p.: 204° C.

Mass (ESI−): 579 (M−H)

¹H-NMR (300 MHz, DMSO-$d_6$, δ): 2.12–2.28(1H, m), 2.38(1H, dd, J=6, 14 Hz), 3.48–3.59(1H, d, J=14 Hz), 3.62–3.78(1H, m), 3.80–4.01(2H, m), 4.58–4.62(1H, m), 6.95(1H, s), 7.34–7.42(3H, m), 7.45(1H, d, J=6 Hz), 7.52–7.78(5H, m), 8.72(1H, s), 9.08(1H, brs)

EXAMPLE 140

(2R)-N-Hydroxy-1-(5-phenylthiophene-2-sulfonyl)-4-(1-piperidinesulfonyl)-2-piperazinecarboxamide (126 mg) was obtained as an amorphous powder in substantially the same manner as in Example 5.

Mass (ESI−): 513 (M−H)

¹H-NMR (300 MHz, DMSO-$d_6$, δ): 1.24–1.48(6H, m), 2.48–2.62(1H, m), 2.73(1H, dd, J=3, 12 Hz), 2.94–3.08(4H, m), 3.37–3.98(1H, m), 3.52–3.97(3H, m), 4.49(1H, brs), 7.38–7.52(3H, m), 7.58–7.68(1H, m), 7.72–7.80(3H, m), 8.98(1H, brs)

EXAMPLE 141

(2R)-N-Hydroxy-4-(N-methylpropylaminosulfonyl)-1-(5-phenylthiophene-2-sulfonyl)-2-piperazinecarboxamide (140 mg) was obtained as an amorphous powder in substantially the same manner as in Example 5.

Mass (ESI-): 501 (M–H)

$^1$H-NMR (300 MHz, DMSO-d$_6$, δ): 0.78(3H, t, J=8 Hz), 1.37–1.50(2H, m), 2.52–2.70(1H, m), 2.16(3H, s), 2.78(1H, dd, J=4, 12 Hz), 3.00(2H, t, J=8 Hz), 3.30–3.45(1H, m), 3.56–3.97(3H, m), 4.48(1H, brs), 7.38–7.52(3H, m), 7.59–7.67(1H, m), 7.70–7.79(3H, m), 8.97(1H, s)

EXAMPLE 142

(2R)-4-(N,N-Dimethylaminosulfonyl)-N-hydroxy-1-(5-phenylthiophene-2-sulfonyl)-2-piperazinecarboxamide (124 mg) was obtained as an amorphous powder in substantially the same manner as in Example 5.

Mass (ESI-): 473 (M–H)

$^1$H-NMR (300 MHz, DMSO-d$_6$, δ): 2.62–2.74(1H, m), 2.68(6H, s), 2.82–2.91(1H, m), 3.39–3.49(1H, m), 3.60–3.82(3H, m), 4.46(1H, brs), 7.38–7.52(3H, m), 7.58–7.65(1H, m), 7.68–7.78(3H, m), 8.97(1H, s)

EXAMPLE 143

(2R)-N-Hydroxy-1-(5-phenylthiophene-2-sulfonyl)-4-[3-(thiazolyl-2-thio)propanesulfonyl]-2-piperazinecarboxamide (109 mg) was obtained in substantially the same manner as in Example 5.

Mass (ESI-): 587 (M–H)

$^1$H-NMR (300 MHz, DMSO-d$_6$, δ): 2.03(2H, m), 2.80 (1H, dt, J=2, 11 Hz), 3.02(1H, dd, J=2, 11 Hz), 3.15(2H, t, J=4 Hz), 3.25(2H, t, J=4 Hz), 3.56(1H, d, J=11 Hz), 3.60–3.80(2H, m), 3.84(1H, d, J=11 Hz), 4.47(1H, brs), 7.38–7.53(3H, m), 7.62(1H, d, J=2 Hz), 7.65–7.70(2H, m), 7.71–7.79(3H, m)

EXAMPLE 144

(2R)-N-Hydroxy-4-[3-(4-methyl-1,2,4-triazolyl-3-thio)propanesulfonyl]-1-(5-phenylthiophene-2-sulfonyl)-2-piperazinecarboxamide hydrochloride (91 mg) was obtained in substantially the same manner as in Example 5.

Mass (ESI-): 585 (M–H)

$^1$H-NMR (300 MHz, DMSO-d$_6$, δ): 2.00(2H, m), 2.80 (1H, dt, J=2, 11 Hz), 3.03(1H, dd, J=2, 11 Hz), 3.10–3.24 (4H, m), 3.56(1H, d, J=11 Hz), 3.60(3H, s), 3.64–3.80(2H, m), 3.85(1H, d, J=11 Hz), 4.48(1H, brs), 7.38–7.53(3H, m), 7.63(1H, d, J=2 Hz), 7.69(1H, d, J=2 Hz), 7.71–7.79(2H, m), 8.98(1H, s)

EXAMPLE 145

(2R)-N-Hydroxy-4-[3-(imidazolyl-2-thio)propanesulfonyl]-1-(5-phenylthiophene-2-sulfonyl)-2-piperazinecarboxamide hydrochloride (90 mg) was obtained in substantially the same manner as in Example 5.

Mass (ESI-): 570 (M–H)

$^1$H-NMR (300 MHz, DMSO-d$_6$, δ): 1.86(2H, m), 2.81 (1H, dt, J=2, 11 Hz), 3.04(1H, dd, J=2, 11 Hz), 3.15(2H, t, J=4 Hz), 3.23(2H, t, J=4 Hz), 3.30–3.70(1H, overlapping with H$_2$O), 3.65–3.80(2H, m), 3.84(1H, d, J=11 Hz), 4.48 (1H, brs), 7.38–7.50(3H, m), 7.63(1H, d, J=2 Hz), 7.68(1H, d, J=2 Hz), 7.70–7.79(4H, m)

EXAMPLE 146

(2R)-N-Hydroxy-4-methoxycarbonyl-1-(5-phenylthiophene-2-sulfonyl)-2-piperazinecarboxamide (110 mg) was obtained as an amorphous powder in substantially the same manner as in Example 5.

Mass (ESI-): 424 (M–H)

$^1$H-NMR (300 MHz, DMSO-d$_6$, δ): 2.85–3.07(1H, m), 3.12–3.25(1H, m), 3.52(3H, s), 3.56–3.93(3H, m), 4.01–4.11(1H, m), 4.29(1H, brs), 7.36–7.52(3H, m), 7.57–7.68(2H, m), 7.77(2H, d, J=8 Hz), 8.95(1H, brs)

EXAMPLE 147

(2R)-4-Ethylaminocarbonyl-N-hydroxy-1-(5-phenylthiophene-2-sulfonyl)-2-piperazinecarboxamide (108 mg) was obtained as an amorphous powder in substantially the same manner as in Example 5.

Mass (ESI-): 437 (M–H)

$^1$H-NMR (300 MHz, DMSO-d$_6$, δ): 0.93(3H, t, J=7 Hz), 2.76–3.10(4H, m), 3.50–3.78(3H, m), 3.95–4.08(1H, m), 4.28(1H, brs), 6.35–6.47(1H, m), 7.35–7.52(2H, m), 7.61 (1H, d, J=3 Hz), 7.68(1H, d, J=3 Hz), 7.75(2H, d, J=8 Hz), 8.93(1H, brs)

EXAMPLE 148

(2R)-1-[5-(4-Fluorophenyl)thiophene-2-sulfonyl]-N-hydroxy-4-[3-(1,2,4-triazolyl-3-thio)propanesulfonyl]-2-piperazinecarboxamide hydrochloride (102 mg) was obtained in substantially the same manner as in Example 5.

Mass (ESI-): 589 (M–H)

$^1$H-NMR (300 MHz, DMSO-d$_6$, δ): 1.99(2H, m), 2.79 (1H, dt, J=2, 11 Hz), 3.03(1H, dd, J=2, 11 Hz), 3.05–3.20 (4H, m), 3.55(1H, d, J=11 Hz), 3.60–3.70(2H, m), 3.84(1H, d, J=11 Hz), 4.46(1H, brs), 7.33(2H, t, J=8 Hz), 7.59(1H, d, J=2 Hz), 7.68(1H, d, J=2 Hz), 7.80(2H, dd, J=4, 8 Hz), 8.45(1H, s)

EXAMPLE 149

(2R)-1-[5-(4-Fluorophenyl)thiophene-2-sulfonyl]-N-hydroxy-4-[3-(4-methyl-1,2,4-triazolyl-3-thio)propanesulfonyl]-2-piperazinecarboxamide hydrochloride (88 mg) was obtained as an amorphous powder in substantially the same manner as in Example 5.

Mass (ESI-): 603 (M–H)

$^1$H-NMR (300 MHz, DMSO-d$_6$, δ): 1.93–2.08(2H, m), 2.72–2.88(1H, m), 3.03(1H, dd, J=6, 14 Hz), 3.10–3.25(4H, m), 3.48–3.90(4H, m), 3.62(3H, s), 4.48(1H, brs), 7.33(2H, t, J=8 Hz), 7.60(1H, d, J=4 Hz), 7.69(1H, d, J=4 Hz), 7.77–7.86(2H, m), 8.98(1H, s)

EXAMPLE 150

(2R)-1-[5-(4-Fluorophenyl)thiophene-2-sulfonyl]-N-hydroxy-4-[3-(imidazolyl-2-thio)propanesulfonyl]-2-piperazinecarboxamide hydrochloride (73 mg) was obtained in substantially the same manner as in Example 5.

Mass (ESI-): 588 (M–H)

$^1$H-NMR (300 MHz, DMSO-d$_6$, δ): 1.87(2H, m), 2.82 (1H, dt, J=2, 11 Hz), 3.04(1H, dd, J=2, 11 Hz), 3.17(2H, t, J=4 Hz), 3.25(2H, t, J=4 Hz), 3.50–3.90(4H, m), 4.48(1H, s), 7.34(2H, t, J=8 Hz), 7.60(1H, d, J=2 Hz), 7.68(1H, d, J=2 Hz), 7.73(2H, s), 7.82(2H, dd, J=4, 8 Hz)

EXAMPLE 151

(2R)-4-[3-(Benzimidazolyl-2-thio)propanesulfonyl]-1-[5-(4-fluorophenyl)thiophene-2-sulfonyl]-N-hydroxy-2-piperazinecarboxamide hydrochloride (79 mg) was obtained in substantially the same manner as in Example 5.

Mass (ESI−): 638 (M−H)

¹H-NMR (300 MHz, DMSO-d₆, δ): 2.08(2H, m), 2.83 (1H, dt, J=2, 11 Hz), 3.06(1H, dd, J=2, 11 Hz), 3.23(2H, t, J=4 Hz), 3.44(2H, t, J=4 Hz), 3.58(1H, d, J=11 Hz), 3.64–3.80(2H, m), 3.85(1H, d, J=11 Hz), 4.47(1H, s), 7.25–7.37(4H, m), 7.54–7.63(2H, m), 7.66(1H, d, J=2 Hz), 7.80(2H, dd, J=4, 8 Hz)

EXAMPLE 152

(2R)-1-[5-(4-Fluorophenyl)thiophene-2-sulfonyl]-N-hydroxy-4-(pyridine-3-sulfonyl)-2-piperazinecarboxamide (110 mg) was obtained as an amorphous powder in substantially the same manner as in Example 5.

Mass (ESI−): 525 (M−H)

¹H-NMR (300 MHz, DMSO-d₆, δ): 1.98–2.12(1H, m), 1.98–2.11(1H, m), 2.20–2.31(1H, m), 3.65–3.85(2H, m), 3.96(1H, d, J=15 Hz), 4.49–4.56(1H, m), 7.35(2H, t, J=8 Hz), 7.44(1H, d, J=5 Hz), 7.47–7.54(1H, m), 7.62(1H, d, J=5 Hz), 7.71(1H, d, J=5 Hz), 7.73(1H, d, J=5 Hz), 8.01(1H, m), 8.62(1H, d, J=5 Hz), 8.78(1H, brs)

EXAMPLE 153

(2R)-4-(N-Ethylaminosulfonyl)-1-[5-(4-fluorophenyl)thiophene-2-sulfonyl]-N-hydroxy-2-piperazinecarboxamide (143 mg) was obtained as an amorphous powder in substantially the same manner as in Example 5.

Mass (ESI): 491 (M−H)

¹H-NMR (300 MHz, DMSO-d₆, δ): 0.94(3H, t, J=7 Hz), 2.45(1H, dd, J=3, 8 Hz), 2.72–2.87(2H, m), 3.23–3.42(1H, m), 3.58–3.91(3H, m), 4.15–4.41(1H, m), 4.48(1H, brs), 7.26–7.38(2H, m), 7.61(1H, d, J=3 Hz), 7.72(1H, d, J=3 Hz), 7.76–7.85(2H, m), 8.94(1H, s)

EXAMPLE 154

(2R)-1-[5-(4-Fluorophenyl)thiophene-2-sulfonyl]-N-hydroxy-4-(1-piperidinesulfonyl)-2-piperazinecarboxamide (157 mg) was obtained as an amorphous powder in substantially the same manner as in Example 5.

Mass (ESI−): 531 (M−H)

¹H-NMR (300 MHz, DMSO-d₆, δ): 1.28–1.52(6H, m), 2.52–2.64(1H, m), 2.75(1H, dd, J=3, 12 Hz), 2.95–3.08(4H, m), 3.85–3.96(1H, m), 3.50–3.96(3H, m), 4.45–4.51(1H, m), 7.33(2H, t, J=8 Hz), 7.62(1H, d, J=6 Hz), 7.74(1H, d, J=6 Hz), 7.82(1H, d, J=6 Hz), 7.85(1H, d, J=6 Hz), 8.98(1H, brs)

EXAMPLE 155

(2R)-1-[5-(4-Fluorophenyl)thiophene-2-sulfonyl]-N-hydroxy-4-[N-methyl-N-(methoxycarbonylmethyl)aminosulfonyl]-2-piperazinecarboxamide (68 mg) was obtained as an amorphous powder in substantially the same manner as in Example 5.

Mass (ESI−): 549 (M−H)

¹H-NMR (300 MHz, DMSO-d₆, δ): 2.58–2.73(1H, m), 2.76(3H, s), 2.82–2.93(1H, m), 3.41–3.51(1H, m), 3.58–3.83(3H, m), 3.36(3H, s), 4.45(1H, brs), 7.33(2H, t, J=8 Hz), 7.56–7.64(1H, m), 7.67–7.73(1H, m), 7.75–7.86(2H, m), 8.97(1H, brs)

EXAMPLE 156

(2R)-4-[N-(Aminocarbonylmethyl)aminocarbonyl]-1-[5-(4-fluorophenyl)thiophene-2-sulfonyl]-N-hydroxy-2-piperazinecarboxamide (69 mg) was obtained as an amorphous powder in substantially the same manner as in Example 5.

Mass (ESI−): 484 (M−H)

¹H-NMR (300 MHz, DMSO-d₆, δ): 2.89(1H, dt, J=2, 11 Hz), 3.06(1H, dd, J=2, 12 Hz), 3.50–3.60(2H, m), 3.50–3.71(2H, m), 3.83(1H, d, J=12 Hz), 4.10(1H, d, J=12 Hz), 4.28(1H, brs), 6.81(1H, t, J=4 Hz), 6.95(1H, s), 7.08(1H, s), 7.33(2H, t, J=8 Hz), 7.59(1H, d, J=2 Hz), 7.68(1H, d, J=8 Hz), 7.82(2H, dd, J=4, 8 Hz), 8.95(1H, s)

EXAMPLE 157

(2R)-1-[5-(4-Fluorophenyl)thiophene-2-sulfonyl]-N-hydroxy-4-[N-(2-hydroxyethyl)aminocarbonyl]-2-piperazinecarboxamide (138 mg) was obtained in substantially the same manner as in Example 5.

Mass (ESI−): 471 (M−H)

¹H-NMR (300 MHz, DMSO-d₆, δ): 2.85(1H, dt, J=2, 11 Hz), 2.95–3.05(3H, m), 3.25–3.40(2H, m), 3.52–3.65(2H, m), 3.74(1H, d, J=11 Hz), 4.06(1H, d, J=11 Hz), 4.28(1H, t, J=2 Hz), 6.46(1H, t, J=4 Hz), 7.32(2H, t, J=8 Hz), 7.58(1H, d, J=2 Hz), 7.67(1H, d, J=2 Hz), 7.81(2H, dd, J=4, 8 Hz), 8.94(1H, s)

EXAMPLE 158

(2R)-4-Ethylaminosulfonyl-N-hydroxy-1-[5-(4-trifluoromethyl-phenyl)thiophene-2-sulfonyl]-2-piperazinecarboxamide (32 mg) was obtained as an amorphous powder in substantially the same manner as in Example 5.

Mass (ESI−): 541 (M−H)

¹H-NMR (300 MHz, DMSO-d₆, δ): 0.95(3H, t, J=8 Hz), 2.40–2.49(1H, m), 2.60–2.69(1H, m), 2.73–2.85(2H, m), 3.33–3.42(1H, m), 3.59–3.87(3H, m), 4.48–4.54(1H, m), 7.32(1H, t, J=8 Hz), 7.74–7.88(4H, m), 7.94–8.02(2H, m), 8.96(1H, brs)

EXAMPLE 159

(2R)-N-Hydroxy-4-(N-methylpropylaminosulfonyl)-1-[5-(4-trifluoromethylphenyl)thiophene-2-sulfonyl]-2-piperazinecarboxamide (170 mg) was obtained as an amorphous powder in substantially the same manner as in Example 5.

Mass (ESI−): 569 (M−H)

¹H-NMR (300 MHz, DMSO-d₆, δ): 0.88(3H, t, J=8 Hz), 1.48–1.65(2H, m), 2.59–2.75(2H, m), 2.78(3H, s), 3.14(2H, t, J=8 Hz), 3.38–3.52(2H, m), 3.93–4.10(2H, m), 4.70(1H, brs), 7.38(1H, d, J=3 Hz), 7.66(1H, d, J=3 Hz), 7.71(4H, m), 9.43(1H, s)

EXAMPLE 160

(2R)-4-(N,N-Dimethylaminosulfonyl)-N-hydroxy-1-[5-(4-trifluoromethylphenyl)thiophene-2-sulfonyl]-2-piperazinecarboxamide (106 mg) was obtained as an amorphous powder in substantially the same manner as in Example 5.

Mass (ESI−): 541 (M−H)

¹H-NMR (300 MHz, DMSO-d₆, δ): 2.68–2.77(1H, m), 2.69(6H, s), 2.92(1H, dd, J=3, 12 Hz), 3.42–3.51(1H, m), 3.61–3.82(3H, m), 4.49(1H, brs), 7.75(1H, d, J=4 Hz), 7.79–7.87(4H, m), 7.95–8.02(2H, m), 8.97(1H, brs)

EXAMPLE 161

(2R)-1-[5-(4-Chlorophenyl)thiophene-2-sulfonyl]-4-(N,N-dimethylaminosulfonyl)-N-hydroxy-2-piperazinecarboxamide (136 mg) was obtained as an amorphous powder in substantially the same manner as in Example 5.

Mass (ESI−): 507, 509 (M−H)

$^1$H-NMR (300 MHz, DMSO-d$_6$, δ): 2.60–2.76(1H, m), 2.76(6H, s), 2.88(1H, dd, J=4, 12 Hz), 3.40–3.51(1H, m), 3.56–3.81(3H, m), 4.46(1H, brs), 7.55(2H, d, J=8 Hz), 7.62–7.73(2H, m), 7.80(2H, d, J=8 Hz), 8.97(1H, s)

EXAMPLE 162

(2R)-1-[5-(4-Chlorophenyl)thiophene-2-sulfonyl]-N-hydroxy-4-(N-methylethylaminosulfonyl)-2-piperazinecarboxamide (110 mg) was obtained in substantially the same manner as in Example 5.

m.p.: 170–172° C.

Mass (ESI−): 521, 523 (M−H)

$^1$H-NMR (300 MHz, DMSO-d$_6$, δ): 1.02(3H, t, J=7 Hz), 2.53–2.64(1H, m), 2.67(3H, m), 2.78(1H, dd, J=3, 12 Hz), 3.08(2H, q, J=7 Hz), 3.35–3.45(1H, m), 3.58–3.82(3H, m), 4.44–4.49(1H, m), 7.54(2H, d, J=8 Hz), 7.68(1H, d, J=3 Hz), 7.73(1H, d, J=3 Hz), 7.76–7.83(2H, m), 8.97(1H, brs)

EXAMPLE 163

(2R)-1-[5-(4-Chlorophenyl)thiophene-2-sulfonyl]-N-hydroxy-4-[3-(1,2,4-triazolyl-3-thio)propanesulfonyl]-2-piperazinecarboxamide hydrochloride (122 mg) was obtained as an amorphous powder in substantially the same manner as in Example 5.

Mass (ESI−): 605, 607 (M−H)

$^1$H-NMR (300 MHz, DMSO-d$_6$, δ): 1.92–2.08(2H, m), 2.78–2.89(1H, m), 3.04(1H, dd, J=6, 14 Hz), 3.07–3.20(4H, m), 3.50–3.88(4H, m), 4.47(1H, brs), 7.55(2H, d, J=8 Hz), 7.60–7.72(2H, m), 7.78(2H, d, J=8 Hz), 8.46(1H, brs)

EXAMPLE 164

(2R)-1-[5-(4-Chlorophenyl)thiophene-2-sulfonyl]-N-hydroxy-4-[3-(4-methyl-1,2,4-triazolyl-3-thio)propanesulfonyl]-2-piperazinecarboxamide hydrochloride (70 mg) was obtained as an amorphous powder in substantially the same manner as in Example 5.

Mass (ESI−): 619, 621 (M−H)

$^1$H-NMR (300 MHz, DMSO-d$_6$, δ): 1.92–2.08(2H, m), 2.72–2.90(1H, m), 3.03(1H, dd, J=6, 14 Hz), 3.10–3.26(4H, m), 3.50–3.90(4H, m), 3.61(3H, s), 4.48(1H, brs), 7.53(2H, d, J=8 Hz), 7.61–7.72(2H, m), 7.79(2H, d, J=8 Hz), 9.04(1H, brs)

EXAMPLE 165

(2R)-1-[5-(4-Chlorophenyl)thiophene-2-sulfonyl]-N-hydroxy-4-[3-(imidazolyl-2-thio)propanesulfonyl]-2-piperazinecarboxamide hydrochloride (67 mg) was obtained as an amorphous powder in substantially the same manner as in Example 5.

Mass (ESI−): 604, 606 (M−H)

$^1$H-NMR (300 MHz, DMSO-d$_6$, δ): 1.79–1.94(2H, m), 2.74–2.90(1H, m), 3.06(1H, dd, J=6, 14 Hz), 3.12–3.29(4H, m), 3.35–3.88(4H, m), 4.99(1H, brs), 7.54(2H, d, J=8 Hz), 7.62–7.75(4H, m), 7.82(2H, d, J=8 Hz)

EXAMPLE 166

(2R)-4-[3-(Benzimidazolyl-2-thio)propanesulfonyl]-1-[5-(4-chlorophenyl)thiophene-2-sulfonyl]-N-hydroxy-2-piperazinecarboxamide hydrochloride (75 mg) was obtained as an amorphous powder in substantially the same manner as in Example 5.

$^1$H-NMR (300 MHz, DMSO-d$_6$, δ): 1.98–2.16(2H, m), 2.78–2.93(1H, m), 3.09(1H, dd, J=6, 14 Hz), 3.17–3.28(2H, m), 3.38–3.51(2H, m), 3.54–3.92(4H, m), 4.49(1H, brs), 7.30–7.39(2H, m), 7.55(2H, d, J=8 Hz), 7.58–7.71(4H, m), 7.75–7.82(2H, m)

Mass (ESI−): 654, 656 (M−H)

EXAMPLE 167

(2R)-1-[5-(4-Chlorophenyl)thiophene-2-sulfonyl]-N-hydroxy-4-methoxycarbonyl-2-piperazinecarboxamide (98 mg) was obtained as an amorphous powder in substantially the same manner as in Example 5.

Mass (ESI−): 458, 460 (M−H)

$^1$H-NMR (300 MHz, DMSO-d$_6$, δ): 2.83–3.08(1H, m), 3.12–3.27(1H, m), 3.49–3.92(3H, m), 3.50(3H, s), 4.00–4.13(1H, m), 4.22–4.34(1H, m), 7.54(2H, d, J=8 Hz), 7.66(2H, s), 7.78(2H, d, J=8 Hz), 8.95(1H, brs)

EXAMPLE 168

(2R)-4-(N,N-Dimethylaminosulfonyl)-1-[5-(4-ethoxyphenyl)-thiophenesulfonyl]-N-hydroxy-2-piperazinecarboxamide (254 mg) was obtained in substantially the same manner as in Example 5.

Mass (ESI−): 517 (M−H)

$^1$H-NMR (300 MHz, DMSO-d$_6$, δ): 1.18(3H, t, J=7 Hz), 2.69–2.79(2H, m), 2.85(3H, s), 3.50–3.59(1H, m), 3.70–3.86(3H, m), 4.03(2H, q, J=7 Hz), 4.45(1H, bs), 7.23(1H, dd, J=10, 10 Hz), 7.49–7.59(2H, m), 7.63(1H, d, J=4 Hz), 7.70(1H, d, J=10 Hz), 9.00(1H, s)

EXAMPLE 169

(2R)-1-[5-(4-Ethoxyphenyl)thiophene-2-sulfonyl]-N-hydroxy-4-[3-(1,2,4-triazolyl-3-thio)propanesulfonyl]-2-piperazinecarboxamide hydrochloride (107 mg) was obtained in substantially the same manner as in Example 5.

Mass (ESI−): 615 (M−H)

$^1$H-NMR (300 MHz, CDCl$_3$, δ): 1.35(3H, t, J=4 Hz), 1.99(2H, m), 2.28(1H, dt, J=2, 11 Hz), 3.02(1H, dd, J=2, 12 Hz), 3.05–3.20(4H, m), 3.54(1H, d, J=12 Hz), 3.63–3.79 (2H, m), 3.84(1H, d, J=12 Hz), 4.0(2H, q, J=4 Hz), 4.45(1H, brs), 7.01(2H, d, J=8 Hz), 7.47(1H, d, J=2 Hz), 7.64(1H, d, J=2 Hz), 7.67(2H, d, J=8 Hz), 8.45(1H, s)

EXAMPLE 170

(2R)-1-[5-(4-Ethoxyphenyl)thiophene-2-sulfonyl]-N-hydroxy-4-[3-(4-methyl-1,2,4-triazolyl-3-thio)propanesulfonyl]-2-piperazinecarboxamide hydrochloride (84 mg) was obtained in substantially the same manner as in Example 5.

Mass (ESI−): 629 (M−H)

$^1$H-NMR (300 MHz, CDCl$_3$, δ): 1.35(3H, t, J=4 Hz), 1.99(2H, m), 2.28(1H, dt, J=2, 11 Hz), 3.02(1H, dd, J=2, 12 Hz), 3.10–3.24(4H, m), 3.54(1H, d, J=12 Hz), 3.58(3H, s), 3.63–3.79(2H, m), 3.84(1H, d, J=12 Hz), 4.0(2H, q, J=4 Hz), 4.46(1H, brs), 7.01(2H, d, J=8 Hz), 7.48(1H, d, J=2 Hz), 7.65(1H, d, J=2 Hz), 7.68(2H, d, J=8 Hz), 8.88(1H, s)

EXAMPLE 171

(2R)-1-[5-(4-Ethoxyphenyl)thiophene-2-sulfonyl]-N-hydroxy-4-[3-(imidazolyl-2-thio)propanesulfonyl]-2-piperazinecarboxamide hydrochloride (91 mg) was obtained in substantially the same manner as in Example 5.

Mass (ESI−): 614 (M−H)

$^1$H-NMR (300 MHz, DMSO-d$_6$, δ): 1.35(3H, t, J=4 Hz), 1.86(2H, m), 2.80(1H, dt, J=2, 11 Hz), 3.02(1H, dd, J=2, 11

Hz), 3.18(2H, t, J=4 Hz), 3.23(2H, t, J=4 Hz), 3.30–3.60(1H, overlapping with H₂O), 3.60–3.75(2H, m), 3.83(1H, d, J=11 Hz), 4.08(2H, q, J=4 Hz), 4.47(1H, brs), 7.01(2H, d, J=8 Hz), 7.48(1H, d, J=2 Hz), 7.64(1H, d, J=2 Hz), 7.66(2H, d, J=8 Hz), 7.70(2H, s)

EXAMPLE 172

(2R)-1-[5-(4-Cyanophenyl)thiophene-2-sulfonyl]-4-(N,N-dimethylaminosulfonyl)-N-hydroxy-2-piperazinecarboxamide (72 mg) was obtained as an amorphous powder in substantially the same manner as in Example 5.

Mass (ESI–): 498 (M–H)

¹H-NMR (300 MHz, DMSO-d₆, δ): 2.68(6H, s), 2.71–2.79(1H, m), 2.92(1H, dd, J=4, 14 Hz), 3.42–3.52(1H, m), 3.59–3.83(3H, m), 4.46(1H, brs), 7.74(1H, d, J=3 Hz), 7.82(1H, d, J=3 Hz), 7.96(4H, s), 8.96(1H, s)

EXAMPLE 173

(2R)-1-[5-(4-Cyanomethylphenyl)thiophene-2-sulfonyl]-4-(N,N-dimethylaminosulfonyl)-N-hydroxy-2-piperazinecarboxamide (62 mg) was obtained in substantially the same manner as in Example 5.

m.p.: 170–172° C.

Mass (ESI–): 512 (M–H)

¹H-NMR (300 MHz, DMSO-d₆, δ): 2.13–2.25(1H, m), 2.18(6H, s), 2.88(1H, dd, J=4, 14 Hz), 3.41–3.51(1H, m), 3.62–3.82(3H, m), 4.11(2H, s), 4.43–4.49(1H, m), 7.47(2H, d, J=8 Hz), 7.65(1H, d, J=4 Hz), 7.72(1H, d, J=4 Hz), 7.80(2H, d, J=8 Hz), 8.97(1H, s)

EXAMPLE 174

(2R)-4-(N,N-Dimethylaminosulfonyl)-1-[5-(3-fluoro-4-methoxyphenyl)-thiophene-2-sulfonyl]-N-hydroxy-2-piperazinecarboxamide (295 mg) was obtained in substantially the same manner as in Example 5.

ESI Mass : 521 (M–1)

¹H-NMR (300 MHz, DMSO-d₆, δ): 2.61–2.73(1H, m), 2.69(6H, s), 2.88(1H, dd, J=4, 14 Hz), 3.45(1H, d, J=14 Hz), 3.61–3.80(3H, m), 3.90(1H, s), 4.43–4.48(1H, m), 7.26(1H, t, J=8 Hz), 7.54(1H, d, J=8 Hz), 7.59(1H, d, J=3 Hz), 7.69(1H, d, J=3 Hz), 7.72(1H, d, J=10 Hz), 8.98(1H, s)

EXAMPLE 175

(2R)-4-(N,N-Dimethylaminosulfonyl)-N-hydroxy-1-(4-methoxybenzenesulfonyl)-2-piperazinecarboxamide (70 mg) was obtained as an amorphous powder in substantially the same manner as in Example 5.

Mass (ESI–): 421 (M–H)

¹H-NMR (300 MHz, DMSO-d₆, δ): 2.42–2.58(1H, m), 2.68(6H, s), 2.69–2.76(1H, m), 3.33–3.43(1H, m), 3.48–3.62(1H, m), 3.66–3.76(2H, m), 3.86(3H, s), 4.40(1H, brs), 7.12(2H, d, J=8 Hz), 7.76(2H, d, J=8 Hz), 8.90(1H, brs)

EXAMPLE 176

(2R)-4-(N,N-Dimethylaminosulfonyl)-N-hydroxy-1-(4-phenoxybenzenesulfonyl)-2-piperazinecarboxamide (102 mg) was obtained in substantially the same manner as in Example 5.

m.p.: 153–155° C.

Mass (ESI–): 483 (M–H)

¹H-NMR (300 MHz, DMSO-d₆, δ): 2.52–2.63(1H, m), 2.69(6H, s), 2.77(1H, dd, J=4, 14 Hz), 3.35–3.43(1H, m), 3.49–3.78(3H, m), 4.38–4.42(1H, m), 7.06–7.18(4H, m), 7.28(1H, dd, J=7, 7 Hz), 7.43–7.52(2H, m), 7.78–7.85(2H, m), 8.92(1H, s)

EXAMPLE 177

(2R)-1-[5-(4-Cyanophenyl)thiophene-2-sulfonyl]-4-ethylaminocarbonyl-N-hydroxy-2-piperazinecarboxamide (72 mg) was obtained in substantially the same manner as in Example 5.

Mass (ESI–): 462 (M–H)

¹H-NMR (300 MHz, DMSO-d₆, δ): 0.92(3H, t, J=4 Hz), 2.79–3.10(3H, m), 3.03(1H, dd, J=2, 12 Hz), 3.53–3.67(2H, m), 3.71(1H, d, J=12 Hz), 4.05(1H, d, J=12 Hz), 4.27(1H, brs), 6.43(1H, m), 7.23(1H, d, J=2 Hz), 7.33(1H, d, J=2 Hz), 7.95(4H, s)

EXAMPLE 178

A mixture of (2R)-4-[2-(acetylamino)ethanesulfonyl]-N-tert-butoxy-1-[5-(4-fluorophenyl)thiophene-2-sulfonyl]-2-piperazinecarboxamide (130 mg) in anisole (1 ml), trifluoroacetic acid (1 ml) and H₂O (0.02 ml) was stirred at ambient temperature overnight, and then at 50° C. for 5 hours. The mixture was concentrated in vacuo, and the residue was purified by SiO₂ column chromatography, eluted with MeOH in CHCl₃=2% then 5%. The fractions containing the desired product were combined and concentrated in vacuo. The residue was triturated with diisopropyl ether to give 88 mg of (2R)-4-[2-(acetylamino)ethanesulfonyl]-1-[5-(4-fluorophenyl)thiophene-2-sulfonyl]-N-hydroxy-2-piperazinecarboxamide.

Mass (ESI–): 533 (M–H)

¹H-NMR (300 MHz, DMSO-d₆, δ): 1.78(3H, s), 2.80(1H, dt, J=2, 11 Hz), 3.04(1H, dd, J=2, 11 Hz), 3.12(2H, t, J=4 Hz), 3.20–3.40(3H, m), 3.50–3.80(2H, m), 3.83(1H, d, J=11 Hz), 4.44(1H, s), 7.33(2H, t, J=8 Hz), 7.58(1H, d, J=2 Hz), 7.67(1H, d, J=2 Hz), 7.81(1H, dd, J=4, 8 Hz), 8.03(1H, t, J=4 Hz), 8.98(1H, s)

EXAMPLE 179

(2R)-1-[5-(4-Fluorophenyl)thiophene-2-sulfonyl]-N-hydroxy-4-[2-(methanesulfonylamino)ethanesulfonyl]-2-piperazinecarboxamide (132 mg) was obtained in substantially the same manner as in Example 178.

Mass (ESI–): 569 (M–H)

¹H-NMR (300 MHz, DMSO-d₆, δ): 2.84(1H, m), 2.93(3H, s), 3.09(1H, dd, J=2, 11 Hz), 3.15–3.35(4H, m), 3.57(1H, d, J=11 Hz), 3.63–3.80(2H, m), 3.84(1H, d, J=11 Hz), 4.45(1H, brs), 7.18(1H, t, J=4 Hz), 7.33(2H, t, J=8 Hz), 7.58(1H, d, J=2 Hz), 7.67(1H, d, J=2 Hz), 7.81(2H, dd, J=4, 8 Hz), 9.00(1H, s)

EXAMPLE 180

(2R)-N-Hydroxy-4-[2-(methanesulfonylamino)ethanesulfonyl]-1-(5-phenylthiophene-2-sulfonyl)-2-piperazinecarboxamide (157 mg) was obtained as an amorphous powder in substantially the same manner as in Example 178.

Mass (ESI–): 551 (M–H)

¹H-NMR (300 MHz, DMSO-d₆, δ): 2.84(1H, dt, J=2, 11 Hz), 2.93(3H, s), 3.09(1H, dd, J=2, 11 Hz), 3.12–3.35(4H, m), 3.58(1H, d ,J=11 Hz), 3.63–3.80(2H, m), 3.84(1H, d, J=11 Hz), 4.46(1H, brs), 7.18(1H, t, J=4 Hz), 7.37–7.53(3H, m), 7.62(1H, d, J=2 Hz), 7.68(1H, d, J=2 Hz), 7.71–7.79(2H, m), 8.99(1H, s)

EXAMPLE 181

(2R)-N-Hydroxy-4-[2-(methanesulfonylamino)ethanesulfonyl]-1-[5-(4-trifluoromethylphenyl)thiophene-2-sulfonyl]-2-piperazinecarboxamide (106 mg) was obtained as crystals in substantially the same manner as in Example 178.

m.p.: 105–108° C.

Mass (ESI-): 619 (M-H)

$^1$H-NMR (300 MHz, DMSO-d$_6$, δ): 2.86(1H, dt, J=2, 11 Hz), 2.94(3H, s), 3.11(1H, dd, J=2, 11 Hz), 3.15–3.35(4H, m), 3.58(1H, d, J=11 Hz), 3.63–3.83(2H, m), 3.84(1H, d, J=11 Hz), 4.46(1H, brs), 7.18(1H, t, J=4 Hz), 7.73(1H, d, J=2 Hz), 7.78(1H, d, J=2 Hz), 7.83(2H, d, J=8 Hz), 7.98(2H, d, J=8 Hz), 9.00(1H, s)

EXAMPLE 182

(2R)-1-[5-(4-Chlorophenyl)thiophene-2-sulfonyl]-N-hydroxy-4-[2-(methanesulfonylamino)ethanesulfonyl]-2-piperazinecarboxamide (160 mg) was obtained as crystals in substantially the same manner as in Example 178.

m.p.: 118–122° C.

Mass (ESI-): 585, 587 (M-H)

$^1$H-NMR (300 MHz, DMSO-d$_6$, δ): 2.84(1H, dt, J=2, 11 Hz), 2.93(3H, s), 3.10(1H, dd, J=2, 11 Hz), 3.15–3.35(4H, m), 3.58(1H, d, J=11 Hz), 3.63–3.79(2H, m), 3.84(1H, d, J=11 Hz), 4.45(1H, brs), 7.18(1H, t, J=4 Hz), 7.54(1H, d, J=8 Hz), 7.63(1H, d, J=2 Hz), 7.68(2H, d, J=2 Hz), 7.79(2H, d, J=8 Hz), 9.00(1H, s)

EXAMPLE 183

(2R)-1-[5-(4-Ethoxyphenyl)thiophene-2-sulfonyl]-N-hydroxy-4-[2-(methanesulfonylamino)ethanesulfonyl]-2-piperazinecarboxamide (157 mg) was obtained in substantially the same manner as in Example 178.

Mass (ESI-): 595 (M-H)

$^1$H-NMR (300 MHz, DMSO-d$_6$, δ): 1.35(3H, t, J=5 Hz), 2.84(1H, m), 2.93(3H, s), 3.09(1H, dd, J=2, 11 Hz), 3.15–3.35(4H, m), 3.56(1H, d, J=11 Hz), 3.63–3.75(2H, m), 3.83(1H, d, J=11 Hz), 4.09(2H, q, J=5 Hz), 4.44(1H, brs), 7.01(2H, d, J=8 Hz), 7.18(1H, t, J=4 Hz), 7.47(1H, d, J=2 Hz), 7.63(1H, d, J=2 Hz), 7.66(2H, d, J=8 Hz), 8.99(1H, s)

EXAMPLE 184

(2R)-1-[5-(4-Chlorophenyl)thiophene-2-sulfonyl]-N-hydroxy-4-{2-[(pyridine-3-sulfonyl)amino]ethanesulfonyl}-2-piperazinecarboxamide (87 mg) was obtained in substantially the same manner as in Example 178.

Mass (ESI-): 648, 650 (M-H)

$^1$H-NMR (300 MHz, CDCl$_3$-CD$_3$OD 10:1, δ): 2.70–2.85 (2H, m), 3.28(4H, brs), 3.40–3.57(2H, m), 3.96(1H, d, J=12 Hz), 4.12(1H, d, J=12 Hz), 4.63(1H, brs), 5.42(1H, br), 7.26(1H, d, J=2 Hz), 7.41(2H, d, J=8 Hz), 7.49–7.57(1H, m), 7.54(1H, d, J=8 Hz), 7.58(1H, d, J=2 Hz), 8.22(1H, d, J=6 Hz), 8.78(1H, d, J=3 Hz), 9.08(1H, s)

EXAMPLE 185

(2R)-1-[5-(4-Chlorophenyl)thiophene-2-sulfonyl]-N-hydroxy-4-2-[(N,N-dimethylaminosulfonyl)amino]ethanesulfonyl]-2-piperazine-carboxamide (86 mg) was obtained in substantially the same manner as in Example 178.

Mass (ESI-): 614, 616 (M-H)

$^1$H-NMR (300 MHz, DMSO-d$_6$, δ): 2.65(6H, s), 2.84(1H, dt, J=2, 11 Hz), 3.08(1H, dd, J=2, 11 Hz), 3.19(4H, s), 3.57(1H, d, J=11 Hz), 3.63–3.75(2H, m), 3.83(1H, d, J=11 Hz), 4.46(1H, brs), 7.33(1H, t, J=4 Hz), 7.54(2H, d, J=8 Hz), 7.65(1H, d, J=2 Hz), 7.68(1H, d, J=2 Hz), 7.79(2H, d, J=8 Hz), 8.98(1H, s)

EXAMPLE 186

(2R)-1-[5-(4-Chlorophenyl)thiophene-2-sulfonyl]-N-hydroxy-4-[2-(methoxycarbonylamino)ethanesulfonyl]-2-piperazinecarboxamide (107 mg) was obtained in substantially the same manner as in Example 178.

Mass (ESI-): 565, 567 (M-H)

$^1$H-NMR (300 MHz, DMSO-d$_6$, δ): 2.81(1H, dt, J=2, 11 Hz), 3.05(1H, dd, J=2, 11 Hz), 3.13(2H, t, J=4 Hz), 3.20–3.35(2H, m), 3.53(3H, s), 3.56(1H, d, J=11 Hz), 3.63–3.78(2H, m), 3.83(1H, d, J=11 Hz), 4.45(1H, brs), 7.25(1H, t, J=4 Hz), 7.54(2H, d, J=8 Hz), 7.65(1H, d, J=2 Hz), 7.68(1H, d, J=2 Hz), 7.78(2H, d, J=8 Hz), 8.98(1H, s)

EXAMPLE 187

(2R)-1-[5-(4-Fluorophenyl)thiophene-2-sulfonyl]-N-hydroxy-4-{2-[(pyridine-3-carbonyl)amino]ethanesulfonyl}-2-piperazinecarboxamide (56 mg) was obtained in substantially the same manner as in Example 178.

Mass (ESI-): 596 (M-H)

$^1$H-NMR (300 MHz, DMSO-d$_6$, δ): 2.83(1H, dt, J=2, 11Hz), 3.07(1H, dd, J=2, 11 Hz), 3.28(2H, t, J=4 Hz), 3.53–3.80(5H, m), 3.86(1H, d, J=11 Hz), 4.46(1H, s), 7.30 (2H, t, J=8 Hz), 7.50(1H, dd, J=2, 6 Hz), 7.58(1H, d, J=2 Hz), 7.67(1H, d, J=2 Hz), 7.80(2H, dd, J=4, 8 Hz), 8.14(1H, d, J=6 Hz), 8.71(1H, d, J=2 Hz), 8.87(1H, t, J=4 Hz), 8.95(1H, s), 8.99(1H, s)

EXAMPLE 188

(2R)-4-[2-(Benzoylamino)ethanesulfonyl]-1-[5-(4-fluorophenyl)-thiophene-2-sulfonyl]-N-hydroxy-2-piperazinecarboxamide (68 mg) was obtained in substantially the same manner as in Example 178.

Mass (ESI-): 595 (M-H)

$^1$H-NMR (300 MHz, DMSO-d$_6$, δ): 2.83(1H, dt, J=2, 11 Hz), 3.06(1H, dd, J=2, 11 Hz), 3.26(2H, t, J=4 Hz), 3.52–3.80(2H, m), 3.86(1H, d, J=11 Hz), 4.47(1H, s), 7.29 (2H, t, J=8 Hz), 7.45(2H, t, J=7 Hz), 7.53(1H, t, J=7 Hz), 7.58(1H, d, J=2 Hz), 7.67(1H, d, J=2 Hz), 7.75–7.85(4H, m), 8.65(1H, t, J=4 Hz), 9.00(1H, s)

EXAMPLE 189

(2R)-N-Hydroxy-1-(2-phenyl-2-trans-ethenylsulfonyl)-4-methanesulfonyl-2-piperazinecarboxamide (159 mg) was obtained as crystals in substantially the same manner as in Example 5.

m.p.: 94–99° C.

Mass (ESI-): 388 (M-H)

$^1$H-NMR (300 MHz, DMSO-d$_6$, δ): 2.81(1H, dt, J=2, 11 Hz), 2.87(3H, s), 3.05(1H, dd, J=2, 11 Hz), 3.40–3.70(3H, m), 3.92(1H, d, J=11 Hz), 4.39(1H, brs), 7.21(1H, d, J=14 Hz), 7.43(1H, d, J=14 Hz), 7.43–7.51(3H, m), 7.64–7.74 (2H, m), 9.03(1H, s)

EXAMPLE 190

(2R)-1-[5-(4-Fluorophenyl)thiophene-2-sulfonyl]-N-hydroxy-4-[N-(methoxycarbonylmethyl)aminocarbonyl]-2- piperazinecarboxamide (52 mg) was obtained in substantially the same manner as in Example 5.

Mass (ESI–): 499 (M–H)

$^1$H-NMR (300 MHz, DMSO-$d_6$, δ): 2.94(1H, m), 3.06 (1H, dd, J=2, 12 Hz), 3.55(3H, s), 3.50–3.80(5H, m), 4.03 (1H, d, J=12 Hz), 4.27(1H, m), 6.98(1H, t, J=4 Hz), 7.33(2H, t, J=8 Hz), 7.59(1H, d, J=2 Hz), 7.68(1H, d, J=2 Hz), 7.81(2H, dd, J=4, 8 Hz), 8.95(1H, s)

Preparation 146

(2R)-1-tert-Butoxycarbonyl-4-(9-fluorenylmethyloxycarbonyl)-2-piperazinecarboxylic acid (15.6 g) was obtained as an amorphous powder in substantially the same manner as in Preparation 7.

Mass (ESI–): 451 (M–H)

$^1$H-NMR (300 MHz, DMSO-$d_6$, δ): 1.34, 1.44(9H, s), 2.78–3.32(4H, m), 3.64–3.96(2H, m), 4.25(2H, s), 4.28–4.78(2H, m), 7.34(2H, t, J=8 Hz), 7.42(2H, t, J=8 Hz), 7.56–7.72(2H, m), 7.90(2H, d, J=8 Hz)

Preparation 147

(2R)-4-(9-Fluorenylmethyloxycarbonyl)-2-piperazinecarboxylic acid hydrochloride (10.9 g) was obtained in substantially the same manner as in Preparation 9.

Mass (ESI–): 351 (M–H)

$^1$H-NMR (300 MHz, DMSO-$d_6$, δ): 2.90–3.04(1H, m), 3.18–3.40(3H, m), 3.76–3.92(1H, m), 4.12(2H, d, J=12 Hz), 4.24–4.34(1H, m), 4.39(2H, d, J=7.5 Hz), 7.35(2H, t, J=8 Hz), 7.44(2H, t, J=8 Hz), 7.65(2H, d, J=8 Hz), 7.92(2H, d, J=8 Hz)

Preparation 148

(2R)-4-(9-Fluorenylmethyloxycarbonyl)-1-(5-phenylthiophene-2-sulfonyl)-2-piperazinecarboxylic acid (15.5 g) was obtained as an amorphous powder in substantially the same manner as in Preparation 11.

Mass (ESI–): 573 (M–H)

$^1$H-NMR (300 MHz, CDCl$_3$, δ): 2.82–2.97(1H, m), 3.03–3.44(4H, m), 3.56–3.72(1H, m), 4.04–4.18(1H, m), 4.39(2H, d, J=8 Hz), 4.52–4.64(1H, m), 7.11–7.52(11H, m), 7.55(2H, d, J=8 Hz), 7.72(2H, d, J=8 Hz)

EXAMPLE 191

(2R)-4-(9-Fluorenylmethyloxycarbonyl)-1-(5-phenylthiophene-2-sulfonyl)-N-(2-tetrahydropyranyloxy)-2-piperazinecarboxamide (16.7 g) was obtained as an amorphous powder in substantially the same manner as in Preparation 12.

Mass (ESI–): 672 (M–H)

$^1$H-NMR (300 MHz, DMSO-$d_6$, δ): 1.26–1.70(6H, m), 2.92–3.20(2H, m), 3.36–3.95(5H, m), 4.02–4.28(4H, m), 4.32–4.44(1H, m), 4.62–4.85(1H, m), 7.23–7.35(2H, m), 7.35–7.52(5H, m), 7.52–7.68(4H, m), 7.75(2H, d, J=8 Hz), 7.88(2H, d, J=8 Hz)

Preparation 149

(2R)-4-(9-Fluorenylmethyloxycarbonyl)-1-[5-(4-fluorophenyl)-thiophene-2-sulfonyl]-2-piperazinecarboxylic acid (13.3 g) was obtained as an amorphous powder in substantially the same manner as in Preparation 11.

Mass (ESI–): 591 (M–H)

$^1$H-NMR (300 MHz, DMSO-$d_6$, δ): 2.82–3.04(1H, m), 3.11–3.29(1H, m), 3.38–3.50(1H, m), 3.60–3.75(1H, m), 3.85–4.00(1H, m), 4.22(3H, m), 4.32–4.48(1H, m), 4.60(1H, brs), 7.28–7.45(6H, m), 7.28(1H, d, J=3 Hz), 7.35–7.83(2H, m), 7.88(2H, d, J=8 Hz)

EXAMPLE 192

(2R)-4-(9-Fluorenylmethyloxycarbonyl)-1-[5-(4-fluorophenyl)-thiophene-2-sulfonyl]-N-(2-tetrahydropyranyloxy)-2-piperazinecarboxamide (12.9 g) was obtained as an amorphous powder in substantially the same manner as in Preparation 12.

Mass (ESI–): 690 (M–H)

$^1$H-NMR (300 MHz, DMSO-$d_6$, δ): 1.25–1.78(6H, m), 2.90–3.20(5H, m), 3.72–4.42(7H, m), 4.62–4.85(1H, m), 7.24–7.45(6H, m), 7.50–7.69(4H, m), 7.74–7.85(2H, m), 7.88(2H, d, J=8 Hz)

Preparation 150

(2R)-4-(9-Fluorenylmethyloxycarbonyl)-1-[5-(4-trifluoromethyl-phenyl)thiophene-2-sulfonyl]-2-piperazinecarboxylic acid (1.18 g) was obtained as an amorphous powder in substantially the same manner as in Preparation 11.

Mass (ESI–): 641 (M–H)

$^1$H-NMR (300 MHz, CDCl$_3$, δ): 2.82–3.00(1H, m), 3.12 (1H, dd, J=6, 14 Hz), 3.29–3.43(1H, m), 3.61–3.73(1H, m), 4.05–4.18(1H, m), 4.30–4.47(3H, m), 4.54–4.68(2H, m), 7.15–7.50(8H, m), 7.55–7.68(4H, m), 7.74(2H, d, J=7 Hz)

EXAMPLE 193

(2R)-4-(9-Fluorenylmethyloxycarbonyl)-N-(2-tetrahydropyranyloxy)-1-[5-(4-trifluoromethylphenyl)thiophene-2-sulfonyl]-2-piperazine-carboxamide (1.20 g) was obtained as an amorphous powder in substantially the same manner as in Preparation 12.

Mass (ESI–): 740 (M–H)

$^1$H-NMR (300 MHz, DMSO-$d_6$, δ): 1.28–2.63(6H, m), 2.95–3.23(2H, m), 3.38–3.92(5H, m), 4.01–4.28(4H, m), 4.32–4.46(1H, m), 4.60–4.68(1H, m), 7.25–7.45(4H, m), 7.52–7.62(2H, m), 7.62–7.81(1H, m), 7.76–7.90(5H, m), 7.97(2H, d, J=8 Hz)

Preparation 151

(2R)-1-[5-(4-Chlorophenyl)thiophene-2-sulfonyl]-4-(9-fluorenylmethyloxycarbonyl)-2-piperazinecarboxylic acid (6.16 g) was obtained as an amorphous powder in substantially the same manner as in Preparation 11.

Mass (ESI–): 607, 609 (M–H)

$^1$H-NMR (300 MHz, CDCl$_3$, δ): 2.82–3.00(1H, m), 3.14 (1H, dd, J=5, 15 Hz), 3.20–3.42(1H, m), 3.52–3.74(3H, m), 4.06–4.15(1H, m), 4.30–4.43(2H, m), 4.60(1H, brs), 7.05–7.18(1H, m), 7.22–7.55(11H, m), 7.74(2H, d, J=7 Hz)

EXAMPLE 194

(2R)-1-[5-(4-Chlorophenyl)thiophene-2-sulfonyl]-4-(9-fluorenylmethyloxycarbonyl)-N-(2-tetrahydropyranyloxy)-2-piperazinecarboxamide (6.67 g) was obtained in substantially the same manner as in Preparation 12.

Mass (ESI–): 706, 708 (M–H)

$^1$H-NMR (300 MHz, DMSO-$d_6$, δ): 1.32–1.67(6H, m), 2.97–3.25(2H, m), 3.38–3.93(5H, m), 4.06–4.28(4H, m), 4.32–4.44(1H, m), 4.62–4.75(1H, m), 7.27–7.46(4H, m), 7.50–7.68(6H, m), 7.73–7.92(4H, m)

Preparation 152

(2R)-4-(9-Fluorenylmethyloxycarbonyl)-1-[5-(4-ethoxyphenyl)-thiophenesulfonyl]-2-piperazinecarboxylic acid (7.80 g) was obtained in substantially the same manner as in Preparation 11.

Mass (ESI–): 617 (M–H)

$^1$H-NMR (300 MHz, CDCl$_3$, δ): 1.45(3H, t, J=7 Hz), 2.87–2.97(1H, m), 3.10–3.18(2H, m), 3.30–3.43(2H, m), 3.62–3.71(1H, m), 4.00–4.09(2H, q, J=7 Hz), 4.05–4.11(1H, m), 4.39(2H, d, J=6 Hz), 4.63(1H, bs), 6.90(2H, d, J=8 Hz), 7.05–7.10(1H, m), 7.21–7.56(9H, m), 7.73(2H, d, J=8 Hz)

EXAMPLE 195

(2R)-4-(9-Fluorenylmethoxycarbonyl)-1-[5-(4-ethoxyphenyl)-thiophenesulfonyl]-N-(2- tetrahydropyranyloxy)-2-piperazinecarboxamide (8.76 g) was obtained in substantially the same manner as in Preparation 12.

Mass (ESI−): 716 (M−H)

¹H-NMR (300 MHz, CDCl₃, δ): 1.48(3H, t, J=7 Hz), 1.50–1.88(6H, m), 3.00–3.26(2H, m), 3.39–3.52(2H, m), 3.62–3.97(3H, m), 4.07(2H, q, J=7 Hz), 4.05–4.11(1H, m), 4.15–4.28(1H, m), 4.35–4.46(1H, m), 4.51(1H, bs), 6.87 (2H, d, J=8 Hz), 7.10–7.21(1H, m), 7.25–7.67(5H, m), 7.70(2H, d, J=8 Hz)

EXAMPLE 196

A mixture of (2R)-4-(3-chloropropanesulfonyl)-1-[5-(4-fluorophenyl)-thiophene-2-sulfonyl]-N-(2-tetrahydropyranyloxy)-2-piperazinecarboxamide (200 mg), piperidine (279 mg) and potassium iodide (65 mg) in DMF (3 ml) was stirred at ambient temperature for 2 days. The mixture was concentrated in vacuo. The residue was partitioned between AcOEt and H₂O. The organic layer was washed with saturated aqueous NaCl solution, dried over MgSO₄, and concentrated in vacuo. The residue was purified by SiO₂ column chromatography eluted with MeOH in CHCl₃ gradually from 0% to 5%, to give 165 mg of (2R)-1-[5-(4-fluorophenyl)thiophene-2-sulfonyl]-4-[3-(1-piperidino)propanesulfonyl]-N-(2-tetrahydropyranyloxy)-2-piperazinecarboxamide.

Mass (ESI+): 659 (M+H)

¹H-NMR (300 MHz, CDCl₃, δ): 1.35–1.47(2H, m), 1.48–1.68(7H, m), 1.70–1.98(5H, m), 2.27–2.45(6H, m), 2.75–2.95(2H, m), 3.00–3.14(2H, m), 3.30–3.50(1H, m), 3.54–3.70(2H, m), 3.85–4.03(2H, m), 4.19(1H, d, J=12 Hz), 4.63(1H, brs), 4.94(1H, s), 7.13(2H, t, J=8 Hz), 7.22(1H, m), 7.53–7.65(3H, m)

EXAMPLE 197

(2R)-4-[3-(N,N-Diethylamino)propanesulfonyl]-1-[5-(4-fluorophenyl)-thiophene-2-sulfonyl]-N-(2-tetrahydropyranyloxy)-2-piperazine-carboxamide (57 mg) was obtained as an amorphous powder in substantially the same manner as in Example 196.

ESI Mass: 647 (M+H)

¹H-NMR (300 MHz, CDCl₃, δ): 0.93–1.07(6H, m), 1.50–1.92(8H, m), 2.43–2.60(6H, m), 2.76–2.92(2H, m), 3.02–3.15(2H, m), 3.30–3.48(1H, m), 3.55–3.70(2H, m), 3.85–4.03(2H, m), 4.20(1H, d, J=12 Hz), 4.58–4.68(1H, m), 4.96(1H, brs), 7.13(2H, t, J=8 Hz), 7.22(1H, d, J=3 Hz), 7.52–7.66(3H, m)

EXAMPLE 198

(2R)-1-(5-Phenylthiophene-2-sulfonyl)-4-[3-(1-piperidino)-propanesulfonyl]-N-(2-tetrahydropyranyloxy)-2-piperazinecarboxamide (150 mg) was obtained as an amorphous powder in substantially the same manner as in Example 196.

Mass (ESI+): 641 (M+H)

¹H-NMR (300 MHz, CDCl₃, δ): 1.36–1.48(2H, m), 1.50–1.66(7H, m), 1.72–1.92(5H, m), 2.27–2.44(6H, m), 2.75–2.94(2H, m), 3.01–3.13(2H, m), 3.33–3.52(1H, m), 3.56–3.68(2H, m), 3.85–4.04(2H, m), 4.20(1H, d, J=12 Hz), 4.08–4.18(1H, m), 4.95(1H, brs), 7.27–7.32(1H, m), 7.36–7.49(3H, m), 7.58–7.67(3H, m)

EXAMPLE 199

A mixture of (2R)-4-(3-chloropropanesulfonyl)-1-(5-phenylthiophene-2-sulfonyl)-N-(2-tetrahydropyranyloxy)-2-piperazinecarboxamide (150 mg), 3-mercapto-1,2,4-triazole (28 mg), potassium iodide (42 mg) and potassium carbonate (53 mg) in DMF (2 ml) was stirred for 14 hours at ambient temperature. The mixture was partitioned between AcOEt and saturated aqueous NaHCO₃ solution. The organic layer was separated, washed with saturated aqueous NaHCO₃ solution and brine, dried over sodium sulfate and evaporated in vacuo. The residue was purified by preparative thin layer chromatography (10% MeOH in CHCl₃) to give 134 mg of (2R)-1-(5-phenylthiophene-2-sulfonyl)-4-[3-(1,2,4-triazolyl-3-thio)-propanesulfonyl]-N-(2-tetrahydropyranyloxy)-2-piperazinecarboxamide as an amorphous solid.

Mass (ESI): 655 (M−1)

¹H-NMR (300 MHz, CDCl₃, δ): 1.50–1.89(6H, m), 2.04–2.20(2H, m), 2.80–2.99(2H, m), 3.10–3.28(4H, m), 3.31–3.42(1H, m), 3.53–3.72(2H, m), 3.87–4.00(2H, m), 4.10–4.22(1H, m), 4.60–4.69(1H, m), 5.00–5.07(1H, m), 7.30(1H, d, J=3 Hz), 7.40–7.49(3H, m), 7.58–7.67(3H, m), 8.10(1H, d, J=3 Hz), 9.38–9.53(1H, m)

EXAMPLE 200

(2R)-1-(5-Phenylthiophene-2-sulfonyl)-N-(2-tetrahydropyranyloxy)-4-[3-(thiazolyl-2-thio)propanesulfonyl]-2-piperazinecarboxamide (139 mg) was obtained in substantially the same manner as in Example 199.

Mass (ESI−): 671 (M−H)

¹H-NMR (300 MHz, CDCl₃, δ): 1.50–1.90(6H, m), 2.05–2.28(2H, m), 2.75–2.93(2H, m), 3.14–3.48(5H, m), 3.55–3.70(2H, m), 3.84–4.05(2H, m), 4.20(1H, d, J=12 Hz), 4.55–4.67(1H, brs), 4.9, 4.99(1H, brs), 7.21(1H, m), 7.29 (1H, d, J=2 Hz), 7.39–7.50(3H, m), 3.55–3.68(4H, m), 9.19(1H, brs)

EXAMPLE 201

(2R)-4-[3-(4-Methyl-1,2,4-triazolyl-3-thio)propanesulfonyl]-1-(5-phenylthiophene-2-sulfonyl)-N-(2-tetrahydropyranyloxy)-2-piperazinecarboxamide (102 mg) was obtained in substantially the same manner as in Example 199.

Mass (ESI−): 669 (M−H)

¹H-NMR (300 MHz, CDCl₃, δ): 1.50–1.90(6H, m), 2.23 (2H, m), 2.80–3.00(2H, m), 3.23(2H, t, J=4 Hz), 3.33(2H, t, J=4 Hz), 3.46(1H, m), 3.53–3.70(2H, m), 3.60(3H, s), 3.84–4.05(2H, m), 4.17(1H, d, J=12 Hz), 4.64(1H, brs), 4.97(1H, brs), 7.28(1H, d, J=2 Hz), 7.38–7.49(3H, m), 3.57–3.65(3H, m), 8.13(1H, s), 9.45, 9.50(1H, brs)

EXAMPLE 202

(2R)-4-[3-(Imidazolyl-2-thio)propanesulfonyl]-1-(5-phenylthiophene-2-sulfonyl)-N-(2-tetrahydropyranyloxy)-2-piperazinecarboxamide (108 mg) was obtained in substantially the same manner as in Example 199.

Mass (ESI−): 656 (M−H)

¹H-NMR (300 MHz, CDCl₃, δ): 1.50–1.85(6H, m), 1.85–2.13(2H, m), 2.77–3.48(7H, m), 3.54–3.70(2H, m), 3.85–4.05(2H, m), 4.12–4.26(1H, m), 4.63, 4.67(1H, brs), 5.04(1H, m), 7.06(2H, br), 7.30(1H, m), 7.39–7.49(3H, m), 7.58–7.65(3H, m), 9.62(1H, br)

EXAMPLE 203

(2R)-1-[5-(4-Fluorophenyl)thiophene-2-sulfonyl]-N-(2-tetrahydropyranyloxy)-4-[3-(1,2,4-triazolyl-3-thio)

propanesulfonyl]-2-piperazinecarboxamide (121 mg) was obtained in substantially the same manner as in Example 199.

Mass (ESI−): 673 (M−H)

$^1$H-NMR (300 MHz, CDCl$_3$, δ): 1.52–1.90(6H, m), 2.00–2.20(2H, m), 2.77–2.99(2H, m), 3.05–3.45(5H, m), 3.52–3.73(2H, m), 3.85–4.03(2H, m), 4.10–4.20(1H, m), 4.64(1H, brs), 5.04(1H, brs), 7.14(2H, t, J=8 Hz), 7.23(1H, d, J=2 Hz), 7.55–7.65(1H, m), 7.58(2H, dd, J=4, 8 Hz), 8.08–8.14(1H, br), 9.40, 9.47(1H, br)

EXAMPLE 204

(2R)-1-[5-(4-Fluorophenyl)thiophene-2-sulfonyl]-4-[3-(4-methyl-1,2,4-triazolyl-3-thio)propanesulfonyl]-N-(2-tetrahydropyranyloxy)-2-piperazinecarboxamide (128 mg) was obtained in substantially the same manner as in Example 199.

Mass (ESI−): 687 (M−H)

$^1$H-NMR (300 MHz, CDCl$_3$, δ): 1.50–2.00(6H, m), 2.23 (2H, m), 2.80–3.00(2H, m), 3.23(2H, t, J=4 Hz), 3.33(2H, t, J=4 Hz), 3.48(1H, dt, J=2, 12 Hz), 3.54–3.70(2H, m), 3.60(3H, s), 3.85–4.03(2H, m), 4.17(1H, d, J=12 Hz), 4.64 (1H, brs), 4.93–5.00(1H, m), 7.13(2H, t, J=8 Hz), 7.22(1H, d, J=2 Hz), 7.53–7.65(3H, m), 8.18(1H, brs), 9.50–9.65(1H, br)

EXAMPLE 205

(2R)-1-[5-(4-Fluorophenyl)thiophene-2-sulfonyl]-4-[3-(imidazolyl-2-thio)propanesulfonyl]-N-(2-tetrahydropyranyloxy)-2-piperazinecarboxamide (96 mg) was obtained in substantially the same manner as in Example 199.

Mass (ESI−): 672 (M−H)

$^1$H-NMR (300 MHz, CDCl$_3$, δ): 1.50–1.85(6H, m), 1.85–2.13(2H, m), 2.75–3.50(7H, m), 3.57(1H, d, J=11 Hz), 3.66(1H, d, J=11 Hz), 3.86–4.05(2H, m), 4.12–4.27(1H, m), 4.62, 4.66(1H, brs), 5.00–5.09(1H, m), 7.08(2H, br), 7.15 (2H, t, J=8 Hz), 7.23(1H, d, J=2 Hz), 7.55–7.65(3H, m), 9.45–9.60(1H, br)

EXAMPLE 206

(2R)-4-[3-(Benzimidazolyl-2-thio)propanesulfonyl]-1-[5-(4-fluorophenyl)thiophene-2-sulfonyl]-N-(2-tetrahydropyranyloxy)-2-piperazinecarboxamide (121 mg) was obtained in substantially the same manner as in Example 199.

Mass (ESI−): 722 (M−H)

$^1$H-NMR (300 MHz, CDCl$_3$, δ): 1.45–1.83(6H, m), 2.05–2.30(2H, m), 2.72–2.93(2H, m), 3.19–3.40(5H, m), 3.50–3.72(2H, m), 3.86–4.00(2H, m), 4.10–4.24(1H, m), 4.54–4.68(1H, brs), 5.02(1H, brs), 7.13(2H, t, J=8 Hz), 7.15–7.25(3H, m), 7.53–7.65(5H, m), 9.34–9.40(1H, br)

EXAMPLE 207

(2R)-1-[5-(4-Chlorophenyl)thiophene-2-sulfonyl]-N-(2-tetrahydropyranyloxy)-4-[3-(1,2,4-triazolyl-3-thio) propanesulfonyl]-2-piperazinecarboxamide (149 mg) was obtained in substantially the same manner as in Example 199.

Mass (ESI−): 689, 691 (M−H)

$^1$H-NMR (300 MHz, CDCl$_3$, δ): 1.50–1.90(6H, m), 2.13 (2H, m), 2.78–3.00(2H, m), 3.08–3.30(4H, m), 3.38(1H, m), 3.55–3.70(2H, m), 3.85–4.00(2H, m), 4.15(1H, d, J=11 Hz), 4.63(1H, brs), 5.01(1H, s), 7.26(1H, m), 7.41(2H, d, J=8 Hz), 7.53(2H, d, J=8 Hz), 7.63(1H, m), 8.13(1H, d, J=2 Hz), 9.45–9.62(1H, br)

EXAMPLE 208

(2R)-1-[5-(4-Chlorophenyl)thiophene-2-sulfonyl]-4-[3-(4-methyl-1,2,4-triazolyl-3-thio)propanesulfonyl]-N-(2-tetrahydropyranyloxy)-2-piperazinecarboxamide (110 mg) was obtained in substantially the same manner as in Example 199.

Mass (ESI−): 703, 705 (M−H)

$^1$H-NMR (300 MHz, CDCl$_3$, δ): 1.50–1.90(6H, m), 2.23 (2H, m), 2.80–3.00(2H, m), 3.23(2H, t, J=4 Hz), 3.33(2H, t, J=4 Hz), 3.37(1H, m), 3.55–3.70(2H, m), 3.59(3H, s), 3.85–4.05(2H, m), 4.15(1H, d, J=11 Hz), 4.64(1H, brs), 4.96(1H, m), 7.26(1H, m) 7.41(2H, d, J=8 Hz), 7.54(2H, d, J=8 Hz), 7.62(1H, m), 8.13(1H, s), 9.50, 9.58(1H, brs)

EXAMPLE 209

(2R)-1-[5-(4-Chlorophenyl)thiophene-2-sulfonyl]-4-[3-(imidazolyl-2-thio)propanesulfonyl]-N-(2-tetrahydropyranyloxy)-2-piperazinecarboxamide (100 mg) was obtained in substantially the same manner as in Example 199.

Mass (ESI−): 688, 690 (M−H)

$^1$H-NMR (300 MHz, CDCl$_3$, δ): 1.50–1.85(6H, m), 1.85–2.13(2H, m), 2.75–3.50(7H, m), 3.54–3.70(2H, m), 3.85–4.04(2H, m), 4.12–4.25(1H, m), 4.63, 4.67(1H, brs), 5.03(1H, m), 7.08(2H, br), 7.27(1H, m), 7.42(2H, d, J=8 Hz), 7.54(2H, d, J=8 Hz), 7.62(1H, m), 9.60–9.75(1H, br)

EXAMPLE 210

(2R)-4-[3-(Benzimidazolyl-2-thio)propanesulfonyl]-1-[5-(4-chlorophenyl)thiophene-2-sulfonyl]-N-(2-tetrahydropyranyloxy)-2-piperazinecarboxamide (100 mg) was obtained in substantially the same manner as in Example 199.

Mass (ESI−): 738, 740 (M−H)

$^1$H-NMR (300 MHz, CDCl$_3$, δ): 1.45–1.80(6H, m), 2.10–2.25(2H, m), 2.73–2.92(2H, m), 3.15–3.43(5H, m), 3.52–3.70(2H, m), 3.85–4.00(2H, m), 4.17(1H, d, J=11 Hz), 4.61, 4.65(1H, brs), 5.01(1H, m), 7.12–7.30(3H, m), 7.30–7.45(1H, m), 7.41(2H, d, J=8 Hz), 7.52(2H, d, J=8 Hz), 7.60(1H, m), 7.66(1H, m), 9.47(1H, brs)

EXAMPLE 211

(2R)-1-[5-(4-Ethoxyphenyl)thiophene-2-sulfonyl]-N-(2-tetrahydropyranyloxy)-4-[3-(1,2,4-triazolyl-3-thio) propanesulfonyl]-2-piperazinecarboxamide (122 mg) was obtained in substantially the same manner as in Example 199.

Mass (ESI−): 699 (M−H)

$^1$H-NMR (300 MHz, CDCl$_3$, δ): 1.45(3H, t, J=4 Hz), 1.50–1.90(6H, m), 2.00–2.20(2H, m), 2.78–2.96(2H, m), 3.10–3.40(5H, m), 3.52–3.72(2H, m), 3.85–4.01(2H, m), 4.08(2H, q, J=4 Hz), 4.16(1H, m), 4.63(1H, brs), 5.04(1H, brs), 6.94(2H, d, J=8 Hz), 7.17(1H, d, J=2 Hz), 7.51(2H, d, J=8 Hz), 7.60(1H, m), 8.11(1H, m), 9.35–9.53(1H, m)

EXAMPLE 212

(2R)-1-[5-(4-Ethoxyphenyl)thiophene-2-sulfonyl]-4-[3-(4-methyl-1,2,4-triazolyl-3-thio)propanesulfonyl]-N-(2-tetrahydropyranyloxy)-2-piperazinecarboxamide (94 mg) was obtained in substantially the same manner as in Example 199.

Mass (ESI-): 713 (M-H)

$^1$H-NMR (300 MHz, CDCl$_3$, δ): 1.44(3H, t, J=4 Hz), 1.50–1.90(6H, m), 2.23(2H, m), 2.78–2.98(2H, m), 3.22(2H, t, J=4 Hz), 3.33(2H, t, J=4 Hz), 3.44(1H, m), 3.55–3.70(2H, m), 3.58(3H, s), 3.85–4.03(2H, m), 4.08(2H, q, J=4 Hz), 4.17(1H, d, J=11 Hz), 4.63(1H, brs), 4.97(1H, m), 6.94(2H, d, J=8 Hz), 7.16(1H, d, J=2 Hz), 7.51(2H, d, J=8 Hz), 7.58(1H, m), 8.13(1H, s), 9.43, 9.47(1H, brs)

EXAMPLE 213

(2R)-1-[5-(4-Ethoxyphenyl)thiophene-2-sulfonyl]-4-[3-(imidazolyl-2-thio)propanesulfonyl]-N-(2-tetrahydropyranyloxy)-2-piperazinecarboxamide (108 mg) was obtained in substantially the same manner as in Example 199.

Mass (ESI-): 698 (M-H)

$^1$H-NMR (300 MHz, CDCl$_3$, δ): 1.45(3H, t, J=4 Hz), 1.50–1.85(6H, m), 1.85–2.15(2H, m), 2.75–3.50(7H, m), 3.52–3.70(2H, m), 3.86–4.05(2H, m), 4.09(2H, q, J=4 Hz), 4.13–4.27(1H, m), 4.62, 4.66(1H, brs), 5.04(1H, m), 6.94(2H, d, J=8 Hz), 7.03(1H, br), 7.12(1H, br), 7.18(1H, d, J=2 Hz), 7.52(2H, d, J=8 Hz), 7.59(1H, m), 9.50–9.65(1H, brs)

EXAMPLE 214

To a solution of (2R)-1-(5-phenylthiophene-2-sulfonyl)-4-[3-(benzyloxycarbonyl)propane]sulfonyl-N-(2-tetrahydropyranyloxy)-2-piperazinecarboxamide (350 mg, 0.56 mmol) in MeOH was added dropwise 1N aqueous sodium hydroxide solution (1.0 ml, 1.12 mmol) at 0° C., and the solution was stirred for 3 hours at room temperature. The resulting mixture was evaporated to remove MeOH and acidified with 5% aqueous citric acid solution. This solution was extracted three times with AcOEt. The combined organic layer was washed with brine, and dried over MgSO$_4$. The solvent was evaporated to give 357 mg of (2R)-1-(5-phenylthiophene-2-sulfonyl)-4-(3-carboxypropane)sulfonyl-N-(2-tetrahydropyranyloxy)-2-piperazinecarboxamide as a colorless oil.

Mass (ESI-): 600 (M-H)

$^1$H-NMR (300 MHz, CDCl$_3$, δ): 1.54–1.91(6H, m), 1.92–2.08(2H, m), 2.47–2.58(2H, m), 2.76–2.95(1H, m), 3.10–3.21(2H, m), 3.45–3.56(1H, m), 3.62–3.70(2H, m), 3.88–4.07(2H, m), 4.17–4.25(1H, m), 4.56–4.71(0.5H, m), 4.94–5.02(0.5H, m), 7.24–7.47(3H, m), 7.57–7.67(2H, m), 9.39–9.56(1H, m)

EXAMPLE 215

(2R)-4-[N-(Carboxymethyl)aminocarbonyl]-1-[5-(4-fluorophenyl)-thiophene-2-sulfonyl]-N-(2-tetrahydropyranyloxy)-2-piperazinecarboxamide (608 mg) was obtained in substantially the same manner as in Preparation 127.

Mass (ESI-): 569 (M-H)

$^1$H-NMR (300 MHz, DMSO-d$_6$, δ): 1.35–1.75(6H, m), 2.60–3.95(8H, m), 4.09(1H, t, J=12 Hz), 4.28(1H, d, J=10 Hz), 4.35(1H, t, J=4 Hz), 4.68, 4.75(1H, brs), 6.82, 6.92(1H, t, J=4 Hz), 7.33(2H, t, J=8 Hz), 7.55–7.65(2H, m), 7.75–7.85(2H, m)

EXAMPLE 216

To a mixture of (2R)-1-(5-phenylthiophene-2-sulfonyl)-4-[3-(benzyloxycarbonyl)propane]sulfonyl-N-(2-tetrahydropyranyloxy)-2-piperazinecarboxamide (352 mg, 0.58 mmol), morpholine (61 mg, 0.70 mmol) and HOBt (87 mg, 0.64 mmol) in DMF (3 ml) was added WSCD.HCl (135 mg, 0.70 mmol) at 0° C. and the resulting mixture was stirred at room temperature for 4.5 hours. After evaporation of DMF, the residue was diluted with AcOEt (10 ml) and the solution was washed with 5% aqueous citric acid, saturated aqueous NaHCO$_3$ solution and brine, and dried over MgSO$_4$. The solvent was removed under reduced pressure. The residue was purified by SiO$_2$ column chromatography to give 343 mg of (2R)-1-(5-phenylthiophene-2-sulfonyl)-4-[3-(4-morpholinocarbonyl)propane]sulfonyl-N-(2-tetrahydropyranyloxy)-2-piperazinecarboxamide as a slightly brown oil (yield 87%).

Mass (ESI-): 699 (M-H)

$^1$H-NMR (300 MHz, CDCl$_3$, δ): 1.55–1.91(6H, m), 2.00–2.14(2H, m), 2.45–2.54(2H, m), 2.78–2.91(1H, m), 3.12–3.22(2H, m), 3.31–3.48(3H, m), 3.57–3.71(10H, m), 3.85–4.07(2H, m), 4.20–4.27(1H, m), 4.55–4.68(0.5H, m), 4.94–5.02(0.5H, m), 7.24–7.49(3H, m), 7.60–7.67(2H, m)

EXAMPLE 217

(2R)-1-(5-Phenylthiophene-2-sulfonyl)-4-(3-carbamoylpropane)-sulfonyl-N-(2-tetrahydropyranyloxy)-2-piperazinecarboxamide (324 mg) was obtained in substantially the same manner as in Example 216.

Mass (ESI-): 599 (M-H)

$^1$H-NMR (300 MHz, CDCl$_3$, δ): 1.48–1.88(6H, m), 1.93–2.04(2H, m), 2.37(2H, t, J=8 Hz), 2.78–2.92(2H, m), 3.06–3.18(2H, m), 3.42–3.69(4H, m), 3.88–4.03(3H, m), 4.20(1H, d, J=12 Hz), 4.55–4.69(0.5H, m), 4.95–5.02(0.5H, m), 5.57–5.63(0.5H, m), 6.05–6.20(0.5H, m), 7.27–7.49(5H, m), 7.60–7.67(3H, m), 9.52–9.63(1H, m)

EXAMPLE 218

(2R)-1-(5-Phenylthiophene-2-sulfonyl)-4-[3-(N-methylcarbamoyl)-propane]sulfonyl-N-(2-tetrahydropyranyloxy)-2-piperazinecarboxamide (330 mg) was obtained in substantially the same manner as in Example 216.

Mass (ESI-): 613 (M-H)

$^1$H-NMR (300 MHz, DMSO-d$_6$, δ): 1.50–1.91(6H, m), 1.93–2.07(2H, m), 2.32(2H, t, J=10 Hz), 2.70–2.95(2H, m), 2.79(3H, s), 3.01–3.18(2H, m), 3.26–3.69(3H, m), 3.85–4.05(3H, m), 4.21(1H, d, J=12 Hz), 4.53–4.76(1H, m), 4.87–5.03(1H, m), 5.85–6.12(1H, br), 7.24–7.50(5H, m), 7.55–7.66(2H, m), 9.26–9.50(1H, br)

EXAMPLE 219

(2R)-4-[N-(Aminocarbonylmethyl)aminocarbonyl]-1-[5-(4-fluorophenyl)thiophene-2-sulfonyl]-N-(2-tetrahydropyranyloxy)-2-piperazinecarboxamide (154 mg) was obtained as amorphous powder in substantially the same manner as in Preparation 12.

Mass (ESI-): 568 (M-H)

$^1$H-NMR (300 MHz, CDCl$_3$, δ): 1.50–1.90(6H, m), 2.78 (1H, m), 3.02(1H, m), 3.36(1H, m), 3.61(1H, m), 3.70–3.98 (4H, m), 4.12(1H, d, J=11 Hz), 4.32(1H, d, J=11 Hz), 4.58(1H, brs), 4.89, 4.97(1H, brs), 5.58(1H, brs), 5.95(1H, brs), 6.58(1H, brs), 7.13(1H, t, J=8 Hz), 7.23(1H, d, J=2 Hz), 7.55(2H, dd, J=4, 8 Hz), 7.62(1H, d, J=2 Hz)

Preparation 153

2-(2-Pyridyl)ethanesulfonic acid (1.00 g) was suspended in thionyl chloride (5 ml). Catalytic amount of DMF was added to the suspension. The mixture was stirred at 50° C. for 30 minutes, and was concentrated in vacuo. The resulting solid was recovered and washed with Et₂O to give 1.41 g of 2-(2-pyridyl)ethanesulfonyl chloride hydrochloride as a solid.

¹H-NMR (300 MHz, DMSO-d₆, δ): 2.98(2H, t, J=4 Hz), 3.34(2H, t, J=4 Hz), 7.88(1H, dd, J=4, 6 Hz), 8.03(1H, d, J=6 Hz), 8.48(1H, t, J=6 Hz), 8.77(1H, d, J=4 Hz)

EXAMPLE 220

2-(2-Pyridyl)ethanesulfonyl chloride hydrochloride (214 mg) was added to a solution of (2R)-1-(5-phenylthiophene-2-sulfonyl]-N-(2-tetrahydropyranyloxy)-2-piperazinecarboxamide (200 mg) and triethylamine (188 mg) in CHCl₃ (3 ml) with cooling on an ice bath. The reaction mixture was stirred at ambient temperature for 1 hour. The mixture was concentrated in vacuo, and the residue was purified by SiO₂ column chromatography eluted with MeOH in CHCl₃ (1%) to give 184 mg of (2R)-1-(5-phenylthiophene-2-sulfonyl)-4-[2-(2-pyridyl)ethanesulfonyl]-N-(2-tetrahydropyranyloxy)-2-piperazinecarboxamide as an amorphous powder.

Mass (ESI-): 619 (M-H)

¹H-NMR (300 MHz, CDCl₃, δ): 1.45–1.87(6H, m), 2.73–2.98(2H, m), 3.13–3.25(2H, m), 3.30–3.72(5H, m), 3.81–4.04(2H, m), 4.27(1H, m), 4.64(1H, m), 4.92, 4.98(1H, brs), 7.13(1H, dd, J=3, 6 Hz), 7.17–7.32(2H, m), 7.37–7.48 (3H, m), 7.55–7.66(4H, m), 8.49(1H, d, J=3 Hz), 9.24(1H, brs)

EXAMPLE 221

(2R)-4-[3-(4-Morpholino)propanesulfonyl]-1-(5-phenylthiophene-2-sulfonyl)-N-(2-tetrahydropyranyloxy)-2-piperazinecarboxamide (380 mg) was obtained as an amorphous powder in substantially the same manner as in Example 220.

Mass (ESI+): 643 (M+H)

¹H-NMR (300 MHz, DMSO-d₆, δ): 1.52–2.12(9H, m), 2.65–2.73(1H, m), 2.80–2.98(3H, m), 3.10–3.25(1H, m), 3.51–3.92(4H, m), 4.45–4.60(3H, m), 4.65–4.78(1H, m), 7.28–7.36(2H, m), 7.41–7.54(3H, m), 7.75(2H, d, J=8 Hz), 8.04–8.12(2H, m), 8.45(2H, d, J=3 Hz), 8.90–9.02(1H, m)

EXAMPLE 222

(2R)-4-(3-Chloropropanesulfonyl)-1-(5-phenylthiophene-2-sulfonyl)-N-(2-tetrahydropyranyloxy)-2-piperazinecarboxamide (800 mg) was obtained as an amorphous powder in substantially the same manner as in Example 220.

Mass (ESI-): 590, 592(M-H)

¹H-NMR (300 MHz, CDCl₃, δ): 1.53–1.86(6H, m), 2.10–2.28(2H, m), 2.75–2.93(2H, m), 3.14–3.28(2H, m), 3.56–3.70(4H, m), 3.86–4.08(2H, m), 4.16–4.28(1H, m), 4.57–4.69(1H, m), 4.95–5.02(1H, m), 7.28–7.32(1H, m), 7.40–7.50(3H, m), 7.58–7.66(3H, m), 9.20(1H, brs)

Preparation 154

(2R)-1-[5-(4-Fluorophenyl)thiophene-2-sulfonyl]-N-(2-tetrahydropyranyloxy)-2-piperazinecarboxamide (5.90 g) was obtained as an amorphous powder in substantially the same manner as in Preparation 157 to be mentioned later.

Mass (ESI-): 468(M-H)

¹H-NMR (300 MHz, DMSO-d₆, δ): 1.38–1.69(6H, m), 2.48–2.60(1H, m), 2.68–2.95(2H, m), 3.00–3.12(1H, m), 3.38–3.60(3H, m), 3.81–3.95(1H, m), 4.08–4.22(1H, m), 4.74(1H, d, J=14 Hz), 7.33(2H, t, J=8 Hz), 7.59(2H, d, J=3 Hz), 7.75–7.84(2H, m)

EXAMPLE 223

(2R)-1-[5-(4-Fluorophenyl)thiophene-2-sulfonyl]-4-[2-(4-pyridyl)ethanesulfonyl]-N-(2-tetrahydropyranyloxy)-2-piperazinecarboxamide (405 mg) was obtained as an amorphous powder in substantially the same manner as in Example 220.

Mass (ESI-): 637(M-H)

¹H-NMR (300 MHz, DMSO-d₆, δ): 1.32–1.70(6H, m), 2.80–2.98(3H, m), 3.05–3.28(1H, m), 3.32–3.95(8H, m), 4.42–4.54(1H, m), 4.66–4.75(1H, m), 7.22–7.38(4H, m), 7.53–7.67(2H, m), 7.72–7.86(2H, m), 8.39–8.50(2H, m)

EXAMPLE 224

(2R)-4-(3-Chloropropanesulfonyl)-1-[5-(4-fluorophenyl)thiophene-2-sulfonyl]-N-(2-tetrahydropyranyloxy)-2-piperazinecarboxamide (1.47 g) was obtained as an amorphous powder in substantially the same manner as in Example 220.

Mass (ESI-): 608, 610(M-H)

¹H-NMR (300 MHz, CDCl₃, δ): 1.52–1.91(6H, m), 2.08–2.28(2H, m), 2.75–2.92(2H, m), 3.15–3.26(2H, m), 3.33–3.46(1H, m), 3.57–3.69(4H, m), 3.85–4.08(2H, m), 4.15–4.28(1H, m), 4.56–4.68(1H, m), 4.93–5.02(1H, m), 7.14(2H, t, J=8 Hz), 7.21–7.26(1H, m), 7.52–7.64(3H, m), 9.23(1H, brs)

EXAMPLE 225

A solution of phenyl isocyanate (38 mg) in CHCl₃ (1 ml) was added to a solution of (2R)-1-[5-(4-fluorophenyl)thiophene-2-sulfonyl]-N-(2-tetrahydropyranyloxy)-2-piperazinecarboxamide (150 mg) in CHCl₃ (3 ml). After stirring for 30 minutes at ambient temperature, the reaction mixture was concentrated in vacuo to give 203 mg of (2R)-1-[5-(4-fluorophenyl)thiophene-2-sulfonyl]-4-[(N-phenyl)aminocarbonyl]-N-(2-tetrahydropyranyloxy)-2-piperazinecarboxamide as an amorphous powder.

Mass (ESI-): 587 (M-H)

¹H-NMR (300 MHz, CDCl₃, δ): 1.50–1.93(6H, m), 2.70 (1H, m), 2.95(1H, dd, J=2, 12 Hz), 3.24(1H, m), 3.65(1H, m), 3.88–4.03(2H, m), 4.17(1H, d, J=12 Hz), 4.47(1H, d, J=12 Hz), 4.67(1H, m), 4.94, 5.04(total 1H, s), 6.99(1H, m), 7.15(1H, t, J=8 Hz), 7.20–7.35(5H, m), 7.58(2H, dd, J=4, 8 Hz), 7.64(1H, d, J=3 Hz), 7.80–7.90(1H, m), 9.32, 9.41(1H, s)

EXAMPLE 226

(2R)-1-[5-(4-Fluorophenyl)thiophene-2-sulfonyl]-4-[3-(3-pyridyl)propionyl]-N-(2-tetrahydropyranyloxy)-2-piperazinecarboxamide (190 mg) was obtained as an amorphous powder in substantially the same manner as in Preparation 8.

Mass (ESI): 601(M-H)

¹H-NMR (300 MHz, DMSO-d₆, δ): 1.32–1.68(6H, m), 2.52–2.83(4H, m), 3.02–4.12(7H, m), 4.20–4.52(2H, m), 4.61–4.75(1H, m), 7.18–7.38(3H, m), 7.52–7.68(3H, m), 7.75–7.86(2H, m), 8.32–8.45(2H, m)

EXAMPLE 227

(2R)-1-[5-(4-Fluorophenyl)thiophene-2-sulfonyl]-4-[3-(3-pyridyl)-acrylyl]-N-(2-tetrahydropyranyloxy)-2-piperazinecarboxamide (190 mg) was obtained as an amorphous powder in substantially the same manner as in Preparation 8.

Mass (ESI): 561(M-H)

¹H-NMR (300 MHz, DMSO-d₆, δ): 2.19(6H, t, J=7 Hz), 1.89–2.06(2H, m), 2.76–2.88(1H, m), 2.95–3.28(1H, m), 3.49–3.80(3H, m), 3.88(1H, d, J=12 Hz), 4.49(1H, brs), 7.33(2H, t, J=8 Hz), 7.55–7.63(1H, m), 7.69(1H, d, J=3 Hz), 7.78–7.86(2H, m), 9.01(1H, s)

EXAMPLE 228

(2R)-1-[5-(4-Fluorophenyl)thiophene-2-sulfonyl]-4-(N-propylaminocarbonyl)-N-(2-tetrahydropyranyloxy)-2-piperazinecarboxamide (175 mg) was obtained as an amorphous powder in substantially the same manner as in Example 225.

Mass (ESI): 553 (M–H)

$^1$H-NMR (300 MHz, DMSO-$d_6$, δ): 0.74, 0.76(3H, t, J=7 Hz), 1.23–1.40(2H, m), 1.44–1.72(6H, m), 2.78–2.98(3H, m), 3.02–3.17(1H, m), 3.46–3.96(5H, m), 4.03–4.18(1H, m), 4.22–4.31(1H, m), 4.69, 4.77(1H, brs), 6.35–6.52(1H, m), 7.34(2H, t, J=8 Hz), 7.57–7.67(2H, m), 7.75–7.85(2H, m)

EXAMPLE 229

(2R)-1-[5-(4-Fluorophenyl)thiophene-2-sulfonyl]-4-(N-methylaminocarbonyl)-N-(2-tetrahydropyranyloxy)-2-piperazinecarboxamide (165 mg) was obtained as an amorphous powder in substantially the same manner as in Example 225.

Mass (ESI): 525 (M–H)

$^1$H-NMR (300 MHz, DMSO-$d_6$, δ): 1.37–1.69(6H, m), 2.48(3H, d, J=7 Hz), 2.83–2.98(1H, m), 3.02–3.14(1H, m), 3.45–3.96(5H, m), 4.02–4.18(1H, m), 4.22–4.31(1H, m), 4.69, 4.78(1H, brs), 6.32–6.48(1H, m), 7.34(2H, t, J=8 Hz), 7.56–7.67(2H, m), 7.75–7.85(2H, m)

EXAMPLE 230

A solution of ethyl chlorocarbonate (42 mg) in $CHCl_3$ (1 ml) was added dropwise to a solution of (2R)-1-[5-(4-fluorophenyl)thiophene-2-sulfonyl]-N-(2-tetrahydropyranyloxy)-2-piperazinecarboxamide (150 mg) and triethylamine (39 mg) in $CHCl_3$ (2 ml) with cooling on an ice bath. The reaction mixture was stirred at said temperature for 30 minutes and the reaction was quenched by adding 3-(N,N-dimethylamino)propylamine (0.5 ml). The mixture was concentrated in vacuo, and the residue was partitioned between AcOEt and 5% aqueous citric acid. The organic layer was washed with saturated aqueous $NaHCO_3$ solution and saturated aqueous NaCl solution, dried over $MgSO_4$, and concentrated in vacuo. The residue was purified by $SiO_2$ column chromatography eluted with AcOEt in hexane gradually from 40% to 60%, to give 142 mg of (2R)-4-ethoxycarbonyl-1-[5-(4-fluorophenyl)thiophene-2-sulfonyl]-N-(2-tetrahydropyranyloxy)-2-piperazinecarboxamide.

Mass (ESI-): 540 (M–H)

$^1$H-NMR (300 MHz, $CDCl_3$, δ): 1.20(3H, t, J=5 Hz), 1.50–1.90(6H, m), 2.90–3.20(2H, m), 3.45(1H, m), 3.64(1H, m), 3.77(1H, m), 3.83–4.00(2H, m), 4.02–4.15(2H, m), 4.37–4.58(2H, m), 4.92, 4.98(1H, s), 7.12(2H, t, J=8 Hz), 7.21(1H, d, J=2 Hz), 7.51–7.65(3H, m),

EXAMPLE 231

(2R)-4-Butyryl-1-[5-(4-fluorophenyl)thiophene-2-sulfonyl]-N-(2-tetrahydropyranyloxy)-2-piperazinecarboxamide (168 mg) was obtained as an amorphous powder in substantially the same manner as in Preparation 8.

Mass (ESI): 538 (M–H)

$^1$H-NMR (300 MHz, $CDCl_3$, δ): 0.92(3H, t, J=8 Hz), 1.50–1.94(8H, m), 2.18–2.38(2H, m), 2.45–2.72(1H, m), 2.94–3.12(1H, m), 3.25–3.41(1H, m), 3.54–3.98(4H, m), 4.28–4.42(1H, m), 4.46–4.59(1H, m), 4.90–4.98(1H, brs), 7.08–7.28(3H, m), 7.52–7.68(3H, m), 9.20(1H, s)

EXAMPLE 232

(2R)-4-(N,N-Dimethylaminosulfonyl)-1-[5-(4-fluorophenyl)thiophene-2-sulfonyl]-N-(2-tetrahydropyranyloxy)-2-piperazinecarboxamide (240 mg) was obtained as an amorphous powder in substantially the same manner as in Example 230.

Mass (ESI): 575 (M–H)

$^1$H-NMR (300 MHz, $CDCl_3$, δ): 1.52–1.92(6H, m), 2.60–2.76(2H, m), 2.82(3H, s), 2.84(3H, s), 3.39–3.52(2H, m), 3.55–3.69(1H, m), 3.82–4.09(3H, m), 4.52–5.64(1H, m), 4.92–5.00(1H, m), 7.13(2H, t, J=8 Hz), 7.20–7.24(1H, m), 7.51–7.61(3H, m), 9.18(1H, brs)

Preparation 155

Sodium hydride (60% in oil dispersion, 1.22 g, 50.9 mmol) was washed with dry tetrahydrofuran (20 ml×3) under nitrogen atomosphere. Freshly distilled tetrahydrofuran (50 ml) was added and the mixture was cooled to 0° C. with an ice bath. To this mixture was added portionwise solution of benzyl alcohol (5 g, 46.2 mmol) in dry tetrahydrofuran (10 ml) and the mixture was stirred for 1 hour at said temperature. To the resulting mixture was added γ-thiobutyrolactone (5.2 g, 50.9 mmol) slowly and the resulting mixture was warmed to room temperature. After stirring for 1 hour, $H_2O$ (30 ml) was added carefully and tetrahydrofuran was removed under reduced pressure. The residue was extracted three times with AcOEt. The organic layers were combined, washed with brine, and dried over magnesium sulfate. The solvent was evaporated to give 9.96 g of benzyl 4-mercaptobutyrate as a colorless oil which was taken to the next step without further purification.

$^1$H-NMR (300 MHz, $CDCl_3$, δ): 1.37(1H, t, J=9 Hz), 1.93–2.04(2H, m), 2.50(1H, t, J=9 Hz), 2.59(1H, t, J=9 Hz), 5.13(2H, s), 7.34–7.40(5H, m)

Preparation 156

To a mixture of benzyl 4-mercaptobutyrate (9.96 g, 47.4 mmol) and potassium nitrate (12 g, 118 mmol) was added dropwise sulfuryl chloride (16 g, 118 mmol) at 0° C., and the mixture was stirred for 10 hours at room temperature. The resulting suspension was adjusted to pH 7 with saturated $NaHCO_3$ solution. The organic layer was separated, washed with saturated $NaHCO_3$ solution and brine, and dried over $MgSO_4$. The solvent was removed under reduced pressure. The residue was dissolved in $CHCl_3$ and the solution was passed through short $SiO_2$ column to give 9.85 g of benzyl 4-chlorosulfonylbutyrate as a slightly brown oil.

$^1$H-NMR (300 MHz, $CDCl_3$, δ): 2.30–2.45(2H, m), 2.67 (2H, t, J=10 Hz), 3.80(2H, t, J=10 Hz), 5.15(2H, s), 7.38(5H, s)

EXAMPLE 233

(2R)-1-(5-Phenylthiophene-2-sulfonyl)-4-[3-(benzyloxycarbonyl)propane]sulfonyl-N-(2-tetrahydropyranyloxy)-2-piperazinecarboxamide (1.11 g) was obtained in substantially the same manner as in Example 220.

Mass (ESI-): 690 (M–H)

$^1$H-NMR (300 MHz, $CDCl_3$, δ): 1.51–1.90(6H, m), 1.95–2.14(2H, m), 2.48–2.56(2H, m), 2.76–2.88(1H, m), 3.09–3.20(2H, m), 3.33–3.46(1H, m), 3.57–3.67(2H, m), 3.86–4.04(2H, m), 4.17–4.23(1H, m), 4.57–4.65(0.5H, m), 4.93–5.01(0.5H, m), 5.12(2H, s), 7.27–7.48(3H, m), 7.56–7.65(2H, m), 9.19(1H, br)

EXAMPLE 234

(2R)-1-[5-(4-Fluorophenyl)thiophene-2-sulfonyl]-4-(1-propanesulfonyl)-N-(2-tetrahydropyranyloxy)-2-piperazinecarboxamide (95 mg) was obtained in substantially the same manner as in Example 220.

Mass (ESI–): 574 (M–H)

$^1$H-NMR (300 MHz, CDCl$_3$, δ): 1.02(3H, t, J=7 Hz), 1.52–1.92(8H, m), 2.75–2.91(2H, m), 2.97–3.10(2H, m), 3.35–3.47(1H, m), 3.57–3.70(2H, m), 3.85–4.05(2H, m), 4.14–4.25(1H, m), 4.57–4.69(1H, br), 4.92–5.00(1H, m), 7.09–7.19(2H, m), 7.21(1H, d, J=4 Hz), 7.53–7.64(2H, m), 9.15–9.24(1H, m)

Preparation 157

(2R)-4-(9-Fluorenylmethyloxycarbonyl)-1-(5-phenylthiophene-2-sulfonyl)-N-(2-tetrahydropyranyloxy)-2-piperazinecarboxamide (16.5 g) was dissolved in a solution (160 ml) of 20% piperidine in DMF at room temperature. After stirring for 30 minutes at said temperature, the solution was concentrated in vacuo. The residue was purified by SiO$_2$ column chromatography (eluent: 1% MeOH in CHCl$_3$, then 4% MeOH in CHCl$_3$) to give 9.57 g of (2R)-1-(5-phenylthiophene-2-sulfonyl)-N-(2-tetrahydropyranyloxy)-2-piperazinecarboxamide as an amorphous powder.

Mass (ESI–): 450 (M–H)

$^1$H-NMR (300 MHz, CDCl$_3$, δ): 1.46–1.90(6H, m), 2.67–2.92(3H, m), 3.24–3.50(2H, m), 3.52–3.68(1H, m), 3.74–3.82(1H, m), 3.86–3.98(1H, m), 4.38(1H, brs), 4.92–4.98(1H, m), 7.28(1H, d, J=3 Hz), 7.35–7.48(3H, m), 7.58–7.64(3H, m), 8.02(1H, s)

EXAMPLE 235

(2R)-1-(5-Phenylthiophene-2-sulfonyl)-4-[2-(4-pyridyl)ethanesulfonyl]-N-(2-tetrahydropyranyloxy)-2-piperazinecarboxamide (186 mg) was obtained as an amorphous powder in substantially the same manner as in Example 220.

Mass (ESI–): 619 (M–H)

$^1$H-NMR (300 MHz, DMSO-d$_6$, δ): 1.32–1.69(6H, m), 2.65–2.73(1H, m), 2.80–2.98(3H, m), 3.10–3.25(1H, m), 3.51–3.92(4H, m), 4.45–4.60(3H, m), 4.65–4.78(1H, m), 7.28–7.36(2H, m), 7.41–7.54(3H, m), 7.75(2H, d, J=8 Hz), 8.04–8.12(2H, m), 8.45(2H, d, J=3 Hz), 8.90–9.02(1H, m)

EXAMPLE 236

(2R)-4-(N-Ethylaminocarbonyl)-1-[5-(4-fluorophenyl)thiophene-2-sulfonyl]-N-(2-tetrahydropyranyloxy)-2-piperazinecarboxamide (164 mg) was obtained as an amorphous powder in substantially the same manner as in Example 225.

Mass (ESI): 539 (M–H)

$^1$H-NMR (300 MHz, CDCl$_3$, δ) 1.08(3H, t, J=7 Hz), 1.50–1.68(3H, m), 1.72–1.90(3H, m), 2.58–2.72(1H, m), 2.85(1H, dd, J=3, 8 Hz), 3.08–3.31(3H, m), 3.57–3.68(1H, m), 3.84–4.08(3H, m), 4.22–4.34(1H, m), 4.58(1H, brs), 4.96(1H, d, J=2 Hz), 5.18–5.30(1H, m), 7.14(2H, t, J=8 Hz), 7.22(1H, d, J=3 Hz), 7.52–7.76(3H, m), 9.35, 9.42(1H, s)

EXAMPLE 237

(2R)-4-[(N-Cyclohexyl)aminocarbonyl]-1-[5-(4-fluorophenyl)thiophene-2-sulfonyl]-N-(2-tetrahydropyranyloxy)-2-piperazine-carboxamide (190 mg) was obtained in substantially the same manner as in Example 225.

Mass (ESI–): 593 (M–H)

$^1$H-NMR (300 MHz, CDCl$_3$, δ): 1.04–1.43(6H, m), 1.50–1.95(10H, m), 2.65(1H, m), 2.84(1H, dd, J=2, 12 Hz), 3.23(1H, m), 3.50(1H, m), 3.63(1H, m), 3.84–4.07(3H, m), 4.28(1H, m), 4.58(1H, d, J=7 Hz), 4.91, 5.00(1H, s), 5.15 (1H, d, J=5 Hz), 7.15(2H, t, J=8 Hz), 7.22(1H, d, J=2 Hz), 7.52–7.65(3H, m), 9.28, 9.42(1H, s)

EXAMPLE 238

(2R)-1-[5-(4-Fluorophenyl)thiophene-2-sulfonyl]-4-methoxycarbonyl-N-(2-tetrahydropyranyloxy)-2-piperazinecarboxamide (160 mg) was obtained as an amorphous powder in substantially the same manner as in Example 230.

Mass (ESI): 526 (M–H)

$^1$H-NMR (300 MHz, DMSO-d$_6$, δ): 1.33–1.68(6H, m), 2.85–3.22(2H, m), 3.42–4.15(6H, m), 3.49, 3.51(3H, s), 4.22–4.35(1H, m), 4.62, 4.71(1H, brs), 7.33(2H, t, J=8 Hz), 7.59(2H, d, J=3 Hz), 7.74–7.85(2H, m)

EXAMPLE 239

(2R)-4-Dimethylcarbamoyl-1-[5-(4-fluorophenyl)thiophene-2-sulfonyl]-N-(2-tetrahydropyranyloxy)-2-piperazinecarboxamide (179 mg) was obtained in substantially the same manner as in Example 230.

Mass (ESI–): 539 (M–H)

$^1$H-NMR (300 MHz, CDCl$_3$, δ): 1.50–1.93(6H, m), 2.82 (6H, s), 2.85–3.10(2H, m), 3.20–3.50(1H, m), 3.44(1H, d, J=12 Hz), 3.63(1H, m), 3.82(1H, m), 3.95(1H, m), 4.21(1H, t, J=12 Hz), 4.61(1H, m), 4.96, 4.99(1H, s), 7.12(2H, t, J=8 Hz), 7.19(1H, d, J=2 Hz), 7.50(2H, dd, J=4, 8 Hz), 7.65(1H, m)

EXAMPLE 240

(2R)-4-(2-Benzyloxycarbonylaminoethanesulfonyl)-1-(5-phenylthiophene-2-sulfonyl)-N-(2-tetrahydropyranyloxy)-2-piperazinecarboxamide (199 mg) was obtained in substantially the same manner as in Example 220.

Mass (ESI): 691 (M–1)

$^1$H-NMR (300 MHz, CDCl$_3$, δ): 1.50–1.61(4H, m), 1.70–1.87(2H, m), 2.72–2.88(2H, m), 3.20–3.40(3H, m), 3.49–3.69(4H, m), 3.84–4.05(2H, m), 4.14–4.24(1H, m), 4.56–4.67(1H, m), 4.94–5.00(1H, m), 5.08–5.11(2H, m), 5.49–5.61(1H, m), 7.25–7.31(1H, m), 7.31–7.38(5H, m), 7.40–7.48(3H, m), 7.58–7.63(3H, m), 9.18–9.28(1H, m)

EXAMPLE 241

(2R)-4-[5-(Isoxazol-3-yl)thiophene-2-sulfonyl]-1-(5-phenylthiophene-2-sulfonyl)-N-(2-tetrahydropyranyloxy)-2-piperazinecarboxamide (285 mg) was obtained as an amorphous powder in substantially the same manner as in Example 220.

Mass (ESI–): 663 (M–H)

$^1$H-NMR (300 MHz, CDCl$_3$, δ): 1.48–1.89(6H, m), 2.42–2.64(2H, m), 3.45–3.70(3H, m), 3.84–4.07(2H, m), 4.27–4.40(1H, m), 4.65–4.72(1H, m), 4.92–5.00(1H, m), 6.40(1H, d, J=8 Hz), 7.17–7.12(1H, m), 7.28–7.60(8H, m), 8.28(1H, s), 9.05(1H, brs)

EXAMPLE 242

(2R)-1-(5-Phenylthiophene-2-sulfonyl)-4-(1-piperidinesulfonyl)-N-(2-tetrahydropyranyloxy)-2- piperazinecarboxamide (192 mg) was obtained as an amorphous powder in substantially the same manner as in Example 220.

Mass (ESI−): 597 (M−H)

$^1$H-NMR (300 MHz, CDCl$_3$, δ): 1.47–1.93(14H, m), 2.58–2.77(2H, m), 3.09–3.28(4H, m), 3.33–3.68(3H, m), 3.82–4.13(3H, m), 4.55–4.67(1H, m), 4.96(1H, d, J=8 Hz), 7.24–7.32(1H, m), 7.36–7.48(3H, m), 7.55–7.66(3H, m), 9.19(1H, brs)

EXAMPLE 243

(2R)-4-(N-Methylpropylaminosulfonyl)-1-(5-phenylthiophene-2-sulfonyl)-N-(2-tetrahydropyranyloxy)-2-piperazinecarboxamide (175 mg) was obtained as an amorphous powder in substantially the same manner as in Example 220.

Mass (ESI−): 585 (M−H)

$^1$H-NMR (300 MHz, CDCl$_3$, δ): 0.88, 0.89(3H, t, J=8 Hz), 1.48–1.93(8H, m), 2.58–2.75(2H, m), 2.78, 2.81(3H, s), 3.06–3.21(2H, m), 3.36–3.52(2H, m), 3.55–3.70(1H, m), 3.84–4.08(3H, m), 4.54–4.55(1H, m), 4.92–4.99(1H, m), 7.28–7.31(1H, m), 7.37–7.48(3H, m), 7.57–7.63(3H, m), 9.08(1H, brs)

EXAMPLE 244

(2R)-4-(N,N-Dimethylaminosulfonyl)-1-(5-phenylthiophene-2-sulfonyl)-N-(2-tetrahydropyranyloxy)-2-piperazinecarboxamide (172 mg) was obtained as an amorphous powder in substantially the same manner as in Example 220.

Mass (ESI−): 557 (M−H)

$^1$H-NMR (300 MHz, CDCl$_3$, δ): 1.52–1.92(6H, m), 2.62–2.76(2H, m), 2.81(3H, s), 2.84(3H, s) 3.36–3.51(2H, m), 3.55–3.70(1H, m), 3.82–4.09(3H, m), 4.52–4.65(1H, m), 4.91–5.00(1H, m), 7.28–7.32(1H, m), 7.35–7.48(3H, m), 7.55–7.64(3H, m), 9.18(1H, brs)

EXAMPLE 245

(2R)-4-Methoxycarbonyl-1-(5-phenylthiophene-2-sulfonyl)-N-(2-tetrahydropyranyloxy)-2-piperazinecarboxamide (150 mg) was obtained as an amorphous powder in substantially the same manner as in Example 220.

Mass (ESI−): 508 (M−H)

$^1$H-NMR (300 MHz, CDCl$_3$, δ): 1.50–1.90(6H, m), 2.88–3.16(2H, m), 3.48–3.52(1H, m), 3.56–4.00(4H, m), 3.63, 3.66(3H, s), 4.41–4.59(2H, m), 4.89–5.02(1H, m), 7.28(1H, d, J=3 Hz), 7.35–7.48(3H, m), 7.56–7.65(3H, m), 9.14(1H, brs)

EXAMPLE 246

(2R)-4-Ethylaminocarbonyl-1-(5-phenylthiophene-2-sulfonyl)-N-(2-tetrahydropyranyloxy)-2-piperazinecarboxamide (160 mg) was obtained as an amorphous powder in substantially the same manner as in Example 220.

Mass (ESI−): 521 (M−H)

$^1$H-NMR (300 MHz, CDCl$_3$, δ): 1.10(3H, t, J=7 Hz), 1.52–1.91(6H, m), 2.58–2.72(1H, m), 2.85(1H, dd, J=3, 16 Hz), 3.08–3.30(3H, m), 3.56–3.68(1H, m), 3.85–4.10(3H, m), 4.22–4.33(1H, m), 4.55–4.62(1H, m), 4.88–5.01(1H, m), 5.18–5.30(1H, m), 7.30(1H, d, J=3 Hz), 7.37–7.48(3H, m), 7.56–7.65(3H, m), 9.34, 9.40(1H, brs)

EXAMPLE 247

(2R)-1-[5-(4-Fluorophenyl)thiophene-2-sulfonyl]-4-(pyridine-3-sulfonyl)-N-(2-tetrahydropyranyloxy)-2-piperazinecarboxamide (213 mg) was obtained as an amorphous powder in substantially the same manner as in Example 220.

Mass (ESI−): 609 (M−H)

$^1$H-NMR (300 MHz, CDCl$_3$, δ): 1.52–1.91(6H, m), 2.46–2.68(2H, m), 3.38–3.52(1H, m), 3.55–3.68(2H, m), 3.82–4.00(2H, m), 4.20–4.38(1H, m), 4.58–4.68(1H, m), 4.86, 4.94(1H, brs), 7.10–7.20(3H, m), 7.33–7.45(1H, m), 7.49–7.59(3H, m), 7.97–8.06(1H, m), 8.64–8.76(1H, m), 8.89–8.97(1H, m), 9.07(1H, brs)

EXAMPLE 248

(2R)-4-(N-Ethylaminosulfonyl)-1-[5-(4-fluorophenyl)thiophene-2-sulfonyl]-N-(2-tetrahydropyranyloxy)-2-piperazinecarboxamide (203 mg) was obtained as an amorphous powder in substantially the same manner as in Example 230.

Mass (ESI): 575 (M−H)

$^1$H-NMR (300 MHz, CDCl$_3$, δ): 1.17, 1.18(3H, t, J=7 Hz), 1.50–1.92(6H, m), 2.18–2.32(2H, m), 2.98–3.13(2H, m), 3.45–3.70(2H, m), 3.84–4.02(2H, m), 4.12–4.28(1H, m), 4.32–4.67(2H, m), 4.88–4.98(1H, m), 7.08–7.18(2H, m), 7.20–7.25(1H, m), 7.52–7.62(3H, m), 9.24(1H, brs)

EXAMPLE 249

(2R)-1-[5-(4-Fluorophenyl)thiophene-2-sulfonyl]-4-(1-piperidinesulfonyl)-N-(2-tetrahydropyranyloxy)-2-piperazinecarboxamide (240 mg) was obtained as an amorphous powder in substantially the same manner as in Example 220.

Mass (ESI−): 615 (M−H)

$^1$H-NMR (300 MHz, CDCl$_3$, δ): 1.48–1.93(14H, m), 2.18–2.26(2H, m), 3.10–3.28(4H, m), 3.36–3.70(3H, m), 3.86–4.12(3H, m), 4.55–4.67(1H, m), 4.92–5.00(1H, m), 7.14(2H, t, J=8 Hz), 7.19–7.25(1H, m), 7.52–7.62(3H, m), 9.16(1H, brs)

EXAMPLE 250

(2R)-1-[5-(4-Fluorophenyl)thiophene-2-sulfonyl]-4-[N-methyl-N-(methoxycarbonylmethyl)aminosulfonyl]-N-(2-tetrahydropyranyloxy)-2-piperazinecarboxamide (120 mg) was obtained as an amorphous powder in substantially the same manner as in Example 220.

Mass (ESI−): 633 (M−H)

$^1$H-NMR (300 MHz, CDCl$_3$, δ): 1.50–1.90(6H, m), 2.66–2.82(2H, m), 2.88, 2.92(3H, s) 3.38–3.68(3H, m), 3.75(3H, s), 3.85–4.22(5H, m), 4.58–4.70(1H, m), 4.92–5.01(1H, m), 7.14(2H, t, J=8 Hz), 7.22(1H, d, J=3 Hz), 7.52–7.65(3H, m), 9.26, 9.32(1H, brs)

EXAMPLE 251

(2R)-4-[N-(Ethoxycarbonylmethyl)aminocarbonyl]-1-[5-(4-fluorophenyl)thiophene-2-sulfonyl]-N-(2-tetrahydropyranyloxy)-2-piperazinecarboxamide (829 mg) was obtained as an amorphous powder in substantially the same manner as in Example 225.

Mass (ESI−): 597 (M−H)

$^1$H-NMR (300 MHz, CDCl$_3$, δ): 1.25(3H, t, J=4 Hz), 1.50–1.90(6H, m), 2.23(1H, t, J=12 Hz), 2.93(1H, d, J=12 Hz), 3.27(1H, t, J=12 Hz), 3.64(1H, m), 3.75–4.08(5H, m), 4.16(2H, q, J=4 Hz), 4.88(1H, m), 4.61(1H, d, J=8 Hz), 5.01(1H, s), 5.74(1H, m), 7.15(2H, t, J=8 Hz), 7.23(1H, m), 7.52–7.65(3H, m), 9.33, 9.40(1H, s)

EXAMPLE 252

Phenyl chloroformate (60 mg) in $CHCl_3$ (1 ml) was added to (2R)-1-[5-(4-Fluorophenyl)thiophene-2-sulfonyl]-N-(2-tetrahydropyranyloxy)-2-piperazinecarboxamide (150 mg) in pyridine (0.5 ml) and $CHCl_3$ (0.5 ml) dropwise with cooling on an ice bath. The reaction mixture was stirred at said temperature for 2 hours. The mixture was concentrated in vacuo, and the residue was partitioned between AcOEt and 5% aqueous citric acid. The organic layer was washed with 5% aqueous citric acid, saturated aqueous $NaHCO_3$ solution and saturated aqueous NaCl solution, dried over $MgSO_4$, and concentrated in vacuo to give 202 mg of (2R)-1-[5-(4-fluorophenyl)thiophene-2-sulfonyl]-4-phenoxycarbonyl-N-(2-tetrahydropyranyloxy)-2-piperazinecarboxamide.

Mass (ESI−): 588 (M−H)

$^1$H-NMR (300 MHz, $CDCl_3$, δ): 1.50–1.90(6H, m), 3.00–3.40(2H, m), 3.50–3.70(3H, m), 3.75–4.20(3H, m), 4.44–5.03(3H, m), 7.00–7.35(8H, m), 7.58(2H, dd, J=4, 8 Hz), 7.52–7.70(1H, m), 9.13(1H, brs)

Preparation 158

(2R)-N-(2-Tetrahydropyranyloxy)-1-[5-(4-trifluoromethylphenyl)thiophene-2-sulfonyl]-2-piperazinecarboxamide (770 mg) was obtained as an amorous powder in substantially the same manner as in Preparation 157.

Mass (ESI+): 520 (M+H)

$^1$H-NMR (300 MHz, $CDCl_3$, δ): 1.46–1.88(6H, m), 2.78–2.90(2H, m), 2.93–3.07(1H, m), 3.25–3.48(2H, m), 3.52–3.68(1H, m), 3.72–3.83(1H, m), 3.86–3.99(1H, m), 4.34–4.42(1H, m), 4.74, 4.95(1H, brs), 7.35(1H, d, J=3 Hz), 7.58–7.75(5H, m)

EXAMPLE 253

(2R)-4-Ethylaminosulfonyl-N-(2-tetrahydropyranyloxy)-1-[5-(4-trifluoromethylphenyl)thiophene-2-sulfonyl]-2-piperazinecarboxamide (68 mg) was obtained as an amorphous powder in substantially the same manner as in Example 220.

Mass (ESI−): 625 (M−H)

$^1$H-NMR (300 MHz, $CDCl_3$, δ): 1.18, 1.23(3H, t, J=8 Hz), 1.49–1.88(6H, m), 2.28–2.87(2H, m), 2.99–3.15(2H, m), 3.52–3.68(2H, m), 3.86–4.03(2H, m), 4.12–4.15(1H, m), 4.28–4.45(1H, m), 4.55–4.68(1H, m), 4.86–5.00(1H, m), 7.30–7.40(1H, m), 7.60–7.78(5H, m), 9.17(1H, brs)

EXAMPLE 254

(2R)-4-(Methylpropylaminosulfonyl)-N-(2-tetrahydropyranyloxy)-1-[5-(4-trifluoromethylphenyl)thiophene-2-sulfonyl]-2-piperazinecarboxamide (235 mg) was obtained as an amorphous powder in substantially the same manner as in Example 220.

Mass (ESI−): 653 (M−H)

$^1$H-NMR (300 MHz, $CDCl_3$, δ): 0.90(3H, t, J=7 Hz), 1.48–1.93(8H, m), 2.61–2.76(2H, m), 2.79, 2.82(3H, s), 3.08–3.22(2H, m), 3.38–3.70(3H, m), 3.85–4.08(3H, m), 4.65(1H, brs), 4.92–5.00(1H, m), 7.33–7.40(1H, m), 7.58–7.67(1H, m), 7.71(4H, s), 9.18(1H, brs)

EXAMPLE 255

(2R)-4-(N,N-Dimethylaminosulfonyl)-N-(2-tetrahydropyranyloxy)-1-[5-(4-trifluoromethylphenyl)thiophene-2-sulfonyl]-2-piperazinecarboxamide (150 mg) was obtained as an amorphous powder in substantially the same manner as in Example 220.

Mass (ESI−): 625 (M−H)

$^1$H-NMR (300 MHz, $CDCl_3$, δ): 1.52–1.92(6H, m), 2.62–2.77(2H, m), 2.85(3H, s), 2.87(3H, s), 3.40–3.72(3H, m), 3.88–4.09(3H, m), 4.57–4.67(1H, m), 4.92–5.00(1H, m), 7.38(1H, d, J=3 Hz), 7.60–7.76(5H, m), 9.16(1H, brs)

Preparation 159

(2R)-1-[5-(4-Chlorophenyl)thiophene-2-sulfonyl]-N-(2-tetrahydropyranyloxy)-2-piperazinecarboxamide (4.20 g) was obtained as an amorphous powder in substantially the same manner as in Preparation 157.

Mass (ESI+): 486, 488 (M+H)

$^1$H-NMR (300 MHz, $CDCl_3$, δ): 1.48–1.98(6H, m), 2.66–3.04(3H, m), 3.23–3.49(2H, m), 3.53–3.68(1H, m), 3.73–3.83(1H, m), 3.86–3.98(1H, m), 4.38(1H, brs), 4.76, 4.97(1H, brs), 7.22–7.28(2H, m), 7.36–7.44(2H, m), 7.48–7.62(3H, m)

EXAMPLE 256

(2R)-1-[5-(4-Chlorophenyl)thiophene-2-sulfonyl]-4-(N,N-dimethylaminosulfonyl)-N-(2-tetrahydropyranyloxy)-2-piperazinecarboxamide (210 mg) was obtained as an amorphous powder in substantially the same manner as in Example 220.

Mass (ESI−): 591, 593 (M−H)

$^1$H-NMR (300 MHz, $CDCl_3$, δ): 1.52–1.93(6H, m), 2.62–2.77(2H, m), 2.84(3H, s), 2.86(3H, s), 3.38–3.70(3H, m), 3.84–4.10(3H, m), 4.54–4.67(1H, m), 4.93–5.00(1H, m), 7.28(1H, d, J=3 Hz), 7.41(2H, d, J=8 Hz), 7.54(2H, d, J=8 Hz), 7.57–7.62(1H, m), 9.18(1H, brs)

EXAMPLE 257

(2R)-1-[5-(4-Chlorophenyl)thiophene-2-sulfonyl]-4-(N-methylethylaminosulfonyl)-N-(2-tetrahydropyranyloxy)-2-piperazinecarboxamide (181 mg) was obtained as an amorphous powder in substantially the same manner as in Example 220.

Mass (ESI−): 605, 607 (M−H)

$^1$H-NMR (300 MHz, $CDCl_3$, δ): 1.18(3H, t, J=7 Hz), 1.50–1.92(6H, m), 2.57–2.75(2H, m), 2.80, 2.82(3H, s), 3.18–3.32(2H, m), 3.35–3.70(3H, m), 3.85–4.08(3H, m), 4.53–4.66(1H, m), 4.90–4.99(1H, m), 7.28(1H, d, J=3 Hz), 7.42(2H, d, J=8 Hz), 7.53(2H, d, J=8 Hz), 7.61(1H, d, J=3 Hz), 9.14(1H, brs)

EXAMPLE 258

(2R)-1-[5-(4-Chlorophenyl)thiophene-2-sulfonyl]-4-(3-chloropropanesulfonyl)-N-(2-tetrahydropyranyloxy)-2-piperazinecarboxamide (840 mg) was obtained as an amorphous powder in substantially the same manner as in Example 220.

Mass (ESI−): 624, 626 (M−H)

$^1$H-NMR (300 MHz, $CDCl_3$, δ): 1.51–1.91(6H, m), 2.10–2.27(2H, m), 2.76–2.90(2H, m), 3.15–3.27(2H, m), 3.32–3.48(1H, m), 3.58–3.70(4H, m), 3.86–4.08(2H, m), 4.15–4.27(1H, m), 4.56–4.68(1H, m), 4.92–5.00(1H, m), 7.28(1H, d, J=3 Hz), 7.42(2H, d, J=8 Hz), 7.54(2H, d, J=8 Hz), 7.57–7.66(1H, m), 9.18(1H, brs)

EXAMPLE 259

(2R)-1-[5-(4-Chlorophenyl)thiophene-2-sulfonyl]-4-methoxycarbonyl-N-(2-tetrahydropyranyloxy)-2- piperazinecarboxamide (138 mg) was obtained as an amorphous powder in substantially the same manner as in Example 5.

Mass (ESI−): 542, 544 (M−H)

¹H-NMR (300 MHz, CDCl₃, δ): 1.48–1.88(6H, m), 2.90–3.18(2H, m), 3.37–3.54(1H, m), 3.58–3.69(1H, m), 3.65, 3.68(3H, s), 3.70–4.00(3H, m), 4.40–4.58(2H, m), 4.88–5.01(1H, m), 7.25(1H, d, J=3 Hz), 7.40(2H, d, J=8 Hz), 7.52(2H, d, J=8 Hz), 7.57–7.65(1H, m), 9.16(1H, brs)

Preparation 160

(2R)-1-[5-(4-Ethoxyphenyl)thiophenesulfonyl]-N-(2-tetrahydropyranyloxy)-2-piperazinecarboxamide (3.76 g) was obtained in substantially the same manner as in Preparation 157.

Mass (ESI−): 494 (M−H)

¹H-NMR (300 MHz, CDCl₃, δ): 1.42(3H, t, J=7 Hz), 1.49–1.88(6H, m), 2.65–2.85(2H, m), 2.88–3.01(1H, m), 3.24–3.49(2H, m), 3.52–3.67(1H, m), 3.72–3.82(1H, m), 3.86–3.97(1H, m), 4.05(2H, q, J=7 Hz), 4.34(1H, bs), 4.78 (1H, bs), 6.91(2H, d, J=8 Hz), 7.13(1H, d, J=4 Hz), 7.52(2H, d, J=8 Hz), 7.56(1H, d, J=4 Hz)

EXAMPLE 260

(2R)-4-(N,N-Dimethylaminosulfonyl)-1-[5-(4-ethoxyphenyl)thiophenesulfonyl]-N-(2-tetrahydropyranyloxy)-2-piperazinecarboxamide (350 mg) was obtained as an amorphous powder in substantially the same manner as in Example 230.

Mass (ESI−): 601 (M−H)

¹H-NMR (300 MHz, CDCl₃, δ): 1.47(3H, t, J=7 Hz), 1.52–1.95(6H, m), 2.65–2.87(2H, m), 2.88(3H, s), 2.90(3H, s), 3.35–3.51(2H, m), 3.56–3.70(2H, m), 3.85–3.96(1H, m), 3.97–4.10(3H, m), 4.09(2H, q, J=7 Hz), 4.62(1H, bs), 4.97 (1H, bs), 6.91(2H, d, J=8 Hz), 7.17(1H, d, J=4 Hz), 7.51(2H, d, J=8 Hz), 7.57(1H, d, J=4 Hz)

EXAMPLE 261

(2R)-4-(3-Chloropropanesulfonyl)-1-[5-(4-ethoxyphenyl)thiophene-2-sulfonyl]-N-(2-tetrahydropyranyloxy)-2-piperazinecarboxamide (658 mg) was obtained in substantially the same manner as in Example 220.

Mass (ESI−): 634, 636 (M−H)

¹H-NMR (300 MHz, CDCl₃, δ): 1.44(3H, t, J=4 Hz), 1.50–1.92(6H, m), 2.08–2.25(2H, m), 2.75–2.90(2H, m), 3.20(2H, t, J=4 Hz), 3.38(1H, m), 3.55–3.70(4H, m), 3.85–4.10(2H, m), 4.08(2H, q, J=4 Hz), 4.21(1H, m), 4.59, 4.63(1H, brs), 4.98(1H, m), 6.94(2H, d, J=8 Hz), 7.17(1H, m), 7.51(2H, d, J=8 Hz), 7.59(1H, m), 9.20(1H, s)

EXAMPLE 262

2-Aminoethanol (129 mg) was added to a solution of (2R)-1-[5-(4-fluorophenyl)thiophene-2-sulfonyl]-4-phenoxycarbonyl-N-(2-tetrahydropyranyloxy)-2-piperazinecarboxamide (250 mg) in DMF (2 ml). The reaction mixture was stirred at 80° C. overnight. The mixture was concentrated in vacuo, and the residue was partitioned between AcOEt and H₂O. The organic layer was washed with saturated aqueous NaCl solution, dried over MgSO₄, and concentrated in vacuo. The residue was purified by SiO₂ column chromatography eluted with MeOH in CHCl₃=2%, then 4%, to give 138 mg of (2R)-1-[5-(4-fluorophenyl)thiophene-2-sulfonyl]-4-[N-(2-hydroxyethyl)-aminocarbonyl]-N-(2-tetrahydropyranyloxy)-2-piperazinecarboxamide.

Mass (ESI−): 555 (M−H)

¹H-NMR (300 MHz, CDCl₃, δ): 1.52–1.90(6H, m), 2.68 (1H, t, J=11 Hz), 2.93(1H, d, J=2, 11 Hz), 3.20–3.50(4H, m), 3.57–3.70(3H, m), 3.85–4.00(2H, m), 4.10(1H, d, J=11 Hz), 4.30(1H, d, J=11 Hz), 4.93, 4.99(1H, brs), 5.62–5.78(1H, m), 7.15(2H, t, J=8 Hz), 7.24(1H, d, J=2 Hz), 7.57(2H, dd, J=4, 8 Hz), 7.60(1H, d, J=2 Hz), 9.40, 9.45(1H, s)

EXAMPLE 263

(2R)-1-[5-(4-Hydroxyphenyl)thiophene-2-sulfonyl]-N-hydroxy-4-methanesulfonyl-2-piperazinecarboxamide (35 mg) was obtained in substantially the same manner as in Example 5.

Mass (ESI): 460 (M−1)

¹H-NMR (300 MHz, DMSO-d₆, δ): 2.66–2.80(1H, m), 2.87(3H,s), 2.97(1H, dd, J=6, 14 Hz), 3.51(1H, d, J=14 Hz), 3.68–3.77(1H, m), 3.80(1H, d, J=14 Hz), 4.52–4.48(1H, m), 6.84(2H, d, J=8 Hz), 7.40(1H, d, J=3 Hz), 7.57(2H, d, J=8 Hz), 7.61(1H, d, J=3 Hz), 9.00(1H, brs), 9.93(1H, brs)

EXAMPLE 264

(2R)-1-[5-(4-Hydroxymethylphenyl)thiophene-2-sulfonyl]-N-hydroxy-4-methanesulfonyl-2-piperazinecarboxamide (27 mg) was obtained in substantially the same manner as in Example 5.

Mass (ESI): 474 (M−1)

¹H-NMR (300 MHz, DMSO-d₆, δ): 2.68–2.80(1H, m), 2.86(3H,s), 2.99(1H, dd, J=6, 14 Hz), 3.53(1H, d, J=14 Hz), 3.70–3.78(2H, m), 3.81(1H, d, J=14 Hz), 4.43–4.49(1H, m), 4.54(2H, d, J=8 Hz), 5.30(1H, t, J=8 Hz), 7.41(2H, d, J=8 Hz), 7.58(1H, d, J=3 Hz), 7.67(1H, d, J=3 Hz), 7.71(2H, d, J=8 Hz), 9.00(1H, brs)

EXAMPLE 265

(2R)-4-(N,N-Dimethylaminosulfonyl)-N-hydroxy-1-[5-(4-hydroxyphenyl)thiophene-2-sulfonyl]-2-piperazinecarboxamide (80 mg) was obtained as an amorphous powder in substantially the same manner as in Example 5.

Mass (ESI−): 489 (M−H)

¹H-NMR (300 MHz, DMSO-d₆, δ): 2.58–2.67(1H, m), 2.68(6H, s), 2.83(1H, dd, J=4, 14 Hz), 3.38–3.49(1H, m), 3.56–3.81(3H, m), 4.45(1H, brs), 6.84(2H, d, J=8 Hz), 7.42(1H, d, J=3 Hz), 7.57(2H, d, J=8 Hz), 7.64(1H, d, J=3 Hz), 8.96(1H, s)

EXAMPLE 266

(2R)-4-(N,N-Dimethylaminosulfonyl)-N-hydroxy-1-[5-(4-hydroxymethylphenyl)thiophene-2-sulfonyl]-2-piperazinecarboxamide (63 mg) was obtained as an amorphous powder in substantially the same manner as in Example 5.

Mass (ESI−): 503 (M−H)

¹H-NMR (300 MHz, DMSO-d₆, δ): 2.60–2.75(1H, m), 2.69(6H,s), 2.88(1H, dd, J=4, 14 Hz), 3.40–3.50(1H, m), 3.60–3.82(3H, m), 4.44–4.49(1H, m), 4.54(2H, d, J=6 Hz), 5.30(1H, t, J=6 Hz), 7.42(2H, d, J=8 Hz), 7.62(1H, d, J=4 Hz), 7.68–7.76(3H, m), 8.97(1H,s)

EXAMPLE 267

(2R)-4-Ethylaminocarbonyl-N-hydroxy-1-[5-(4-hydroxyphenyl)thiophene-2-sulfonyl]-2-piperazinecarboxamide (19 mg) was obtained in substantially the same manner as in Example 5.

Mass (ESI−): 453 (M−H)

$^1$H-NMR (300 MHz, DMSO-d$_6$, δ): 0.93(3H, t, J=4 Hz), 2.77–3.05(4H, m), 3.50–3.73(3H, m), 4.01(1H, d, J=12 Hz), 4.23(1H,m), 6.40(1H,m), 6.83(2H, d, J=8 Hz), 7.40(1H, d, J=2 Hz), 7.55(2H, d, J=8 Hz), 7.60(1H, d, J=2 Hz), 8.93(1H, s)

EXAMPLE 268

(2R)-N-Hydroxy-1-[5-(4-hydroxyphenyl)thiophene-2-sulfonyl]-4-{2-[(pyridine-3-carbonyl)amino]ethanesulfonyl}-2-piperazinecarboxamide (32 mg) was obtained in substantially the same manner as in Example 178.

Mass (ESI−): 594 (M−H)

$^1$H-NMR (300 MHz, DMSO-d$_6$, δ): 2.82(1H, dt, J=2, 11 Hz), 3.05(1H, dd, J=2, 11 Hz), 3.27(2H, t, J=4 Hz), 3.53–3.80(5H, m), 3.86(1H, d, J=11 Hz), 4.45(1H, s), 6.84 (2H, d, J=8 Hz), 7.39(1H, d, J=2 Hz), 7.51(1H, dd, J=2, 6 Hz), 7.56(2H, d, J=8 Hz), 7.61(1H, d, J=2 Hz), 8.14(1H, d, J=6 Hz), 8.71(1H, d, J=2 Hz), 8.88(1H, t, J=4 Hz), 8.97(1H, s), 8.99(1H, s), 9.92(1H, s), 10.79(1H, s)

EXAMPLE 269

(2R)-4-[2-(Benzoylamino)ethanesulfonyl]-N-hydroxy-1-[5-(4-hydroxyphenyl)thiophene-2-sulfonyl]-2-piperazinecarboxamide (22 mg) was obtained in substantially the same manner as in Example 178.

Mass (ESI−): 593 (M−H)

$^1$H-NMR (300 MHz, DMSO-d$_6$, δ): 2.81(1H, dt, J=2, 11 Hz), 3.05(1H, dd, J=2, 11lHz), 3.25(2H, t, J=4 Hz), 3.52–3.80(5H, m), 3.86(1H, d, J=11 Hz), 4.45(1H, s), 6.83 (2H, d, J=8 Hz), 7.38(1H, d, J=2 Hz), 7.42–7.58(5H, m), 7.61(1H, d, J=2 Hz), 7.80(2H, d, J=8 Hz), 8.65(1H, t, J=4 Hz), 8.99(1H, s), 9.92(1H, s), 10.79(1H, s)

EXAMPLE 270

(2R)-1-[5-(3-Fluoro-4-hydroxyphenyl)thiophene-2-sulfonyl]-N-hydroxy-4-methanesulfonyl-2-piperazinecarboxamide (121 mg) was obtained in substantially the same manner as in Example 5.

Mass (ESI): 478 (M−1)

$^1$H-NMR (300 MHz, DMSO-d$_6$, δ): 2.67–2.81(1H, m), 2.87(3H,s), 2.98(1H, dd, J=6, 14 Hz), 3.52(1H, d, J=14 Hz), 3.68–3.85(3H, m), 4.43–4.50(1H, m), 7.03(1H, t, J=9 Hz), 7.39(1H, d, J=8 Hz), 7.50(1H, d, J=3 Hz), 7.59–7.68(2H, m), 9.00(1H, brs), 10.28–10.85(1H, m)

EXAMPLE 271

(2R)-N-Hydroxy-4-methanesulfonyl-1-[5-(4-methoxycarbonylmethoxyphenyl)thiophene-2-sulfonyl]-2-piperazinecarboxamide (69 mg) was obtained in substantially the same manner as in Example 5.

Mass (ESI): 532 (M−1)

$^1$H-NMR (300 MHz, DMSO-d$_6$, δ): 2.64–2.80(1H, m), 2.86(3H, s), 3.98(1H, dd, J=6, 14 Hz), 3.52(1H, d, J=14 Hz), 3.65–3.85(6H, m), 4.42–4.50(1H, m), 4.89(2H, s), 7.03(2H, d, J=8 Hz), 7.49(1H, d, J=3 Hz), 7.63(1H, d, J=3 Hz), 7.70(2H, d, J=8 Hz), 9.00(1H, brs)

Preparation 161

2-(4-Isopropoxyphenyl)thiophene (1.88 g) was obtained in substantially the same manner as in Preparation 43.

$^1$H-NMR (300 MHz, CDCl$_3$, δ): 1.36(6H, d, J=7 Hz), 4.54(1H, m), 6.88(2H, d, J=8 Hz), 7.00–7.03(1H, m), 7.18–7.21(2H, m), 7.49(2H, d, J=8 Hz)

Preparation 162

Sodium 5-(4-isopropoxyphenyl)-2-thiophenesulfonate (1.28 g) was obtained in substantially the same manner as in Preparation 56.

$^1$H-NMR (300 MHz, DMSO-d$_6$, δ): 1.32(6H, d, J=7 Hz), 4.45(1H, m), 7.06(1H, d, J=4 Hz), 7.13(1H, d, J=4 Hz), 7.42(2H, d, J=8 Hz), 7.55(2H, d, J=8 Hz)

Preparation 163

5-(4-Isopropoxyphenyl)-2-thiophenesulfonyl chloride (1.35 g) was obtained in substantially the same manner as in Preparation 44.

$^1$H-NMR (300 MHz, CDCl$_3$, δ): 1.35(6H, d, J=6 Hz), 4.61(1H, m), 6.92(2H, d, J=8 Hz), 7.19(1H, d, J=4 Hz), 7.54(2H, d, J=8 Hz), 7.78(1H, d, J=4 Hz)

EXAMPLE 272

(2R)-1-[5-(4-Isopropoxyphenyl)thiophene-2-sulfonyl]-4-methanesulfonyl-N-(2-tetrahydropyranyloxy)-2-piperazinecarboxamide (246 mg) was obtained in substantially the same manner as in Example 4.

Mass (ESI−): 586 (M−H)

$^1$H-NMR (300 MHz, CDCl$_3$, δ): 1.37(6H, d, J=7 Hz), 1.55–1.91(6H, m), 2.74–2.90(2H, m), 2.88(1.5H, s), 2.93 (1.5H, s), 3.35–3.49(1H, m), 3.58–3.72(2H, m), 3.85–4.03 (2H, m), 4.24(1H, d, J=13 Hz), 4.55–4.64(2H, m), 4.92–5.01 (1H, m), 6.90(2H, d, J=8 Hz), 7.14(1H, d, J=4 Hz), 7.48(2H, d, J=8 Hz), 7.57(1H, d, J=4 Hz), 9.15–9.27(1H, m)

EXAMPLE 273

(2R)-1-[5-(4-Isopropoxyphenyl)thiophene-2-sulfonyl]-4-methanesulfonyl-N-hydroxy-2-piperazinecarboxamide (195 mg) was obtained in substantially the same manner as in Example 5.

Mass (ESI-1): 502 (M−H)

$^1$H-NMR (300 MHz, DMSO-d$_6$, δ): 1.34(6H, d, J=7 Hz), 2.60–2.74(1H, m), 2.81(3H, s), 3.35–3.49(2H, m), 3.60(1H, d, J=13 Hz), 3.77–3.95(2H, m), 4.22(1H, d, J=13 Hz), 4.54–4.62(1H, m), 4.70(1H, bs), 6.90(2H, d, J=8 Hz), 7.14 (1H, d, J=4 Hz), 7.48(2H, d, J=8 Hz), 7.68(1H, d, J=48 Hz)

This application is based on application Nos. PO 4249, PO 7156 and PO 8568 filed in Australia, the contents of which are incorporated hereinto by reference.

What is claimed is:

1. A compound of the formula (I):

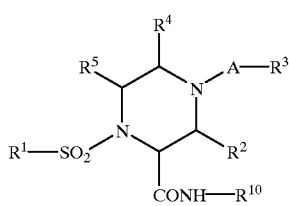

(I)

wherein

A is a sulfonyl;

$R^1$ is a lower alkyl optionally substituted by halogen, a lower alkenyl optionally substituted by aryl, or a heterocyclic group optionally substituted by a substituent selected from the group consisting of halogen, cyano, nitro, amino, acylamino, lower alkylamino, carbamoyl, hydroxy, lower alkoxy, aryloxy, lower alkyl, aryl, heterocyclic group, haloaryl, hydroxyaryl, lower alkoxyaryl, lower alkylaryl, nitroaryl, biphenylyl, aryloxyaryl, trihaloalkylaryl, cyano(lower)alkoxyaryl, cyanoaryl, cyano(lower) alkylaryl, lower alkanoyloxyaryl, lower alkanoyloxy(lower)alkylaryl, di(lower) alkylaminosulfonylaryl, hydroxy(lower)alkylaryl, lower alkoxycarbonylaryl, lower alkoxycarbonyl (lower)alkoxyaryl, lower alkylsulfonyloxyaryl, aryl substituted by halogen and hydroxy, aryl substituted by halogen and alkanoyloxy, aryl substituted by halogen and lower alkoxy, lower alkyl-heterocyclic group, and aryl-heterocyclic group;

$R^2$ is a hydrogen or lower alkyl;

$R^3$ is a lower alkyl optionally substituted by a substituent selected from the group consisting of halogen, heterocyclic group, carbamoyl, lower alkylcarbamoyl, carboxy, protected carboxy, heterocyclic-carbonyl, di(lower)alkylamino, protected amino, arylcarbonylamino, heterocyclic-carbonylamino, lower alkanoylamino, lower alkylsulfonylamino, di(lower)alkylaminosulfonylamino, heterocyclic-sulfonylamino, heterocyclic-thio, lower alkylheterocyclic-thio, and heterocyclic-thio, a lower alkoxy, an aryloxy, an aryl(lower)alkoxy, a heterocyclic(lower)alkenyl, said heterocyclic group being unsaturated 5- or 6-membered heteromonocyclic group containing 1 to 4 nitrogen atoms, a heterocyclic group, said heterocyclic group being selected from the group consisting of unsaturated 5- or 6-membered heteromonocylic group containing 1 to 4 nitrogen atoms, saturated 5- or 6-membered heteromonocyclic group containing 1 to 4 nitrogen atoms and unsaturated 5- or 6-membered heteromonocyclic group containing a sulfur atom, which is optionally substituted by heterocyclic group, said heterocyclic group being unsaturated 5- or 6-membered heteromonocyclic group containing 1 or 2 oxygen atoms and 1 to 3 nitrogen atoms, or a group of the formula:

wherein $R^8$ and $R^9$ are the same or different and each is hydrogen, lower alkyl, carboxy(lower)alkyl, lower alkoxycarbonyl(lower)alkyl, carbamoyl(lower) alkyl, hydroxy(lower)alkyl, aryl, cyclo(lower)alkyl, heterocyclic-(lower)alkyl;

$R^4$ is a hydrogen or lower alkyl;

$R^5$ is a hydrogen; and $R^{10}$ is a hydroxy or a protected hydroxy, and the above-mentioned heterocyclic group is each selected from the group consisting of unsaturated 3- to 8-membered heteromonocyclic group containing 1 to 4 nitrogen atoms, saturated 3- to 8-membered heteromonocyclic group containing 1 to 4 nitrogen atoms, unsaturated condensed 7- to 13-membered heterocyclic group containing 1 to 5 nitrogen atoms, unsaturated 3- to 8-membered heteromonocyclic group containing 1 or 2 oxygen atoms and 1 to 3 nitrogen atoms, saturated 3- to 8-membered heteromonocyclic group containing 1 or 2 oxygen atoms and 1 to 3 nitrogen atoms, unsaturated condensed 7- to 13-membered heterocyclic group containing 1 or 2 oxygen atoms and 1 to 3 nitrogen atoms, unsaturated 3- to 8-membered heteromonocyclic group containing 1 or 2 sulfur atoms and 1 to 3 nitrogen atoms, saturated 3- to 8-membered heteromonocyclic group containing 1 or 2 sulfur atoms and 1 to 3 nitrogen atoms, unsaturated 3- to 8-membered heteromonocyclic group containing a sulfur atom, unsaturated 3- to 8-membered heteromonocyclic group containing an oxygen atom, saturated 3- to 8-membered heteromonocyclic group containing an oxygen atom, unsaturated condensed 7- to 13-membered heterocyclic group containing 1 or 2 sulfur atoms and 1 to 3 nitrogen atoms, and unsaturated condensed 7- to 13-membered heterocyclic group containing 1 to 2 oxygen atoms, or a pharmaceutically acceptable salt thereof.

2. The compound of claim 1, wherein $R^1$ is a lower alkyl optionally substituted by halogen, a lower alkenyl optionally substituted by aryl, a heterocyclic group selected from the group consisting of unsaturated 5- or 6-membered heteromonocyclic group containing 1 or 2 sulfur atoms and 1 to 3 nitrogen atoms and unsaturated 5- or 6-membered heteromonocyclic group containing a sulfur atom, each of which is optionally substituted by a substituent selected from the group consisting of halogen, cyano, nitro, amino, acylamino, lower alkylamino, carbamoyl, hydroxy, lower alkoxy, aryloxy, lower alkyl, aryl, haloaryl, hydroxyaryl, lower alkoxyaryl, lower alkylaryl, nitroaryl, biphenylyl, aryloxyaryl, trihaloalkylaryl, cyano(lower)alkoxyaryl, cyanoaryl, cyano(lower) alkylaryl, lower alkanoyloxyaryl, lower alkanoyloxy(lower)alkylaryl, di(lower) alkylamino-sulfonylaryl, hydroxy(lower)alkylaryl, lower alkoxycarbonylaryl, lower alkoxycarbonyl (lower)alkoxyaryl, lower alkylsulfonyloxyaryl, aryl substituted by halogen and hydroxy, aryl substituted by halogen and alkanoyloxy, aryl substituted by halogen and lower alkoxy, heterocyclic group selected from the group consisting of unsaturated 9- or 10-membered heterobicyclic group containing 1 or 2 oxygen atoms, unsaturated 5- or 6-membered heteromonocyclic group containing 1 to 4 nitrogen atoms, unsaturated 5- or 6-membered heteromonocyclic group containing 1 or 2 oxygen atoms and 1 to 3 nitrogen atoms, unsaturated 5- or 6-membered heteromonocyclic group containing 1 or 2 sulfur atoms and 1 to 3 nitrogen atoms, and a lower alkyl- or (phenyl-) heterocyclic group, said heterocyclic group being unsaturated 5- or 6-membered heteromonocyclic group containing 1 or 2 oxygen atoms and 1 to 3 nitrogen atoms, or a pharmaceutically acceptable salt thereof.

3. The compound of claim 2, wherein $R^3$ is a lower alkyl optionally substituted by a substituent selected from the group consisting of halogen, heterocyclic group, carbamoyl, lower alkylcarbamoyl, carboxy, protected carboxy, heterocyclic-carbonyl, di(lower)alkylamino, protected amino, arylcarbonylamino, heterocyclic-carbonylamino, lower alkanoylamino, lower alkylsulfonylamino, di(lower)alkylaminosulfonylamino, heterocyclic-sulfonylamino, heterocyclic-thio, lower alkylheterocyclic-thio, and heterocyclic-thio, a lower alkoxy, an aryloxy, an aryl(lower)alkoxy, a heterocyclic(lower)alkenyl, said heterocyclic group being unsaturated 5- or 6-membered heteromonocyclic group containing 1 to 4 nitrogen atoms, a heterocyclic group, said heterocyclic group being selected from the group consisting of unsaturated 5- or 6-membered heteromonocyclic group containing 1 to 4 nitrogen atoms, saturated 5- or 6-membered heteromonocyclic group containing 1 to 4 nitrogen atoms and unsaturated 5- or 6-membered heteromonocyclic group containing a sulfur atom, which is optionally substituted by heterocyclic group, said heterocyclic group being unsaturated 5- or 6-membered heteromonocyclic group containing 1 or 2 oxygen atoms and 1 to 3 nitrogen atoms, or a group of the formula:

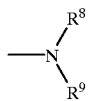

wherein $R^8$ and $R^9$ are the same or different and each is hydrogen, lower alkyl, carboxy(lower)alkyl, lower alkoxycarbonyl(lower)alkyl, carbamoyl(lower) alkyl, hydroxy(lower)alkyl, aryl, cyclo(lower)alkyl, heterocyclic-(lower)alkyl;

said heterocyclic group each being selected from the group consisting of unsaturated 5- or 6-membered heteromonocyclic group containing 1 to 4 nitrogen atoms, saturated 5- or 6-membered heteromonocyclic group containing 1 to 4 nitrogen atoms, unsaturated 5- or 6-membered heteromonocyclic group containing 1 or 2 oxygen atom and 1 to 3 nitrogen atoms, saturated 5- or 6-membered heteromonocyclic group containing 1 or 2 oxygen atom and 1 to 3 nitrogen atoms, unsaturated 5- or 6-membered heteromonocyclic group containing 1 or 2 sulfur atom and 1 to 3 nitrogen atoms, unsaturated 5- or 6-membered heteromonocyclic group containing a sulfur atom, and unsaturated 9- or 10-membered heterobicyclic group containing 1 or 2 oxygen atoms, or a pharmaceutically acceptable salt thereof.

4. The compound of claim 3, wherein $R^1$ is a heterocyclic group selected from the group consisting of unsaturated 5- or 6-membered heteromonocyclic group containing 1 or 2 sulfur atoms and 1 to 3 nitrogen atoms and unsaturated 5- or 6-membered heteromonocyclic group containing a sulfur atom, each of which is optionally substituted by a substituent selected from the group consisting of halogen, phenyl, halophenyl, hydroxyphenyl, lower alkoxyphenyl, lower alkylphenyl, nitrophenyl, biphenylyl, phenoxyphenyl, trihalo(lower) alkylphenyl, cyano (lower) alkoxyphenyl, cyanophenyl, cyano (lower) alkylphenyl, lower alkanoyloxyphenyl, lower alkanoyloxy (lower) alkylphenyl, di (lower) alkylaminosulfonylphenyl, hydroxy (lower) alkylphenyl, lower alkoxycarbonylphenyl, lower alkoxycarbonyl (lower) alkoxyphenyl, lower alkylsulfonyloxyphenyl, phenyl substituted by halogen and hydroxy, phenyl substituted by halogen and lower alkanoyloxy, phenyl substituted by halogen and lower alkoxy, heterocyclic group selected from the group consisting of unsaturated 9- or 10-membered heterobicyclic group containing 1 or 2 oxygen atoms, unsaturated 5- or 6-membered heteromonocyclic group containing 1 to 4 nitrogen atoms, unsaturated 5- or 6-membered heteromonocyclic group containing 1 or 2 oxygen atoms and 1 to 3 nitrogen atoms, unsaturated 5- or 6-membered heteromonocyclic group containing 1 or 2 sulfur atoms and 1 to 3 nitrogen atoms, and a lower alkyl- or (phenyl-) heterocyclic group, said heterocyclic group being unsaturated 5- or 6-membered heteromonocyclic group containing 1 or 2 oxygen atoms and 1 to 3 nitrogen atoms;

$R^2$ is a hydrogen;

$R^3$ is a lower alkyl, a halo (lower) alkyl, a heterocyclic (lower) alkyl, said heterocyclic group being selected from the group consisting of unsaturated 5- or 6-membered heteromonocyclic group containing 1 to 4 nitrogen atoms, saturated 5- or 6-membered heteromonocyclic group containing 1 to 4 nitrogen atoms, and saturated 5- or 6-membered heteromonocyclic group containing 1 or 2 oxygen atoms and 1 to 3 nitrogen atoms, a carbamoyl (lower) alkyl, a lower alkylcarbamoyl (lower)-alkyl, a carboxy (lower) alkyl, a phenyl (lower)-alkoxycarbonyl (lower) alkyl, a heterocyclic-carbonyl (lower) alkyl, said heterocyclic group being saturated 5- or 6-membered heteromonocyclic group containing 1 or 2 oxygen atoms and 1 to 3 nitrogen atoms, a di (lower) alkylamino (lower) alkyl, a phenyl (lower)-alkoxycarbonylamino (lower) alkyl, a lower alkoxycarbonylamino (lower) alkyl, a benzoylamino (lower)-alkyl, a heterocyclic-carbonylamino (lower) alkyl, said heterocyclic group being unsaturated 5- or 6-membered heteromonocyclic group containing 1 to 4 nitrogen atoms, a lower alkanoylamino (lower) alkyl, a lower alkylsulfonylamino (lower) alkyl, a di (lower) alkyl-aminosulfonylamino (lower) alkyl, a heterocyclic-sulfonylamino (lower) alkyl, said heterocyclic group being unsaturated 5- or 6-membered heteromonocyclic group containing 1 to 4 nitrogen atoms, a heterocyclic-thio (lower) alkyl, said heterocyclic group being selected from the group consisting of unsaturated 5- or 6-membered heteromonocyclic group containing 1 to 4 nitrogen atoms, saturated 5- or 6-membered heteromonocyclic group containing 1 to 4 nitrogen atoms, unsaturated 9- or 10-membered heterobicyclic group containing 1 to 5 nitrogen atoms, and unsaturated 5- or 6-membered heteromonocyclic group containing 1 to 2 sulfur atoms and 1 to 3 nitrogen atoms, a lower alkylheterocyclic-thio (lower) alkyl, said heterocyclic group being unsaturated 5- or 6-membered heteromonocyclic group containing 1 to 4 nitrogen atoms, a heterocyclic-thio (lower) alkyl, said heterocyclic group being unsaturated 9- or 10-membered heterobicyclic group containing 1 to 5 nitrogen atoms, a lower alkoxy, a phenyloxy, a fluorenyl (lower) alkoxy, a heterocyclic (lower)-alkenyl, said heterocyclic group being unsaturated 5- or 6-membered heteromonocyclic group containing 1 to 4 nitrogen atoms, a heterocyclic group, said heterocyclic group being selected from the group consisting of unsaturated 5- or 6-membered heteromonocyclic group containing 1 to 4 nitrogen atoms, saturated 5- or 6-membered heteromonocyclic group containing 1 to 4 nitrogen atoms, and unsaturated 5- or 6-membered heteromonocyclic group containing a sulfur atom, which is optionally substituted by heterocyclic group, said heterocyclic group being unsaturated 5- or 6-membered heteromonocyclic group containing 1 or 2 oxygen atoms and 1 to 3 nitrogen atoms, a mono- or di (lower) alkylamino, a carboxy (lower) alkylamino, a lower alkoxycarbonyl (lower)-alkyl (lower) alkylamino, an N-(lower) alkyl-N- (lower) alkoxycarbonylamino, a carbamoyl (lower) alkylamino, a hydroxy (lower) alkylamino, a phenylamino, or a cyclo (lower) alkylamino;

$R^4$ is a hydrogen, $R^5$ is a hydrogen, and $R^{10}$ is a hydroxy, a lower alkoxy, a phenyl (lower) alkoxy, a fluorenyl (lower) alkoxy or a tetrahydropyranyloxy, or a pharmaceutically acceptable salt thereof.

5. The compound of claim 4, wherein $R^1$ is a thienyl substituted by a substituent selected from the group consisting of halogen, phenyl, halophenyl, hydroxyphenyl, lower alkoxyphenyl, lower alkylphenyl, nitrophenyl, biphenylyl, phenoxyphenyl, trihalo(lower)alkylphenyl, cyano (lower) alkoxyphenyl, cyanophenyl, cyano (lower) alkylphenyl, lower alkanoyloxyphenyl, lower alkanoyloxy (lower) alkylphenyl, di (lower) alkylaminosulfonylphenyl, hydroxy (lower) alkylphenyl, lower alkoxycarbonylphenyl, lower alkoxycarbonyl (lower) alkoxyphenyl, lower alkylsulfonyloxyphenyl, phenyl substituted by halogen and hydroxy, phenyl substituted by halogen and lower alkanoyloxy, phenyl substituted by halogen and lower alkoxy, heterocyclic group selected from the group consisting of unsaturated 9- or 10-membered heterobicyclic group containing 1 or 2 oxygen atoms, unsaturated 5- or 6-membered heteromonocyclic group containing 1 to 4 nitrogen atoms, unsaturated 5- or 6-membered heteromonocyclic group containing 1 or 2 oxygen atoms and 1 to 3 nitrogen atoms, unsaturated 5- or 6-membered heteromonocyclic group containing 1 or 2 sulfur atoms and 1 to 3 nitrogen atoms, and a lower alkyl- or (phenyl-) heterocyclic group, said heterocyclic group being unsaturated 5- or 6-membered heteromonocyclic group containing 1 or 2 oxygen atoms and 1 to 3 nitrogen atoms, or a pharmaceutically acceptable salt thereof.

6. The compound of claim 5, wherein $R^1$ is a thienyl substituted by a substituent selected from the group consisting of halogen, thienyl substituted by oxazolyl, a mono- (or di) (lower)-alkylamino, a carboxy (lower) alkylamino, a lower alkoxycarbonyl (lower) alkylamino, an N-(lower)alkyl-N-(lower) alkoxycarbonyl(lower)alkylamino, a carbamoyl (lower)-alkylamino, a hydroxy(lower)alkylamino, a phenylamino or a cyclo(lower)alkylamino, and $R^{10}$ is a hydroxy, or a pharmaceutically acceptable salt thereof.

7. The compound of claim 5, wherein $R^1$ is a thienyl, a halothienyl, a phenylthienyl, a halophenylthienyl, a hydroxyphenylthienyl, a lower alkoxyphenylthienyl, a lower alkylphenylthienyl, a nitrophenylthienyl, a biphenylylthienyl, a phenoxyphenylthienyl, a trihalo(lower) alkylphenylthienyl, a cyano(lower) alkoxyphenylthienyl, a cyanophenylthienyl, a cyano (lower)alkylphenolthienyl, a lower alkanoyloxyphenylthienyl, a lower alkanoyloxy(lower) alkylphenylthienyl, a di(lower) alkylaminosulfonylphenylthienyl, a hydroxy(lower)-alkylphenylthienyl, a lower alkoxycarbonylphenylthienyl, a lower alkoxycarbonyl (lower)alkoxyphenylthienyl, a lower alkylsulfonyloxyphenylthienyl, a phenylthienyl wherein the phenyl group being substituted by halogen and hydroxy, a phenylthienyl wherein the phenyl group being substituted by halogen and lower alkanoyloxy, or a phenylthienyl wherein the phenyl group being substituted by halogen and lower alkoxy, or a pharmaceutically acceptable salt thereof.

8. The compound of claim 1, wherein $R^1$ is a lower alkyl optionally substituted by halogen, or a lower alkenyl optionally substituted by aryl, or a pharmaceutically acceptable salt thereof.

9. A pharmaceutical composition, comprising (1) the compound of claim 1 or a pharmaceutically acceptable salt thereof and (2) a pharmaceutically acceptable carrier or diluent.

* * * * *